US012767975B2

(12) United States Patent
Chenchik et al.

(10) Patent No.: US 12,767,975 B2
(45) Date of Patent: *Oct. 20, 2026

(54) MULTIPLEX PREPARATION OF BARCODED GENE SPECIFIC DNA FRAGMENTS

(71) Applicant: Cellecta, Inc., Mountain View, CA (US)

(72) Inventors: Alex Chenchik, Redwood City, CA (US); Costa Frangou, Sunnyvale, CA (US); Mikhail Makhanov, San Francisco, CA (US); Russell Paul Darst, IV, San Bruno, CA (US); Donato Tedesco, Berkeley, CA (US); Lester Kobzik, Mountain View, CA (US)

(73) Assignee: Cellecta, Inc., Mountain View, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 17/892,550

(22) Filed: Aug. 22, 2022

(65) Prior Publication Data

US 2023/0227889 A1 Jul. 20, 2023

Related U.S. Application Data

(60) Continuation of application No. 17/587,500, filed on Jan. 28, 2022, now abandoned, which is a division of application No. 16/543,211, filed on Aug. 16, 2019, now Pat. No. 11,274,334.

(60) Provisional application No. 62/799,448, filed on Jan. 31, 2019, provisional application No. 62/765,124, filed on Aug. 17, 2018.

(51) Int. Cl.

*C12Q 1/68* (2018.01)
*C12Q 1/6806* (2018.01)
*C12Q 1/686* (2018.01)

(52) U.S. Cl.

CPC .......... *C12Q 1/6806* (2013.01); *C12Q 1/686* (2013.01)

(58) Field of Classification Search

None

See application file for complete search history.

(56) References Cited

U.S. PATENT DOCUMENTS

| | | | | |
|---|---|---|---|---|
| 5,994,076 | A | 11/1999 | Chenchik et al. | |
| 6,265,165 | B1 * | 7/2001 | Xu | C12N 15/1096 435/6.16 |
| 2003/0082758 | A1 | 5/2003 | Rosen et al. | |
| 2003/0186246 | A1 | 10/2003 | Willey et al. | |
| 2006/0121452 | A1 | 6/2006 | Dhallan | |
| 2008/0050393 | A1 | 2/2008 | Tang et al. | |
| 2013/0123120 | A1 | 5/2013 | Zimmermann et al. | |
| 2013/0244897 | A1 | 9/2013 | Lueking et al. | |
| 2013/0274117 | A1 | 10/2013 | Church et al. | |
| 2015/0038343 | A1 | 2/2015 | Eamon et al. | |
| 2015/0087535 | A1 * | 3/2015 | Patel | C12Q 1/6806 506/4 |
| 2016/0251714 | A1 | 9/2016 | Conant et al. | |
| 2016/0257993 | A1 * | 9/2016 | Fu | C12Q 1/6869 |
| 2016/0362748 | A1 | 12/2016 | Mongan et al. | |
| 2016/0376664 | A1 * | 12/2016 | Chenchik | C12Q 1/6806 506/4 |

FOREIGN PATENT DOCUMENTS

| | | | |
|---|---|---|---|
| CN | 107385042 | A | 11/2017 |
| WO | WO2004051218 | A2 | 6/2004 |
| WO | WO2008069906 | A2 | 6/2008 |
| WO | WO2011014811 | A1 | 2/2011 |
| WO | WO2013081864 | A1 | 6/2013 |
| WO | WO2013128281 | A1 | 9/2013 |
| WO | WO2013138510 | A1 | 9/2013 |
| WO | WO2016172126 | A2 | 10/2016 |
| WO | WO2017210469 | A2 | 12/2017 |
| WO | WO2018119447 | A2 | 6/2018 |

OTHER PUBLICATIONS

Giardina et al., Whole genome amplification and real-time PCR in forensic casework, BMC Genomics, Biomed Central, 2009, vol. 10, No. 1, p. 159.

Lin et al., Multiplex genotype determination at a large number of gene loci, Proc Natl Acad Sci USA, 1996, vol. 93, No. 6, p. 2582-2587.

Langmann et al., Real-time reverse transcription-PCR expression profiling of the complete human ATP-binding cassette transporter superfamily in various tissues, Clin Chem, 2003, vol. 49, No. 2, p. 230-238.

Myllykangas et al., Chapter 2 Overview of Sequencing Technology Platforms, Bioinformatics for High Throughput Sequencing, 2012, p. 11-25.

Clarke et al., Modular tagging of amplicons using a single PCR for high-throughput sequencing, Molecular Ecology Resources, 2014, vol. 14, p. 117-121.

Parkinson et al., Preparation of high-quality next-generation sequencing libraries from pictogram quantities of target DNA, Genome Research, 2012, vol. 22, p. 125-133.

(Continued)

*Primary Examiner* — Suryaprabha Chunduru

(74) *Attorney, Agent, or Firm* — Jonathan Mares; Bret E. Field; Bozicevic, Field & Francis LLP

(57) ABSTRACT

Methods of preparing a plurality of sample-barcoded anchor-domain-flanked gene specific deoxyribonucleic acid (DNA) fragments from a template nucleic acid, e.g., ribonucleic acid (RNA), sample are provided. Aspects of the methods include employing a set of gene specific primer pairs, wherein each pair of gene specific primers is made up of a forward primer and a reverse primer, at least one of which includes a sample barcode domain. The methods find use in a variety of different applications, including high-throughput sequencing, e.g., expression profiling, applications, including of small biological samples, e.g., single-cells.

24 Claims, 87 Drawing Sheets

Specification includes a Sequence Listing.

(56) References Cited

OTHER PUBLICATIONS

Head et al., Library construction for next-generation sequencing: Overviews and challenges, BioTechniques, 2014, vol. 56, No. 2, p. 61-77.
Blomquist et al., Targeted RNA-Sequencing with Competitive Multiplex-PCR Amplicon Libraries, PLOS One, 2013, vol. 8, No. 11, e79120, 14 pages.
Markoulatos et al., Multiplex polymerase chain reaction: a practical approach, Journal of Clinical Laboratory Analysis, 2002, vol. 16, p. 47-51.
Shen et al., MPprimer: a program for reliable multiplex PCR primer design, BMC Bioinformatics, 2010, vol. 11, p. 143.
Zhao et al., Comparison of RNA-Seq and Microarray in Transcriptome Profiling of Activated T Cells, PLOS One, 2014, vol. 9, No. 1, e78644, 13 pages.
CoPrimers by Co-Disgnotics Inc., downloaded in Apr. 2015, 1 page.
Karn, High-Throughput Gene Expression and Mutation Profiling: Current Methods and Future Perspectives, Breast Care, 2013, vol. 8, p. 401-406.
SureSelectXT RNA Target Enrichment for Illumina Multiplexed Sequencing: Strand-Specific RNA Library Prep and Target Enrichment Protocols, Agilent Technologies, Version FO, Apr. 2018, 67 pages.
SMARTer® Target RNA Capture for Illumina® User Manual, Clontech Laboratories, Inc., 23 pages.
Gaublomme et al., Nuclei multiplexing with barcoded antibodies for single-nucleus genomics, Nature Communications, 2019, vol. 10, p. 1-26.
Mamanova et al., Target-enrichment strategies for next-generation sequencing, Nature Methods, 2010, vol. 7, No. 2, og. 111-118.
SeqCap RNA Enrichment System User's Guide, Version 1.1, Roche Sequencing Solutions, Inc., 2017, 51 pages.
Samorodnitsky et al., Evaluation of Hybridization Capture Versus Amplicon-Based Methods for Whole-Exome Sequencing, Human Mutation, 2015, vol. 36, No. 9, p. 903-914.
Stoeckius et al., Cell "hashing" with barcoded antibodies enables multiplexing and doublet detection for single cell genomics, Genome Biology, 2018, vol. 19, p. 1-16.
Xu et al., Detection of splice isoforms and rare intermediates using multiplexed primer extension sequencing, Nat Methods, 2019, vol. 16, No. 1, p. 55-58.
Zheng et al., Anchored Multiplex PCR for Targeted Next-Generation Sequencing, Nature Medicine, 2014, vol. 20, No. 12, p. 1479-1486.

* cited by examiner

FIG. 7

TABLE 1

| | | | |
|---|---|---|---|
| | GGCAGCAACTCGGG | CTGGAAGAACCCGC | AGCTGTGCGCAAGA |
| GCCCAGGAAGCCGA | CCGCCTACAGAGGG | CACGCGACGATACC | GGCGGAACCTCATG |
| CCACGGCCAACGCC | GGAGATAGGCGCCC | GGCGATCAGGGCAG | GAGTAGGGTGAGGC |
| GCCAAGGGACCAGC | CAAGTGGCCGGCGG | TACACGAGAACCGA | ACCGTGACGGCAGT |
| GACCGCAGCCGAGG | GCGACGAGGCCACT | GACACCTCCCCAAA | CCCACAGCAAAATT |
| ACCACAGAACCCAA | AGCGAGACGGTGCC | AGCGCGTCGAACAG | ACCGAAATCCTCAC |
| CGACAGGGGGAGAG | TCGGCAGAACGCCG | AATCCCCCGCCCAA | AGACCAAGGGAGTT |
| GGAAGAGCACCGGG | CCGAACCGGGTGAA | CAGCAACGAAACGT | TAAAGGCCGAATGG |
| GCCCGAAGCACGGA | GACCAATACACGCC | ACCCGCAAAGGTGG | CACCCCGTTGGAAA |
| GACAGCCGACCAAC | AGGAGCCGGTAAAA | GCATAAACGGACCA | GTAGCCCCACAAAT |
| GAGGCAAGGGGCCC | CAGTAGCCCGAGAA | ATCCAGAGCCAACC | TGAGGGCGTAACAC |
| ACGAGCAGCAGAGG | CGCACACATCACGC | CAACCGGTCACGGG | AGGGACGCTGCGTG |
| CCCCAGCGCAGACA | GCTCAGCGCCAAAG | GGAGGCCAGCCTAG | ACCAACTGACGCTC |
| AGACAAAGCCGAAG | GAGAAACAAGATGC | CAGAACTAGCACGA | GCAATCACGCGTAA |
| CACCGAGGGGAACG | CCAAATAACAAAAG | AGACCCGCAATCAG | TCTCCGGACGCACC |
| CAAGCGCGACACGA | AACAGCGACACGGT | ACCCCCTCGACCGC | CGGGTCGCCTGAAA |
| CACCCGAAAGCCAG | ACCAAGACGACCAT | AACCGTCCGCAGCG | GAAAAAGTAGGATG |
| GCGAGCGAGACGAG | GCAAGACCCTCACC | AGAGCACGTAAGGG | GAGGCGGTCATAAA |
| AGAGGAGCAAGGGA | ACCATCACCAAGCC | AGACGGGCACATGC | GTGGTAGCGCGCGA |
| GACGGTCCCGACAC | CGAGACCCTCCAGA | GATAAAGGAGCCCC | AATTCCACACAAGA |
| ATACGAACGACGGC | GCTCCAGGCAGCCA | CACAGCTGGAACCA | CAACGGCGTGGAGT |
| AGCTCGGCCAAGAA | AGCTGAGGACCAAG | GAAAGACAACGAGT | ACGGGTCATGGGAC |
| ACGAGAGTAGCCGA | CCACCCTGGACACG | CGAGGAAAAGGTTA | GGACCTGGACACGT |
| ATGAGCGGAAAGAA | CCAGGAAACACCTA | AACCCAAGTGTAAA | GAAAAATACGGTCG |
| GGCAAAAACCCATC | CAGGAATCCGGCCA | GCAAACTCCGGGAT | CGCAGGACATTCCC |
| AGGGGAGACCCGTC | GTGGCCGAGGCAGG | GCCACTTGGGCCAG | GTTACCGCAGGGCG |
| AGCAAGGGCCTGCG | CAAGGCAGCGGTGC | AGGCCCACAGCGTT | GACAAGCCCGTTGA |
| GCCGCAAAGTGGGA | AAGCCGCACACTCC | TGCTACGGCACACA | TGCGTGGCGACGAC |
| GCCCAAAGTCGAAC | AGCCAGGCAACTAC | CTCTCAAAGAAAGA | ATCAGAACATAAGA |
| CAAGGTCGCCGGGA | CTCCAAGCCCCGGA | GCACCCCTCACAGT | ACAAGCCGCATGTC |
| AATGACGGCAAGCC | CGTGAACCCCACCC | ATCCAGGCAGAGTG | TAGAGGCGGGCCTC |
| GAGCCACGAGTCAC | GTACAAGCCGGCCA | CAGGATAAAGACTG | CATAGAAGCCGTAA |
| GAGGCGCAATACAC | ACAGACGAACACTC | CTCCAACTCGGGGG | CCGTAGGACAAGTG |
| TAGGGAACCACACC | CAAACAAAGCGATG | TATGGGAGCCAACG | TGAGACGCGAGCAT |
| GGGGAATGACCAGA | AAGCGGTGACAGGC | TCCACGCGCTGCAC | CCACACAAATCTAG |
| ATGAAGAAACAAGG | TAGCACGCCGACAG | TCTAAGCGCGCGAG | ACGCCGTCCAGCTG |
| AACACGAGCGGTAG | GTACCCCAGCGGAC | GGGGGAACTAGGTG | AGAGGGACCTTCAC |
| GGGGACGACTACGA | CACAGGCGGTGGGC | AGGCGCAGAATAAT | CTAGGCATAGCCAG |
| GGAGACAAGGGGCT | CACAGGAGACACTC | ATCACCAAGTCCGG | GAGCACGTCCATCC |
| CCTGCAAAGGAACG | AAGCACCATGCGGA | CACAGTACGAAGAT | ACAAATTCAGCGAC |
| GCGAATGGAAAGCA | GCACTACCAGGCAA | GCGCAACCGTTAAC | AGAACATGGGTCCG |
| CGGGCTCGGACACA | GGCGAGGGAGGTCA | CCCCATACCCACGT | CGCGATGCCGCACT |
| GGAGCGACGTAAAC | GGTACAAACAACCG | GGTTAGAAGCCCCG | GCGGAGTGTAACAA |

FIG. 7 (Cont.)

| | | | |
|---|---|---|---|
| CTTACACCGGAAGC | GGCACTGCTGACAA | CGCCCATGCCGTAG | GAAGCTGTAGGGCG |
| AATGGAGAAGCCTA | CTAACCACACTCAA | CTGCACCACTGGGA | CCGGACTCGACCTA |
| GAGCGACACGCTAT | CGCTGCATGGGACC | CAGCGGGTCGATCA | CCTCCGACGGTGAG |
| ATGGTCAAAAACGA | GAGCATACGCATAG | AGGGCACACCTTCG | AAGGACAACAATAT |
| CCGGACGTGTAAAC | AAGACCTAAAGACT | GAGTGGGCAGCGGT | GAGCAGAGTCGCGT |
| ATGCGACAAATAGC | GGCCAAATCCACTG | AACAACTCCGTGGC | TGACCGCAGCACCT |
| CGTTCGAGGAGCAC | AATTGGAACGCGCC | TGTAAAGCCCCCGC | GGCGACCGACCTAT |
| CGTCGGAACAACAT | CGCGAGCTACCGGT | GCACACGTAAAGTG | TCAGGCCAGACAGT |
| TGCATCGGCCACCG | ATCGCAGGGCGTGC | AACGGCCTCCTCGC | AGAATCCGCAGTGA |
| TTCGCACACCAAGC | AGGGACCTTCAACA | CTCCGCTACGCGAA | GACAGAATGGCAAT |
| GATGACCCGAAGAT | AGAGACCTCGGCTG | ACTGAACCACTGGA | ACTGAACTGAGGAC |
| GCTTGGGAGAGGGC | CCCGACCCGTTCAG | AGACGGTCCGGTAG | AGAAAGGGACGTAT |
| AACACCTGGATGGG | ACTTCACCGCAAAG | AGGGTAGTGAGCGG | CATCCGCAGCGTAA |
| CCACTCGCTCCGCA | ATGAAAAACTGGCC | GGAGCGCTGCATCC | CCTAGTGACGGCCG |
| ATCAAGCGGTGAAG | CGCGTACGCTAACG | TTACCCAGGCAAAA | ATAGCCATAGAGCA |
| AGCAGGCGAAGTTA | GCTCCCGCTCAGGA | GTCAGAGATACCGC | AGCCGTGAACGTCG |
| CGAGGGTCGAGTCG | AGTCGACCTGAGCA | AGCGGAGGTACGGT | AACAGAAATCAGTC |
| ACCCAAAAACTTCG | AAACGAAGCGGCTT | CTCCGAGCTAGGAC | TACAAAGGCTAGCA |
| AGGCTGGAGGATAG | CGCAACTAGGATAC | CCAAAGATAGATCA | CGATGCGACCAACT |
| TGATCCAGAGGCCA | CGTATGGAAAACAG | GGGCGAAAGGTACT | AGGCCGACTCATAC |
| AAGACCACTTCCCA | CGCAGTCGGTCCAG | GTTGCAGGGAACCC | CTGCGGCACCGTGG |
| AGATGTAGCGGAGG | AAGCGTCGTACGGG | GTCTGGCAGCAGAA | AAATAAATCGGGAT |
| GAAACGCACCTGCT | GCCGGTGCGTAAAC | TCGGAGAACGTGAG | ATATGGTGAGCAAC |
| AGGGCAGTAGGACT | GGACTACACACGTG | CGGTGGAGCGCTCA | ATGCCAGAACATAT |
| GATCCTAACCAACC | CGTGAACGAAGTCA | GAGCGCCTTAGCAC | TCAAAGTAACATAA |
| CAGCGTCGCGAGTG | CATACCGGACACCT | TGGCCAGAGTCGCC | GGGCAAGCTCTGTG |
| GTACTAACACAGCA | CAGTAAGCCCAATG | GCAAGTCGGCGCTC | GAAGGGGCTTCCTC |
| AGAGGTGAACAAAT | CTCGAAGCCTACGG | CCCAATCGTAGGAA | CTAGAGGGAGCTTG |
| CCCCTAAGGGCCTG | GGAATGGCGTACCA | CGTGGGGAACGGCT | AGAGAATTTAGGCG |
| TGCCGTCGCGAAAC | GGTCGAGGGACGTA | ACCACCGACTGGAT | CCGTAACCGCCCTT |
| CCACATCGCAACCT | ACGTGAGATAGCAC | CAACCAGCGATTAG | TATGTGCAGGGGAG |
| GCGGCTGCCTCACG | TGAGACATCCCGAG | GGCACCCTCTGAAC | AACGGTGGGTTCCA |
| CACTACAAGGGGAT | GTCCGCGATAAGCG | TAAAAAGACGCGTA | ATAAATCCAATCAC |
| TAGACCCCCTGACC | GAACTGGCTCAAGG | ACCAGCCAGCTCAT | TAGCTGACTCGGGG |
| ACCGGGAACTTACC | CATAGGTAGGGCAC | GACAACGGGTGTGC | GATTGACGGGCTCC |
| TAGATAACCGGGCA | CAATGATGCGAAAC | CTAGCCCAATCCGA | ACTTATAAGGCAAC |
| CTGGGGGAAGCAAT | GTGCCCGTCCCAAG | CTATCCAAACGAGC | CTTGCTACACCCAC |
| CGGCTATGGCCCAG | ACGACACGCGTTGA | GAAGCGTACGCTCC | TACCTCAAAAATGA |
| TCTGCGAGGGGCGA | CTTCAGACAAACAC | ACGTTCGCAGGAAA | TGAAGTTCAGGCGA |
| CCCAGGGGCTTCGA | GAGAAGAAGCTTAC | GAATGACGATAAGG | TGAGCCCACTTACC |
| TGGGGACCTGCGAC | GGAGGTCTAAGCGG | GAAATAACGATCAG | ATTAAGCAATACCC |
| GCATTAGCAGAGCG | AAGCCCGACATGTA | CAATGCAACATGGC | GAAATCTTCCGCGA |
| TGAGACCACAGTCG | GAAGCGAGGTTCCA | CTACAACGGCTGCG | GAGGTAGAACAATT |

FIG. 7 (Cont.)

| | | | |
|---|---|---|---|
| CTCGGCGATCTCAA | ACCGATCGTATCGC | TCACAATATGACAC | GGGTACAGTCGGTG |
| CGGTATTGAGAGCG | CTATACGGCCTACC | CTATTGCGGGAGAA | CTGTAGGGCGTCAA |
| CCTTGGTCCCGAAG | GCTAACACGGCTTC | GAGATCCGCTGTAC | GTAAATCCCCTACC |
| TGATCGACCTCGGC | ACGTAGGAGCGTAT | AAATCGATGGCGCT | GACCATTGACGGTG |
| TGCGGGTGGTGACC | GGATGGGCTAGATC | TCACGAGATCCGTA | AATGGCGAGGTGTG |
| TCCACCTAGGGCTG | CCTAATGTGGCCCA | CTATGCCGGGCCAT | TACTGAATAACAGG |
| GCACCTGCTGGATA | GGTGAGTTACACAC | TAGTCCCTACGGAC | ATCATAGCTCCCAC |
| GCCCTGCCGCTTGA | AAGCTACCTCACCT | AGGATGAGTTGGCG | GCGTCCTTCCCCAC |
| GGGCATCTAGAATA | GCACATTCGATGAC | GCGGCTGTGAACCT | GCTACAACTGACTG |
| AGGTTGTGGGCGGG | CAATCGCTAATCGC | TTGAGCGAAGGTCA | GTGGAGGCTTCAGC |
| TACTCCCGTCAACA | GCGCTGGCTTCGGA | GTATCCCGGATAGA | CGATCTATCACCCC |
| TAAAGCTGAGTCAA | TGCGTCGGGTAACA | AACGCCATATCGCT | CCCGTCTAGGCGTA |
| GTACGCAAATTAGC | CTGGGAACAGTTCC | TCTATAACGGCAGA | GGCTGACCTAAGTC |
| GTAAGTGGGCTAGG | AGAGCTGCACTGGT | GCTCACTGACTACG | CGACTGGAAGTTCA |
| TATGGCGCAACGTA | GAACTAACTTGCCC | CGTCGCACAATTCG | AGCTCAAGTTCGAG |
| ACCAGACGTCTGTA | TGAGTACCCAGCCT | AGTAGAGTAATGCC | CGTTGCGGCTGACA |
| GGTAATACGCTACG | CTCGCTGACGGCTG | GTGCTCATAACAAA | GCCTACCGGTCCGT |
| ACTCCCCTCGTAAC | CCAATATCCGCATG | GGGTTGCAAGAACT | GGCATACCCTTGGG |
| CACGTGGCTCCGCT | TAGAATGACAATGA | CCTGACATTCCCCA | GAAAACACTTGTCA |
| ACGGCGTACTATAC | TCAGCGTAGTAGGA | GGCAATTCCGATCA | GCTACGTACAGCTA |
| GCCAACGTATATCA | TACCGCGACTCCAT | GCACAGTATCTCGA | TACATGACATACAA |
| CTTAAACCCGTCAG | CTAGGTACTCGCCA | AGGGGCTATGTCGC | AAATGTTACCCCGA |
| CCTGTTGCGGAAGG | CCGTCGGTGTCGCG | GCGCTGGAAGTAGT | CCCCTGATGATGAA |
| ACATTGCGGTCCGC | GAAGACCTACGGTT | TCGTGTCGACGCCA | GACTCTCCATGCCC |
| GAGACACTGCTTCG | GAATGTCACTGAAA | CTACCATTGCCGGA | ACACCTTCCCGGGT |
| ACTATACCCGGTCA | ACAAACTAAATCCT | CACTGCAATCAAAT | GACGGCTGATATGA |
| GTCCACCTGTGACA | TGTGGTGGCGGCCA | AAGTCACCTTAGAG | GGGAGAGGATGATT |
| GCATCAGGCGGTTC | TATATCCGCAACCC | AAGGCATTATAACG | AGATAATGGAAAGT |
| ATCAAGGAGGCTTC | TCGCTATAAGGACA | ACCTAGACCGCTTC | ACCGTAAACGGTTG |
| GTGCCTTAAAGGCA | ATCCAGACGCGTTA | AGCGGACTAGTCGT | TTATAACAAAGGCA |
| TGGCCTCCACAGTG | CATATCCCACCATA | TGGACTCACGTCCC | GATGCTGACAGTCA |
| TGAGGAGGACTTCG | TCCGAGGCCCTTGA | ATAGTCCGCCTAGA | GCAACAATTCCTCA |
| GTCCCGAGCTCGTC | CAAGCTGGGGGTGT | CATTCACCCCGTCA | GACGTCATACCTAC |
| CAGCTATTCCGAGG | GTGAAATCAGTGAG | TTAGCACCGGTGCC | GACTGGTGAAAATG |
| TAAGATCCCAAGCT | GGGATTACATAACG | CCATGACCCTTCAA | CTCCATCGAATCAA |
| ACCCCATAGCTGCT | GATCCCTGCCGGTA | ATCAGTTCAACGCC | GGTCGGGGATCTCA |
| AGCTGCCTGTACCA | ACACTCCCATTGAA | CCACATATCGCGTA | ATACGCGAAGTGCT |
| TCAGACATTAAAAA | CTGGACCGGAGTTA | AAAGACTCAATTAG | ACCGGCTCGGTCCT |
| AGTAGAGGTGGTAG | CGACAGCTTATGGC | GTCCGGATTAAAAA | TAAATACGGTACAC |
| ATGTGCTACGCCCG | AGGTGGGTGCCTCC | TTACGCTCGGAAGG | TGGGACTGAGCTCC |
| CGCAGAAATATTCG | ACGACCGCCTTTAG | ATCGCCGTCACTAC | GTTCCAACGCCAAT |
| CGGTGCCTATAGGG | TGGGAGTACTGCCA | CGTGCCCTTAGCAA | CTAAGGTAATACCG |
| CCCCGTCTGACTCA | GCGTAGGATCCATG | CCAAATTCGGATGA | CCTCCTCGGAGGGT |

FIG. 7 (Cont.)

| | | | |
|---|---|---|---|
| GTAGCAGATGACGT | AATAGTGCGCTGAA | CCTACACCTAGAGT | ACGGTATCTATACG |
| AGGAAAGGCATCTT | GACAGGTATCAACT | CACGATTTGGAGAA | ATACTACTAAACTA |
| GAACAGCATTGTAA | GAATCACTTCAAGC | CCTCAGAGTAGTGG | CTACGGTGTACTAC |
| CCCGATCTAAATGC | CACTATAAAACTGG | TATCGCAACAGATC | TGCTATAAAGGACT |
| CGGTGCCCAAGATT | ATGGAAACTACGCT | CAGCGCTGGGTTAA | AAGACTTTCATCGG |
| GAATCCGCAGTTCA | GCGTCGCATTGCGC | CGATCCGATGTCCA | CTTCCGGACCCTAT |
| GTAACAGCCTTGCA | CCTGGGTATAGCGA | CCATTCGATACAAA | TAAAATGCACTTCC |
| TATTAAAGCGAAGG | CGGACTGGGTAATG | ATCACAAATATGGA | AAGTCTTAGTCCGG |
| GAACTGAGTGAGTA | CCACCTGTACGGTC | CGAATAGCTTCCCG | AATTCTAGTACGCC |
| TCCAAGACTGACGT | GTGGCCATGGATAG | CGGAATTTGGGACA | GGCCGACGCGTTTT |
| CATAAGATTCGCAC | CCAAGTTACGAGAT | GAGGCTCGGTCTGG | TGGCATAGCGTGTC |
| AGGGCTGATGTGAA | CAAGGGTGAGGGTT | GGTATCGAGGCTAA | TATTGCCCCAGTAG |
| AGACCATACTAATG | CGCTAAGGACGTGT | CATGTAAAACGTAG | TACAAGTCTCTGAG |
| GAACCGGACATCTT | AGTTATAAGAAGCA | ATGTACAGCAAATG | AAAACTGTACCTGT |
| AATACTGAGGTCCG | TGTGACAGACGCTA | CCACCGTGATATCT | TCCTACGGTGTCGG |
| ACGTTGGTCGAAGA | GGAGGGCATTGCTG | TCGAGAAGACTTTC | TGTAAGCTCAGCGT |
| GCTAGTGGACCGTA | CCCTGTGATAAAGG | CCCTGGTTACCAGT | CGTACGGTACCGTT |
| AGACGCCTATCGTG | CGCCTTAAAGCTAA | GCTTATCCCGAGAT | TGGAGGGTATAATG |
| GTCAGACAAGCTCT | CATAAGAGTATGCA | GGGAGTGGCTTCTG | ACGCAATTCTAAAT |
| GTTGCAAGTCCGCA | TGAAGCGAGAGATT | AAGGACGGTCTATT | ATTATGGGAGATCA |
| GCGAACCATATTGC | ACGAGCGTTCACAT | TTATCACGAGCGCT | TCAATGCTATAGGC |
| TTCATAGAGGCACG | GATGCCAAGTATCG | AGTAACGTTGATCA | CGTAGTTGAGTGGA |
| TTCACCGGGAGTAA | GGGCTGCCCCATGT | CCTTAGTATGCAAA | ACTTATACCAGCTA |
| GACTTGAATCGGAA | GCAACCTAACTAGT | CCAGTATGTGGGAT | GAATAGTAACGCTT |
| CTTGGGAGTGAGAC | CTGCCTCTCGGCCG | TTAGTAACAGACTC | ATTGGAACTGTCAC |
| GCCAGATAATGCAT | CGCGCAGTGTTCGG | GCAGGTTCACCGTT | AGTACTACAGATTG |
| ACTAAACCGTTCCC | CGACGGGGTTACTC | GTGCTCTACTGCAC | ACCCGCTATCCTCT |
| TCGCGCTGGCACTG | GTGAAACTTCGGCA | ACATATGCGCTCGT | TAAACTAATTGCGG |
| TACACGTACGTCCG | CTACTACCCTACCG | ATTGTAATGCCCCA | AATACTCCAATGGT |
| AGAGCCGGTTTCAA | AACTAAGTATGGGA | ACACGCTGTAACTT | GTTCCAGCAGTTAC |
| CAAATACTGCTGGA | CCGGATGTGATGGG | GACACCATTGCTGT | TCGCATGTAAGATA |
| CTCGCGACAGTCGT | TAAAACAACCTGTG | GCAGTCTATGTAAC | TTTGCGAAGATACG |
| GAATCTACCGCTGC | CAAGAATATGTGCA | TTAGAGATGACGGT | GACCCGTGTTAAAT |
| CCAGGGGAAATTAT | CAACGTGGTCCCGT | TCTTAGACCAAACT | AGTGAGTGATTGGG |
| TCGTTAAGCGCACG | AGTGGAAAGCCTTG | ACGCGGTAATAATT | TGTGTCGCTCCACA |
| CAAGAGGCTCTAGT | CCCGATGTAGCGAT | TTCGCTACTAGGGC | ATGATCACATGGGT |
| CTAGTGAACTGAGG | CACCGCTCTATAAG | CGATTGCGGACTCT | GTACTGGGTGCAAT |
| CCCGAAGTTCACTC | CCCGAGTTGTCAAA | GATATAGCAACTGT | GACCACTTCTGCTC |
| TAACGAGTGGATAG | AACGCCCTTCCTCA | CCTAATGCCCGGTT | GTACGTCAATAGTG |
| CGACGTTTGCGAGA | ATATCCACGGATGA | AGAGGTCGGTTTAC | TGGCCCTCCGTTCC |
| AGTACTGAATCCCA | ACTAGATCATCGGA | TTACAAATCGCTGG | CTGGACAGTGTCTG |
| GAACGTCGGCTGAT | GTAGCGGCATGGTC | CTTATGATACCAAC | GGACAGTGTTCGTA |
| AGGGTGCGGCACTT | TTGGGCGAACACGT | GATGTCGTGGTCCA | TAGTGCCAGGGTTC |

FIG. 7 (Cont.)

| | | | |
|---|---|---|---|
| TTAGGGTCGCCGTC | GGTTGGTCCACGGT | ATCTTCCTGCCACA | TCGGGTGCTCCCTG |
| ATACAGTTCCAGTG | ATGGGCCTCAAATT | GACCTTGCTATCAG | TACATTGTGAACGG |
| ATGCCTGCTCAGTC | GATATCACCCTGAT | TCCACAATCTTAAA | TAGGTTCAACGTCA |
| CTTTAGCCATCACG | CGTGGTAACCTTCG | AGTGAGTTCCCATG | CCAATTGATGAATC |
| CTGAAAAATCTGAT | GCTTTATAGCGAGA | GTTCTTAGCGAGGC | GAAACTGGTTCTCG |
| ATGTAGGCCCTGGT | ATTCTACGTGAACG | TACCAGATGGGTGT | TGGTTGTCCGAAGC |
| TACCTTAAGTGGAA | ATGGACATGTGATG | GCATTCGGGTATAA | TGTGGCTCATCCGA |
| TTCGGACAGGTCCT | GTGGGGCTCTCCCT | CAGTACCCTTCATA | CAGAGCGTAGTTAT |
| GGTCTGTCGGCTCA | CCCGTCAGTGCTCT | GCAGCCATCCATTT | AATTTAGGCCCATC |
| CCCTCAGCAGTTCT | ATATCCAAAGCCTT | GGCCACTGTTTAAA | ATGAGGCGTACATT |
| CCGTGCACCGGTTT | TTGCTAGAAGCGTG | GCATCATGTAAAAT | TGTATAAACTGCAC |
| GTTATTCCGCGAAG | TAGCTTACAATCCG | TACGTGTGTACAGC | TACCTAGATCCTAC |
| ATTTAACGGAATAC | GGGTCATCCGTGCT | TATACTGCCGCATG | TCCAGCCATATGCT |
| CAGAGATTTCTGAG | AGTGTCACTATGGG | CATCATCGCTTACG | TATTAGCTCACGCG |
| CTCATGACTGAATC | TACGTAGTAGCCAT | CCCAATATACTTAC | TCGATTCGGTGCGG |
| GTGGCTGCCGGTTC | ATACCATGGTTAAC | TCTCAATTCGCGAA | CTAAATATGAGAGT |
| GTGCAGGAATTGTG | CTTCTCCGATCCAA | GATAATTCTGCGAA | GGGTGCTTTCGACA |
| CAAATGTACTCGTG | GGCCTTTTACCCCG | CGCTTGTAAGAGTC | AACAGATTTACATG |
| GTTAGGTAACGTCA | TGAAACTTCTCAAC | ATCGGGTTAAGATG | AAATAGCTACATCT |
| TCTAAGTGTAGCAC | TTAGAACTGGATAC | GGGCTCACGGATTT | AATCCCTGGGCTTA |
| TCAGTGACTACCAT | TGAACATTAGTAAC | TATGTCGCGAATAG | CCTAACAGCTCCTT |
| GTCTTCAACAGCTG | GAATGAATACCTGT | ACTGACTCCTGATG | TACAGATCTCGATA |
| ATAAAACTCTAGCT | AACTCAATGCCTTG | CTGTTTACAGGCGA | AGACATGTCTTAGA |
| CTGGGTGTTGGCGC | GTTGCGCAGTTGAG | GCCAATCTTCAGTC | TAATTCCCCTGGCG |
| GGCTCATAGTGAGT | GCGTCGATTGTACC | TCACGCGTAATTCC | GTGTAGATTCGACG |
| GTGCAGTTGTAGGG | TCGAAAAAGTGTAT | ACTGGTTACCCAAT | CGTAGATATTCCGA |
| TCGCAAGACTTATG | GTCACGCGGTCCTT | TGCGTAGTTAAGGA | CTTACAATCGCCTG |
| CGCATTTAGCAGTA | TTTAATCGAAAGAC | CGCCTCGATCTTGA | CGTACCTGGGTTGG |
| CTTCAGGGAATGGT | CTAGGCTGGATACT | TGGTCGTCCCGGTG | AATCCCTATAGTCC |
| AGCACATTTGGCTC | AGGAGTCAATGCTT | GTGGTTGTCCCGGC | CGTCCTTCAATCAA |
| ACCCGAGATTTTAC | TCTAGGGTTAGGCA | TACGGACCCGTATT | TCGGAGAGTCGTTG |
| GGTAGCAATGTATC | CTCCTCACAGGTGT | TGCCATCTGGATGG | GTGTGTTCAGAGGG |
| GGAATGTAGCTATC | TCTCATCCCACATC | CGGCTTCTCCCTGC | CGGTAACAATCTTC |
| GAGATTCTAACAAT | TAGTGAGGCGATTG | CGGTATGCTTAACA | GAGCTAGTAATGTA |
| CGCTCATCATATCG | CTAAGGGCTGCATT | GGGGAGGTTTTCAG | TGTGCTCGGTACAA |
| AAAAGTAGTTCGTC | AAAATCACTGTTAC | ACGGTGGTACTGCT | TGCTCTCACATAGG |
| ATGACAACTAATGT | GGTTTGGTAACGGA | AATCACATTGGGCT | CATAGCGTTTGCCA |
| AATTGAATCCTAAC | CAGTTATATAAGCG | TCGTACTCCGTCAC | ATACCACACTTCGT |
| TCTGGAAAGAGTCT | AGCATAATCATGCT | TTCCCGCTCGTAAA | GGACCGATTTATAG |
| ATGTACCGATAGTC | AGTCTCTAAGATCC | TCGCAAATTAATGC | ACATGTGTTCCCCG |
| ACTAGGCGTTCCGT | TGTAACTCCGGCTA | CACCGTTCCTTCGG | CTGGGTTCGTCCCA |
| GGTCGCACTTAATG | GACTCGTTAGCCAT | GGTCCTAGGTGACT | GCGGACCTCCTCTT |
| TCGTATAACGGCTC | GGTCGGTTGCCCTA | CAACATTCTTAAAG | TGCTCCTAACGATA |

FIG. 7 (Cont.)

| | | | |
|---|---|---|---|
| TCCGACAGGTGCTT | GTGGCAGTGATTAC | GCACTTAATTATCC | TCTAGACCAATTAT |
| ATGGAGTTCAGCTC | GTAGCCGTCATCGT | CATACGCATGTCTT | GGATCCCTTCTTAA |
| CGGCTTACTCAGAT | TAGATCGCTAACTG | CACTGTTTTGCAGA | TTGATCGGGCTGTC |
| CTGTCACTGCATAC | TCCCAACATATAGT | TTACCCGGATTCGT | GAGCCGTTGTTCCT |
| GGCGTTTCACTAAA | TCCTCGTACTGTGG | CTGGTGCTAATCAT | GGACTTCGCTGCTT |
| ACATTTTACGCAGC | GTTGGTCAGGGTTA | TGCCTATCTCAGTC | TATCGTGATTGGGG |
| CATTCATAACATGA | GGTTGGACCTTTAA | TGACTAATCGTGTA | TTCCGGGTCGCTGT |
| AATATATGCGAATG | CCTCCTCCTGCTTA | CCGATATCATGTTC | GCGATCGGTTTGCT |
| CGTTTAACCACATA | TTTCCGACTAGTAA | GTAGGAGTTCTCTG | CCCGCTTTCTCTGA |
| CGAACTAGTTGAAT | ACGAATTACGTATT | GATAGCCTTCATTA | GTACGCGTTTCGTC |
| GATTTAAGACGGTC | GAACATCGTATTTA | TGCTTAGCAAATAT | AATTCAGAATCTTC |
| ATTAGCGCACTCTG | GTCTCTTACAACTC | ACCTCTAATGTTCG | CCATCATGGCATTT |
| ACTTTGCCTAAAGA | TTCTAATCACGCTG | TCATACCGGACTTT | TGTAAACATCCTAT |
| TTGCTGCCTGCCCG | ATAATCAGTACTGT | GTGTATATCTAAAC | ACTTAAATGTACAT |
| CCACATTGTCATGG | GGGCTAAACTTTTC | TGAACCAGCTATTT | GTTAGTCCTACGGT |
| CCTATCCCGCTCCT | ATACACTGAGATTT | CGTTTTGGCCAGAT | CTGTAATGTATCGC |
| CGTATCGATTCGCA | TGTCTAAGTCGTGG | TTCTAATATGAGAA | CATCTCTTGGGCGT |
| CGTAAGTGTGAGTG | TTTAACTCACAGTC | GTCTACTCGGTTAG | ATGTGACCTATTGG |
| GTCCGATGACTCAT | ATGTCTTCAAGCAT | AATATTACAGTCCT | GAGAATCTCTTATA |
| TCGAACCCTTGTAC | TTCTTGCAAAGCTC | TAACAGAAGTTGTT | GGTCTTAGCACTTA |
| AACCTCTATACCGT | GTAGTATATAGGTC | TCATCGATACTTGG | AGTCTTGACGCTCT |
| CGTTGCAGCACGTT | AAATTTCTCTACGG | TTCCCGATTGCGAT | CCTATTTCTCCCAA |
| TCGTTCGTCGGGCG | GTCTCCGCTAGTCT | CTCTCGGGCTTTGC | TATGTATAAGCTAC |
| CGGTAAATTATGAG | TTTCATCCACGCGT | CTTCGGCTGGGATT | ACTACTGCTTCGTA |
| ACTGACGCGATTTA | GCTCGAATCTATCT | CCGAGGTTGTGATT | TCGTCAGTTTGGCA |
| CTGTAGATGCCCGT | CATGTTCCCGCTAT | CTTTGCAGTTGGGG | TAACTGTGGTGGCT |
| CCTAAGTTCGACGT | GTCTTGGACACTCT | TGTTATCCGGGATC | GTCGATTTATGCAG |
| ATGAGTCTCGCCTG | GTGAATCGGTTTCA | ATGTAGTAAGTTCA | CGTATATGTCATAC |
| AATGTAAATCTGCA | TACATGCTTTCGCC | AAGACGTTTGCTCT | TTATCGTCCGGATC |
| CCTCTACCCAATTC | GGTGGACTTATCCT | GTGGATCTTATAGA | TTATGGGTACGAGT |
| GTTGGTCGCAAGTG | CGCTTGGAGTTACT | ATCTGGGGACATTT | TGTTTCGTCCCCGG |
| CGCTGCCTACTTAG | TCTGGGTACCTTGG | CGTTCCTCTGCCTC | TCTCAGACTTCTGC |
| TTAACAGAGATTGG | CGGAGTATTGATTC | AATACCTCTCTCTA | CTACCATATGTCTG |
| TCAGTTAGGTAGCG | CAGTTGAATGTGAT | CGTCGCTTCGTTAG | GAGTTGGACGTTTC |
| CACAATGTTCTCGG | GATATAGGCTTGTC | TGACCTTATCCGTG | ATTAGCCTCTTCAG |
| ATCGCTAGATACTA | TACATCTCCATTAG | TGCCCATTGATGGT | CTATTATGATACGA |
| ATCTCGCTTAGACC | TGCGCAAATTTCCT | GGTGATGCCTTAAT | GTATCATACCTTGA |
| CGTCTCGTCGGGCT | ACGTAGTCATATAT | TGTGGAATCCGCTT | TTGTATAAACCCTG |
| CATTCAGCGCAGTT | GAAATACGTGTTCT | CCATTAATCCTAAT | TTCCGCGTAAACTT |
| TGGCGGTTGTGCAC | CTCAGGTAGGTTTG | TCAACGAAATTATT | TACTTGTAAACTAA |
| ATAGGTGTCATAAA | GATCGTTGCGATGT | CCGCTCTTTGGGTA | CCCCTTTTTCAGGA |
| ACCGTCTCAAGTTG | GGAGTTTGTATAGA | CTTGCCATGAGATT | TTTAGTGAGAGCCT |
| AAAGTCCTTTCGAG | GATTCAACTTCTAG | GTATTGCAGCTTCC | AACTTTTCATAGAC |

FIG. 7 (Cont.)

| | | | |
|---|---|---|---|
| CGCCTATATGGTTC | TCATGTATATCTGA | TTCTACTGTAGACT | TCGCTTAGTAAGTT |
| AGTCTTCGCCATTC | AAGCTGTCATTTTA | GTCGGCCTTTGTTC | TAAACATGCATTTT |
| TTAGACTAGAATCT | TTCCTTCTCCAGTA | CATGACTTCTGTCT | GTTTATCCCTTCGA |
| TGGAGCCTTAACTT | ATATCACGATTTTA | ATGCTGTCTCTGCT | CGATTGATTCTTCC |
| TCCGGCTGTCATAT | GATCTCATTTTAAG | TGGCGAGTTTTTGC | ACTGTCATCTTGTA |
| ACGTTATTGTCCGA | ATCTATGAATTGAT | ATTCGTTATCTGCC | GACTTCGTTTGCGT |
| TCTGTCCAACATAT | TCTTGTGTCGCATA | TTTTTGAACTGGGC | TTATATGAGGTTGT |
| TGACATCATTTAGC | CGTGTTTTCAGTAG | CTTCGGAGCTTTTG | TTTCAAGATTCTTC |
| TGATTTCCGCTAAA | CGTTTCACTCATCT | CGTGATATTATTGA | TGATTTATTCCATG |
| TTATTCGTAAGCGC | TTCATCCACTCCTT | CTATCGGTAGTTAT | TTAGAGCTTCTTCT |
| TTTCAAACTGACCT | TTCTTATGGTCAGC | CTATTAGTTTGAGG | CGAATGTGTTTTTA |
| TGTAACTAATTGCG | TCTATGCGATTTAA | TTAACTCTCCGTGT | GATGTCTACTTTTG |
| TCACTTTTGGCCGC | TTCTCATATCCCGT | TGCTTCTGAGTTAA | TCTGTTCGCTCATT |
| TGGTTCTGACCGGT | TACGTCTATTATAA | TCTCACGTTAGTTC | TTTGGTTCAGTGTG |
| ACGTGATCTTGGAT | TGACTCTCTCGTTG | CCTGTATTGTACTA | GCTACTCCTTTTAT |
| GCTTGTTCCTAACG | GTTTAACGTATATA | GTCATTATATCTAG | ATTGGTATTATGAT |
| CTTACTATAGGGCT | TTGATATCTCGTCA | TTTATTGATGAGGG | CGATTACTATTTGT |
| TTAAGGGATAGTTA | TAATAGTCTCCTCT | TTGTATTTCAACGA | TTAGCATATCATTT |
| GGCTTCTTCGCAAT | TGAAGTGTTCATGT | AAACTATTTCTGTA | TGTTCGAATCTTTG |
| ATCATGCTTGAGTA | TAATTTCGTCATAG | ATTTCTCAAGTCTC | CCCTTGTTCTTCTG |
| ATCGTCTCTATCAA | TATTAAGCTTTGGA | CCTGATGTATACTT | ATGTCTGTTGTTAC |
| TTTGACTTCCAAGA | CGTGTTGATCATTC | ATTAACTATGTGAT | TATGTTTTACACTA |
| TGTGGCCTGTTGCC | ACTTAGTTGTTAGC | ATGTGGTGTAATTC | TTTACCTGTTAATG |
| TTGCCTAGGATGGT | TTAGTCTGGGAGTT | TATTCACACTTATC | ACTTTATGTGTTAG |
| TGTCGTGACTTAAC | AATATTCTGTTGCG | TTCTATTGCGCTCG | ATGTGTTCCTGTTA |
| ATCTTAGTAACTGA | GTCGTCATGTTGCT | TTCATATACCATTA | CTCCCTTACCTTTT |
| CCCTTTCTACGTGA | TATCTAGTCCTTGG | CTGTCCTTCTGGTA | TGTCGTTGTTGTGC |
| CTATGATACAGCTT | AGATCATTGTTGTA | TTTAACAGTCTTGC | AATTTGCGTTTTAC |
| CTGTTTGGGCCGCT | ATTTTCCCTCGATC | CGTATTTAAGGTTG | TTTTTCCGACTGTG |
| CGGTCATGTCCTTC | AGATTTCCAGATTT | CTAGGGATTTGTAT | TTTTAGAGTTTCCC |
| CGATACTGTTACAT | TCATTATACTGATA | CGTCTATTTTGACA | GGCGTGTTATTGTT |
| GCTTCCTCACTTCC | TCCTCTTTGGGGAT | CGTACCTTCTTCGT | TGTGAACTTTTTAG |
| CTTGGATGCTTGAC | GACATTATCTAGTT | CTTACATGAAATTT | TCCAACATTTTTCT |
| TTCCTTCCGGCTCT | GTTCCATTGAATTG | TAATTAGGTTGTCA | TATTTTTGGCCACT |
| TCGCGTGATGTTGT | GTGATATTCACTTC | TTATATTTAGGCCC | GATAGTTATCTTAT |
| AAGCGTTACATTTT | GCTTATGCTTCCTG | CTTTGTGTCAACAT | GTTATCTTATGCCT |
| TTTTCCGACTGTAC | AGTTCGCTTTGGTG | TCTGGTTGTGCACT | GTTTTCTGCTTAGC |
| AGTTTCCTGCGTGT | GTTGTATAACCCTT | CTAACATGTCTATT | ATTTGGGAGTGTTT |
| TACAGTACTATTTG | GATTTCTTTCCAGC | CTAGTATTCTGTCC | TGTTATGTGCTGTC |
| GTCTGATTGGGTGT | CAGCTTCATCTTCT | TAAGACTATGCTTT | GGGTGTATATGTTT |
| CGAACTTTTCTGCT | TTCGTATTGAGCCT | TTCTGTATGAACCT | TGTGTCTTATGGTA |
| GAATATGTGTAGTT | TAGGTGTTTAGTGA | ATGTTGCATACTTA | TATTGTACTCTACT |
| GGTTGCCTTTCTCG | CCCATAGCTTTTTA | CAGTTTATTCATAC | CCTAATGATTTTTC |

FIG. 7 (Cont.)

| | | | |
|---|---|---|---|
| GACTGATTTTGATT | AAGGGGAGGCCCGG | CGACCCAAGAGAAA | ACCACACTCAACCA |
| TTTGGATTTGGTCT | GAGCAAGGGCACCG | AAACCCACGAAACG | CTAAACCCGGGGGG |
| CTTATTTTGCATTG | GGCCGACACAGCGC | GAACGCGAGCCGGA | CGGCATCCGACGAC |
| CTCTTGACATTTTT | CAACACGCGGAAGC | CACGCAAAAGAGGA | GCCGATAGCCCGAC |
| CATTTACCTATTTT | GAAACGGCCGCGGA | GCGGCACACGAGGA | AAGATCCGGACGGC |
| TTTGAATAGTTGTT | CACCAGAGGACGGA | AGGACGCAGCCACA | CAGCAGGTAGCGAA |
| TGGTTTATGAATTT | AACAACGGCGCCCG | GGAACGGGCAGAAG | GACACCCCAAATGC |
| TATTTGTTCTCTAC | ACACCCACACCCCG | CCACGGAGGAAGGC | GACTAGCCACCACA |
| TTTTGATACTTCTG | CACGAGGCCAAAAC | CCGACACAAGAGCG | GCGCAGCTACCAAC |
| GTACATTTTTCTGT | AAAAGGCACCCAAC | GGAGGGGGAGACCC | ACGATCCGGGACCG |
| TTGGTTTTTGACTG | CAACACCGAGCCGA | AAGCAGCCGGGGCC | CGCCAACCAGATCA |
| CTCTTTCGTTTCCT | GGCAAGACAAGAGA | CGCCAGCCAGGAAC | GGCAGCCGGATGAC |
| TTTTATGCTCTTAT | ACGACGACCCAGCG | AGGACGGCAGGCAG | GAGAACGCGGTCGG |
| CGTCATTCTTTTTT | CACACCGAGGCCCA | CACGACCAACCAGG | ACCACCCGAACATA |
| GCCGCAACACCCGA | AAAAGGACGAGCAA | CAGCCAGCACCCCC | GACAATAGCAACAC |
| GCGGAGCCAGAGAC | AAGCAAAACGAAAG | ACCCACGAGAGCAA | ACAAATGAGCAAGG |
| GAACCAAAACGCGC | AGCACGCCAGACGA | GGGCAAGGAGGGAC | AGATGACCAACCAC |
| CGAACACCAGCCCC | GAAGCACGCAGCAC | ACCGGAGGGGAGGC | AGGGACTGGCGGGG |
| GGGAACCCCACGCG | CCGCACAGCACGCC | GCGAGAACGCCGAC | AGGACCGGACCCTC |
| AACGCCAGCGACCC | ACGACGACACGAGC | CGAGGAGAGCAGCA | GCAAATCAAGGCGA |
| CCAGAAAGGAGAGA | CGGGGAGCAGAAGA | AAACCGAGCCAGGA | AAGACAAAAGGCTA |
| ACCCACGGCGAGGA | CCCAAAGACAGCGC | CACCACGCGACACG | TCGACCGACCGAAC |
| ACACAACAAGAGGA | CCGGAGCACCACCG | CAAAAACGCGAGGA | CAGGTCCCCAGGAC |
| ACACCCAGCGCAGA | GCCCAGCAAAAGAG | AAGAAAAGACGCCG | GCGGATCCCACCGG |
| GGAGACCGCCAACG | AGCAGACGCGACGC | GCACAAAACAGCAG | ACAGGACTAACACA |
| GCAGGGACCCCACG | AGCGAAAGACACAG | CCCCAAGGGAGGAG | GAAGGATGCCACGC |
| GGACCGCAAAAGCC | ACAGGAGGCGGACC | AACAACGAGCAGCC | AAAAGAGCCTGCAG |
| AGCCAAGCGGGGGA | AGCACGCAAGGGCG | CCAGAGAAAAACCC | GAGCGGAGCTAGCA |
| AACACCACGCGAAC | GAAAGCCCGACGCA | ACGGAAGAAAAAAG | ATCGAGCGCGCGCA |
| CGCACAGGCGGAGA | GAAACGCAGACCGG | GGAAAGCGCACAGA | GAACACCCTCCGCC |
| AGACCGGACGGAGA | CAAGCCACGCAGAA | ACCAAAAACAGACG | CCGCACGCTCAACC |
| CGCAGAGAAGAGAA | GCGACCCGGAGAAA | AAACCAACAGAAAC | CGAAGAAGTGCAAG |
| GCGGGAAGACAGCG | GCGAAAGGCGCGGA | GACGGACGGCAGGG | GTGCAAAAAGGACC |
| GAAAGAGGGGGCGG | ACACACAACAGAGC | GGGAAAGAAGCGCG | GGCCCAACCCTAAG |
| CAAAGACCGCGCCA | CCCAGAACAACGCG | CCACGGAGGCCAAA | GCAAAGAAGGTCAA |
| AGGCAACAGAGGGC | AAAACGGGAACGCC | CGGAACCCACCCAA | GAGACAATCCCCAG |
| GGAACAACGCCCAA | GAGACCAACGGAAA | AAAACGGCAAAAAG | CAGCCAAACAGTAG |
| CGCCAGCACCCACG | GAGAGCCACGAGCA | GCCTGAGGCGACAC | AGGTCAGGGACGAC |
| AAAGCGGCGCCGGC | CGGAAACGAGGAAG | CAGGGGTCCCAGCG | CAACAGCCGCCGTA |
| CGGAGGGGAAGCCG | CAAGAGAGGGCAAG | GCGACTAAAACACC | CCGCCAGGACTCGA |
| AAAAAGAACAAGGC | CGACGCGAAAGCGG | GAGAGGGGTAGGGA | GTCCCCAACGAAGC |
| GGGACAAGAAGCGA | CACGGCACGCGACA | GAGTCGCGAAGAGG | ACGGGCACAAGCAT |
| CGAGGCCAAAACAA | CAGAGCCGCAGCAA | AAGGAATCACCGCC | ACCCGATGGCCAGG |

FIG. 7 (Cont.)

| | | | |
|---|---|---|---|
| AACACGCTCCGGGA | ACCCTGCGGGACAC | GAATGCAACGAACG | CCAACACGGCCATC |
| TCAGGGGCAAGCCC | GAGGCAACGCAATA | CGCCCAAAACAGAT | CCCAGCACGTGGGG |
| GAGGAGGTGCCCGA | AGCGTAAGCCCAAC | GCAGAGCCCGACGT | ACGCATGACCCCCC |
| ACGCTCCACAGCGA | GAGACCCTAGACGA | GACCGAGGACCTGC | CCCTCCACCGAACA |
| GGCCAGGCGATCGA | GCCAACCCACACCT | AGAGTCCCAAGAAC | GAGCCCGAAGAATA |
| GGCTCGGAGGAACC | CGAACCGTCAACAG | GACCGCACATCCCC | CCAGCATAACGGGC |
| CCAGAGACCGGTAC | AACGCTGGCAGAGG | ACAGGGAGGTGCAG | ATCACAGCCGAGCC |
| CCAACGAGGGCTCG | CACAGCGGTCAGAA | CATCGGCAAGCAGC | GCCACCCAGCCTCC |
| CAATCCGACAGAAG | CACTAAGCGGCGAC | CGGACATACGCACG | GGATAACCCGCAAA |
| ACGCTCACGCCGGC | GCCCGTACCGCACA | CTGGGAAAGCCACA | ACGCATCCCGCCAA |
| CGCCGATCGGAGGC | AGCCCGTGACAAAG | CCACCCCACTAAAG | ACGAAAACAGTACC |
| AAATAACGCACCGG | CTGAAAAGAGACGA | CCGCCATCAGGCAC | TGACAGGACACGAG |
| AGGTAAAGCGACAA | GGGAACCAGCTGCC | GAAGAGAGATAAAA | GCAGGCAAAATGGG |
| CCCGAGCCTGCAGG | CACCTCACCGCGCA | GCAGCGGTCGAAGG | ATGACACGGAGAGC |
| CAGGCCACCCTAGC | GCCCCTCCGAGAAC | ATCGACCAGAGGGG | ACAGGTGCCGACCA |
| GGCACCCGGAACCT | CCGAAAGGCATAA | AGGCCTCAAAGAAC | GCCGAACGGCACAT |
| AGTGCGGAGACAGC | GAAATCCGACACCG | CCAAGCGTCGAAGC | AAGTGGGCCGGCCA |
| GGGGCACTCCCAAC | TGGAAGACGGGAGC | ACCGACAACTCGGA | GCGAACGCTGGCCC |
| CAGCTCGGACAAGA | TGGGACCACCCAAA | GGAATAAGGAGACC | GCAAAAACGACGTA |
| TCACGAAACCGAAA | CGACAATAGCCAAA | CTCCGACCACCCGC | GGAACAAAAGTGGC |
| AAGCTGGCAACCAA | GCATGGAAGGCGCG | CGACGTCCACACCC | ACGGGCAGGAAGTC |
| AGCGGGTAGCGCAC | AGAGACGGATGGAC | CAAAGCACCAATAA | CCCACGAAATCGCC |
| ACCAGGGTCGGGCC | CATAAGGCGGAGCG | GGTGCAGGGGCAAG | TCCGCAGCCAGGAC |
| CTGCCGACGGGAGA | AGAGGCCGTGGGGA | GCAAGCAGGGGGTG | TCCGAGGAGCACAA |
| GCGCTAGAGGGGCC | TGGGACCGGGACGC | CCGGGACAGACGCT | CACACCAGTAGAGA |
| GGTAGGGCAGCACG | CAAAAGGCCTCCCA | CACCGCGTCAGCGA | GCCCGAGTCCGAGA |
| GCAACGGCATCACA | TGGGACACAACGGA | CAAAACCTGAACCG | CGCGACCGCATGCC |
| CGAGAAAGCAAGTG | AACACGGTCCCACC | GCACCCATAGGGAC | CACCAAATACCCAC |
| AGACGCCTGCAAGG | GACGCTCAACAAAG | CTACACACAAGAAG | AGACCTACGCCAGA |
| CATAAAACGAGCGC | CACATGGGAGCCAC | GTGCAGAGGGACAG | CCCGAGGACTGGAC |
| ATGAACACCGACGC | CGAGAAACATACAA | CAAACCCCGATAGG | GATAACCGGGAAGG |
| CCCGGTGGAGAACA | AGACACGTACCACC | GGGTACACGAGACC | ACCTCGGAACAAGA |
| TGGACAGCAACAGA | AAGCGCGAACCTCA | CGAGGTCACGGCCC | GCGAGCGCAGATGG |
| ATCACCGGAGAACG | AGCCCAGCCTGCAA | GTGAGAACACGAGG | CCCGCACCTCAGCA |
| CACGCCTCGGCAGC | GTGGCACCAGGAAC | CAAGAGTCAGACAC | TGCAGGGAGGACCA |
| GAGCGCAGGATCGG | AGCCTAGGAGCGGG | CGAGAGTGACGCAG | CCGACAGACCATGG |
| AGCCACCATAGAAG | CAGACGCCCATCCC | CAGAGTCAACACAA | GACGGCAGTGCAGA |
| TCACGCCAACACCA | AGAAAGTCACAACG | CTAAAACAAAACGC | CACAAGAAATGGGA |
| AAAGCGTGCACAAC | AGGCAGTCCCGAGA | AAACAGGGCCATAG | AACGGCCAAGCACT |
| ACGAGCCGATGGGC | CGGTCACGACACCA | AAACCAGACCCTGC | GAAGGGCTGAACGA |
| TCCCCCAAACCAGG | GTAACCACAACAGC | CGAGGGGACAGATA | CAGCACACCATGAG |
| GTACCCGGAAGACC | AACTGGACCCACAG | AGGGACCAGGGTAA | GGGAAAGCGGAAAT |
| GCGTGACAAACCAG | CTCAAAGCGCGAAA | CAGCCTACGAGGCA | GGGAGGACGCAGTG |

FIG. 7 (Cont.)

| | | | |
|---|---|---|---|
| GGAGGAATCGAACA | ACGAGAGACAAATC | ACACCGAACGTGCC | CGGAGTGCCGGAAG |
| AAAACAGCGCAACT | GGTCCCCCAAGAAG | ACCGACCAATGCCC | GGAGCGATCCGCAC |
| TCCAGACCGGAGAA | GTAGGAAAGACAGG | CCACGACGGTACGA | AGAACCAACATGAA |
| ACTGCGCACAGGAG | GTGACGGCAAGCCC | ATGCAAGGAAAACA | GGGACCCATAGACG |
| CAAAAACCTAGGAC | AACCGAGCCCCAAT | GCAGCGCCACTGCC | AATAAAGAGCCCAC |
| AGCAAGAATGAACC | GACGGACCGAGGTA | TACCAGAGACGAGA | TGGACGGAGAGCGG |
| CAACCGCGATCAAA | AAAAGGATGACAGC | CCATCAGGAGCAAA | GAGACCACCGATCG |
| GAGGGACCCCTCCG | AGAAGATGCACAGC | GAGCGATGGGCGGC | CGCGAGCGCAACGT |
| CACTGCCCAACCAG | CGAGAAGCGCCGAT | CCGCGATGCAGCAG | AGCCCGATAAACAA |
| CGGAACGGCGAGAT | GCACGCACTGCCGA | AAAGCACCGATCGA | TGAGAAGCAAAAAC |
| AAAAGACGGCCCGT | ATGCCCCAAACCCG | CCCAAATGCGGGCC | AGTCCAGCGCCGCG |
| GACATACAGGCCGC | AAAACGCCACGATA | CAGCCCAATCCGGC | CGACCTGCCCGAAC |
| CGACGAGATAAACC | CCGGATAAGGGGCC | AGAACGAGTAACCA | GAAAAACCGTGAGA |
| ATCACACCCGCAGA | GACAAGTCGGACGC | AGGGCGAAACACTA | AGACGTCCGAGACC |
| ATGGAAGACGGAGA | ATAAACGCACCAGG | CGATCAGCGGGACA | CCACTGCACGCACA |
| CTGCGGGAGCAGAC | AAGTCAGACCGCCC | GGCCTAAGGCAGGA | CACAGAGTCCAGCG |
| AACAAAAGATCACA | GGCGTGCAACGGAG | CCAATACAGAGACG | CCTAGAGAGCCAGA |
| CAACAACACGTACC | GAGAGACCCCAATC | GAAAAGGCGAAATA | CAGGGATAGAGCGG |
| GGGCACAACAGCTA | CCCAGCCTCAGGGC | AATGAACGAGACAC | CAGGCAGCCGCAGT |
| GCCTGCAAGCGCCA | GGGAAATCCAGCAG | GCTCAAACAGCCAC | GCACGCACGTACCG |
| TGGGCGAGCCACAG | AAACACAGGCAGCT | AAGCGCGACGAACT | CAAAAGGTACACCC |
| ACCTGAGCCCCCGA | CCACGGTACCAAGG | CGCAAGAATAACGA | CCATAAGAAAGAAC |
| AACAGGCAGGACGT | CAGTGCGGGACGCG | AGAGCCGTGGGGAG | CACCTCCGGAGCAG |
| AGGCGGAATCCCGC | CGAGCGTAAGGCGA | GGACCCACGCAGTC | TGAAGCAAACAAGA |
| ATCCGAGGCCCCCG | GGAACCCTAAGGGA | ACCGTAGCCAAAGG | CCATGGCACAAACC |
| GCGCCATGGCGAGC | GGGATGAACAAGAG | GAACGCACGGGCTC | AACGGGGACCGATC |
| CGCGTGGACCACGA | GCGGTGCGCAAGGG | ATGCACAGGCCAGG | AACTAAACGCAGGA |
| CAAACTACCCACGA | CAAACCAACTGGCG | AGGCAAAAGCATGG | CGTGGCCAGAGGCA |
| GCAGCCGACCCACT | GCCGAAGGAACGTG | TACCGAGGCGGGGA | CCCCTACGAACGAA |
| AGTGGCCCACGGGG | GCACGAAGACCCTA | GGACGATGGCACAA | CTGAGAGAAAGCAA |
| ACAAACGGAGCAAT | GAGCCTAGCGCCGG | AGAGCATAGCGGAA | TCGCCCAGAAGCCC |
| GACACTGCGAGCGA | TACAAGCACACCGC | AGCCGGACACCCTA | GATCACGCACGCGC |
| CCACGAGCGGCTGC | GCCGCAAATACCAC | AATAGAGGACAGGG | CACGCACTGGCACA |
| AGGAGAGCGCTCCA | CACTCACAGCCAGC | CTGGCGACGACCAG | GGGAGCCCAAATAA |
| CAGCAAGAGTAAGA | CAGAACCCTCGCCG | CGCAACGCTGCCGA | ACACAGCAAGGTCC |
| GGGAAGTGCCGGGC | AACCACCCCTAGAC | ACCGCGATGCGCCC | AAAGGAAGAATAGA |
| CTCGAACCGACCCC | GATCGCCAAACCGG | CCGCAGCAGCGATC | CGACGAATCGACAC |
| CCGTGCAAGACAGG | TAACCAGAAACACC | GGATGAGACACCCC | GCGCTGAGCGGAGG |
| GCACGGATAAACCA | CACCTAGGCCGGAC | CACCGTAACACCCC | GCGAGAACGGGCCT |
| ATGGCAAGAACCAC | ACGCAAATGCAGCC | GCGTCGCGGAACAC | CGCAGCGCACGAGT |
| GAGCGCCTACAGCG | AAGCGGACCGCTGA | GCCCGAACAGATCC | GTCCGGACGGCAGC |
| GCTGCCCAACCGGG | TGCCAAGGGCCGGC | AGGGAAGAGCTAAA | CTGAGCCAGACACC |
| GAGGGAGAGAGTAA | CCCGAGTAGCGCGG | ACGAACCTAAACAG | AACCATCGGGCACA |

FIG. 7 (Cont.)

| | | | |
|---|---|---|---|
| GGCAGAATAGGGGA | GTCCCAGACGCCCC | GAAGCACGCGAGTG | CACATACGCCCCAG |
| GTCCAAGAACAGGC | AAACGCGCGCGGTG | ACGGAAACAGGCTG | AGGCCCAAATACAG |
| AACAAAGCAATGAG | GGGAAGCAGGCATC | AACATAGGGAAAAG | CGGGCAATCAGAAA |
| GCCGAGTCGGAAAG | ACGAAAGCATGCAC | GCGAGAGACGTAGG | GGAATCAGAGAAAG |
| ACAAGACCACAGTC | ACGCAGTGGAAGAG | GAGTACGGAAGCCA | GAAGATACAACCAA |
| TGCCGGACCCGAGC | AATACGAAAACACG | GATCACAGAAAGAG | CCGACTCGAGGGAC |
| CTGGAAGCAAGGCA | CGCGGAGAGAGCCT | GAAGGGCTGGGGCC | TGGGCGAACCCAGC |
| CCAAAACGACGTGC | CATAAGCGCACACC | CCAGGAGCCGTAAG | AGCCTCGGCAGCAC |
| AACGACAATGACGA | GGCAAAAGTAAGCA | AGACTCGCCAGGCA | ACTGCCCAGAAAGG |
| AAACAAGCGCACTA | CAGAGTGGCGCCCC | GGACAGTCCCCACC | CACCCCCACCAGTC |
| GAGGGGTACCCAAA | GCACCCTCAGACCC | GCGCCACCGAGTGA | CCCAGAGAACGATG |
| CCGACGCACGACTA | GAAAACCGCGACAT | GCAGCCCAGAACTC | CGTAGACACCAAAC |
| GCAAAGATGAGGAG | AAAAGTGGCGCAAG | ACAGGAAGTCACCC | CAGCCATACGCGGA |
| AAAGACTAGGAAAA | CACAAAGAGCCGTG | ACTAGCCCAACAGG | GGGTAACAGAGAAG |
| TGACCAGAGGGCGC | AACCTACAAGCGCA | GGCCAAGAGCATAA | CACCTGCACCGAGA |
| TCGCAGGGGAAAGA | CAGATAAGCCCGCC | CACAAAAGAAATAG | GAGGATAAGAGAGA |
| CGATGGAGGAAAAG | CAAAAACCACATCG | TGAGCGGAAGACAG | GGGAGACACCAGGT |
| GACCTCCCAGCGAC | CAACCCCACCCCCT | CGAAGAAACCACTG | CCGACAAGCAATCC |
| AGCAATAACAGGGA | CCGCGACCTAACAC | CGGAATGAAGCAGA | CCAGATGCTAAGGC |
| CACCGGAGGTCACC | AGCGAGAAATCGAC | ACCCGTGAGACCCG | AGGATATCAGAGCA |
| GAAGACTGAACACC | ACAAGACAATAACG | TACCCGCAACAGCG | GTACACGAGGACCT |
| GGAAATCGCAGGAC | GACTACACGACCGA | TAACCGGGCGGCAC | CGAGTCCGGTCGAC |
| AAAAACAAGGACTG | AACAACGCGACTAA | GAGAAACCCTCGAC | GCATGGACTCAAAC |
| GGCGGTGCAACCCA | CGCGTAGGGCAGAG | ACGGCAAGGAATGA | GTAGGTGACGCGAG |
| GGTGCCACGACACG | AAACGGGAATGAAG | GAGAATACACCCCC | GAGCGGGAGTGCTA |
| ACCCAGTGGACACC | GGCCAGCAACGTGC | AGGGTCCAGGCACG | GGAAGGCTGGCGTA |
| GCAGCATAAAACAG | GAACCGAAGGGAAT | GGGTAAGCAAGGGG | AGCAGGGGGTCTCG |
| GCAGCGAGAAACGT | ATAAAAAGCAACCC | CATGGAGGGCGAGG | TAGAGAAGGAGGTC |
| AGCGACATCAAAAC | CGGAGCACGATAAC | GGACCGAAACGTCG | GGAGGCCCTGGTCC |
| CAAGATGCAGGAAA | CAACAGTGCCCAGA | CGACCAAGCTACGG | AGTGCGACCGAAGT |
| GCGACCAGCAAGTA | CCAGGCCACGTCGG | CGGAAAGTGGAGGA | CTAGCAGCAAGCTG |
| AAAACCTACGAAGG | CGCGTGCCCAGAGG | CCAGGGACCGTGGA | AGTTGCCAGAGCGG |
| AAAGGATGAAAGCC | CACCGCACACATGG | CCGACGCTGGAACC | CTACCACGGGGTCC |
| TCGAGGGCACGCGG | GAGGTCAAGCAGGG | ATAAAAGAAACCCG | TAGTAAGAAGGCAC |
| CCACAGACTCCCAC | ACCCCGACTGCCGG | GGGAGACACATAAA | CGTAGGACGGCTGG |
| CACGAGCGAAAGTG | CACCTGCACACGAC | GCGCGTACACCCAG | AGTCGTACCCGGCC |
| ACCGGAGGGAGCTA | GAGAAAAAGAAATC | AGGACCATAAACCC | TACCGCCTGGCACG |
| GGACGTCCGGCAAG | AAGCGCAACCCGTG | GGGGTACGCCAGCA | GTTACACACGGCGC |
| AGCACACGCTGGCA | AAGAGATAGACGAC | AGGCCCAAGAGCCT | TGCATACCGCGAGC |
| TAAACGGCGGGCCG | GCATCGAACCGCGA | CGGAATGAGAAGCG | TCAGGCGAGGGTAC |
| GCGATGGAGCCCGG | CATGGACAAAGACG | ATGCCGAGGCACGC | AGCAGTACCGTCAG |
| CGTCAAGAAACGCC | CGAATAGAAACGGA | GGGAAAATAAGAAC | CGGGAGCGATAATC |
| GCATACCAGAAACG | TCAGAAAGGGCACC | CAGCGCAAGACTAC | CCGGTACCGTAGGG |

FIG. 7 (Cont.)

| | | | |
|---|---|---|---|
| ACCGGTATGCGAGA | GTGTGCACCCGGGC | CCGGTCCATGACAC | TGGAGGATCACAAG |
| AGTCACCCCTAACA | CGCTCGCGAGATGG | CCGTCGAATCGGCA | AAGCCACGGTATAC |
| ACGAAAACCCATTA | GAGAAGTTACAAAG | CCGAGTAACGCTGC | AAGGCTGGAGCCCT |
| CTACCTGAAGAACA | GAAGTCACAAGCGT | CCGCTGATGGACGG | AGTACCCGTGCGAG |
| GCAAGTCGCGATCC | GCATAGAGCAGGTC | CGGTGTAACCGCAG | GGAGCCTACCCGTC |
| TGGCACCGAAATAG | AGTTCGCGGGCCCA | TGCACCGAGCTGAG | AATCACGGGTCAAG |
| CCCTCGTGGGGACA | AGTCACAAACTCAA | ACGTGGCCTGCAAA | ACAGTACGAGTGGG |
| GGATCTGCAACACG | GAGGAGCGTACGTC | CGCCCACACTTGAC | CGCGAGACTTAAGC |
| GTGGACCATAACAG | TCGGAGCGGCTGGC | ACAACTATCCGAAC | GTAGAGACGCCTGC |
| CGGCTGCCAAGGCT | CGCGATACGCCTGA | TGACTACGACCCAC | TAAGCGAAACTGGC |
| CGACTCATACAACA | CAACGGGCTAGTCA | CGCGCAGCTCATAC | AAACCCAGATTGCA |
| GTAAGCTAGGGAAG | CCTCCATCGAAGCC | CCTCGAGGTCAGAG | ATCGAATCGACAGA |
| ACGAACGGAGTTCG | TAAGGTGAAAAGGA | TGCCTCCAGGACCG | AAACGTAGACGTAG |
| ACACTGGGACGAGT | CCTACCTAACCCCA | ATGCCGAGGTGGCA | TAACGGCACTACAG |
| AGCATGATGCCGCC | CTCGTCGAAACAAG | GAGTATCGCCAAGG | CGATCACACGGGGT |
| GATCCAGCCGGGTG | AGGATAAACCGATA | GCATCTCGCCCCAA | AAGCTAGGGCGTGA |
| GTCGACTCAAGGGA | GACACAGTATACGG | GAGGATCGATGGCG | GTAGGTAACCGAGC |
| AAAGAGACCCGATT | ACTGACCAGCTACA | ACATAAGTGGAAAA | GGTCAACGCCTGCC |
| GGCAGCTCTGAAGC | TCATACGACGAAAG | ACGACAGCGAGTAT | GATCACGTCAGACA |
| CCGGTCTCAGCACA | ACGCGACGTTGAGG | CCGACACCCTCCTG | CAGCATGCTGGGCG |
| GACAGGATCAGTCC | CAGATAAAAATCGA | ATCCCACGTCACCA | CGAGCTAACGATAC |
| CCGATCGAAATACG | GGTGTGAAAGGCAC | AGAACCACCCGTTC | GCTGGAAACGTCCG |
| GCCGGTCGATCCAA | AGATACGCCAGAGT | ACACAGAGCTCTGG | GGGTGAGGTCAGAC |
| GACCAGCTCCTGAC | AAGGTCCCGCATCG | GAAAAACTTAAGGG | GGTCTACCGCAGAG |
| ATTAAGAGAACGAG | AGTACATAGGCGGG | GGGACGCCGATAAT | TTGAGCAGCCAAAC |
| CGTACAAGGATGGC | CCGCGTGAACGAAT | CGAACTCAGTAGCC | ACCCCGAGAGTGGT |
| TAGTCGCCAGCCAA | CTCGAGGGTCGGCA | GCTAACATCCAGCG | GCCCCACTACGTCA |
| GCCCAAGTGATACA | TGAACACATACCGA | TGCCCAGGTAAAGG | CTAGACCGATGACA |
| GAACGCGGTGTAAG | GACTGAGCTCGCAC | ATATAGGAACCGCC | AGCATGGAAGGTGA |
| GGCTAATAAAAAAC | ACTGGAAGACGGTA | GAGCTGGGATGCGC | TGCGCCAATACAGA |
| CAGACGGCACCTTA | AAGCCGCTACCCTG | ATGCGTCGCCAAGA | CGCCCTTCACGGCA |
| AACGGCGTTGACAC | GCGACGCTAGGGTG | GGAATGCCTAAGAA | GTGGTCGCGGAGCC |
| CCATATGGAGGCGC | ACCTCCTAGGAGGC | AAACGCCCAGTATA | GGTTGACCACAACC |
| GTAAGTACAAGGAG | TCTGGGGGAGGGAG | ACTACCGCACGTAA | AGGAGAAGATTGGA |
| GATGCGACCCGTCC | GCCGATGACATGCA | CCGGTGAGAGGTAA | CTCGTCGGCGAAAC |
| GCTGGGTAGGCCGG | CTCCACACGGACTA | TCGGCCTCACACGC | CCCATAGTACCACA |
| ATCCCCTCCGGGGA | ATAACCGGGGGGCT | CATGAAAAGCACCT | AAACCGAGGCTTCG |
| TAGCCCTCACGCCG | ACAAGTAAAGTAGC | GCATGCAGGGTAGC | CGCATCGGGGTGCG |
| TGCGCGAGAGAATG | ACCCGGATATCGAA | TACGCTGGGAAGCA | GTCCGGACGCACCT |
| CGATCGAAAACTCA | CATGCCTGGAGGCG | ACTACCAAGGATCA | AAGAAGGTCACGTG |
| GACACACCAGCGTT | ATAAGTCGACGACG | TACGAGTAAGGGCC | CCCGGACAAGTGTA |
| GAACCACCAAGTTG | AGCCTGCGGTGGGG | GTCCTACAACACAG | GCGAGCTCAACCCT |
| CGCAGCGCGTCATC | GCGTGCGCAATAGA | GTCACAAGACCTCG | CAAGACGATCAGAT |

FIG. 7 (Cont.)

| | | | |
|---|---|---|---|
| AGAAAGCACGTCTA | GCGCTCGCACTCCC | TACGGCAGGCACGT | TAGGAATGGACGGA |
| TAGGACACGGGCTA | ACTCACCCGTGGAG | CCGAGCATACCTGG | CCAACTATGGAGAC |
| CTGAGACCTGGAGA | ACCACTCCAAGTCA | AAGCTGTGGAGCCA | TGGAAAACACGCAT |
| AAAGATAAGATGCC | GTAAAATCACAAGC | ATGGGGGAGCTGCA | AAAACAAGATACGT |
| AAACAATCATAGGG | GGAAACATAACTCC | AAGGGACGTCATAG | TAACGCTGGAAGAA |
| GAGAGGGTGTCACC | GTGCGGCACAAGAT | GTGGAGAACCGGTA | GACGCGAATAGATG |
| CTCAGTGGACGCGC | AACGTATAAAGAAC | CGTACTAACGGACC | CAGGGCGATTCCGA |
| CCTTAGGCGAACCA | GGAAGGAACCCTGT | CCGTAATAGAACCC | TCACGCACGATAAA |
| GCCCCTAGACAATG | TAAGACGGGTACGA | GTGAACATGCGCGG | TATACAGGGGGAGC |
| AAGGGAAAACTATC | CCGCACCTGCGTCG | GCAAAAGGTGAGTG | CGGTCTCCGGAAAA |
| GGTATACCGACCCC | TACCCCTGCACCAG | GGACCGCACTCTCA | GGTCATAGACCGCA |
| TACCCTAGCAGAAA | GTCACGAACCGCCT | AACAGCACCTACTA | CTCGGGAGGTCCGA |
| GCTGACCACGGCTA | CCGCCACTCCAGTG | GCAGATCATAGGGG | GTGAAGGTGGGGCC |
| TGCGGCAAACGGGT | CTGCAAGGTCGCAC | GCGCCTTCGCACGA | AACTCGAGGAACTG |
| GCGTGGCACGTCCC | CCTCACGGCCTGGC | AATGTGGCACGACA | GTAGGGACGGTCCG |
| CGAACGCTGCGCTA | TAACCAATAGGAGG | AAAAAGCGTGCATG | ACCAGGCCTTGGAC |
| GGTAGCGGCACACT | GCAGGAGAGTACAT | ACCGATAAAGATAC | AACTGGTCCGGGAC |
| TTAGCCGCAAAGCC | GACGAGAAAACCTT | CCGCACTAGAGACT | AAGATCGGCGTACC |
| CGGCCATATGAGAC | AGAGCCACCAAGTT | GCCACTGTACGCAC | TCCCGAGCATCGAC |
| GGTCGGCCTACCCA | ACTAAGACGCAATC | GCGCTGGCGAACGT | GGCCAGTCAGTGCA |
| CATCCATCCCCCAG | CGTGGAGGCCCATA | GCTCCCGGATAACA | CGAGAATCGTGGCA |
| GCCGGATCGACCAT | CGGGGTTAGGCGGC | AACCTGGTCCAGAA | GGAACTAGCGTAAC |
| ACCCCAGGCTGACT | CACGAAGTCACGTC | CTTACCAGCAGCCG | GAAACTATGAAACA |
| AGAGGGGAATCTCC | GGCCTGTACGGGAC | CTGCCAAGGCAGTA | TGAAACCCTGACCC |
| CAATGTGAGGAAAG | CAATTGACGCACAC | AAAGCCTTAGGCAC | CAGAGCTGCCCATG |
| CTGCAGTCGCACCG | CTCACGGCTCACCC | GGAATTGCCGCAGG | ACCGGGAATCGGAT |
| AGTAATAAAAGCAG | ACAAGGGGAGTGTA | ACGATAAGTGGAAA | GCTATCGCGAAGGC |
| ACCACGCCGTCTGA | ATGGTCACCCCAAG | CGGCAAGTAATCGG | GACAGATAACTGCA |
| AAGCTCAAGGTAGC | CTAGCCCTCCGACC | CTACGGAACGGGAT | TGACAAAGAAGCTG |
| GGTCGAAATGACGA | ACACTATACACCAC | CCCGGAATAGCTAC | GGAAGAGTCGTGAG |
| ATAGGCAGACATGG | ATAAGCCATGCGGG | CCTCACCGAGTCCC | GGCGCTATGGGAAA |
| TGGCATACCCCCCA | TGTAGACAAGAAGG | CCGGAGTAAGCTAG | GAAACCGACAATCT |
| AGCCACTACGCTGC | CCCACACCGCTTAA | TAGAACGGAATCGC | CCCCTCTCACACAG |
| AGCCCCAAGTGGTA | AACCATCCAACGTC | AATCGGGCGGCGAT | CTAGGACGAATGAG |
| TAGGACGTGCGACG | CATGAGTGAAAACA | CGAAGCCGTCAATC | GGGGTGAGGACCTG |
| CTAAGAATCCGCGC | AGGCTCCGTCAGAC | AGCGGAAGCAGATT | CGTCCAGTGACCCA |
| CTTCGAACCACCGA | AACGCCTAACTCGG | CAGTGTGGGCACGA | GGACGCGGAAATAT |
| GTCACTACCCCGAG | AATCAGTACGGGAG | CGTGACGGGTGCCC | AGAAAAGACCTTGG |
| GCAGGAAGCTGGGT | CACCTAAACGGCGT | GTAAGAAAGCTCGA | AACCGGGTGAATGA |
| AATACGGCCATAGA | CCATAGAAACTAAG | AGACTACTAGCAGC | CGCACGGCCTACGT |
| TCAGGCCTCGCGCC | GTCAGTGCACAACG | CAGCGCTATGGACG | GACCACATGGTGCC |
| GGCCTCAAGCGTGG | TGGACCGGTGAGCC | TGGAGTAGAGAACC | CACGAACAGTTGCC |
| TCCCGCATCGAAAG | GATGGCGCTAGCAG | AATACACGGGACTA | CATCTACAACAGCC |

FIG. 7 (Cont.)

| | | | |
|---|---|---|---|
| GAGTGTGACCCACC | TATCAGAGCACCAC | GAACCCGGTAGGGT | GACATAAGTACGGG |
| GCCTGCATAACGAC | CACTCCAGCTCGAA | TTCACAAAGGGGGG | CTAAGGACAAGTGC |
| AAGGACCCTGATAC | CAGAGGCACAATTC | AGGAGGCCTCAGAT | ACTCAGCAACGGTA |
| GATAGTCGAAAAGA | GGGTAGCTGCGCAC | CCGAGCCGTGGTCG | GGCACCGGTCGTCG |
| GCGGGTCAACTCGC | CGATCGCAGGTAAG | CGAATGAATGGGAC | GTTCAGAAGAGGCG |
| CGTTGAGCACACAG | CCACGCTTACGCCG | CCACAGGTTACCCG | TGACGCTACGGGGG |
| AGTCGCGAGGACGT | GAACCCTCCATACC | GTCGCACAAATGCC | TCCGCGTCACGGAG |
| CAGGACAAGGTTGG | AAACATGCGAGGGT | GCGCTAAGAAAACT | AAGAACTGCACCTA |
| ACGACGGCTGATCA | GTGCGTGGGAGAGA | TCGTGCCCCAAGGA | TACAGCCATGACAA |
| AAATCATGACAACA | TACAGAGGCCTAAA | TTGCACCCAGGAGA | TGCCCTAAGAACCC |
| CGGCGTACAAGCGT | GCGGCAAAGCTTGG | CGGACGAGTAAGGT | CGAGCACTGAGTAC |
| GTTCGGGAGACAAA | TGGACATCGCGAAA | GAATCAGGGGAGGT | CGCTAAACACTGAC |
| CTCGTCAGAAGGCA | AAGATTGGACGAAC | CAAGCATCCAATAC | GGCTATGGCCGCGG |
| ACGATGAGCGTGCA | AAGACTAAGAAGTA | ACACTCGTGCACAG | TTGGCGCAAGAAGA |
| GGGACCACGTGTGC | TGGAGAGAGCATAG | CAGGCGTGCGTGAC | TCTACCGCCAGACG |
| TACAGTGACAGACG | CTGGGTAAAAGGGA | AGGTCCGGACGTGA | GCTATAACCAGAAC |
| TAAAGGACGCGAGT | GACTACCGAGGGGT | GCTCGCCCAGGTGC | TAACGATCCGCGCC |
| GTTGAAGGAACAAC | CCCAGCACGCACTT | GATCCTCCCAAGGG | CCAAGGCATAACAT |
| CGAACTGGATCGAA | GAATGGGACCGTGC | CGTGCGCAGAAATA | TGCCCGTGCAACCA |
| AAGTTCCACCCAGA | CATCGAAAGATAAA | TAGTAACCGAAACA | ACATGCTGGCGAAA |
| CCTAGGGAAACACT | AGTAGGCTAGAGAG | TAATGGGCACAGAG | ATAGGGAATAAAAG |
| AACAATCATGGGCA | CGAGTATACACACA | AACTCCGACCACAT | GGGAATAGTGAAAA |
| CGGCTGTAGGCAGA | AGGATTGAGACCGA | CGCCAGGTGGCATG | GCATCACCGGCAGT |
| GCACGTCACCGGTA | CTCACAGCGGCCAT | ACTCGGAGTACAAC | AAACCGCCGGGCTT |
| TAGCGGAGGGATGC | TCTGAACGGCAACG | GCCTATAAGAGCAC | TGACACAATCACGC |
| GAACCCACCTCCTG | AATCGGGACTCAGA | GCAGGAGGATGTAC | TAACGGTGGACCCG |
| CCAAGATGAAACTA | GAAAGTGGGTGGCC | TCATACGGACAAGA | CGACAAAGGTCAGT |
| TCCGTGCGCCAACA | CACTCGACGCGTAG | AACGCGCTGTGCGG | GAGTCGAGCACCTC |
| GACAGCGAGGTTAG | GCCTATGGGGCGGG | AACTCAGCGATCAC | AGATGGATACAGCA |
| GAGATGAGGAATCC | CCTAACTACGGAGG | CCCCAGTAAATGCC | GCAATGCCCAGAGT |
| GCCACCGCGTACAT | AAGTCTCCCGCACG | TAACGAGAAAACAT | CTCACCCACCCGGT |
| CTGACACGCCGTCG | TCGGCCACCAATAG | CCCCTCGGGTCAAC | GCACATCCTCACAA |
| CCACTAGAACTACC | GAGAGCTGGCTGGA | CGACTCTCAACCAC | GTCTGGAAAGCCCC |
| CCCATAAATAAGAC | AATGCGACGCACAT | CCTAGGGGCAGTGC | GAAAAGTCGGCAAT |
| AATCCCGAGCGAGT | GCCCACACGTGTCC | CGCAGGGTGGAAAT | GTGTGACCGGACGA |
| TTCGGACCCAAGAG | GATAAAAATACCAG | TAGCCCCACCATGG | CCGGTGCACCTGGA |
| CTAGGGGCACACTA | GTCACGCTGGGAGA | GACGAAGGTTGACG | CGGGACAGAACCTT |
| ACGTCCGTGCAACC | AGGCAGTATAAGCA | GTAGAGGGACTCGA | AGTGTAGCCGCCGG |
| ATGGCGCAGGGGAT | TACAACATCGAACC | ACCTGCCGAGTAAG | GGTGCCACCAGTGA |
| GAGCCGTATCGAGA | CCGAAGGGTATAAC | CGCTAACGTACAGC | TCAGGCCCAGACAT |
| AACCTGGGAATCGG | GTTGAGGGCCGCAG | AGCGGATGCGCTCC | GGGTCCCCAGACTG |
| ACCCGACTTGACGG | GCCAACTGCAAAAT | ACTACCACCACAAT | ACTGGGGAGCAATG |
| ACGATTAGGCGGCC | CGGCAATCCGTAAC | TGGACGGAAACGAT | CCCCGTCAATGCCA |

FIG. 7 (Cont.)

| | | | |
|---|---|---|---|
| CTCGGCACACAATC | CCGGGTCTACCGCA | GCCAACTACACTGG | GGCCCTGTCGAACG |
| AGAACCGTCCTCGC | GCTGAGTCGGGCCC | CCCTCGACTAACCG | CAACTTGCGGCGGG |
| ACAACGTGCATCGA | GGCTAGATAGAGGC | AATCCAGCTAACGG | AGTCCACGACGTCC |
| TACAGCGCAGGCTC | GAAGCAGTGTCAAA | CTGAAGGCGAGCAT | ACCTCGAGGTAGAA |
| CGGGTAAGGAATAC | AAAGTGCCATACGC | CGGCCAATCACGTC | CCTAACCGGAAATC |
| ATTACGGAAAGGGC | TCGATGGCGAAACC | ACCTCGCTCGCCGC | CCCAGCCGTGTCGC |
| CAGATGATGGCACA | CCCCGACTGCTGGC | GGGGCACATAATCA | CCGGTCGATCGAGA |
| GCAAAGGCGGTTGC | AATGGCACAGGTCG | CGGTACACCAAGGT | CCTATCGCCGACGA |
| TACAGGAAAGTGGG | TCCGAAGCGTGACA | CTCCCATGCGAACA | GGCGTCTGACGCGA |
| CTCTGGAAGCGAGG | GATATGAACACAGA | GGAGATGAAATGAC | GAACTCGGGACTCC |
| CGAGTAGGAGCCCT | CCGAGCTCGGCAGT | TAAAAATCGCAGAA | GAAGCCGAGCTTAC |
| TCCACCAGGCTCCA | GACGGTAGAAGTCA | AATGAAAGTAGAAA | GAATGCCCGAGAAT |
| TCTACAAAACAAAA | AAACTTAAGACCCA | GTATGAAGCGCGCA | GGGAACATGAACAT |
| CACCAACAGATCTA | GACCCGGAGACTAT | TAGGGCCTAAGAAG | TGATCACGGCAAGA |
| GCAGTGATGCCGCA | CGCACGACCATTAG | GGATGCGTACGCCC | CCCATCCCCTAAAC |
| GGGCGTTGCACACA | CAAAATCATCAAGA | AAGGACGTATACGG | GGAATCGGAGGTCC |
| CGGTCCAAGGCTGC | GGTCTACGAGCAAA | CCGAAGGGCTCATG | TACATAAGAGGAAC |
| GCCGGTGAAAGTAG | TCACCGCAGAGATA | GTACTGAGCAACGG | AAACTCATCACCGG |
| ATAACGAAGCCGGT | TGGCGAGCGGCATA | CATGAAATCCGGCA | CCCGGTACAATGAC |
| CAATCGAGTCGGGG | GTTGCCAAACAGAA | CGTATAAACGAAGA | GGCTACCCGCTCGC |
| CTCCAGGCCAGCTG | CTGGTAGGGGCCAC | AGTAACTGAGGACG | ACTCAGCGAAACTG |
| ATTGGGACCAGGGA | GAAATCGACTACAG | CGACGCGTCCGTGC | ACTGTCACGGGGGA |
| CAGACTGCGGATAG | TGACCTCAGGGGAG | CCTACCCCAAACTA | AAGGCTGCGTGAAA |
| CGTAACAGGAGGCT | ACACGTGTCGGGGG | GAGTGCAGAGTGCC | AGTCTAAGACACCA |
| AGCCAGTTGCCGAG | CCTCGAGCATGACA | AAAGTCGGCAGCTG | ATCTGGAGGGAGCC |
| GGACGACGATTGAC | CCCGCTTAGGGAAG | TCCGGCATGAGGCG | CCGGAGACATTGAA |
| AATGCATACACAGA | TGTGAGCCGACACC | GTCGGGAAGAGGTC | GGAGACCCATTCAC |
| TCGAACATAGGGCC | GGCGGTTGGGAGCC | CCTGTACGAAACGG | CATCGTCGGAACCC |
| CGACGATCGGCCAT | GGAATCGAAACCAT | TGGAGGCCAATACG | AAAATAGGTGCGAA |
| CAAAAAGCTACATG | ACACTAGACGATCA | ATGCACCCGGAGAT | AAAACCAGATCTAG |
| AATGGTCAGCCGGG | GACTGAGCGCATCG | CTCGCCAGCATCGA | CGCACCTGAAGGAT |
| GGGGTAACCATCAA | ATAAGGGGATGCCC | TGCTCCGACGGGCC | TACTACCACCGGGC |
| GATCGGGATCCCCG | TCACCAACCGGCTG | GTACGGGTCGAAAC | TCTCCGCCAAAGCA |
| AAGGGAGTCCATGA | GGTTCGGCACGGAC | GAAGGAGACGTATA | TACCACCGAATACC |
| TCGGTGCGGACCCA | AAACATGGATCAGC | CTCACGCCGAGTCG | CGCGGATAGACATC |
| CAGGAGAGCCTTCC | AGCAAGTACTCCAG | AAGCAATGCGATCA | AAGAGTCAAGTGCG |
| AAAGAACGGCTTGC | ATCAAGTCCCGCGC | GAGGTCAATCGACC | AAAGAGATTACACG |
| CATAACATCGCGGA | GACGCTGGAACCTC | AGGACGTACCAATC | GCAGACCACGCTAT |
| AACCAGGCATGCCT | AAAAGCGCAGATCT | CGTCCAGCATAGGG | CACGCTGTGCGGAC |
| CGCAAGCTGCTAGC | AAAGTCAACTAACA | CAGCAAACTGCATC | CCTCGGAGACCTCG |
| GCTAGATGCAGGCG | CTAACTAACCCCCG | TGGGTACGGGGACA | AGGGGAGCATTAAC |
| GGACTGGGTAGCCG | TAAGCCGTGACCCC | ACTACACTACCGCC | GCATTGGACGGGGG |
| CGGTAGCACAGTAC | ATGGCCCTGGGCGA | CGTCCGCAACTCGC | TGAAAAGAACAGTC |

FIG. 7 (Cont.)

TAGCACTGAGGAAG
TGGGCATCCACGCA
CCTAAAAATCAAGC
GTCGTACCCCCACA
GTGCGAGCACGGAT
CAAGATGGCCACTG
CGTCGAGCCTCCAC
GAGGGTTCGAGAAG
CGACGTGAGACCTA
GAGGCCGATGATCC
CACCTCCGTCCCCA
GAATGGAGCTCGGG
ACTGAGTGGCCCCG
AGACTAGCCACATC
CACGATGATCCACA
ACAACCGTACAATA
GAGAGCGGTCGCTC
CCAGGCCAAGCTTC
GTGACGTGCCCGCG
TGGAACAGCCGTGG
CCCAACTTAACGGA
CATCGAAAGGCCTC
GAAGCTAAAACAGT
ATGCTCCCACCCGA
AGCACAGTGTGGAC
GGCTGAGACGGTGA
TAATGCGCGGCCGC
TGCCACGCACATCG
GCCTGTACCAGGAA
GCGGGTACACGTCC
GGGACCGAGCAGTT
TGGGGCAAGGTGAC
CAAGGCATCTCGCA
AAAGTGAGCCGTCA
GAATTCGGCACCAA
CGAAGTAAGGTAAA
AAGACCGTGACGAT
TACACGACCTCACA
TTGCAAGGGGGCGA
GACTAAACAGCCCT
CAACAACACTAGTG
AAGGGAAATACTGA
AGACTGGTAAAGCG

ATGAGGGCCTCAAG
GGGAGGTCCTAAGA
TTGGCACAGACCGC
CACTTGACAACCGC
AACATACGCAGCGT
CACACAGGCAGGTT
CACCCCACGACTTA
GGGCACTGTCACAG
CTATAGCAACAGGA
CTATAAGCGCACCC
AACGAGCATAGAGT
AGTGCAGCGTACCA
CTAAGGAGCGTACG
CGTTCCGAGCCGAA
GGATAAATACGCAA
CGTCCCGAGTAACG
TAACGTCCCGGACA
CTACCCGACCTGAA
GATAGATAAAACAA
ATACCGACTGACAA
TAACGCTCCCCCGG
CACTCTAGCGGCCG
AAGGGAGCGATTCG
GACCGAATCGAGGT
CACGTAAGAAGCTC
AACGAGGGATACTC
CAGTCACGCGCCCT
GCAAAGTGCTCCAC
GCACGCAGACGTCT
AGAGCGCGATGCCT
AATGAGCTCAAAAA
AACCTGAGCGCCTC
CCCCAGTGGCAATA
GACCGCAGGAATTC
TAGCCACAGCGGTC
AAAGTCAGGCACTA
CGACCAGGGCTATA
CCATAAGCTCAGAA
AGGCCTAGAGACTC
TAACAGGGAAAATG
TACGGAGGAATCCC
CACTGGGTAAACGG
CTTAGCGCGCGGCC

GGCCACTAGATGGG
CTGAGCGCTCCCGG
AAGCGTCAGCCCTC
CATAGCCACCTCGA
GACTGACATCCAAG
TACAGACAGATAAC
GCAACTATCAGCGG
TGCGGACATAGACC
CGAAGCATGAAACT
CAAACAAGGAATTA
GGAATATGCAACCA
AGCGCGAAGTATCC
CTTCGAAAACGGAA
AGGGATCAAGTCCA
CATAGAGTAGCAAG
GGCTAAGAAACCGT
GAGCCTAAGATAAG
ACTCCCTAGCGCAC
CTGGACCCCCTGCG
TAACACGAGACTGG
CCCATAATCGGGAA
CGGTAAGGGTACGG
CAATGGCACGCTAG
GATAGAGTCCCAGC
CATCCTAGACGGAC
TTACCCAACACACG
CCACCAGTATCACG
AGCGACCGTTCGAA
AAACACGTTACGAA
GAAAGCCAGGCATT
GGGGCTAAGAGTCC
ACAGAACGTCGTCA
GGCGCTCAGCTAGC
ATATACCCGGCGCC
GACTACAGGCTCCG
ACGTACTAAAGGCC
AACCGCCAGTGTAA
CGACGTGGCGTGCA
TCCAGACGCCCACT
CTAGGGGGTCAACC
CGATAGAACTAGGG
CGAGGTAGCAAAGT
GCGGAAATCAGACT

CCCACCACCCGTCT
TGACCGGGTCAGCA
CACTTAAACGCAAA
CTCCCTGCCACCAA
CGCAGGTCCATGGC
GGTGTGAGAGCGGG
TGAGAAGGCGCCTG
GCATAATGGCCGAG
ACTGCCGGTGGGCA
GAGCAACGGGGGTT
GAGTCCACTGGAGG
CCAGTTCCCCAAAA
CGAAAGGCATCAGT
AACTAGACAAAGCT
AAAAACCTCGCTCC
GCCGTAGATGGAGG
CTACCGATAAAAGG
GAACTGATGAGAGG
GAATACTCCAACAC
GACATAGATAAACA
AAGCCGGTTAGGCG
GCCATCCAGCGGTG
ACGTGCGACCTGGG
AACCCTCGAGGTGG
AGGCCACCGCTCAT
AACACGCATTAAAC
CCCCCATCAACGGT
TCATAGCCAGGGAA
AGTTAGGGCCGCCA
CGGAATGAATGGAC
CGAATAGGGCGAAT
ATTGAGAACGCCGA
TAATCCAAGAACGC
CAGGGCCTTAAGCA
TGAGGTACCGGGAC
AAAGGCTTGCCGAA
TGGCCACGGCTACG
AATCGTGCGGGAGA
AGGGGAAGCTACTG
GTCTCGGGGAGGAC
ATCAGTGGGGGCCG
CCCCTGGGAGAGCT
ACAATACAATGGAC

FIG. 7 (Cont.)

| | | | |
|---|---|---|---|
| AATCGAAAGTACCG | GCTCAGAACCGGAT | ACCTCAGGCCTGAC | GGTCCGCACTGCAC |
| GCCGTACCAAATAA | CTAGTGGGCAACAA | CTAATAGACAAGCC | GGTTGCGACGCGCG |
| ATAAAGCTGAGCGA | CCTGTAGCCCCCCA | CATGGGCGAATGGA | CCTCGGCAGGTCAA |
| AACTCCGGAGGTAC | TAACAGGATGGCCA | CCAAGACCTAATGA | TGCGTGCCCCACAC |
| TCCCTAGCCGAAAA | CGGGAACTGAGAGT | GAGCCGACTGAACT | TCGGAGTGACAACC |
| CGGCTGCACAGCTG | CTGCGCAGCCCACT | TAACTGCAACGACC | TGGCGCAACACGCT |
| CTGCCAAACTACCA | CCGGACATAAGTAC | GAACGATAGTCACG | ATAAACAACGATAA |
| AAATTGCGCGAACG | GTCCAACATGCACA | TAGCGTGGAAAAAC | CACGTCCCCATACA |
| AGGTAGCGAGTCGG | TGACAAGTAGAGAA | CCACCAGACGCGTT | ACTCGGACGGACTA |
| CGAAACGCGCTTAC | TTCGACGACCGGAA | AAATGAAGTAAGAA | CCTTGACGAAAAAC |
| GCATACAACTCCCA | CGACTGCCACCCGT | AAGAACCTATGGCA | GCCGTGATCGGCCG |
| CGGACGATCGTCAC | AACTAACTAAACGC | CAGTCCGACCCCTA | AATAACCAAGTCGG |
| CTGGCAGCTGCGAA | CAAGAGAGGTGGGT | GAGAGATAGGAGTG | CCCTGCGTAGGCAC |
| GCGAAATCCTACCA | TCGGTCAGACCAGA | GCTCAACAGCGTGG | CTAGGACAGCGGGT |
| ATCCCCAGAAGTGA | CGGATCGAAGGAAT | GGCAAAGATATAAG | AGCCGGTTAGGCCA |
| TAACAACTGAGCAC | CATGAAACTGCCGG | CTCCCAGATCGAGA | AACTATGGGCGGCA |
| CGACCCAAGCTGGT | CGCATTCGCCGCCA | GGACTCCGTGACAA | ATGAGGAAAGGGCT |
| GCAGGGGGATAATG | ACTAACCTGCCCGG | GCATAATGCCGCCA | CGATAGATGCGACA |
| GGGAGTCGGCCTAA | GCACCGACCTTGAA | GGGAGTCCGTGGGA | CTGAACACTACCCC |
| TATCAAGCAGAACA | ACTGCCCCAGTCAG | TAACGACAGCTACA | TGAAACACGGTGAA |
| CCGGCAAATACGTG | ATACCCGACGGTCG | AAAACTCAGACAAT | AATATGGAACCAGC |
| ATAATAGGGAAGGA | TGAGCCTAAAAAGC | ATCCCCGACGCATA | CAGTAAGGAAGGTC |
| GTGAGATGGAACGG | GATCGCGCACTAAA | CATGACGCAATACC | TAACCCGGTCCGAG |
| CCCAGTGAGCGGGT | TAACACGGCCGCTA | ACACTGGCGACTCA | CTGCCGTACGGGCC |
| AAATGCTGGGGCCG | TCGCGAGCCCACTA | CCCCGACGTAGCGT | GTGAGGACGGGTAA |
| ATGTGGCGGCCGCG | GGCCCTGACACCTG | TCATAAGAGAAGGA | CAGCCTCAGCAGAT |
| TCCTCCAGCCCGCC | CGATAGGGAAACCT | GGATGCAAATCCAG | CACTCAGCCTCCGC |
| ACAGCATAATGCCA | TGACTCCAAAGAGA | GGCAGGCTCCATCG | TGAAAAGGTACGAC |
| TGGCGAGACCTCGG | GCGCCATTAGACGG | AGCTAAAAGGCTGA | GGGTCCCCACTGGA |
| GATAGACAGTGGGG | CCCCAAGGATAGTC | ATTAACGAGCCGGA | CACAACGCGCATGT |
| GGACCCGTTGACGG | CAAAGTGAGCGTAC | TTAAGAGACCACAC | ACGATGGCGCGCTA |
| GGATGGAAATGACA | CCATAATACGCGAC | GGTATGGACCGGCG | GTAGCGTAGACGCG |
| CCTACCACACGGTC | AGGGGTCTAGCGGG | TAACGAAAGTGAGC | CCACCACAGATAAT |
| AACGGAAGAGAGTT | CGGACAGAGATCTC | AAGAATTCGACCAG | CGACGTGGTAGAAA |
| GAGTACGTGACCAC | GTACAGCACGTCAG | ACCCGCACCTTGAG | GCGCACGCATGCTG |
| GAGACTGCGACTCC | AGGCACATGGTGAG | GTAAGAGGCAAGAT | CGTTAGCGGCAGCC |
| CCCTGCGCACGTCG | TAAGAACAATACCA | AAGCCAGATTGGAA | TAGGATCGCCACCA |
| GGTGGAGAAAGAAT | AGAGCTAAGATCAG | GGCCTTAACAACAA | TCAGCCCGACCTCG |
| GTAACGTCAGCGCC | GCTCCACGTAAGAA | CCTGGATGGCGCAA | CGAAACGAGTTCGG |
| GGGCAGGCATATAA | ATTGACAACGAGCG | CAAATGACCATAAC | CCCCGTCCTCCAAC |
| GCAGCGGATCTGAG | CCACAAGATTCCAA | TGCTCAAGCGGGAA | GGTGACGTGAAACC |
| CTGACTCGGGCGGA | ACACCTCGGTGCAA | GAAACGGTAAAGGT | ATCTACACAAGGAC |
| CTGACCTGCAAAGC | CTGAGCCAGCGGTA | GCATCAGAGCCATA | AGCGAAATGTCGGG |

FIG. 7 (Cont.)

| | | | |
|---|---|---|---|
| GGGCAATTGGACCA | ACTGAGACCATGAC | AAACGCGTGCCCCT | TCTGCCGATAACAG |
| CCCGGAATATGCGG | GGAGAATGGATGCC | CGGCACATTACCAA | GAGCAATCTGCTGG |
| CAATGGGTAACAAA | CGCACGTACCTAAA | ATCGCGAATCCGCC | ACCTGTATCAAGGC |
| GAAATTGCCCGACA | GCCACGCTTAAAGG | GGCGAGTCCCCTAG | ACTTTGACCCCGAA |
| GGGATCCATGCAGA | GACATACAGCAGCT | GAATCGCATAACAA | TCGGCCAGATGGTG |
| TGCCGGAGACCAAT | AACCATGATCGAAC | AAGCTATAACCGAG | TCCTGATAAAGGGA |
| TCTGAAGAAAGAGA | AAGAGTCCGGGAAT | ACTCAAGGATACAA | ACGAGGCAGTCTTC |
| GACCCGTAGGGTCG | ACTCGAGCGGATCG | TCACCATCGGGACC | AACGATTGGCTAGA |
| CCACTTGGCAGACG | TTAAAAGGCACCGA | TCCTGACGCCGGAG | TAGCTGCCCATGAA |
| ATCTGACGCGGCCA | GGGATAAATCAGCC | CCCACCTGGCTAAC | TAGCAAATCTCCCG |
| AAGGATACGGCCGT | CTATCGAAAGAGAC | CCTACCCACAAACT | AGTAGCATTCGACG |
| ACGAAGGCCTGAGT | AACCACACTCATCC | ATAGCGAAGCATAA | AGCTGGTACAATAG |
| CCACTCCCGATACC | AATCGTCGGGAAAG | AGATCCCCATGCAA | TCGCATTAGCGGGC |
| ACGTCCCGTAACGG | AATAAGGGGGTGGC | TGGAACCGAAGATA | GAAGGATTTGAAGG |
| AAATCTGAGCGGAG | TAGAACAAGATACA | AGATAGGTAAAAGC | CCGCTCGGGTAGTG |
| CCGCGTTCCCCAGA | ACTCGCGAGTAAAA | CCCACATCGCCACT | TCTCCAACAATAAC |
| AGAGTGCTCCCGAA | GCGGGTCACCCTCG | CTACCCTACCGCGG | GGATGTGCGGTCCA |
| CGCAGCGTCAGTCG | GCATCTGCGCGGCA | CGGAAAACGGTATA | AAAGAGTACAACTT |
| CGCGACTCTCGGCC | GTTCACAGGAAAGC | AGAGCGGTGGTCCA | GCTTATACACGAGG |
| ACTGTCGACCGGGC | CCCGTACATAGAAA | GGACCTAGCATGGG | AGATCAACTAGAAT |
| GGGGGTAAGACAAT | CCCGCAACCTGTAA | CGATAGGAAACATG | CGTGCTTGCGCAAA |
| CAAAACCTATGCAC | GCGTTACCCGCCGC | CGTCACACGTGGGA | CTCAAGTGCCCCTA |
| AAAAAGTTGCGCCG | GTAGCACGATGCGG | ACACGAGCCGAATT | GTGCAACGCTTGGG |
| AACCGGCTAGGTAC | CGGATAAAGAGCAT | TACATCAGGAGACG | TCCCACAGCATTGA |
| GGCCGTACAAGATG | AAGTACGCCTCCAA | CGGAACCGACGTCT | GAATAGACGATTCA |
| CGCACCTCAGTCGC | GGAAACGACATTCA | GCAGGACTTCGGAC | ATGCCCAGCATTAG |
| AGTTCAGAGCGGGC | GGAGTGCTGGGCAA | TAGATAAGGAAAGA | CTAAGTCGGAATCG |
| GCAACTGACTGCCA | AACGGGGTGCGTCG | CATCGACAAACGAT | TCCAGTTAACCCGG |
| TAGGCGACACTAAG | GATAAGCCCTGGCA | CTCGTACGGCGGCC | ATAGGAGCGAATAT |
| CCTACTCGCCGAAG | GGGTGACTCACAGG | AAAAGTCAGCCTCA | TCGCCGTGCCTGGA |
| AGCGCAGATATACA | TGAGCTAGAAAAAA | ATCCAATAGGAATA | CACCGTCCGGTTGA |
| GGGGTAACGCTACC | CAGCCTGCCACATC | GAGGTGTAGTAACA | GTTCTCGACCAACG |
| CAGTCATACAGACA | TAATCAAACAAGCA | CGCTAAATCTGAAG | CTAATCCAACCGTC |
| GCTTCGCCACGCCA | CACGTGGGCAATGG | CTAAGCCGCTGAAT | AAATAACATGCACT |
| ACAGCGCGTCGGTG | GGCCTAGAGTCCAC | TCTCGTAAAGCGGA | GGATAGGGGTTAAA |
| GAGACAAATCCGTA | CCCTTCGGAGGGGG | ACGTCATGAGAATC | CACCTTGAGAATAC |
| GCCAGAACGGTTGG | AGCATAGAGATAGC | GATTAGAACCATGA | TGGACTAACTCGCA |
| CCCCACCTCGCTAC | CACAGAATATGGAC | TGAGTGAAGAGTAG | GCGAGTTGTGCGCA |
| TCAAGACTACGGCG | AAGTACCACCGTCG | CGCATTCAAAAAGT | GGCCATCGTGGGAT |
| GCGGAGTACCCTGC | TCAACTAAGAGGGC | TCAGAATACCTCGC | GCTGAGAATTGAGG |
| CCCATGTCGCAAGC | GGGGCAAGCATATG | CCAGGTAAGCATCT | GCAGATTTAAGACG |
| AGCCTCGGAAATCA | TGTAGCAAACCGCC | GTGCGGGTAGACGT | AGACATTCAAGTGG |
| GGCGAGATCGATAA | CCCAACGACATTAA | TGAACGCATGCTAG | TAACTTGACCAGCA |

FIG. 7 (Cont.)

| | | | |
|---|---|---|---|
| GCTTATAAACACCA | ATGGCGGATACCTG | CCTGTTAGGCGACA | AGAATATCCCTGGA |
| TGGCAGGTCCCCGT | CAAGATATCATCCG | AGACGCTATGAAAT | CCACAACCTACTCT |
| CGTGTAGCAATAAA | ATGCAGTGCGCTAC | GCCTGACAATCGGT | ATTCGCCCTAACAG |
| ATGAGACTAAGTAG | CAGCCGCTGATATG | CGTAAGCAAGATTA | GGATGCCACATCAT |
| GTTGAACCTGGGAA | CCCGTTCAGCATAG | AAGATGTCCAATAC | AGAGTAAATCACGT |
| ACGCGGATCATTCA | GACCAAGTTGGCTA | CCGTAGCTAAAAAT | ATAGTGTCAAGGGG |
| TAGGTCAGTGAGAA | CGCGGAACGCTTTC | ACCCCTGCAATACT | GACTTCGGAAGATC |
| TTTCCCCGGGCGGC | GGTTGGCCTGGCGG | AGCCAACCCCTATT | CATCTAACGCATGA |
| GACCGTTTGCGCAG | GCTATGATCGCCAA | GATGCTTAGGGACC | TAACTAGCACCAGT |
| TCGGGGACATCAGT | AGCGCTTTAGCACG | TACCAGTAGAAGTA | CTAAGCACCGCTTC |
| CATACCTTAGGACC | CTGCTCTGACGGAG | GGCAGCCGTTATAG | ACAGACTGATAGGT |
| GCACTCTGCAGTAC | TGGGGCATGCTCGG | GCTCGGCTTGCGGG | AAGTCAGCTCCTAA |
| GCCTAGCGTCGCTC | CTTGCCGGAACTCC | CGAGCCTCCTGCTG | GACTCCCACACATT |
| CTAACGGTGTAGCA | GCTGCACATCTCCC | TTGCCCACTGAGAC | GTACATGTACCGAA |
| CGCAAACGTTTCAA | CGAATTTGCCCCAC | GGCCTAATGACCCT | GGTCGGCTAGTACA |
| GCAGGCGTGATGAT | CGGATGTAACCTGC | GTAGTATCGGAAAC | TGATGCGGACGGAT |
| TAACAAACAATGGT | CACCAATCGTGAGT | AGTTACGCAGTCCA | AAACAAGTAACTCT |
| TTCCACAAGGTCGG | ACAAGATAGTTAAA | CATCAAGATAGGGT | AAATTTCCGACAGC |
| GAGCTCCCTACACT | TTCTGGGAAGCGGA | ATCCTAACCATAAA | GAATTGATAGGCCC |
| GTGCTACGAACGTC | CATGGAATAAACGT | GGCATAATACTCAC | CAACACAATGGATT |
| GTTCCCGCTACCAC | CTGTCAAGAACACT | TGGGCCTATCGGGC | CACTTGGAACGTAC |
| CCCCAATAGTCTCC | CAGATGGATCTACC | TAAGATGAAGCATG | GAGTTGACCTACCC |
| AGTAGGAAGATCGT | ACGAGATATGGTGC | CGTCAACCATTGAA | GGGCCACCTTATGC |
| GACGCCTTGCGCTA | TTACTGCGCACAAA | ACAGCATCGAGATT | TTGACCAAAATGGG |
| TCGATCCACGCAAT | GTCAATCTAAGAAA | GGTTAGCTGAAGAA | ACGGTGCGATAAAT |
| TGCTGCGAAGTCCG | GGGAGCGTGTGGAT | TAGTCCCAGTAAGA | CAGTGCATAGGGGT |
| TATCCATGACCAGA | TGACACATCTGCGG | ACGGGTGCCAATTG | GGCACGGTGCTCAT |
| GGAAGATTATCCCA | TTACCGCCACGTAG | GGCACATCGTTCAG | CAGTGAAGTCCCTG |
| TAACGGGCATTACA | AGTACATCCAGTCC | AGCAACCTACTATA | TTCCGGTGCAAAAG |
| CTGGGGAGCCTCTA | CTCAACGACGTCTC | GAGCCCATCTGTGG | GCGTCTGGACAACT |
| ACTAAATAGGGCTC | GAATCGCATGGGTC | GACAGTGTAGCTAC | CGGACCATCGGGTT |
| TTCCCGCAATCGAC | TGGACACGAGCCTT | CATACTGGCTGCGG | CATTTCAGCCGCAC |
| TGACCCCCTAGCGT | CCTACGTTGGCAAG | GTCGGCTGAGGAAT | CATCGCGCTGATGA |
| ATGTCCAGGCGCTA | GTCACCGATTGCGA | AATGCGATCTGAGC | GTGATGGCCACGGT |
| CCAGATCCCCCTTG | CGGGTCCTAACATC | GTCGCAGACAAGTT | GATACGCGTGCTCA |
| CGTGGACGGTTAGA | TTGTCCGCACCACC | ATTGGCCCCCCGCT | TCTGGTAGGCCCGC |
| TCCCTGGCTCGCAA | CCAGCCACTTCTGG | GCGTAGTTAACGCG | TCTAAGAAAATCGC |
| ATACACCGTATGAC | AGACATACCTGGTA | GGGTGCTAGGATAA | CGGACGGAGGTTCT |
| ACGATTACCACCTC | GCTAACCGTCGCAT | AACACTACTTAACG | GGCTCACCTCGTGG |
| AGTAATAGCATACA | TGTGGAAGCATGAG | TCCCACACCTCAGT | GATGTCATCAAAGG |
| GAAGGTCTGACTAC | CAGGCCTGTACCGT | TTCATCGAACAAAA | ATACGTCCAGAAGT |
| TGGCCAGGTGCTAA | TCTGTCCGAAGGAC | TCTAGCAGCGGCTC | CGCAGCTTAGCCTA |
| ATGTGGCGAATCCA | ACAACGTGCTGATG | CCTGCCCGTCATCC | ACGTAGGGTAGATA |

FIG. 7 (Cont.)

| | | | |
|---|---|---|---|
| GGCCTTCAGAGTCA | GTCACAGTTCAAAC | GAGTTGCCATCAAG | TGGGAACGTCAGGT |
| CCCACGCGTCAATT | CAGGGCGTTATAAC | TCAGCCCCTAGATG | GTGGGCGTGCAATC |
| CCATAGACGCGGTT | CCGGAATGCTCTAA | GTGTGCGGTACAAC | ACGCCACTTAGCTA |
| TTCACAAACACAAT | ACCTTCCAGACTAG | GGAGTGTGACATCA | GCCCTTGCAACGTA |
| AGCTATTCACCCAA | TCAAATCAACTACG | ATTGCGGCAATGCA | CTTACCACCTAGCC |
| TCGGGGTAAACATA | CAGTGGCTCTCGGC | CCCAGGTTTGAGCA | GTCTGCTAGCCAAC |
| CTGGGGCTGCTACG | TAGTGTCAAACACA | CTCCGACGATAAGT | CGGCGTCCCTGTAA |
| CGCTGATGTGGCAA | TGAGAAAATGCAGT | GATAGCAGTCTCAA | CGCCTGACTGCCAT |
| CGTCCCTGTCGCCC | TCAATCTAGAGGAA | CGCCTCCCGTGTAC | GGAGGGTCAAACTT |
| TTGAGAGTGACCCG | CGCCTGTGATCGCG | CAGCTACAGACATT | ACCGATTCTGGCCG |
| CAAGAATTACAAGT | ACTACTTAAAAGGA | TGATCTCGCGCCCG | ACTCGCACATTCGA |
| ATGACGGGTCGTCC | GCGATAATTCACAA | CAGCCTGGTCATAA | CCGCCTAGCTAAAT |
| TCTTGCAAACCCAA | ACGAAGGGTTACCT | TCCGATCGCCGCGT | TGTCTCCACACAAG |
| ATTGGAGTGGGCAG | GGGCAGAATAATGT | GCTAGCGGGTGCCT | GCGTGCTGCACTAG |
| ACGAGGTCGCTGGT | CCGGATCACTTAGG | TCAAAACGTTAAGG | CATTAACACACATG |
| GGCAGTACACCTAT | CTCCCAATGCTCCC | GCTGGCAGAATCTA | AGGCCCTTAATGCA |
| TCTCGGACGTAACC | GGGTTCAGGTCGAA | TCCTGGCGTCCGCA | CTGCACGCACTAAT |
| GCTGCTGTCCCCGG | CGTGCATACCGCAT | GTATAACCCAACCT | TCGAAATGCGGTAG |
| AGGTGGATACGCGT | CTCTCGCCACTAAC | GAAGTACCGGTATG | CCCAGACCTGCCTT |
| CGTCGTAGAGATAC | CCTTCGAGTGCCGC | CAAGCTACTGCATA | TGATATCGACAGGG |
| GTAACACGCCTCAT | GTTGGTGGACGACC | AGGCGGTCTGCCTG | TGTACAACGCACTC |
| CGAACTACGAACTT | CCCGTGGGTGACTA | ACACGGACGGTTAT | ATCATGATCAGCAA |
| TAAGCAAGTTCACG | GTAAACTGTCCCGC | CCAGTTAGCCGCTC | TGCTGACTCGGCGG |
| ACAGGTGCGCGTTA | ATGGAGGGGTTCAC | TAAAAATAGACCCT | ACACCTGGTCCATC |
| CACCTGCCTAAATA | ATGCGGCTCGGGGT | TCGTCAGACTACAA | TTAAGGCAAAAATC |
| CGCCAGCAGTGGTT | AGCGCGTACGCGTT | ACATCGGCTCGTGG | AATGTTACGCGGAC |
| GTGAGATACTCGGC | ACGAGCATGTGCTA | ACGCCGTTTGAAGC | TAAGATTACGGCAC |
| TGCCAGCTAAACTC | CCCGATTCATGAGC | CTCTGAGGAGCTCA | CAGAAAGATTATAC |
| CTGAACTCAGCTGC | CGACTTCGTCGGGC | GTCGGCGTCGTAGA | GGATTAGATAAGGC |
| ATTGTCCACGGAAG | CACCTATTAAAGGC | TAGCATTCCCAGAC | GCTTCGGGTCCGGG |
| ATCGTCGTAGGCGG | ACTGTGTGGCAGGA | GTAGTTCCCGGCCG | CGTACTGCTACAGG |
| CCTGGGCATCCGTA | TATGGAAATCACGC | TGCTGCACCCAATA | ATGGCCTGGAAATA |
| CGTCCAAGACCATT | CGATACCCCGTCGT | CAACCCCTTGACTC | TGACGGAATTAAAC |
| CGGGTCTTCCGCCA | GCGCGATGGAATTA | AGGTGTGGACTCAC | AGCCGTAGCTTAAA |
| GATGGTGAGAACTA | AGGGTTTAAAGGAA | ACGCCTCATAAGCT | AAGTCCGTCGCATC |
| CCATAACTAGGCTA | GGGTTGGTGCAAAA | GAGATCGATCCGAT | TGCCGAGTTCGAAC |
| TAGAAGGCTTCGAA | TAACACCCATGATG | CGGCTAGCGGGTGT | AGGCCTCAGATTGA |
| CACGAATGTGCACT | GCTAGGGCGATTAA | AGGCCCTACTTCGA | AAAGTCGATGGAGT |
| GTAAACTGATACAG | AGGACAAATGTTAG | GTGCATAACACAGT | GGCCTACTTAGAGA |
| TGTCACATAAGGCA | CTTGAGGAGTCCAG | TTACGATGACGGGC | GCATCTAATCAGGG |
| CCCGTAACCTTGGC | CTCAGATCAAACAT | TTAGGACTCCCGGA | AAGATTCATAGAGG |
| AAAAGTGGCATTCC | TCGGCACGGGAGTT | AACACATGACGTAT | ACTTCACGCCGCGT |
| GACTGGATCATCAA | GCGACCAAGTTCCT | GCCTGATCGATGCC | GCGAGGACTTTGCA |

FIG. 7 (Cont.)

| | | | |
|---|---|---|---|
| TACCGATGTCCCCC | TGCTCACATCGGCA | AGCCTGGATCGATG | CTTGCCCATGAGAG |
| GAGAGTATAAACTG | CATGGCTAACGCGT | CCGTTCAGCCAAGT | AGCCTCTGCGTCCA |
| ACAAGTGCGTCTAG | CTGCATAGATGCGC | CCAATGGTCACATC | CTTATAACCCGGGA |
| GTCCTGAGAGTCAA | TCCGAGTGAGGCTG | GTGGAGCCATTCGG | GACTGCTTGGAGAG |
| GAATCGCTGTGACG | TGTCGACAGCGTAC | TGCCAGGGGAGCTT | GGTTCCCAAATACC |
| ATTAGGGAAGTAAA | CCCCTACACCCCTT | GATCCGCAAATTAG | CCTGCAGTGACAGT |
| GCCTAGTCAATCAA | CTGTCTAAGGAGCA | GTCTACACACATGA | CCAATCGCGAATTA |
| ATGCGTACAGTGCA | CACCGTCATGTGAC | GGGCATATAATGGC | CGGCCATAATGTCA |
| AATAAGTGATGAAC | TTCCGCACTAGACC | ATCCGTAACGATAG | ACTAACCTGGGATA |
| TAACACTACTAAGA | CCAGATGTCGATCG | ACACATTTACCCGG | AATGCACTTCGGAA |
| GAGGACTGTAGATG | TTATGCAGCAGCAG | GTCCTGTCCCAAAC | GAGTGAGCCATGTG |
| ATACTAAATGCAGG | GTGGACAAACTCTC | GAGCCTGATGCGTC | CTCACCGTATCCAC |
| CGACTTAAAAACTC | GCCACCTCAATGTA | AATGTTCGCAGGGC | AAACGCTCATGTGA |
| TTAACCCAGGTAAC | CTTCGAGACGTGCG | TCGCTTCCGGGAAA | AGCTAATAAGCGTG |
| CCGCTAATAATAGC | GACTAACCGATAGT | GTTAGGGAGGCGGT | TGAAAAGGGTGTGA |
| CCGGCAATGGGTGT | GAGTCAAAACTTCC | AGGTGCTCGATGGC | AAGATTAACCTGAG |
| CGTTAAAGTAAACG | CGTAAGTGCCGAAT | CGGCTATCACTACA | GGCAACTTCATACC |
| GCCTAAGCTACGAT | GTAAGCTCTAAACG | CGCTCGAGCGTATC | GCTGCACGTACACT |
| ACAGCGGCTATATC | CGAAAATGGTATAG | ACCTCACATACATC | TCGTGGGATCACCC |
| TGATAACAGTCGAC | GGGATTGCTAGCGC | GGGACCGTCCGTTA | GAACGGATCGTGTG |
| AGGGCTCTCTCCAG | ACTCAAGAATCAGT | GGGTGCGCCTCAGT | GACCTCATTGACCG |
| CAGGGAGGAGTCTT | CGCCGAAAGTGTAT | GGGTCCAATCCTAG | GAGCGTGTGACGTG |
| GCGATGTCCGACTG | CGCGTTACTACAAG | GTGATCGTACGGGA | CCAGAGAATATGGT |
| GAGCCTCCTCTAAA | TATGGTAAGGGCCG | CAAGCAGGTATCCT | GTCAAGATGCAGAT |
| ATGAGTAAGCTAAC | TCTGACTGCGCCGA | TCCCCTCCCTAAGC | TCTCGTGGGACAAG |
| CACAAGGCAATCTT | CCAGTGCTATGAAG | TCCAGAGACTTGCG | AGTTTGCGACAGAA |
| TCAATCCCCCACTA | ACCTACAAGCATTC | TCGGTGGATGCCAA | AGCAAGCTGGGCTT |
| CGAATTCTCGGACG | GGATTATAACCGCA | GCTAGCTCGGTAAC | AATTAGGGTAACCG |
| GGACTCCTTGGGCG | TCCTAAAGAGCTGG | CAGAGGCTTGACTG | TTTGGACGGAGGCG |
| CAAATTAGGCCTAG | GCTAAATGAATCAG | AAGGTGGCCTTACG | CCTTGAGACAGTAG |
| CCATCAGTCTGCGA | CTAAACCTCCCCAT | TCAGGTACCTGCGG | ACACTAGTTGGAGA |
| CCATTTGGGAAAGC | ATGATGACGTAACA | AATACTAAGTGAGA | TCGCGTCTAAACGG |
| GGAGTAAAGCTGTA | TCGGCGAAGTCTAG | TAGGAGTAGCCACT | CTCGAGCTATACCG |
| CCTCCCGAAATTGC | GCACCTCTTCCGCG | GATCCCTGGAACAT | GGAGGATAATTAAG |
| TGAGAGGACCTGTA | TACAATGGCGGTAC | ATGCTATGCCCACA | AAGGTTCCTGCCAG |
| ATACGCTGCCGCTC | CGTACTCTGCACAG | CAACAGCGATTGCT | AAACTATGCATAGG |
| TCACCCGATTCACA | AGGATCCGATCTCA | GCAGTTAGGATCAA | TCGCCCATAAAGGT |
| AGCTAGCCTGGGTA | CCCGTCCCTACCTC | GTCATGGCCCTGCC | AGTGGCTGGTACCG |
| AATAGCGATCCATG | CGGTATCTAAGCGA | TAGAATGGGTCAAC | TGGCGTAAGAGATA |
| ATCCCGCATGAATG | CACGTTCCACACTC | GGGCGATTCGGTAC | CTTAGCACATCCCG |
| GTCAATGCTCGGAC | CGGATTCCCCACTG | CAGACTACTAGCTC | CAAATGCCGGTTAG |
| CGATACGTGTCCAA | CCCCTCAACCTGTA | CCGTCAATAGTCCG | CCACCTGACTCTGG |
| CAGTATGTGGGGGC | CAAGGTACATGGTC | GCCAAGCCGTAATT | CTGCTTAACCGGCA |

FIG. 7 (Cont.)

| | | | |
|---|---|---|---|
| ACATTGGCGAAGTC | ACGCATAGTCTGAA | ACACCAATTACCAT | TGGGTGGTAGACGC |
| TAAAGATCCTACGA | TCGTTGAAAAACAA | GCCTCGGTCCATAA | TCCGCTTAGACGCC |
| CTATTAAGACCGAA | GCGAGGAGTTAAGT | AGGAACCCATCATT | GCGATTCGCCTCAC |
| ACGTCCATCGATGG | CGAAGTGATCGGTA | GGCGTCCCGATTAG | CGGCCTACTTCACC |
| TCAATAATCGAAGG | TCTGCGCAGCCGCT | TTCAATCACACGAG | ATCGGTCACTCACA |
| GTCCATATCGCCCG | GAGCACTGATCAGT | CACCCCTTACCTAG | CCACACTTGGTAGA |
| GACTTCACATGGGC | GCACGTGGAGTGGT | TACGGTCCACTGAG | TCCAGACTGACATA |
| CACGGGTGTTCGAA | GACCTCTAGCCACT | AGCCGACACTACTT | CGGAGCAGTTCTCC |
| AAGTTCTCGGCAAC | TCGATTGCCAGCAA | CGGCTAAGTGTACG | ACGTACGTCTCGGC |
| GCGGTAGTATACCC | CCTTAAAAAGTACA | GATGTGCGCTCGCG | GATGATGGGTCGAA |
| GTAAGTGACAAATA | GTCAAGGAGTTACG | GACCTCTTAAACAA | CACCCGTACAGATT |
| CATTAGAGGTCCGG | AAATGGCATCTCCC | GCCCTATACGTGCA | AGATAGTCTGCGGC |
| CACTGCCATTCGCA | CAGGTTGCAGTAGC | GCCCTTATAAGGAG | TTCACCCAATGAGC |
| GCACCGTCCTAATC | CGAATTACACCTCA | CCTCAAAATGTGAC | GCACCGAATATTAC |
| CCTGTGCCACGGGT | GCTGCAGGGCTGTA | GAGAATTCCTGGGG | GGAACCCCGTTCTA |
| AAGAGCGCTGCTTA | CGCCCTCTCAAATA | GCCATTACTGGGCG | CACTAGGACGGTTG |
| GTGGGCATACCGAT | CCGTTAGGATCACC | GGTCCCTAGGCGCT | CAGCCCCAATTTGA |
| CTTTCCCACCACGC | TCCGGGATGATCGA | AATGACTATCGCCG | TTAATGACCCAAGA |
| ATTCGTGAAAAAAG | ACGTATAGGTGAGC | AGTACCGGGTTAGC | ACCCACATTCAATG |
| AAGACTTGGCCTGC | TCCACCAGGTCGAT | CCGTCCAGATTAAA | GGCGAATAGGCTAT |
| ATGTGCACGCAACT | CCAACCCTTTAGAA | TGCGCCATCTAGAA | CAAGTCCCACTTGA |
| AATAATGCTCACCA | ATAGTAGGACTGAC | TCCAGCGCTGGAAT | CGATCGGTTGCGCC |
| GCACAGTTAGGCCT | AGCGCATCTCCAGT | CGTGACGTAGGCGT | GTGTAACAGTGCCA |
| AAAATCTACATGCG | CTTACAAAGACTAA | GTATATCAGCCAGA | TCGCGCAACTTGGC |
| AAGAAATGGTGTCC | GATGCACCTGCCTC | GGTAGGCAGTGACT | TAGGTCCCGTCCAC |
| ACACGCCAGCGTTT | AGGGAGCCCTTGCT | GTCCTTAAGCCGCC | TTCCGTGGAGGGAC |
| CTGAAATTCGCGCA | TAGATGCATCCCGA | CATGGGCGATGCTG | GCTTGCCAGGAGCT |
| CGATCAGATCCAGT | AGCGTGTTCACGCG | GGTCCAAATGCATG | AATCCTATCGCGCG |
| AGGTGAAATCGTCC | AGTTCGACCGGCTC | TAACGACCTTCGAA | GGGTCCTAATCCCA |
| TAGAAAGGAGAATT | CCAAGCGCTTTGAG | TCGGTAAGCTACGC | TCTACAGGGTAAAG |
| AGCCCGTTGGATAC | AGGACGGCTTGATC | GGAATTCCATCGGC | AATGCCCAGTGCTA |
| CCGTCTACCTGCCC | TCACTAAGAAATAA | ATCAGTGTGGAGGA | AGCCCTTGACCGGT |
| CAAGAGTTTCCGGG | CGCTGGATGACGTG | GGCGGTGCCATTAC | AGTGGTCACATACC |
| GATCGCTGAAGTCG | TACGAGCTGCCTAG | GCCTTCAAACTAGA | CTGAGGAAATCGTA |
| GCGGTCAAGGGTTA | CGCTCCGGTATGGG | CCTTGCGTGCAGGC | CCCGCTCGGTAGTC |
| ACACTTTGGAGGGG | CTCGCCTATAGCCC | CGTTACTGGCCACG | CACGCGAACTCTGT |
| TAGCATAGAACGCT | GGAGGCTCTCTCCG | GTGTACAAGTAGCC | CCAACTGAGATGTA |
| GACCGTAGTAAGCT | AAAGTGCAAATTAC | TTCGGCTGGGCCGG | GGCGAGTGCGTAGT |
| TACGGGGTTAGAGG | TAAAGACTAGGTGA | ACGCGAGTCATCTG | AGAGATAATTGACG |
| GCACCTAGGCGGTT | GACAACCAATTCTA | GTACACGTGGCTAG | GCCATCCTAGTACA |
| AAACCGTACCGTTA | GCAGCCTGAGGCTT | TACCCTGATGAGAA | CCGGCTATTCGCCG |
| CGGGGTGTACCTAC | GGTAGAAAATATGC | CCTGGCCTGGAGTA | CAGGTGGGGTCCCT |
| GGCGCATTTCCGAA | ATCTACGAGATCGC | AGCGAGGATCACTT | TACAACTAACCTCA |

FIG. 7 (Cont.)

| | | | |
|---|---|---|---|
| GGGGTGGGCAATCT | GATTTCGCACACCA | TCTGCCGTCGGCAC | TGGGAGATTGGGCG |
| TCGCGGTCTACGAC | ATGTTGAAGGGCCA | CTAGAGATAATAAA | TACCAATAACGAAT |
| TCCCAACTATAACG | TTACAGCGCGAAGT | CCGTGCGATGTGCC | GATGGAAGGCTGCT |
| TGTCACACGCCATC | TATGAGCCTACCAA | AGATCGCCATTACG | GAACCTCTCGAAAT |
| AGTGCTCAAGAGGT | TCAGGTGGCTCGAA | TGTCAGCGGGTCAG | ATGTGAACAACCTG |
| TCCCGGAGTAGATG | ACCTAATACGGCGT | GCTTCCAGCAATAC | CCCGGATTCAGGTG |
| AGCTCCCGTAGGTC | GGCCAGAAATCTTG | GCTTAAGAGGCTAG | AAACCCCAGGTTCT |
| CCTGCCTCGCTAGG | GTCGTATGCGCGAA | CTTTGCGCCGCGGA | CGGCCTGACTACTC |
| TTTCCCAAGCGCCA | CAGCTAGGTGTGGC | TAGAAGTGACACTA | GGCTTCGGGGTCAC |
| TCCACAGTGCGTCG | GACCTGGGCCTATG | TCGAGTACGGTGGC | AACGATTCCGAATC |
| ACGGCTGGTTGGAG | AAAGGATAGTCTGC | GGTACATCCGCTAG | TGGTACGATAGAAC |
| GCTCCAAGATCTGG | TGAGGCAGGTCGTA | GCGCTAAAGTCCGT | GAATCCTAGATCCG |
| ACCGAATGACAATT | CCCGTTTGCACGGC | CGTCTCCATCGGAG | AGAACCATTTAGGG |
| TAGAGCAAACAGTT | GCTACCAAGTGATC | CCCTACCAATGAGT | GTACGATAACCTAA |
| GGGGTCGTCGTGAA | AGTGCTGTAAGCCG | CCACCGCTCTGCAT | GCGTAAATGCAATG |
| GGGGGACCAGATTT | GCGACTGATCTGCC | CCTCACCAGGCTCT | TAGCTAAATACAAA |
| TCAGTCACAGTGCA | CCGCGTTACTCGAC | GTATTCACGAAACA | CCGCGTTACCTCCG |
| CCTTCCGTAGCCGG | GGGTGGAGTATGAA | TTGCTAAAGAGCCC | CCGGTACAGTGTCA |
| CGTACTCCCACTCA | TCCAAACGCATTCC | GCGACCGTACTGAT | TTCAAACGACAAAT |
| GTAGGCTGAACGTA | CCCTCAAGCCTCTG | CGCTCGCTAGGATA | TGCGGTTGACAGGA |
| GCCTAGACCTTACG | CTTCGCCTAAGCCC | GACCATGTTGCAAG | ACTCCCTAAAAAAT |
| AACAATCATCCTAG | ATCCTAGCGGGCTG | CCGTCTGCGCCAGT | CCGGTGAGCTCTCG |
| TATCTACCCGGCGG | AGACGGCTTGAATC | CATCCCGATTACAC | TCGAGATCCAATGC |
| GGGGAGCCTCTTAC | TCCGTAGCGTCCGG | GATGAAAGAGGTGT | AACGCGTGTCGGGT |
| AAAGAACCGACTTT | CGAACCCGTCCTAT | GGTACTAATCCCGA | CCGACCTTGATCGC |
| TAGAGTCTGGAAGA | CTAGTTCGACCCGG | AACGTTCCTAAGGA | GGCTGCTATACGCC |
| GTTAGACTAGAGCC | ATCCATTGCACGAA | AACGGGTGGAGTAT | AGACCTCGAATGCT |
| ATCGTCCAGCGCCT | ACAGTCATAACTAA | GGAGTATGCGCTGG | ATGGAGACAGGTGT |
| CGGGCATCATCATC | CTTAGCTGCGACGG | ATCCTTCCGAACGG | CCTTGACGTGCGAA |
| ATATGGAAGAATGC | TAATTAACCCAGGG | CCCTCGCTCACGTA | CGCCGTCTTCCGGG |
| CTGTGAGGGTGGAC | CACGATACAGTGCT | ATACTTAAGGGCAC | CGATACACGTATCA |
| TGGAGTTACAGGGC | ACTGCTGGAATCAA | TCGTACCAAATGAG | CAGGAACTTGAGAT |
| GGCCAGGTTCCACT | TGTAGGGCCTGGGA | CCCCAAAGGAATTT | GAGGTTAGCGTGCG |
| AGGAGATGTCCATA | CGGTCACCTACGTA | GATCCGTTAAGGAA | CAGTACGGCTACCT |
| GCTCGTGATGAAAC | AAAGCGCTCTATCG | TAGGCGACCCCGTT | AACCAGGCTCTCTG |
| GCACGCGATTGTAG | CTATGAGAAGTCCC | TTTACGCACGGACG | AAGTCAAACATAGT |
| ACACCAACACATTT | AACCACCAGCTTTG | TGGTTGCAGACAAC | GCAGACTTTCAGCA |
| GCGAGCCTCCCTTC | AGTCTACAGCCATA | AAGAGGTATCGTAA | GTAGCTCAGAATGA |
| GTTCGTCACCCCGC | CAAATAACTCTACA | ACCCGTGGGAAGTT | GAATAACTATCGCC |
| ATACCCCGTACATG | CAATGCCCACTGAT | CACACGCCCTTGTG | TCAAGTAGGCCGCT |
| CGTCCCTCGTCGAG | AGCTCCATCCCCGT | ACACAACTGGGTTG | AGGCATGGTCGACT |
| ATAAAACACCCTTC | TAGCAGATAGAGTC | ACCAAATCAATTGA | CAACGTGTAGCATC |
| CATTTGCCGCAACA | CCAGTTTAGAGCCA | CGTGCCTACGAGTA | CGTGGGTACTCACC |

FIG. 7 (Cont.)

| | | | |
|---|---|---|---|
| CAACTTTAACAAAC | TGTCTAACCGCCAA | TACCACCCCAAATT | ATCTTGCAGGGAAC |
| CGGTGCTGCCATGC | GCTAGAAATATGGC | ATGGTCCCAGTGAC | CGGAATCATGCTAC |
| ATGCGCATTCGGAG | CTCGAAACCATTAC | GAATCCTGGTCCAC | ATTCGACAATCGCC |
| CACGAATACATTGA | ACTGGATGGATCGC | TGCAGGTCATCGAG | GATTTCGCAGCAGG |
| AACGTCACTCAGTG | CAGATAGTCAAACT | TAGATATCGCCGGC | TTGGCAGGCGGATG |
| AAATTGCAACGGTG | ATGAGGAATTGCAG | CAGCCGTCGCTAAT | ATGTCCCACGATCC |
| GACGACGAACTTCT | GCTATGGCTCACAC | TTGCGGGAGAATGG | TCGAACGATCCCTC |
| ACGTGCCTGTGAAC | GGAAATGTCATCAA | ACGCGTAGTCACGT | GCGGACACACTTAT |
| TCCGCAGCTGCGCT | CGCATTCGAGCGTC | CGCGACTCACTCAT | ACTATTGGCGCGGG |
| AGAGGTTATACGCA | CCCGTGGTGCTCAC | CTACGTAGGTGACA | GGATCCACATATGG |
| AACAAAAATAGCTT | AAAGTACTCCCACT | CTCGCATCGCGGTA | CAGTTGGCACTAAA |
| TGGGAGATAGTCAA | ATTAACTGGAGAAA | CGCTTACACAACTC | TCGCCTGCGCTAAG |
| ATGCGCGATTCACC | AACTCACACATTCA | TAGCGGAGGCTACT | TCGCCGAGCGTTAC |
| GTATAGGGCTCCCG | GCACTTAACGGGCT | AGATTGGACCCTCA | TTGAACAAAACATC |
| GACCAGGCGTATTG | AGGGTGCTAGGGTA | GCCATACCATACTC | CCGTCGGCTTACGA |
| ACCAACCTCGCGTT | ACCGCTGTCGTAGC | GTCCGGCACTATGA | GTTCAAACATAAGG |
| AACAAGTAGTGCTA | TCATATACAAGGCG | CTAAGGTTCAAGGA | ACTGCAACCTGGCT |
| TGTAACAACACTAA | GAAAAGACTCCCTT | TACGAGACGTCATG | GCGGTCGGCCTTGA |
| TGAGTCGAGGCATA | CAGATGTACGGTGA | GTATCAGTCAAACG | AAACACTAGGTGTC |
| CCGACAAGCTTGGT | TGAGTGGACACCGT | GTAGCATGAGTACA | GCGGTTAGTCAAGC |
| CGTTAAGCCGGTGG | TAAAACAGGGGTCT | GGAACGATCTCCCT | TGCGAACATTAAAA |
| CTCCCACAAGCATT | AGACCGTTATCCGC | CGCGGATTCGCGGT | TAAAGAAGATGTCC |
| GGGTTAAGAGGTGC | AGCTATCAAAATAA | CACGTCAAATTCAC | GGTGGCGAATGCTA |
| GAGCCCGTTTCCCG | TTGCGCCACACCTC | CACATACTCAGATC | CACGTCTGGGTCCC |
| ACCGACGTAATGGT | GATAAACGGCGTTC | ACCCTTGAACTGAC | GACGCGCTTGAATA |
| AGGCAATTGACCGT | GTAGTGGGCCAAGT | AAAATGCGCGTGGT | AGTCGGCTCTCCGG |
| ATCTACCCCTGAGG | TGGCACTAACACCT | GTTAAGACGTCCGA | GAGCTTACTAAAGA |
| GTTGAACTGCGAGA | GTCAAAACGCTGTC | CGATGTCGCTACGC | ATGGCTAGTGCGCG |
| GGATCGTCATGAGC | GGGTTACGCACCAT | GATGACGGAATTGA | ACTACAGGCGCATT |
| TGAAACCATGGGAT | TACTGGAGGAGTGA | CGCTCAGTTAACCC | TACGAGGTACTGCA |
| AGACCGCGTCGTGT | GACGAACGAGTTTG | GCCGCTGATGAACT | TGTGCCGAATCGAG |
| TAGCGAGCTGCCGT | AGCCGAATTGGTAA | TCATAAGACCGTCC | GTACCGATGGGCTG |
| ATAAGGTACACGTC | CCGAGCCACTTCTC | GTGACGCAGAGTTC | GTCCAGTACTCCCA |
| GCGGCACCACTATT | GTGCCACCTAGGCT | GGTGAGCACTCCGT | AGGCGACTACAGTT |
| TTGGTGGGGAGAAC | TGATAGTGAGGAGG | AATAAGGTACTCAG | ATCAGGGTGCGCTC |
| GCTCTCTAAAGGGA | GTACTGCCGGTGCA | GTGATGTAGCGCAA | GGAAATTGAAGCGT |
| CTGTACGTAAAAGG | GAGATTTAGCAAGC | GCTGGCTTCAAGGA | GAGATAAGGCTAAT |
| AGCTCCCGAATCGT | TAACCACGTAAACT | CAAATAAGTCAGGT | TTTAGAGCCGACCG |
| AATGTACCCGAGTC | GGTCCCCGATGCGT | AAAGGGGACCTTCT | GTTCGCGACCGGGT |
| GCTTCGTCGCCCAG | GTGAGGAGATTACC | CGACCTTAGGTACC | CATCGTGGAAGAGT |
| GTAGAAGACTGGTG | GCTTTAGGGACAAA | CCCGGTAGCGATTG | AAGTAGTTGCCGCA |
| CCACATGAGATTCC | CTCAAAGGTAAGGT | GTGACTGGGCGGAT | ATGGCTGCATAAGC |
| CATCTTGCGCCCAC | GGGACTAGTGGGTC | CTCCGCATACGCAT | GATGGGGCTATACA |

FIG. 7 (Cont.)

| | | | |
|---|---|---|---|
| GCCATAATCTGCGC | GAGGCTCGTAAGAT | AAGGCTAAATCTAA | AGGATCTTCGGCAC |
| CGGCCTCGATGGTA | TGGGCTGCGGGAGT | CTCAGCTCGCTAGA | CTACCTCCGCTCAG |
| GGTCGTGCGTGGAC | CCTGTACGACCTAC | CTGTGCTACCGAAA | CGATGATTGACGCA |
| GACTGCCTCGTAAC | CCTCGGACATGGTG | CACCAGTATCGTAG | AACTAAACTCGACT |
| CGCCTATAAACCTG | CTTACTGAAACGAG | TTGGCAGGTACGGG | GACTCGTCCCTCAC |
| TGACCCTGATCGAC | GCTGGGACTAGTAC | TATACATACCGGGG | GGTCACAGAGAATT |
| ACTCTCGCCGAGTG | CTCCATCACTCCGG | GAGATGGTGGGAGT | CGGGATACACTGTG |
| CGGTTTCAACCGGG | GTGGGAGTATAAGG | TCCTTCAGGAAAAC | TCGCCAACGTATCA |
| TTGAACGAGAAGGT | AAAGCGTAGGTCAT | CAGACGTCGTTGGA | TTAGGCCGAACTGC |
| GACGGCTATACAAT | TAAAGTGGGACCAT | GATACTATGACGAC | TCACAAGGTAGGCT |
| TTGCTGGCGCCGAG | CGACTCTAGGGGAT | CGCTGCTCTCCGAG | TACCGGCAACTTAA |
| ACACTGGCTTGACC | ACGGCTCTATGACC | CAATGGAAAGAATT | ACAGCTTAATCAGG |
| ACTGCACTCACTAA | TTCGCCTCCCCGGC | ACATGAAATCTCAG | AGTCTAAAGTAAAC |
| AATGCTAGGTAGGG | ACTCCTAGCGATAA | TCCCTGCCCACGCT | CCCCGTGCCCTTCC |
| AATAACGATTGGAG | CTGTCGACCCCTAC | CGGATACCTACTGG | TTAGAAACGCCATA |
| CGCATGTGAGGCGT | CCATGGATCGAGCT | GCACTAGGTATCGC | GCACATACATAAAT |
| GCCGAGGTCGCTCT | GGCGTGCTCAAAAT | CACAGATACTAATA | TATCCGCGTGCAGG |
| ACTCCAGTTCCAGG | CGGCATGATCCCTG | ATTCCTCAGCAGGC | CCGCGTCCGTACTG |
| CATCATGGGCTGAG | TGAATAGCGGTAAG | TATTCGGCGAGAAC | TGAGAATCCTAAGG |
| GATAGACATTAACC | CATTGAGGCAAGGT | TCACCACGCAATTG | TCGACATATCCAGC |
| TGGTGGACTCCACA | ACATTCGAGCGGTA | AGGGGCTTCTAGCA | GTTCTCCGGAGGCC |
| CAGCACCAATCCTT | ATAGCAGGATAACT | GAGGATATGGCTAA | GGACGGATACGGTT |
| GACTTAAGCGTGGC | GACAGACACCTTTG | GTCAGGCGTCATGC | AGATCACACAGTTG |
| ACCTACGAAGGGTT | ATTGCAGTAAAAAA | TGCCGGTCCCTGCG | GGGGGTTTCGGAGG |
| ACCTATAGTGAGAG | CGCATCTTGAGCCC | CCGCTGCATTCAGC | CACAGCTAATTAGG |
| CTCTGCGAGTCCCG | CTATGCAGCTACCA | AAAAGCTTGTAGCG | CGAATGACCGTGTG |
| TCAAGACATTGGGA | GTAGTGCTCAGCGC | GATGGGCTGGTAAG | TACCTGTCAGGAGG |
| ACCCTGGCCGTATC | AAACGAGGTATGTG | CACAGGCAAATTCT | TGACCGTCAGACGT |
| GTGAGTCAGTCCCG | AAAGAGGGGTGTTG | TTGACAATACAACC | GCGGAATTCATGAA |
| AAGACCCGTAGCTT | ACCTTTGCGGGGGC | GCGGATTGGTGAAA | CTGGACCCCTCTAC |
| GAGATTGCGTCCAA | ATTGCACGACATGA | ATGTGCCCGTCGGA | ATGGGGACCGCATT |
| CGAGGTTGTGAGGG | CTTGGCCATCGAGG | GACCTTTGGACAAA | TAACTCGTCGAGGG |
| AGGTAACCACTTCA | ACCTTAACTACCAG | AACGATCCATCTCG | CCTGGGGAGTATGC |
| GGTAGTCATAGCCC | CCTGAATTCCAGAC | CAGGCGATTGCAAT | AGGTCCTCGCCTCG |
| GGGGCTAGATTAGC | GTATGACATAAAAC | CGAGTCATCGATGG | GTTACGCGACAGTA |
| TGCAGATTGCCGGG | GATAGTAACCCGTC | TGGAGGCACTGGAT | TAGGCAGGTCTCAC |
| ACAATGTTGCGAGA | ACCCTGAGCTTCCG | ATCAAAGTAGTCCA | TTCAAGACGTCGCC |
| ACTAGACATACAAT | CACGAATGATTCGG | TTGAAGTGAAGGCC | GGAATCGAAGTGTA |
| GACTCTAGATAGAG | CACTTCCTCCCGGG | GTGCTACATCGAAC | ACAGCGTCGCCTAT |
| GACAAATGAAAGTT | AGACCTGGGTGGTC | GCGGTAGCCCCTTG | GCTAGGAATACTCG |
| CAAAGAGTGATAAT | TAAACTCGGGCTCC | GTTCTGAAACCGGA | GGCATAGGGGCCTT |
| CATCGTATCGGCAA | CATCGCGAGCTTCC | TTAAGGAACATCAA | AGCTTTAACGAGCG |
| CCGCCACTCTGTGC | CAGAATGGACCCTT | CACCTGCCAGTACT | CGGTCGCATACACT |

FIG. 7 (Cont.)

| | | | |
|---|---|---|---|
| GGCGACGTCCAATT | CAGAATAGCTTCAA | GGCCTGGGACTTAC | AGTGCTTGGAAGAC |
| CGAGGCCTCCATAT | TTCGACCGCGTAAG | GTAAGACCGTGGAT | GTAATGATAGAGGG |
| CCCTGTACGTCCAA | AGGTGAGCGTGATG | AGGAGACAGGTTGT | GTCACGCCTATGAC |
| CGTACCTAAACGTC | AAGCCATGCCCGTT | CAGAGTGCTCATCC | GAAGCCTGTTCGGG |
| GGTGAGCGCACTTG | TACCTCGTGCCCGA | AGACTCCGTACCCT | CTGCGCTCGTGGCG |
| CTTATGCGCCAGAG | ACAGCTAAATAGTC | AGATTGCCCCAATC | AGATGTCCTGCGCG |
| ATCGAACGCTATAA | GGATCGAATATCGG | GGAACGGACTGGTT | AAACCAACCTTACT |
| CGGTGATAGTCGAG | AGTTACTGGGACGA | CCCAGCTACTGACT | AGCGATGTATCCGA |
| TCCCCACTGGGTAC | ATCATCAGAGTAGA | TTCTCCCACGAGGA | AGAGCTCCCGTCTC |
| TGAATCACTAGACA | GGAAAAATCAGTGT | CCTCAGAGGTTAAC | AATTGCCTACCCCC |
| AAACGTCGCTCTAA | GGTCCCAGCCTCAT | ACTTCATGCGCCAA | AATGCAAGGTCTCA |
| TAGAGAGTCATCGA | AACTGTTAACGACC | TCGACTAGCAACGT | TAATCAGGCTACCG |
| AGTGGTCGTGCCAA | TGAAAAGTCGACGT | GTTAGAAGATAGAG | GGAGAAAGTTTCGC |
| ATACCGGGTGTGGG | CAAACTTGAATCCA | CTGACTGCCAGAGT | CAGGGTTGATGCAA |
| CCAGTAGCCCATGT | GCTTCGCCAGTAGG | TTACTAGGGCGACC | TATAAGCAAACAAT |
| GTCCCGGAAATTGA | GTGGCCTCGCCTAA | GTGCCATCCGCCTG | GGCAGGTTACAGTA |
| AAGTGGAGGCTGTA | AAGTGTCCGCGTGA | CATAACCTCGATAG | GGGAGGTGACCTCT |
| GTAGAGTAGATAGC | TCACCGCCAATAGT | TCTAAAAACGCTCG | CGGTGAACTTACCG |
| GTCAGCTGCGCCCT | ATTACGACGCATGG | ACCTTAAGCCGGCT | ATCGATCTCAGACG |
| ACGTTCTAACGCAG | GCCACACTAATGGT | ACCGCGTAGACTTA | CACCCTGCCCTAGT |
| CGGACCCCACTTTC | AATCTCGGTGCCGG | ATAGAGTTAGACGG | AACGTCTACCGGTA |
| GGCTTGAGATGAAG | AAATATGCAGGTCG | TTCGCCAGACTACG | CGTTAAGCCAAGTC |
| CGTTACTACGACCC | ATGAAATAGATGGG | ACCGTACTTCGGCG | CGATGCATCTCAGG |
| TGCGTGGCAGGACT | TGCCGAGACCATTC | TATACCCAACTCAC | GTAGCGGAGCTCCT |
| TCATGGCTCAGCAA | CAATTCAGAAGTAA | TATCACCATACCCC | TCCAACCGAAGTAT |
| GCCGTCAACCTCAT | GACGTTCTGAGGCG | TGGGCCTAGCAATG | GACGTTATGGCGGC |
| TCTCCGTAAGGCAG | AATAGCCTTAGGCC | CAATAGTGCGCGCT | GCGGTCTAGCGGCT |
| CCGTGCCGCAACTT | GCGCACATAGGTGT | AACTACTGGGATCC | CGGCAGTGTCGTCA |
| GTTACATGCACGGA | GCCCTGATTGGGGA | AATTAGGGACGGGT | TAATAACCGGAGTG |
| GACGAGTAGATGAT | AGTTCCGTGGCCAC | GGATTCAGAGCGTC | TGTCCGGGTCCAAC |
| TAGGTAAAGCCGAT | AAACCAGTTTCCGA | GTGGCTCGAAAATC | CTCAAATCGCCTGG |
| AATATGGCTACGGG | AGTCGCGTTACACA | CACTCACGACTGGT | TACGACTAACAATC |
| GTGGCGTCGGTCGA | CGTCGGGAGGTGTC | CTTATGGGCAGGCA | GTAGCTGGGAGGTG |
| GCATGACTCAGGCT | TGATAAACCCTGCA | CGACTTACGGCACT | CCCGTTGTCAAACC |
| CGTGACCAGACTTC | ACTGCAAGCTTAGG | CTACACACGATTGC | CCGGACGATCTTCG |
| AACTACTCAAACTG | CAAATAGCATATAA | ATCGTACACACAGT | GAGCTACTTGCGAG |
| TAGGGACGATGAGT | CTGGCCGTACCTGA | AGGTAAGGGCAGTT | GTATCGAATCCCAC |
| TGGATAATAGCAAA | GATATTGACGGGAC | TCGCGAGCCTGGGT | TCGTGGACGCGTGC |
| TGGATCTCAAGAAG | GATATCAAAAGTGC | AGCCGTCCGACCTT | TAAACCTACACATC |
| GGGTATCAGTAGGG | CCCTAATTCGCCCG | AGACCGGTATGGAT | CGATGATGAAGGGT |
| TCACCTCGCATGAA | GGATATGGAAAATA | AGTAAACAACTCTC | ATAATGCTAGGAAA |
| CATGGGACGGGTAT | AGCGCCTACCTACT | CAAACGCCTTCATC | TAGGATCCGTACGG |
| AGAGTTGAGCTCCC | TTGAAGCATGGGGA | CGACCCAGTCACTT | TGCCGCTGACCTGG |

FIG. 7 (Cont.)

| | | | |
|---|---|---|---|
| CACCAAATTCAGCT | CTAACAGTTACAAA | CACCAGATACTGTG | TACCCGTGGCGTGC |
| TGATCCCCACTCCC | ACTACACTAAAATG | CTTGACGCTCGGAG | CACAGTTACCCGCT |
| ATATCCATCAGAGG | GTGGACAGTCCTGA | TAAGCGGGATGTAA | TGTCTAGAGAGCAG |
| CAATCCAGTCCTCA | TTAGTCAGACCGCC | CAGCTAGGTTAAAG | AGATTCACAGTCGG |
| AGTGTACGCCGGTG | CAGAATTAGACATA | CAAAACGATTTGCC | GATGAACTCCAATG |
| TGGACCTGCCCTAA | CACTCTGGAGGGTA | CTTGGAGGGGGGTA | GCGGATAAGTGCTG |
| CAAAATTAGATCGC | AACTGAGGCTTGGG | AGGCCTAGTTAAGA | GCCTGGATGGCCGT |
| GGTATGGGGATGAG | AATAATGGAACATG | GCTGCCTGGTCAGA | TAACAAAGTATCAA |
| GATACGAGATATAC | TAGAGGTAGAGATG | TCCGATAAATAGGG | ATACTTAGCCCGGG |
| CAGCACAGTACTTG | ACCTCGACTGAAAT | CGTGCAATCACTGG | AGTATGAAGCGCTC |
| ATCCCCTGAATCCC | ATTAGGATCGACCC | ACATTGCCCAGTCG | CACTCAGGATACAT |
| CATTGAGGACTGCC | CACTTGCACGGGCT | ACCGTACCTGAGAT | CGGTCATAACTCAG |
| GCGGTGCTACCTGG | ATTGAGAGGTACCA | GCGCGTGTTAAGGC | TACAGTAACGGGTA |
| CATAGTCCTCAAAG | GATAGATAGACAGT | ACAGGTCTCTCAGC | TAGGGGTCGATAGC |
| CCTGCATGCGCGTG | GAAGCATGGGCATT | GAAGTAGAGTCCTG | TCCAGAGCGGTATC |
| CCGGTGCAACCATT | GCAAATCACTCCTG | GTGACCTCCGAAAT | GAACAAACATATTC |
| CGGAAGTTGATCAG | TGCGTCCAGGCTGC | ACGGTCCTGATGCA | GCCCTAGCGTGCCT |
| GAATCTACTAACCC | AGGTCGACGCCATT | TGGACGCTTGAAAA | CTTACCACATGAGA |
| GACTCCCACTATAC | TGGAGGCAAGTGTC | CGTGTCGCAGGTCA | AACCGCTTAGTCAG |
| GGTCTCAAATCGAC | AACCCCGATTAGTG | ACGGTCAGGCTGAT | AACGTCCGTGCATC |
| TTGGGACTAGGGCA | TTGCCATGCGACAC | TCCGACGTACTCAG | TTGAAACACCGTAA |
| TCCTGCGCTACCAC | ATATAAAGCACTAA | CTCGCAAAATATAC | TGAGATAATAGGAA |
| TCACGTCCGCCATA | GGCATAATAGAACT | AAGCTTTAACACCA | CTTAGACAAAGGTC |
| GCCCAGACGTTGGT | GTTAGCGGCTCCGC | GCGGCTAGCGTCTC | CCCGTCAGATTAGG |
| TCACGTTCCCAACC | CTACCCCTAAGGTG | TGGATCCCTCAGGA | CGAGGGTACGTAAT |
| CAGTGGAAGCGTCT | GTATGACAAGTAGA | CTCAGGCTCTACAC | CACGTCTGGCGGAT |
| AACACTGTGGGGTG | TACCTGGCGCTCCC | TCCTGGGACCAAAT | CGTGGTGAGTGAAG |
| ACTATGTGGGGACC | TCGCCCAGCGGATT | AGGTAGCCCTCTGC | ATTGAGAATGGAAC |
| TATGTCAACCGGCG | AGCGCAGATTGTGG | GGACGTTTACAGAC | TTACGAAGTCACAG |
| GCCTGTACAAAACT | CATGCATCTGACAA | ACTTGCGCTGGGAC | TCTGACGTACCGCC |
| CTTCCAGATGCAAC | TGCTAACCTACCCG | ACGATTGAGCCAAT | AGGGACTTGATCCC |
| CCCAAGATTAAACT | CTACTGTAGAGGGA | AGATTGCACCGCGT | AGTAGTCCGGTAGC |
| CTTAGTAACAAGCG | AGTGAGAACAGGTT | GACCGCTCGTTGGC | GCTTGCCCGAAATA |
| CACTTCAACCCTCC | TAAGAGAACTCTCA | TCACAAGTATACGC | TAGATTCAGCACCG |
| AATTACCGTGGCAA | TGCTCGAAGGATAG | CCGGCTAAGTCGGT | CTGTCATGCGGCGG |
| AGCTACATAAATGG | AAGAAAAGAACTTT | GGATAATGAGGCTC | AGACTAGTGATAAA |
| TCAGGCGATGACTA | TTCGCCCTAGCCCA | ACTGAGCCCAGTGT | CAGTCTAAATCGCG |
| AGTATGTCCCGCAG | CGGATCATCACAGT | CAGATTAACAAGGT | TGAGGTTGGACGAG |
| AGAACTCTGGGAGT | AAGCCGATTGGATA | ATGGACGACCGTTC | TCATTCACGGGGAC |
| ATCCTGACCGTGGG | AGATTCAACGTAAC | GGGGACTCCTCTCA | CAGGTAAGCCATTG |
| CTGACATGCATGAG | ACAAGAGCTTAGGT | CCAAAAGTGATTGA | CGGTGCTAGTGAGC |
| CAGAAAAGTTCCCT | TCCGGCATTCCGGA | GGCGAGTTCGCCTC | ATGCACACGATATA |
| CAGTATCGATCGGA | GTCCTCAGCCTCCC | ATCGTACAATGCAA | GATTGCGTACCGAG |

FIG. 7 (Cont.)

| | | | |
|---|---|---|---|
| CTCCGACAACTGCT | ATCGTCCGACATCC | AGAAGTATTAGCTC | TCATCTGAACCGGT |
| CCACGAGATTGAGT | ACGCCTATATGCGA | CGCCGATTATTAAA | CGCTACTGCTGTAA |
| TCGTCGCCGACCTG | ATCGCACGCTGCTC | TGCAGTATCGCCGT | TAAGTGACAGTTGG |
| TCGGGCTCGTGGGC | TCATTGGGAATGGC | CTAATATCAATGCA | CAGAGGTGAATTTA |
| AGGACGGGTAATTG | CCTTACGCATCGTC | GGGGATGATGGTCT | GCCCCTCATTCGTA |
| AGTATGAAGTAGGA | ACGGGTTGAGATGT | TGTGCGCGAATCTG | CCCTGCTGATACTG |
| TCTTAAGAGACACC | AGAATGAGGGCTTT | CCGCTTGTTGCAAC | AGTTGTCGGTGGAA |
| GCGCGACTTGAGCT | GCTCAATCTTGGGC | CATTGGGGGTATCA | GGAGAGTTGTGTGG |
| ATTGCTCCGGAGCA | GTATGCCTAGCATG | CATAAATCAAGATT | TGCCAGCCCTGTCT |
| GTCGTGCGGAGGGT | TCAAGTCTTGCCAA | GGCCGTAGTCTCTG | GATCATTAGACTGA |
| ATGGCTACCGTCGG | AATATACCGTCAGT | TATATGGACTAAAC | GTTGATACAACGTC |
| AGGATCGGTGGATG | TCAACGTCTCTCCC | TAAACTCCTCCAGT | AGACGCGGTCTTTA |
| CAAACTCGGTCGTG | ATCGTTGATCCGGG | CTCGGGTAATGTCC | AGCTTTAGAATACC |
| GGCGCTAGCATCCT | GTGTATGACAGGCT | GTATGTAGGACCGT | TTCTGCCCATAGCA |
| AGAGAAGAAATATT | TTTGCAACGTGCAC | CTCCATACGTTAAA | ACCTGCCTCCGATT |
| CGTTGGGACGTAGA | ACCTCTGGCACTTA | ATTGCAGCCCACTT | CTCGTCGCGAAGTT |
| GGAACGTCCCCTTA | GCTAAGGATGAATT | CACATCTCCGACTT | AGAAGCTTACTTAA |
| CGGTGCTGGAGGTA | GCGTCTCTCAATAG | ACTCAGCGGTATGT | TTGCTCGCCAAAGT |
| GGGTAACAGGACTT | GCCAATATGTCACT | ATAGATCGTGAGTA | GTTCTTACCCGCAA |
| ACCTCTCTGCACGG | TGTAGGGGACTCCT | TTCAGCCATCGCTG | TCTTCATACCAGCC |
| CACGGTAACTCGTG | ACTCAATCTAGACT | GTCTATGCCGTAGC | GAGCGAATTCTAGT |
| GTCTAGCATGGAGG | AGGTAATCTCACTC | GCCGTAGTTGTGCC | AAGGCGAATTTGTC |
| ATCGTCCGAGCGGT | GTGCGTTAGGATCG | ACTGCGCGTCTAGT | GAAGTCCGTTAATA |
| GTGCGAATACTGCC | ATCAGAGCCGTTAT | TCTGAGTTAAAGGG | ATTTGACCATGAAA |
| CATCCTAGGCTCGA | ATCGCTCCGCCGTT | CCACGCTTGGATAT | TATACAGTAGTGCA |
| CTGAACGAATCTCG | TACGGGGATACGTT | TGTCAATCAGCATG | AATCATCACTGCTC |
| TATGTAAGAACCAA | GATCAACTATTCGC | ACTATTGGTAAACG | GAGACGGGATTTTG |
| CTGAAAAGATCTAC | TCAAGTGTATGAAA | TCGCAATGATTGAA | GATAGCTTCGGATA |
| AGATTACCCCGTAA | CTCCCGAGTCCTGT | TCTTCCGGACTAAG | TACGGACGTTGTAA |
| GATCGCGATATAGC | ATGCTGGTGCCAGT | TCCTGGTTCCACCA | TCCAGTCCAGGGTT |
| GCCACCGAGATTGT | ATAGTGCAAGATTG | CTGATTAGGTAGAA | AATAAGACTGGTTG |
| GGTATCAGATGACA | ATAGGCGTCTAGGT | GTGTCATGGCTAAG | AGTGACTCGCATTC |
| CGGTGGCATCCTGA | TAAAATACCTCTGG | ACGACCTCTAAGTT | CTCCCGCTTCGCCT |
| TACTAACGAGTGAA | GCTCCCATCATCTG | CCTAGTAGATGTCA | TTGGCTGAGCAAAT |
| TCCGCTCCCAGTGG | GCAACTGAATATGT | AAGTAGTTGAAATC | TCCCCACCTTGATA |
| AGATAGAGTTGAGA | GCGCTTTGCGAATA | ACTTCTGACAATGG | AAGGAGTGTTCTCG |
| TAATGCACGGTGCG | CTTAGCGGAGTACT | CCGAATTAATAGGT | ACGGTGGCGTTTAA |
| TCGTTCAAACAACC | TAGCCGGTACTAGT | TACCGAATCAATTG | CTTCACATCGGATG |
| TAGGAACTAGGATC | CGTTAAGTTCCGCG | GTCGACGTGGCGTT | CTTTTCGCGGGCAC |
| CTCGTTCGACAGAA | CTATCTGGCTCAGA | TGTAATGCGAGTAG | TTCGGGGTATCCGG |
| CGGGACTGGATGAT | AGGATTGGAATTGG | ATTAGTTCGCCAGG | CTGCCTGGGTTCAA |
| ACTGTGCCATGCCG | GATCTACGTAATGC | GTCACCTGTCGATA | TTGCCTAAAGCTCA |
| GTTTACGCGAAAAG | TCGTCCGAGGTGTA | TTTGAAAGCCATAG | ACCTAGCATTAGAT |

FIG. 7 (Cont.)

| | | | |
|---|---|---|---|
| GCTTCCCACTTGCA | CGTTGTCTAGAACG | AACCGTGTCCTGTG | CCTTGGAAATTGAC |
| GAACAAGTCTTTCG | GCTGATCGCGTTAA | GGTGCTTCTGAGCG | GACTCCTGTGCGTC |
| ATGCATCAATATGG | TCGGGATTGCGGTA | ACTGTCTGTCCCAC | TAATCAAACCCATT |
| AGCATTATGTACGC | TGGGCGAACGGTTT | ACTAGTACTCATGA | AAATGGTCCTATAA |
| AATAGATCACGTTC | TAACCTTCAGTGAA | ACTCTGGTCTCGAG | ATTCTGGGCCTCAC |
| CGGATAATCTTCCG | GACATACCTTGAAT | CTACAGCATGCTGT | AATTTCCGAAAACT |
| AACATTACGGGTGT | AAGAAATTTCACGT | GTGTCTCAGGGATG | ACGCTATAGGAGTT |
| TCACATATGCATCA | ACCCTAGGTACTAT | CGGGTGTGGTGCTC | TAGGAGGAATTTAC |
| AGTCTGGCCTTGGC | TACGCATAGGTGTA | CAGTGGTCACACTT | CTGCAAGCATATCT |
| ATTAAAGTAGCGGT | ATCGGGGTTCTAAC | GCCTCCGCGTCTTG | TGGGTCACTGCCTC |
| ATCATTCCCCATAC | GAGTGCTGCGGGTT | TGTACGTCCCATGC | GGACGACTTCGTTG |
| TCTCGCCCATCTAG | CCTCCCTCCGAATT | GGAATACCATGTCT | GACACTACTCTGGT |
| ATCACGTGATCAGT | TGCCCTGCGTTGAA | GCCTGATATCATCC | CCATGTCGACTTAC |
| GATAAACACATTAT | AGCGTGCCATCTAT | GGATTCGTGCCGGT | CCAGGCCTTTGACT |
| ATCAAACTGCATTA | TAGCTCAGGTGAGT | TCTAGGCGGTGATA | ATGCGCTCGCGTGT |
| GAGGTATCCTCCAT | GACCCTTTCGCGTA | AATCTCAACCGTAT | GATAACTAGTAGTC |
| AGAATTTGCGAGCT | TTTAAGGTCGAGAC | ATAACACTTCCGTG | GGATATCTGGGTGC |
| GCTAAGTTCCGTCC | CTCGGGCTTACGTC | TCTGTACCGCGTCC | GCTCCGCTATAGAT |
| AGCGGTTCAATCTG | AGTGGGATGTGTAC | ATTGCATATACGAC | CCTCTCCATAACGT |
| GATTGGGATGCTAC | GCTATGTCAGCGGT | GTGGGGAAGTATTA | ACCCGTCAAGTCTT |
| GAGTACTATGTCCA | ACCGGTAATTCCCT | TATGAGGCCTGTGG | ACTGGTCCGTGAGT |
| GTTACCAACCTTCA | CGTCCACTTGGGAT | GGTAGCTTCCTGGG | GTGCATGGGTAACT |
| TCCACCTTTCAGAG | CATCAGTACCTCTA | TAATCGATATAGCC | TCTTGAACTAACGG |
| TGAAACTATCTAAA | TTAGACGATATGGA | AAGCTCGCCTCTTC | CTGCGCTCTTAAAC |
| GGAATATACTATAC | CTGCGCTATATGGC | TATAGTATAACGCA | TCTCCCAAGATGTC |
| TATGGGTAATGAGA | GTGGTTGGAAACAT | TCGTCAGCGGATGT | ATTACTAACCACAT |
| CTTGCTGGACAGGT | TACCTGCGCTACTA | CACTCTTGCCGATC | TTTACAAGCGATGA |
| TTCATCGTCAGGAC | TTATACCAGCCCTC | TTTCAGCTCCGACA | TAGTGTTGCCCGCA |
| GTGTGAATGTCCAA | CTGCTCCTGGAATG | CATACCAACTTAAT | TGAATGGAGCGTCT |
| GTAAACCTAGTTGA | TCACTGTGCGTCAA | TCGTAATGGCCTCC | ATGATGTTACCCCA |
| GTGTCGTACGAGTG | TGTGAACAAAACTT | GCTGCGTAGAATAT | TAGAATTTAAGGAA |
| GCTTAAGTCCGCTC | GGTGTGCCGTCGTC | TATTGCCAACTAGG | TACGCCATAGTCTG |
| GTCTTGGCGTCGGC | CCTTCCAATATAAC | GTCCCTCGCGATCT | GCGTTACCCATATA |
| AAATGCGCTCTTAG | TGTTGATGCAGCAC | GCATTGTCCACTGC | TAGTCCGCCATCGT |
| CGGTCGACTGGTTA | TCTTAGAATCAGAC | CTTGCACGGTCCTG | GTACACACTTTCGG |
| TAGGGCTAAATTGG | GACACTTAATCCGT | GGCTGTGTCCCCCT | TGGGCTTTGGAGGG |
| TTGACGGGCTGGGT | TATGTAGGTAGCGC | GAGTGATTCGTCGG | TATGGCGTTCAAAG |
| CTAAAGCACTTTCC | TACTCCGCCAATTG | TTCCCGTCTACAGG | ACGTCGCTGACTCT |
| ACAAGTTCAAAATT | GCGGGTTCTGTCGG | CATATTCAGCGCTA | CTACGTCCTATGAA |
| TCATAGATTGCCCC | ATTACACCATGCGT | GTGTTCACCGCTGG | GTTTCTAGGCAAAC |
| CGTCCGGCATGTCT | TTGGCAGACGTTCC | TAGACGGTGTACGT | TTACATTGCCGAAC |
| TTCTAAAAGCATCG | ACTGCGTCCTCCTC | CTTGGCAAGTTGAA | GATCTTACACCACT |
| CGTGCAGATTGGTC | ATCCTCGAATCTAC | GCTGAGATAGTTGG | GGATAACTCCTACT |

FIG. 7 (Cont.)

| | | | |
|---|---|---|---|
| AATTCGTTACCAAA | ACAATTGTGGCGTC | TGCCATTCGACAGT | AAATATTGGACGTC |
| TAAACGGTGGCATT | GGTCTAGTACCATC | AATGTGTGAACTGG | CACGAGATTAGTTA |
| AACAGTGAATAATT | AGAATTTAGTCAAC | CTCTGACCCCGGTT | GTCTGGCGATACTC |
| CTATACGTTACGGC | AAGGTAGATGTCCT | ATATACGAATGATG | AAGCCAGCTGTTTC |
| TCACGGTCTGCAGT | TACTCGCTCTAGAG | CTCTCCTTGCAAAG | CTCCAAACTTGTGC |
| ATCGCCTCACATTA | TATTCACGGCTCCC | GGGTAGTTCGGATA | CAACGCCTCTTCGT |
| TAAAAATGATGGGT | TCGGGTCGAATGGT | TAGTTTCGCGGGAG | TCGGATCTAGGCAT |
| GATGTAACTACGAT | GAGTGAGTGTACCT | CGACTTTACTGAGC | GATGGAGTAGTGGT |
| TAGAGATTGTAAAG | AGTGTAGCTAATCG | TCTGACGAAGCTTA | TCCGTATGGCTCGA |
| TGCGACTGTATCAC | GTGACCTTAATAAG | CATCGGCCTTTGGG | TACTTGCTAAAAGA |
| GACCCACTTATAAT | TATTGCACGGAAAT | AACTCCCCCTCTCT | GACCGGGTTTGTGC |
| TCGAAGCATAGATT | GGTTTGCCAATCCG | GTCAAAATTATCGG | AGCACTTTGCGTAG |
| GTAAAGGTTCCGGT | CAGTCGTTCCGCCT | TTGGGGATTAGGAA | AACTTAATCAGTAG |
| GGCGTCATTCGCCT | GACTGGACTGTGTC | TACTGGTCAGTCCA | CTGTTAACTCCACG |
| TCAATAGCCTAGTC | ACCATTTTGACCAA | CGTTGTCATAAGAA | TTAAGGATATCACA |
| CATTTATCCAACGC | CAGTGCAAGTTCTA | TTTCGGGGTAACCA | ATTGTGCGCCCCGT |
| CCCATTCGGATCGT | GCCAAATTTGATAA | ATGTACCATGTAAC | CAGGCATGTTTGCG |
| GCATCTTAACGTAC | TGACGGGTTGGTGG | TGAAGACACATTTC | CAATTCACTAAGAT |
| GGCTTTCCCCCGTA | AACTCCATTATCGC | GAGTGAAATAATTG | ATTTGCGAACGACT |
| CCGTGGTCTATGGG | GGTTGGTAAGTGCC | GCGTGTATGATAAA | AACTTCATGGATAA |
| AATTTACTCGCGGA | ACCAATGAGTCGTT | GAACTAAATACTTC | TTAAGGCACGATCT |
| TACCTCGGTGGCCT | AGTCTTTAGCGACC | CCGCTTCTCATGAG | GTAGTTACATGAGA |
| TCCCCCACACTTTA | CTTGTAGAATCGAA | TTACCCTTACGAGA | GCTTCCTCTACGAA |
| CCCTTGCGTGTACC | TAACACGTCATAGT | CCTTACTTGACAAC | TAAGACGGCCTTAT |
| ATTAACGTCTCACA | CGTAGAGTGAGTTA | TACTTCGACGCATG | TGAGAGGGTTCTGC |
| GCCTTTCGTACGAC | ACGGTGTCCGGTCT | AACAATTTCTCACG | CTTAACGAATAGTA |
| GCATATTGTACCGA | GTCGTGGCTAGATA | GCTTGACCTCGGGT | CATGGTTGTCGAAC |
| TGATTTAGCACGGA | TCATCTACTGCGAG | ACGTGTTGGACGGT | TATCGGAGAAAGTT |
| AGGTTAGTACACTA | GTGAGATTCTGACA | AAAGCCAACTTCTT | TACTTACAGCTGAG |
| TGCGCTCCCTGCTA | ACTGGCGCTTCTCA | TTCAGTCAGTACGC | CGCTTTACCCTACG |
| TACAAGTTCAAAGT | TTCCCCTATAGGAG | CAGCTCATCTACAT | CACTGAGGTATATC |
| ATGGCTGGCCCTTG | CCTATCCACACTTA | ATTTGACACCAGTA | AAATGCTATTGAAC |
| CGCCTAAGATGTTA | TATTCGAGCAGGCT | ACTTTCGGGGTACA | ATAGCCGTTTGACG |
| GTGCCCACTCCCTT | CCTCAACTCCCTGT | GACTTTCTCCGACC | CTTTCGGAATACGG |
| GAAGTGTTAGCGTA | AATCCGTGAATGTG | AGAATTCATAGGCT | AGGCTTATGGAAAT |
| TAGCGTCCTTGAGC | GAGGCTGTTCGTGC | AAGTTTCGGAACAT | TTGAGGCCGTAAAT |
| ACGCTCTCGGTTGA | TGCGATATTAGCCC | GTTAAACCATCGTG | GGTGAAGGATTCCT |
| GCGTTCTTGGGAGG | AGCTAACATTTACG | CCTACGACTTATAA | GAGATCTGGTTCAG |
| ATCTGTCAAAGAGT | TATAATTACGAGCC | AGTGTTTGCGACGC | TTGGTTACGAACAA |
| CTATCCAGAAATGT | GCTGGATTGTCAAC | GAGCTATGTATCCG | TGTAAGGAGATGCT |
| CAATGACCAGTTTG | CTAGGCCCTTCGTG | GTCAACATTAATAC | CGTCGTTAACCCAT |
| AGCATGTCGGAATT | GCCGTCCATAGTGT | GAGCTTTGGAAGTC | TTGGTAAAACTGGA |
| AAGTGGATAGCTTC | CTCACAGGTTCTGG | GTGTCGATCAGCAT | CTGTCAACTTGGGA |

FIG. 7 (Cont.)

| | | | |
|---|---|---|---|
| TTCAGCTTGAGAGG | CTGCGTTTAGCCGG | GCTATTGGGCATAG | TGAATCCTCCATCC |
| GAATTCTGAGATGG | TAGCCTGATCGCGT | CATTTCCGGTGAAA | CGGTGTGCCGTGTC |
| AGTAGGTCAACTAT | ATGGTATAAGGGGT | GGTCTGTGTAGGGC | GGAACGGGTATTGT |
| CGCTTGCTGAGCAT | CTTTTGAACGACAA | ATTGACAGTAGCGT | TTCGCCCTCTACGG |
| ACCTTATTGCAGAA | TAGTCTAAACAAGT | AACAGCTGTTTACC | ACTAGGTGGCTTCA |
| GTGGGCAATAGTAT | AGTCTATTCGGCCG | CTCTGCGAGGATTC | TCTCAGGGCTTCGG |
| TACTACTACATCCC | GAACTAGAGTATGT | AAATTGAGAGTCAT | CTGGTGCCGGTGTG |
| TGGTTCGAGCACAT | GTATAGATCGACTA | AGGATATCTACGTC | ACAAATAGTGATTC |
| GGTCTTCAATGACG | ACACTTCGTTCGCA | AACGTGATATTAAG | ATCATCGTCCATGA |
| ATTCAGACATCGCT | TTGGCCAACCCTCT | AATTACAGATCCTC | AAACAGATTTTCCC |
| GGGGCTCAACCTTT | CATCAGTGGCCTAT | TGCTGTTAGGCAAG | TCCAGGGGTTCTAC |
| AACGACTTTAAACT | TAGCTGTCAGCGCT | AAAAGTCCTTTCAA | CTAAAAGTCAGTTG |
| ATGATAGTCTAAGC | TCAAAAAGTTCTAA | TAGTACGCTAGGCT | TTCTCGAGCCAGGT |
| GTACCACCGCTTTA | ATGATCTCCCTCCG | TAGGACCTGTCTCA | TGGTGTGGTGGGGC |
| GGAACTTTCGGTAA | AGCGACGTTTGCAT | ATGGTTCGGGTAGG | GGCTATTAATGGGC |
| GGCAAGTGTATCTG | CCGTTTAAGCGCGT | CATAAAGGGGTTTA | AGTGCTAGACTTCA |
| GTTCGCATGATACG | GGTGTCACACGGTT | GGCGTGACTATTGC | CCAGGTTGATCATC |
| AGGACCCTCTATTG | ATGTGGTCGTAGAC | GACGTTCACTCGAT | TTCATCCGGAAATA |
| AGTTATCCGTACCG | CTCCGTATTGAGCG | GACATTTGAGATAA | CCTCTATGCTGCGC |
| GCACTCGCGGTATT | TAACTCTCTGCCAA | GACGACCCTTTGTC | TAACATCTGCGGTG |
| CTGCCCGATGTTAG | ACCTGTTAGCACTA | TGGGCTGTTACAAG | TTACTGTAGGCGCC |
| ATACTGATCCGCCT | CAGTCCCTTTGCAG | ATTCAATGATCCGG | ATATCGAGTTCACC |
| AGATTTGTAGGAAC | TGACTATTGCGGAC | AAGAAGCTTATTGG | TCTCTTAAACGCAC |
| GAGTCGCTGTATGC | CCGTTCGTTAACAG | CGGAACTGTTCGGT | GGCTTTTGGAGAGC |
| CGGTTATCGAGATC | TACTAAGTTACCGA | TCGGTCAACATTCC | GTAAGAATGCATCT |
| TCGAGCGGCTGTAT | CAGGATTTGCGCGT | TTGACCCTCACTGA | TGATGTACAAAATC |
| ACGCTGTTAAACAT | GCATTTGCCATGGA | TCCCGATCAGTTAG | CGGGAAGTATTGAT |
| CCGTTTACGATGCG | TGAGCATGTACATC | CTTCTCAAGACTCG | TTCTCGGGGGGCTG |
| CTTGTGACCTCCGC | TTGCGTATGGGCCA | ATTATCCCAACTCC | TCAGGATTAGATCA |
| AAAGTATTGACATC | TACTGAAGTCTGAC | TAGCTACACTGCCT | TCAGTGCTGCGCTG |
| GTGATGAGGTGCGT | CGTCCTGCTCACCT | CTGGGGTTGAATAG | CGGGACTAGTTATA |
| TATAGCGTACGGCT | TGTCTGGTGACAGG | CTCTGTCCGATACA | ATGTCCCCCTTAAA |
| CCTCTAATATCGCC | TATGGATTCAAAAC | CATGGTGGTTCGCG | TGCCGATGTGACGT |
| GTTTGGTCCGACCA | CTGCACAATCGTTA | GCAACAGTAATTTG | TGCTAAATGGCGCT |
| CTTAGCAATCAGGT | CGCAACCTTATCGT | GTGCAGCTTGTCGC | ATCCCTAAAACTTG |
| TATCAGGCTCATAC | TCGGCTATAATCGC | TCCTACTTAGCAAA | CCAGATACGTTATC |
| CTGAACCTAGGCTT | CTGGAAAGACGTTT | ATAAAAAGTGTCGT | CGGCTATAAAATGT |
| ACGTTGAGTGCTGA | ATGTATCCATCCCC | GATACTCGCTGATC | CTGCGAATCTAATC |
| CAGTTCAACTGGTC | CATCTGGTATAACC | CACTCTTAGACGGT | ATACACATTCTACA |
| GTCTATACTCCCGC | CCATATCATCGACT | TGCCCTGGAGGTCT | TCCTAGGCTTAAAG |
| CCGATTGGCCTGTG | AGTCTCAGCTCGCT | AGTGAATATGATAC | GTATACAAGTGTAG |
| ATTCGGTACCCCCT | TCTACTCGAGGAGT | CCTTGGGCCTCGCT | AGAGTCATACTAGT |
| TCATATCATGAGGC | CTCCATGAACAATT | TACGATGCGCGATT | TCCCTCCATTGGGG |

FIG. 7 (Cont.)

| | | | |
|---|---|---|---|
| CATGTGTTCGCCCG | CCAATCGGCTCTGT | CCCATCGTCGCTTG | TTGACATTACCGAG |
| CGATTATCCCGGCT | GCTGTCCTATCAGC | AGTTGGGTCGGACT | TAAGGGTATGTCGA |
| GCCATATATAACTG | CGATGTCCTACTGC | CATTGCTCAACTGA | ATGTGCTTGCACGC |
| AATTGATAGTAGGA | CGAGATGGGTTACT | CAAGAGATGTATTC | GCTCTAGAACTTAG |
| AGTTCAGTGGATGG | TGTTAGCCGCATAG | GAGAATAGCATTTG | TACTACCCTGGTGG |
| CAATGGGTGAGTGT | AGAATCCTGTGATG | CGCCACTTGTAGGT | TAAATTCACGAAGT |
| GATCTAATGCGTAC | TTATCGTAGACCGA | CTACCTATAACGAT | CCCTGCTGGCTTGG |
| TAGCAGGCGTCTGT | GGAGCACGGATTTT | AATTTGGTCGGCAG | GGGTTCGCCTTGCG |
| TAGACTTCTAAGGG | CGATAGAGTGTAAT | CGCAGGTCTGGGTT | TGTCTGGCTGGAGC |
| TTCGGCTCCTGAAG | CAGCCCTTGAAGTT | AAGTAAGTACTTGG | ACATTCTCTGGCGC |
| GGAGCGTGACTATT | ATGGCGACATCTTC | CGTAAAATATCCTC | GAAGTTACTCACAT |
| AGGTATCGGATCTC | CTACTCGCCGTTAC | TTAGTAGCCTCACG | GCGATTTGATCCCG |
| AAACCTACTAATTA | AGAAAATCTTTCGG | CACTGGGGTGTGCT | CCATAGGTCCATTC |
| GCAAGCTGATTTGC | GACAATGGGGTGTT | TTGTGTCGGGGAAC | ATCGCAGCTTCATA |
| ATAACGTGCGTTCC | GCCTTAGCCTGTAG | TACGTATTCGGGCG | GTAGCTCTCCTGAA |
| TCTAATCACCGATA | AACGGAATTTGGTA | CGGAGCTTTACTAG | CATGATGGCCCTGT |
| GTTAAGACCTGATG | TGAACTAGAACTGT | ACGGAGCTTATGAT | AGTCGTTTCACCAA |
| AGTGTCCAATAGTG | ACATGTGGAATCCT | CTGTCTGTGCGAAA | TCCAATCGGTAGGT |
| ATAAGTGAAACTAT | TACAGGCCATCATT | GTGTGGTATAGCCA | AGTCGGTGTCATCC |
| ATAGCCCCTGTCGT | TTCTCTACACGAAA | GATCGTCTCAGGTC | AGGCTTTCAGCATA |
| TGCTGAGCGTGTAC | ACAAAGATTTGAAT | GACGGGCTCCCTTT | TTTATAAGACGCAG |
| TACGCTCGACCTGT | ACCGTTAATAAATA | AACTAATGTTGCAG | CTGGCCTCTATGCA |
| GATCAGTGTGTCAA | ACTGATACTTAGCC | TTACCTGGCCCTCA | GCGTTTGCGGGTCG |
| TCATAATCCAGTGG | TACCCTAGATTCGC | GTGTCAGTGCGGTG | GGATTTTCGGAGGC |
| AGATAAACCATTTC | CCACGATCCTGTTG | TGCGGTCAACTATA | TGCTGGTATGGACA |
| TCGTCTACCCCTGG | TGCCGTTCGCTCGC | TGACGCTTCACTGA | GTTTGGACAATAAC |
| GGACGATGGTGGTT | ATTGATATCCGGGG | TAGACGTAGATTAA | GCGGCATGCATTGT |
| GCCCTGTGACCTGT | GAGTCGCGTCGTCT | TGGAGCACATGTTA | TTCAGTGCCATGGA |
| AAGCGTAAATTGGT | TAGACAGTTCGCTG | TGTACGCCCACATT | GCAGAGTAATTTCA |
| AATAGGTGGTAGAT | AATCTTAGAGGGTA | GCCCCTGATCGTTG | TCTACAAACGTCAT |
| GTTTACGATGGACA | CCTTGAAGAACTGT | TTGGGTTACAGCAG | CTGCCGACGAATTT |
| AACATATAATGGTG | GTCGTGTGTGAGCG | GTGTCGCTACAGCT | CTTGCACGGCTAAT |
| AGTAATGGCTAGTC | CCCTGGACGTATGT | TGCCAATTCAGTAA | ACGTGTCCCATGCT |
| GTTGAGCAAGTTCC | CTACCCGCTCGATT | GCGACTTCGTATAC | TCATCCAACAGGTT |
| ACAACTACTGCTCT | CGTCTGCACTATGG | CAAGCCACGTGTTT | ACTGTGACCCTCTG |
| GTGATAGAGTTGGA | AGTGTATTACAGGG | CAGTCTCGATTACC | ACGGCTTTCGCCTA |
| CTCTATCAGGGTCA | ATGTTAGGAAGAAT | GAATAGACATCTAT | TGATTATCGACAGG |
| CACATCATGTGCTG | TAACCTTCAACCCT | AGGCGTATTAGTCG | CCCAATATTTACAG |
| AGAGTCGTTGCTCG | GTTACGCCTTAGGG | TTGACGGTCGTCCA | GTCATGTACATAAG |
| CCCGAGTCTGTCTC | TACATTTGGCGCCC | CATAATGTAACTAA | CCACCGACTCTTTG |
| CATAGAGATGTTGC | ACTCGACTGCTCTA | AAAGTCGTTCGTAA | CACCTCGTCTTGGC |
| GAGAGTCATACCTT | ATATGCTTAAACCA | GAAGTTGTCTGCAC | AGTAGATTGCAGTC |
| CGGTCTTCGGGCCT | TTAGCTGTGAGCAA | TTAAACATACCCTA | GTACGCTCCGTCTA |

FIG. 7 (Cont.)

| | | | |
|---|---|---|---|
| CCGTTCCTGGCGCT | TGGACATATTAACA | TTATCAGCGAGAGT | CGCGCTGTTCGCTA |
| ACGTTTCGACCGAT | CTACCGCCATTCTC | AACAAATTCGCTGT | CCCCAGGATTGTCT |
| GTGCTTGATCACAA | ATCTTGACTCGCCG | CGCCAACTCATTTC | TCTGACGGTACATG |
| TCACCAAAGTACTT | TAGGCTGATTCAGC | GCATATCTGCACCT | GCCTGAACTTTCGC |
| CGTTAATATAGCGG | TTTGGTGCCAAACA | AGTCGGTCATGCGT | CGCGTCTATAGGTG |
| TATGCAGCTAAATC | CACGATCTTTCCAC | CGGTGACGTTAAAT | AAGAATGGCTTGCT |
| GTGCTTGCTCGACG | ACTATGGTTCGCGG | GATAATTCGCGCAT | GTGAGCAGGCCTTT |
| CCCCGTTGTTGACG | GTCTCCTGATGGAA | ACTAATCTAACCCT | CTACTTAGTGCGCC |
| CCTGCGAAAATCTT | CAATTGTGCAGGTA | GTCCGTTCGTAGCA | ACGTGTGACTTAAA |
| TGTCACACGGGTAT | TACGGCGTGATTGC | GGAATTCCGATGTG | TAACTACATTCCGC |
| AAATCTGCTGTGCC | GAGATTCGTCTGGG | TTGAACCACCTCGT | CTGAGCCCTGTGAT |
| AGGTCTCTTCGAAG | CGGTTAATGCCTAA | TATAACCGTAGTGA | CATCGGATGCTCAT |
| CGACCGTTCCTAGT | GAACGCTATCGTTC | CTTGTACTAGGAGC | CGTGTCCCTGGGTC |
| TCCGCGTCTCCTCA | CTCCTTCTGCGAGG | TCTGCGCGTTAGCG | AATATGGGTAGATC |
| AGTAGTAGTTACGG | CTGTGCATGAATCC | CTCGAGTGCATATG | GCGGTGATGCTCGT |
| GTGATGCAGGCTAT | CAATCTTCTAGGAG | CTATTGCATCGAAA | GGCCTGCTATATCC |
| TCAGCTACAAGTTC | GCTGGCACTACATT | GGTGGTTAGTAAGA | TTCGCACAGAGTTA |
| TCCCTCACCTACTC | TTAGCGCTCGCCTC | ACTACAGTGTTACA | TTGACACCTGAGTG |
| ACTCTTAGTGGCAG | TGGGGGTGTCCTAG | GCATCACAATTACT | CACGCTAGTATGTA |
| GAAGTGATCTTACC | GGCCTTACGGTGTC | GGGTGTGACAGTTG | AAGTCTCGTCGGTA |
| ACGGTTATATAGCA | GTGTGGAGTCCGGT | TTAGCCGTGCCGTA | GGGTATCCCCCTCT |
| GGGTGATTAACTAA | TGTAATGCGTCGCA | ACATGGAACATCTT | TAGTTCAAAAGATG |
| TTAAGATGTAGGAG | CTGAGTGACATGAT | CTGGGACTATGCTC | CAACAAATTTTGGA |
| ACTAAGCTCTCATC | CCTTAATCCGATAA | TGTCACGGTACCGT | GTGGTGAGATATGC |
| CTGGCTTGAATAAA | ATCTTAAACCCGTG | ATACTCTCGGTCCC | GAAACTGTCATGTC |
| AAACCGCTTGTGAT | TCACTCGGTGAGTC | TATCAACTAAGACT | GTCCGGGATCGTAT |
| GTAACGTCTAGGTG | TCACAACAGCTTTC | ATTGGGGGATGAGT | GGTGAAGTGATGTG |
| ACTGTCGAGCCTCT | ATCCTCTGAAAATG | CTCAATGCTAGTGG | CACTTCGAGACCTT |
| ATTTGGGTGAAGCA | CGCGGTCCTTCGAT | TTGGCTCCGAGTAC | TTATGGGCGTGCCA |
| TCGTCTCGCAAATA | CATTACCTTGGACG | ATGGAATAGAGTAT | CTGAACGTGCCTTC |
| AGCTATTATACCGC | CCCGTGCTTACTGA | CACTGAATGGTCTG | CATAGTGGCGAATT |
| CTGGGTAGATAGCT | CGCCACATTAGTCT | TGGAACGCTCATAT | CCAATGCTGGTAGT |
| CCTCCACTTATGCG | CCTGCAGGCTTCTC | ATTCACGAGAGTCT | CGTTTAAGAGGCAT |
| ACTCCTAGGGTATG | CATGTGCTACATAA | ATGGGATGCTGCGT | GCATTCTCGGCGTG |
| CCTTTACTGACGGC | AACTAACTGTATCG | ACATGAAGCTTATC | AAGAGCTTACTCCT |
| ACTGTCGCATAATC | CCCCACTTAATCTG | CGACTGTTCCATAA | CCCCTTTCGCTCCA |
| ATCTCAGTCTCCAG | CATGATTCGACTAC | CTGGAGATAACTCT | GCCACTCTGTGTGG |
| CGCTGGCCTGCTCT | CATTGAGAGTTCAG | TGTGCAGAATAAGT | GAGGGTATAATGCT |
| AACTTTGGGCCTGG | ATCAGCATGCTTCA | ATCGCGTTCCGTCA | CAATTGCTCGATGA |
| CTCGTAATACATGG | TGTTAAAGATCCCG | CACGGGTTGCTATA | TAACCTTCGAGATG |
| AGGACTTTGAATCA | ATGCTCCGGAGATT | CAATCTACCTTAAG | CGGCATTTACGCTC |
| ATGTTAGACGTGAA | CAGAAACTATTGTC | GCTCCATTCTGACG | GGGTTCCGTTGCCC |
| AAAGATTTTGCCCC | CAATTCATGGTAGG | GGTTGCAGACTTGC | TGTAGAGGTCACTA |

FIG. 7 (Cont.)

| | | | |
|---|---|---|---|
| AAAGTACGTATAAT | CACTTTGGCATGCC | CCAAGTTTATAAGG | TGTTGAACCGGGTG |
| TCGAGTTCTAACCA | ACCCTCGTTAAGTA | GGTTCATGCTACGC | GATCTGGAGTTGAC |
| ATGTTAGGTACCCC | TCAATTAAGTGACA | CTTGATACCAATGG | CTGGCGTGTGTAGG |
| ACTCGAGCGTCCTT | CACAAATTTTCGGC | GCTTACTGCGCATG | TGCGTGCGTCGGTC |
| ATGCTACTACTGGG | AACAACGTTTCTGG | ATGATCTGTGGCCA | TGACCACAATTGTG |
| TTGGTCGATAAGAC | CCATGTGTTGAGGA | GGGCTTGTGGTGCG | ACTCCAATAGCTCT |
| CAGTTGTGCCCTGG | CAGCATTTCACAAT | CCAGTACTCATGTA | CGTATCATCAATAC |
| AGTACGATGTACTG | TAGCAGATTTACGA | GTGGAAAATGGTTG | CTTGACGCTACAGT |
| GCTTCGTGAAAGCT | GGTAAATTATCAGG | GTCAAGCATGCGTT | TGAGGCTTAAATAG |
| TGCCACGTCGGTTG | AGGCTGCTGTTCGC | TCCAAATTAACTAC | CTTGAATTGAAGCA |
| CTACTTGCGAGATC | GGTATAGCCCGATT | TCGAATTATCGCAG | GCAGCACGTTTCTA |
| TAAGATTTGGGAGG | AAGTTAGAGGTATG | TCTCGCTACGGCCT | GTTGTGCCCAAATC |
| TACCCAGGTTCGTA | AGACAAATGTCTTC | TGGTGTGCAGGTAA | AGGTCACCGGTTTG |
| TTGGGCTCCCTCAA | GTGCAATCTAGCTC | ATCTCATAATCAAA | GGTAATGACGCGTT |
| ATAACTCACGTTAG | TCGTAGCCGATTAC | TGCTAAACTAGATA | AGCTTAGGCTTCCC |
| GCGTTCAGACCTTG | TACGCATCTTACCG | ACTCAGAATGTCTG | AACGTTAGCTATAG |
| CGATTAAACTCGAT | AGTGGGTCGGTATA | TGGTCGGCGTACTC | AATGATAGTCGCTC |
| ATAATTGACGTACA | ATCGCGGTGGTATG | CGCACTTTTACCCG | GCCACGTTCGTTAC |
| CTGATTTACGGAAC | TGGGTGCTCCGGCT | TCCATTAAGGATCC | GGTCCTCGCATCTC |
| GCACTGTTCGTACG | GTATAGCTATGGAG | CGCATTGTTGCGAG | TCCTTTACACCGGC |
| CTCTCATGACAGTG | TATTGAATGGGCAC | ATAATTAGAGGATC | AGTATTCTGAGAAA |
| TGCCTGGTGCACTG | AGTGAACGTGCTCT | AAGTTATCCGCCTA | GACTCTTCGGATGG |
| TCCTTACGTGGGGA | ACCAGTGGTTTAGG | TATAATCTGCCCCC | CGCGCATGATTACT |
| AAATGCGAGTCTTA | ATCTGAATTGGAGC | TTGGCATCAAAGGT | CTGCGGCTTGCTAA |
| GGGTTCGAGTAATG | GAACTCTGCTAACT | GTTCATAACAATAC | CTAGAATTAGAGTC |
| CTACTACTATCGAG | TGATCGGAGTATCA | CCGGACGAATGTTT | AGCGTCTGTTGAGC |
| AACAAAGGATTTGT | TCCGTCGAATTCCA | CCACTACACGTTGT | TATCTTAGACAAGG |
| AGTGTACTACGCCT | AGTCTTTCCAAACG | GTGCGGAGCGGTTT | TATGCACCCAATGT |
| ATCTACCCAACTGT | GTGATCCCCTAATG | CTCATAAAGCCTTC | TGAAGAGAATTGAT |
| TGGGACGAGCTTGT | AATCTGCAGTTCCA | TAGTCTATCAGGGA | TGCGGTCGAACTTG |
| GTTGGATGATACCA | CTTGACATCGTGAC | CTACACTACCATTC | GATCTTGAAGGTGG |
| AGTTGTTAACGGGA | GATAGTTCGTCCCC | TGCCACGGTCAGTT | CACTATCATATCCG |
| TCATTAGCTGCCGA | TAATCTGGAAGTGC | TTTAGAACTCGGCG | CTGCACATTTCGCG |
| GTTTGTCACCAAAG | ATCCCACGTTGGAT | TCAGAATTGCTAAG | TCTTAAGGGAACTG |
| CTGTTGGCCCACTC | ACGTAATTACTAAA | TTAAATATGCACAG | TGGGTTCCGGACCT |
| TAGGTAAGAGATCT | GTCGAACCTCTGGT | TATTCCACGATGGA | TGTACGGTGCTACG |
| GCGTGAGACCTTAT | TTCTGAAGAGATAC | ATTGGCGCATATAG | ATAGCGTCTAAACT |
| CAATTAAGCATTCG | CATGTTACCAACTA | TTAATAAAGTCGAG | GAGTGTATTGGCGA |
| CGCACGTTAGTTCA | AATGATTCACTAAC | TCTCAAAACACCTT | GATGTACTCCTCAA |
| GAGTCCCACTTCTG | AGGCTTTAAGTCGG | GATTGGCATAAAGT | CTGTCCTCATCCGG |
| TACAATTAGCATGG | GGCGATACTTATAG | ATGGTGGATAGACT | AAGGAATTGTTCAA |
| CTCTCTCCCTACAG | GTTGCCCTCCGTAG | TGCGTCGCATGTGG | CGTTTACACTCCCG |
| TTTAGACCGCTCAC | CTAATAAATGCTCA | AGCTCCGTCCTATG | ATCGGTAGCCTTGA |

FIG. 7 (Cont.)

| | | | |
|---|---|---|---|
| CGACCTACCATTCT | TTCCACTAATAGCC | ATGTAAGAGACCTT | AGTAGTCAACTTGG |
| TTGAAAACGATAAT | TTCACAATGCGCAT | CGAGCATCCTCTCT | TCTCTAGAGTACCA |
| TCGCGTACGGCCTT | TCCCGTGCCATATG | CGACCGTCTTTCCG | TCTGCCATCGAGTG |
| GTACCGGAAGGTTT | ATAGATACTTCCGA | CTTAGTCCCTACCA | TTAACTCAGGCCTA |
| TCATAACCGTGGCT | GGGATCTGTAACGT | CTCAGAGTAGGGTT | TAGCTGGGGAGTTG |
| AATAGTCGACATAT | CTAGTTCCGAAACT | TAGCCACTTCCGCT | ATCCGTAATGCGGT |
| CGTATGCCATGCTC | AGTATGAACCTAAT | GTATCTTCGGACAA | TATATGACGGGTCC |
| GTTTGCGCGACTGC | GGGGCTACTTCTGA | GACCGTTCATAATC | GATCAGTGTACACT |
| AGGAATTTATACCG | TAAACGTCTTAAAA | TGATAGGAGTGCGT | TGAGTAAACTAATC |
| CTTGGCCGTAATGA | AAGGATGTCCGTCT | AGTCCTGTGCTAAC | CTCACCTCGATCCT |
| TCAACAATGGGGTT | CCGGTATAATTCAA | GTCCGTAGTTGAGC | ACGTTAATACCTGC |
| CACCGAGTACATTT | ATAGCGAATCGCTT | GGTGACGTCACTGT | TCCTAAGTAATGCG |
| GCCTGCACTTATAA | TGGATTTCGACACA | TTGTATCGGGCCGG | TAGTGCGCGACTAT |
| GGTGCCAGGTCCTT | ATAAGGTATTCAGA | ATATGAAGGTAGGT | TACGTTCCCAGAAT |
| TCATCATAGGTAGA | AGTCCTGGTCTCGG | TAGACCTGGCGTTG | TCCTTGGATGAAGC |
| AGGACCCTTTCGCT | AGACTAGTGTGTCG | AGATAGAACCATTT | ATCTCCATACACTG |
| AGGTACGACTCTTG | GGTGTACGTTGCAG | TTGTTGGAGCGGCC | CGGCCTATGTGCAT |
| CTGATATAGAACTA | GCCCGTGTTCGGCT | TTGCGGTCTCACGA | GATCCCTCTGTGCA |
| ACTTAGGGTTAGGA | ATATCCCTATGGGC | CCAACACTTTTAGC | AGCTTTGAACTAGG |
| GGTCATGGTCGGTC | GGTCGCGAGATTTG | TTCCACCAAATGTA | TGCAAGTTGCGATA |
| CTGGTCGCTTACGC | TTGATGAGAAACTG | CATATGACTACCCT | TATCCTGTCGGGGC |
| TCGGGCTTGTCCAG | CTTGGATACCGATC | GCCCGTTCAAGTGT | TAAAAACTACACTT |
| CAACGGCTTTCTCG | AAGTTTCGAGCTCC | AAGTGTAGCTTACG | TTGGTACGGCGTAG |
| CGTCATTCGAGGTG | AGATCCATAATATC | CACTCGTCCTGCTA | GTAGAAGTCTTAGC |
| ATCTCAAAATAGCT | ACTGCAATTGCGTA | ATAACCGTTAAAGT | CGATATCACGTTAA |
| TACTTACGAGGTCG | TAGTGCAACTCTAG | TCTCTGAAGGTCCC | ATTAGGATAGGTGA |
| AGCACGAATTTAGT | TCTGTGAAAACTCA | TCACAGGGCTGTTC | ACTGACCGATTTAC |
| CCGTGACTTGAATA | AACCGTCTCGCTCT | AAGTATAACCCTGT | CATAGATTGATCCG |
| GGAATGATCTGATA | TGTTGCTCGCGAGG | CCACTCTCCTCTAA | CTCTTGCTCAAGCC |
| TAATCAACGGTTAC | CCTCACCTCTAGTC | GTAGCCTTTCACAC | CTGCTTCCGTAAGC |
| AGCTTGTGCTACGA | AACAGTTTATACAA | TGTCTCGCGTACAC | TAGTACACTAATAA |
| TATAAACTGCGGAT | TTGCGTAGAACATG | CGTTGACTCCGAGT | CATTTGGCTAAGCC |
| CAGGCCCATAATTT | AGTCCAGATCCCTT | TAACTGGTCGCCTA | CCGTTACTCGCTAG |
| GCATTGGAGTGCTC | ATGTATGCAACATA | AAATCGGTTATGGA | CTCGGATTGCAGAT |
| GACTGCTCCTTACA | CAACGATTGTTCAC | ATGTATACCACTCG | CTGCCTAGTGGGAT |
| GCTGTGCTGGGATC | CAACTTGAATTGCG | CTTGTAAGATGACG | CACTTTCGGGCGAT |
| TCGTGACCGCTTCG | ATCGTACCACGTGT | GCCACGTTCCGATT | CCGTTTGGTGGGCA |
| ACGCTTCATTAAAG | ATTTATGGAACCGC | CTATGCGGTAAATG | GCGGGATGATTCTG |
| AAAAGCTACTATTC | TTCGGACCTACCGT | ATTTAGGTAAGACG | CAGTCTCGTGCTAG |
| TACAGCGCATTTCG | AGTCGGTTGATACC | ATGACACTTGAACT | ACTTGTCTGAACAA |
| TAAGTTCCATAAAG | CACCGTTAACCTTA | CGTTTATGACGAGG | GACTCTCGTATCGA |
| AATTTTGGACGCCG | GTTGGCTGGGCATC | CTGTACTACAATAG | AAGATTGATTACGC |
| CCTCTCTGGATCGA | TTGATCGCACCCAT | CTATGAACTAACTC | ACCTTAATTGGCCA |

FIG. 7 (Cont.)

| | | | |
|---|---|---|---|
| CCCTTCATACCCCT | CGATAAATGCATGT | CTTGAGATGTAAGG | TATAACAAGAGTTG |
| ATGCTTACTGACCC | AGTAGTCACAATTA | ACCCCAACCTTTTC | TTAGGTGACACTCC |
| GAGTCTAGTTGCAC | ATCGGTAATGGATG | GTTCCGAGAGATTG | TTTCACGAGCGGTG |
| GGCACTCTTAGCAT | AATGCACTGGCTGT | TCCGAAATTTCGCC | CCACGGAGGTTCTT |
| AATCATTCCCAAGT | GCTCGGTTAAGCTG | ACGGTAAATAATCT | TATCCCTTGAAACC |
| TGATAGGCAGGTTC | GAGGATTTCACTCG | TGGTGAGCGCTAAT | TGGTCAAGTGGTCG |
| ATCGGCTTGCTGGG | TGATCTGGGACTAA | GTGAGACCGGTTTC | GGGGTTTGTCGCCG |
| GTCTAAGTGAAATC | TATGACTTAGAGAC | GTACTAGGGATATG | GATATCCTAAGGTG |
| ACGGTGAAAATTTG | ACAGTCGAATCTTG | GATCGTCTACCGGT | AATCGCGCTAAATT |
| ATGCCGCTTCTCAA | TATCCTACGCTGCC | ATTGAATGTGAGGG | ATACGTGAATGCGT |
| AATTCGTCGAGGGT | GCTCGGGGTCCATT | TTGCGAGCTCTCCC | GATAACCTCTAGGT |
| CTCTATCGGGCATC | ATCAATCCTGTAGG | ATTTGCTCCAAGCC | ATCCTCAGTTCGGC |
| AGTCTCGCGAGCTT | ATCGACAGTCCGTT | CGCATCTGATGATG | GTATGGAGCGTTAC |
| CCCGTTGGCAGTAT | AGGCTCGTTAATGC | TCGGGATCCTGTCA | GACTCTTCGAGGTC |
| GAACTCTCCAATTG | GAGGGTTTAGGCTC | CACTAACTCTTAGA | GATCATAGAAGTTC |
| GGTGTCAATTCCGG | GTCGCTAGACTTAC | GGTTGTGCCATCGG | ATCCACACTTCTAA |
| TAATCAGGGTTGAA | GGATGGTGCTACCT | CCGCCATATCGATT | GTTTCGTGAGAAAA |
| GTGGCGTCGACATT | ACGTCCCCATTCCT | AGACCGTTGATCTG | TGGGGATAATTCCC |
| ATTGATCTCAACGC | TTAGAAGCCTGTAA | CCCCTCCTGTATGG | TACAGTTACTAGAG |
| CGGGAGCATCGTTT | GAATTACTCATGAG | CCCTTCAGGTGACT | GCCGTTAGCCATCT |
| ATATCCGGCTCCTC | TCAGGACTTATGGG | TGACATGGCCGTGT | CGAGGGTTTATAGG |
| CTGGACCCTCACTT | GGCACTATTATAGC | GAATAGTGTTGACC | ATCCTGAGTGCTCG |
| GGGTAGTCAATGTC | TCTGCGTGCGAGGT | CCATTGATGGCCTA | AACGTTTTCGGAGA |
| TCCGTTACCCCTAA | TGTTCACTACGAAA | TGACCGTATTGCAA | TTACCTCGGGGCGT |
| GCTAGCTCCTCCTA | TATCATCACCTCAG | GCTCCCCCAGTGTT | TTGAGGAGAAGTAT |
| TTAGGTGACCGCTA | TTATGGCCACATCC | AGGCATATTGTCGA | ACTCTATAACCTGA |
| TGCGTGCGACTCGT | TCACGTCTCGGCTC | TACGAAAGATTGTC | TTATCGCTACACAA |
| GAGTCCATTATGCG | CTCTTCATAGACGC | GTCTACACATGACT | AATCATCGGGTCGT |
| CTGACGCCCTCTGT | TCATTCGTACCGAA | ACCCTTTAACGCGT | TGGAGCACGTTGCT |
| CGTAATCAGAATAT | TAATCCCTGAAATG | AGCCATCTTGTACC | TCATTAGGTAAGAG |
| ATCTAGACTCTAAA | TTGACCGGCTCTCC | GCCCATTCATATCG | GCCTGCATTCCCTG |
| TACGTTAGGATGGG | ATGTTCGGTGAAGC | CTACCATGCTGCCT | TTTTGGAGAAGACA |
| CAGTATTACCATCA | GGAGCTAATTCCAT | TGGCGGAATTGTCA | CTTTCGAGAGACCT |
| TCCCTTACTCCACG | CTCTTGTCCCAGGG | AAGTTCCTTGAAAG | TGCTAGGTATCCCC |
| TTCATACGACTCCC | GCCGCACTTTATGA | ACTTCGCTACACTC | ATCGTCCGTTCCCG |
| CCTGGCGAGTTACT | GGAAGTTGCACGTT | CTGTTCATGAGCAA | ATCGCTCCCGTACT |
| AATGAACTGGTCTG | TTACAGAGTAACTC | GCCTACTTTAAGGC | TGTATAAGAAACGT |
| ACTTCTCCATACGA | TTGGCAAAATAATG | CTATGGCTCCACGT | GGCACGCTTGTACT |
| CTACATGATTGCCG | TGCTGGATGTCAAA | CGGCCTCAATTCCT | TAATAGTTGCGAAC |
| ATGGCTTCGGTAAC | TTCTTGGCGGGGAA | CACTGAAGCTTCCT | TCTATCATTCGAAC |
| CACCCCTTGTATCA | GGTAACAGATTTAG | CGATCTAAGTGTGG | GACTCCGTGTTACT |
| TGCACTAATAAATG | ACCCGCTTATCCGT | CTGTCAATGGGCTC | CTAGTAATGGTATC |
| GTCTGTCGTACCCG | CCCATTCAATGATC | GCCTCGTTCCTGGG | ACGGTCTATTCGTC |

FIG. 7 (Cont.)

ACTCGGGTTGTCCT
GGCCGTCAGTTATT
GGTCATTATTACGC
ACGTCGGTATGCTT
GATTGTACATAGTA
TGCTGTCGGAATGT
CCGGGTTCTAGTTC
ATACGATTTCATAC
TGGCTATTCAAGAT
GGACGTGTGTATTC
TATGCGGTAAGTTC
CACGGCGTGTCTTT
ATATATTCCAAGTA
TTCTTAATCCCCGC
GCATGGCTTGTTCG
AGGCACACTTTTTC
GCTCTAACTGTTGC
GATAGGCCCTTCTT
TGATTTGGGGATCG
GATTCAATAGATTA
TTGCAGCGACTGTT
TATGCTGGATATCG
CTACATAATTAGAT
GCTGTCTCATAGCT
CCGACTTACACTTT
TCACTGATCAGTTA
GTTTGAGCGTTACA
AACCTATGGGTTGT
AGATGGCATTTTAA
TATCATGCATACAT
TTAGATATACGTAA
TGCAAGGCTGTTTG
AGCTGGTGTTTGCG
ACTCTATATCAATG
AACTTCCCTTTCCC
GCGCACCTTTCTTA
GTTGACTTGCCTCG
TGACTTGCTAATGA
GCCATTGGATTAAT
TTTACCCTGTGGAG
TCATGTAGTATACG
ACATACTCACTATT
AATCCGGGTTGTTA

TGTCCTACCTATCG
TCTCGTATAGGACT
TTCGCAGGAATTGT
GGTAGATCGTATAT
TTCAATTCAGCCGT
GACTTGTATTCCGA
TCTGTAGGGGTGGT
CACGTATCACTTTG
ATACATAACCTATT
ACCAAGGATATTTT
TTTCAGGTAGATGG
TAGTGTATGCCGGT
CAGGAGTCGGTTTT
TTAAATGCCTGCTC
TTAAATCCAGATTG
TCTTCAATAACGAT
TATAATGGTCAAGT
ACCGTCGGTATTTC
AGAGTACTGTATTA
GACTATGGTCCTAT
TAAATTCACAGTTG
AATTATGCCGCTTA
CAAGCATTGCTCTT
TGGTGGAGTGTCTC
GTCCGGTCAGCTTT
TAGTGACATCGATT
AGATTAGGCTAATT
CTCTTCTGTCCAAA
GGTGTATGTTAGCC
CCTCGAATTTGCTA
CCATTTATGGGTCC
GACGATTTCCTTAA
TGTACCCTAGTTAG
GCTTACCGATGTCT
CATTCATGGTGACT
GAAATGTGGATGTT
TCTAAGTCATCCTG
TGTATATGAACTCA
ACTTCCGGTTCCAT
TTCACTGATATCAC
GTTGTGAGTGCCTA
GTAAGCATTGAGTT
AAGTTATGGATTAA

CAATTCCATTATGC
TCATACTGCTTGGG
GTTTAGTTCCCGAA
TTCGGTGGTAAATC
TCCTCCGCTCTGTG
TGGCGTCTGTCGCT
TACTAGGTTCAATA
GTATTAGGGAGTCT
CGAATTTTAAAGAT
ATCCCTTGTAATCG
CTGTGGCATTAGCT
TTATGGTAATGGAC
TCAGTGTTCCCCCT
TAATCGTGGGTATG
ATTATTCGTCACAA
TATCGTAGCTGCCT
TCCGATACTCTCCT
CAGAACTTTAGTGT
GCGGCAATTTAATT
ACCGCCATGTTTTG
GCTTGTGAATCATC
TTTGTTACCGGAGC
GTATTCGACTAGTC
TTGTAAAACATGTG
GTGGACTTCTCATC
GTCCGTGGTGTCCT
TCTCCGCTTTCCCC
TTTTAGCGCGACTC
TGTGCGATCAATCT
TCTGCTCATATAAA
GTTAGTATCCCTGA
GATTAATTGGAGCT
TACACTCTAATCTC
TTCGGGATGGTTCC
TAGACAACTTTATC
TGACTATCATACTA
GTAATGCCTGTCTC
CTTTAGTTGGGCAA
TAATGCGTATATAA
GATGCCAATATGTT
AGTATTCATGCCTC
CCTTCTCGCCTGTC
ATATGAGTGGTAGT

CGAGTGCTCTCCTT
GTGGATTCACATGT
TTACTGTGGCTAGA
ATTTAAAGTCAGTC
CATCATCTTCATCG
TATAGAAGTGCATT
TCTGGAGTCTCGTC
TATCCACGGTGTGT
TATGTCCGGCTCAT
AGTTTATAAGGACT
CGAGTGTTTCGATA
TGTTACTCAATAAC
ACAGTTTCCATCTA
GTACAATGCCCTTT
TAAGTAGATCTATG
CCTAATTTTGGGGC
CTCATATGCGTAGT
GCTTGCGTCTGTGG
AATGACATTACTTC
CGTGAATATCCGTT
CGTTAGCGACTTTG
TCTATTGTGCAGCA
GATAAGAGGTTATT
CGCTTCTACATAGT
AGGGTCCTTAGTAT
TACTGTAACGTAGT
CATGTTGAGATGGT
ACACATTTATTGCC
TCTGGGCCTTGCTC
GCAATATTTCTAGG
ACTAGTCTGATTCC
CCAATGAAGTATTT
GCGAAATATTTCGT
TATTATCCAACTGC
TCTTTTAGCACCCC
TTTTAAGGATAGGC
CGTAACGCTGTGTT
CTAAACATTTCATC
GAAGTTCTACTATA
GCTGGTATGTTCGG
TCGGATACGATTTG
CTAAAGTTGTCTAC
TCCCATTCTGAAAT

FIG. 7 (Cont.)

| | | | |
|---|---|---|---|
| TGTAAATGCAAATT | CACCTACTTTACTG | TGCACTTTATGGCG | ATAGCTTGATGGAT |
| TCCGATTACAATTG | AATTACTCTTAGGC | ACTATCATATGTGG | GTATCAATGGTTGG |
| TGGCCGTTTTCGAG | TGCTACTTGACCTG | CTTCCTTAGCACTA | CAAGTCTCTTGGTA |
| ATCAACTTCTGGGT | TGCTATGCTATGCC | TCAATTATCTACCC | GTTGATAGTTAAGA |
| TCAGCGGTTGTCAT | TAACGCTTAACATT | AGTCAATAAAGTTT | GTTTAACATCCCTG |
| TATTTCATGCAGAC | TAGGGTATATATGC | TGTAACCCGTATTA | GGTCGAGACTGTTT |
| GCCTTTTCCCGAAT | ATGACTTTAGGTGG | AAGTCTACGATTTC | TTGCGCGTATGGTG |
| TAGTTGGCTGATGA | GTCGCTTAAGGTGT | GCGTCCTCCTATCT | TTGCTGATCGAATA |
| CGGTACGTTCTCCT | TCAGACCTATTTGG | GGCAGGTTATGTGT | GGGTCTTTGAGAAT |
| GGGTTTAACGATAT | CTTTAAGCTGAAAT | GAGTATCATTATCC | ATGGAGGTATATTA |
| TAAATTACATGGAT | GTCTCTTGAGTCCG | TTTAGCCAGACGTT | AATTGCCTTATAAA |
| CGTTTGGATGGCTA | TGCCGCTTGCATCT | CGCACTTTTTAAGA | TCATGAGACTCTGT |
| AGGATGTATTATGG | AATTCTATTCACAG | TTAACTGGTGCGTC | TTAATGACTGGGCT |
| TGTATAGCGGAGTT | GTTCGGACTATGTG | CATTACTGTAATGG | ATTATGGCCTGCCT |
| ATCATTGTCCGACT | TCCTTTAAATCAAG | AATATCTGGCTATC | CTAACTTCCATATG |
| ATCTGGTAGTTCAG | ATCTAGGATTCCTA | CTTCTAGTGGCTGG | CTGCTGTATGAACT |
| GGATAGTACGTTTG | TGGACCTTTTGAGG | CATGTCATGCCGTT | TACGTCTGCGCTGT |
| CTTGCTAGCTGGTA | TGCATTCGTATCCG | CGGTTGGGTTTCCA | CTTGAGCGTTTGGC |
| GGATGTCTTTGGCA | TATGCCTGTACTAC | GGTGGCCAATTTAT | TAGATTAGTCGTAA |
| GATATAAAAGTGTT | CTGTGAATACTATG | TATCGGTCGCGTCT | GTCGAATGGATCTT |
| TTGAGACGTTCTCA | AGTAATCATTTGAA | GTCATGTCATGATC | GTGGCAGATTTGCT |
| TAGAAGAGTGTTGT | GGCTCTCGTTACTG | CTGCGAGTGCTTAT | CCTCTTAGAATCAT |
| TTGTTAACGTGGCG | TATCCCTCCTCTCA | TACATAGTCTCATA | TTCTGTACCGAGTC |
| CTGAGTAGTGTAGT | TGTGTCCGCGTAGT | GGACTCGTCTCTAT | GTGGGTTTGAAGGT |
| TCCCGATAGTTCTA | CATCTCACGTTGTG | GGGGTACTGTTCAT | TCGTTACAGTCTGG |
| ATTCGAGTAAGTGT | TTACGAAATTTCCA | CTCTGTGCCCATTG | GACTGAGTGCTGTT |
| ATTTACCATAAGTG | AGTTAGGAGGTATT | ACGTTTGATATGAG | TCAATACCTATACT |
| GGCTCAGATTCTTA | GTCTTCCCTAAAAT | CATACTATATACTA | TGTTTGGGGAGGTC |
| GGTACTGGTTAGAT | TCGTTGCCACGTCT | TTTGGCAGTTCACA | CACTAACGTTGGTT |
| ACAGGAGTTATTCT | TCTCTGCCCTGGTA | ATCGTGTTCGACAT | TCCTACCTCATATC |
| AGTATACGATTACT | CTTTACCAAATTGA | AACGTGTCTCGTTC | TTGGTCGGTGCACT |
| TACTTCCAATCGTC | ATCGTTTCCCCCTC | GGACGTATTGTATA | TTTAGGTCTGGAAG |
| CTTATACTGTCAAA | GGACTATTAAGTAT | CAATAGTATTAGTA | ACTGTCAGTTGAAT |
| GTTAATGTCACCTC | CTAACCGTCGTATT | TGGTACCTTGGCTA | GGCTATCCTCTAAT |
| TTTCGGTCAATCCC | CGATAGTTAGTGTA | TACGATTTTACGAG | CAACGTTCTCTGTG |
| GCTCCCTTTCGAGT | CTCCCGTTAAATTC | TTTCACTACACGAT | GCTGGTAACAATTT |
| TAGTACTCCCCATT | TTAACCTCCGATTA | AGATTCGCGTTCTC | TTACATATCAGCAT |
| CTGGTTAACCTAGT | CCTAACTGTTTGAC | GTATTTGAGTCACG | CAAATTTCCTATGC |
| AGCCTTGCGCTTTG | ATTGCGTACCTGTA | CAGTTATTATCGAC | GTATAGTTTAACCC |
| TCCTTAGACATTGG | CCTCTGTGTGATCG | ATTCGGTCGACTTA | AATTCCCGTGATTC |
| TTGCTGTCCGGTAA | CTCCCATTGTGATC | GCCTTTCCTGGCGT | TTGACTTAGATAGC |
| CTATCAGATTATCG | TGCCACTTAGTAGT | GTATCATCAGATCT | GACTCACTTTCGTG |
| TGGATCCCGGTTAT | AAATCAATTTGCTG | TATCGTTAGAAAAT | CTATGCGACTTTAG |

FIG. 7 (Cont.)

| | | | |
|---|---|---|---|
| GTGTCTACACTATC | GCGGCTTTCTTGCC | TCGCTTCTGCAACT | AGTAGTCGCTGTGT |
| ATTTAGATACCTGG | TCTCCGTTGAGCGT | TTTATACAGCTAGG | TAGTAATGACTGTG |
| TAATTCTTCGGAGC | ACTTGCCTAGTGGT | TGCAAATTAGATTG | ACGCTCTTTCTCGG |
| ATTTCTCGCGAAAT | TCTCAAGTACTGGT | GCCTCTATATTCCA | TCGGCGTCTTGGTA |
| TACAGATGGTTCAT | AATCAGTTCGTATC | AAGTTCATCCTCTC | TTTAGGAATCGATC |
| TGAAACAGTTTAGT | TTACAAGTGTTCAA | TTGCCAACCTTTGG | ACGCTCATTCGTTC |
| GGCCTTTCCATGAT | TTTCCCGATGTCGA | GTTTTCCGGACCTG | TTAGTTCGATACCC |
| TGTATACAGGTCTA | TCCTCGCAACATTT | TGAAAAATTGTCTC | AATCGATGTATTAC |
| TCTTCTCGTCCACG | AACATGTTACTAGT | AGTACATCATTATG | TTAGATACACTAGT |
| ATTTTTCACAACCG | TTAGTGGAATTAAA | CGTTATCAGGTGGT | TACTCGGGATTCTA |
| GGGTGATATTGCTC | GTATTACTTGCCCA | TGGTTCATAGTACG | TCATCTGCGTGCAT |
| TTGCGAGGTTGACT | TCTATCTGCCAGAT | CGGGGTTTCTACAT | CTGTTAGCCGTTCG |
| TGTAGAGTTACAGT | ACCGATTGGTGTCT | TACCAAGGTTTAAT | GTATCTGTTAAGAC |
| CTTTGAGAGCATCT | TTACATCCGTATAA | CCATTACGTCCTTA | TACTGAAATTGGCT |
| CATATGGTAATGTC | TTTGTGCCCGATGG | CTGAATGTTAAATA | TTTCACCACCATCT |
| ATCGTTTGGAAGCT | GTAATTCGTCAGCT | TTGAATTATGCCCA | ACCTCGGTTGCGTT |
| GGGTTATCATTCGA | CGGCTCTGCCTGTT | TTTAGGCTGCACCT | TCCGAAGTTGGTAT |
| TGCTATGGGTCCAT | ATGGTGTGAGTATC | TGGTAACCCTGTTA | TAATGCCGTGCTTG |
| TGGGGAAATCTTAT | GGTTCTCATCCATC | ATCTCTATGAGTGC | TCCCACCATGGTTT |
| GTTCAATAGGTAAT | ATCGACTACGTTTA | CCTTCTTGATCGAG | ATCTGCTTCACAGT |
| ATAAATTCTGGACT | AGATCTTATGGTGC | GCAGAATATTATTC | GCTTAATGAAATTC |
| GATTCTGCCCTCCT | TTACTCAGCCGGTT | TGGCAGGGATTTCT | GGCTATATGTTCAG |
| GTCCAATCTATTAA | GCAGTATCAATTTC | GCTCCTGTGTCCTA | ATTGTAATTGAGCC |
| ATTCAGTTTACCGC | GTGTAATTCCAGTC | ATTCCTGATGGCCT | TTCTCCGTTGCCGC |
| CGAAATCTATGTTA | AGTCGATCTTTCAA | ACCCCTTATTGAAT | ATTGTCCCGTAGGT |
| TCGTCTGGGAGTCT | TAACCCTAGTCTAT | TAGACACGTTTTGG | ATGGTACGTTTCGA |
| TCGACCTTAGCGTT | TGTATACGTTCGGC | GTAATGATACTTCA | CTTGGTTGGCTCCG |
| CAAAGTATGTTTCA | GCATACTAGTCATT | CTTACGTCCTGTCA | CCGAGGTGTGCTTT |
| GTTGAATCCGTATG | GTCTTACCACCTTC | GCCTGTGGTGATTA | TACTAATCCGGTTC |
| GGCGTATATCCTTG | CTTCGACGTAGTTG | TGTCATATTGCCAG | TGACGTACTGGTCT |
| ACCTTTGCCTATCA | CTCGCCCATTTTCA | TGTTCTATCCAAGC | TTTCGAACCCTGAT |
| TTAATACGCGTCTG | TACTATCTCCCCAT | TCCCCTTATCTACA | CTTCTGCATCATCA |
| TACCGCCTGTGGTT | CTCCCCGTTATGCT | CTTCTAGGAGGTTC | GTTTTTGCCAGCCC |
| TGTCATTGAATAGG | TTTCGACGCTCGGT | ATTCGCGGTGGGTT | CGAGTTCCTTATCA |
| TCGAACTTGCTACT | CATTATAATAGCAT | TACATGTGGCCTTA | TAAGAATTTTGCGA |
| AGTATGCTTATACG | AATGGGTGTGATTG | TGACGTCCCTCTTC | CAATATATTGAGTG |
| TACCATCTCGTCTA | TCAGCTATCATAAT | GTAACCTTAACCTT | ATTGATTCGGACTG |
| ACATTGTTAGTGAG | GCGATGTTAATCTC | ACTGATGTTTCAAC | ACCACTAGATTTCT |
| CTCGCCGAATTATT | TGTCCAGTCTGGTA | CATTTTCAGGAGTC | ACTTTACAAACTCT |
| GGTTTACATGATCG | GGCTATTGATCTAG | ATGGTACGCATTTC | ACTTGACATGATGT |
| TTAAGGAGCTCCTT | ACTAACTATTGTGA | CTCGATGTGCTTCA | GTGATCTTTGCCGG |
| TAATGCCGTTGCCT | TCGGATAAATTACT | CCTCTTTACGCCTC | TGCGCGTTTGGAAT |
| AATCTGATGAGTCT | TAAGCTTCTCGGCT | GTTGTGCCTACTCG | AGTGCCTAGTGTAT |

FIG. 7 (Cont.)

| | | | |
|---|---|---|---|
| CATTTTCTAAGACA | TGATCCGATTCGTC | GTACTCGTATATCG | TCCTTCTCATGACG |
| ACCTGCGCAATTTT | TTTGGCGTTGAGCA | GAATATCTAGTTAG | CCTTACCTCTTCCG |
| CCCGCTAGTTTTAG | GGGTTCCGATTAAT | GGGCACTCGTTGTT | GCTGTCCTGTGTAA |
| GTACTGCACTTATC | TTCAGCTTTAAGCC | GTTTATTGGAGGGG | GATCTCGTATGGAT |
| TCCGAGTTCTTGCG | ATTTGGAGCTAACT | ACCTGTTGACGTTG | TGGTTTGTACGCAG |
| TGCGTAGTACGTTC | GGGCTTTCCTCTAG | CCTGATTAGTTCAC | ATTGGTCGTCCATG |
| CATTGTCGGATATG | TTCGTACTCACTCG | AGCTCTCTCTAAGT | TATACATTCCTACC |
| GGCTTCCTGAATTC | GATTAGTTTAGAAG | CTGGTTCAATGAAT | ATTCGGTTCGTGCA |
| ACACGTTTGTCACT | TGCTCGGTTATCAG | CTACGTCTATGTGC | TGAGCTGTGGTATC |
| GTGCTACTCCGTCT | TACGACCATTTCGT | CTCTGGGTTAGCTA | ACAGTTTAGCCCTT |
| AAATTTTGGGGATA | TGGGATCATATGTC | TCGATAGATTCCCT | CAATTGTACATCCT |
| TATACTAAGGATAT | CTTATGCTGAAGGT | CTATCGTTCAGTGC | ATAACGGCTCTGTT |
| ATCCGTGTATGATA | TGTGACCTTACGCT | GGATTGATGATAAT | CTTTCCTACGTCAG |
| CTCAAATTATCACT | GTTGTTTAGAACAC | TACTGGAGATATCT | TCTAGTCCTGTACA |
| AATGTTGCATCTGA | CAAGACTTTATCTC | TTAGACCAATAGTT | TTGCGGGTGCGTTA |
| AGAAAGTTTTACTA | CTTTGGCTCCCTCA | TTGTTAGCTCAGGC | AGTTTGACTCTAGC |
| GCTTTTGAAGGAAT | TTTATATGGCAGCG | CTTTAATATCACAC | TTACATCAATCCCT |
| GCTTTCAGCTACTA | TGGTCCCTTGATGC | TCAGCTCGTACTTA | CGGTTAGATTGTAG |
| GCTTTACTCTACAC | ATAGTCTGGTGTCA | GGTCTTGCGTAATA | GGGTAGCTTCATTA |
| TTAAGCTACATAGT | GCCACCTATTTTAG | ACAGGGATATTTTC | GGATACGTATTTGC |
| GATTTGGCGGTGCT | ACTCTGCATTGCAT | TTGATGCGTAGTGG | CCATTGGCGTCTAT |
| AAGTTGCCTGGATT | CCTCTGATTCATGC | GCTTTAACAGTCTA | CCGATTGAGTCTTG |
| CACATTATTTGACA | ATGGTGTCTTGCCC | GGCTATACCTCCTT | TTGGAGTAGATCTA |
| TGTACCCGTCTATA | CAGATTTTAGGCAT | CATTGTCCTCCGTC | ATTTGGACTTACGC |
| TTGTCACGTAACAT | CATTTCGTAATCCG | CCTTACGTGCTTAG | TGTCTTAGATAGCC |
| GAGATGAATTGTTC | CCTCGCTTATCATG | GCTTTAAATTCCCC | TTCTGACTACAGGT |
| GATTCCTTGTAAAA | TCAATTTGCAATGG | CCTATGTCTTGACG | CAATTCATGACTTC |
| TCAGACTGTTGATC | TGTATGTAGTACCC | GCTTTTGGGCCCTC | CACTTTGGTAACTG |
| GCGTTCATTTAGAC | CTACGTAACACTTT | GTGAGCTGTATCTA | TTATAGCTGAGACT |
| ATATTCATCGCATA | GGCTCGTTTGGTCC | TATGGATGTATGCA | AAGGATCTTTGCTG |
| CTCTGACTTTACGA | TGTTTTCAAAAGGC | GATCTTCCCGTGTA | GTTTTGACATACAG |
| GCTAGTATGACCTT | ATCCTTGTAGTAAG | CGTTCTATGGTCGC | TACTGTTGTGAGCG |
| TAGTGCACTTACTC | CAATGCTGTCCGTT | TGTTGGTTGCGGCC | TCAGGTTCTACTGG |
| CTTTACCATCTGCC | CTCGCTCTGTAAAT | AGTGTAGAGTTCGT | TACTGTGCGGGTTG |
| TGTCGCTAATGAAT | GTGGTTTGGCCCGT | TTCAGAAGTAACTT | CAGCGTTTTTGCCC |
| GAGCTGAGTTTTGA | TTTCGCTGCTACCC | ACGGGTTTGTACTC | CTCTTCTCAAATAA |
| TTAGCATTCATAGG | CCCTTGGTTAGGGT | TGAGGTTCTCTAAC | CGTGCTGAGTTTCA |
| AATGGTCCTTTACG | TTCATAGGATAATC | CTCCTCCGGGTCTT | TCCTTTCCCGTAAG |
| TATGTAATGAACTC | TAACTTGTTACCAC | ATTTTCAGGTAAGG | GTATGGTGATTCGG |
| GTGGGTAGTCATTG | TGCTGTAACTGTAA | CCCCCTATATCCTT | GTAACGTTTTAAGC |
| CGTATGTCGTCCGT | CAACCCTCTGTTGT | TGCGTGTGCGATTC | GAGTTTAGATATCA |
| GTACTGGTGTGCAT | CCTCGATGTTCGCT | TAATGCGTCTGCTC | GAATTTTTGGCAAG |
| TGACCCTTGTAGTG | TCCGTTTACCAGGT | CCTATCCCATATGT | TTGGAAGTTCGTGG |

FIG. 7 (Cont.)

| | | | |
|---|---|---|---|
| GATTCTCACGTTGG | GGGTCTTCTCGCTA | TCACCATTATCGTA | TGAGTCACTTAAAT |
| AGCTTTGTTAGCAA | GTGTTCACTGGGAT | TAGGAAGTTGATTA | TCAGCCGTTCCTGT |
| GCCTACTATATATG | CGTCGGATTCTATG | TTGGCAGGTTACTA | CTCGAGTACTTGGT |
| AATTTTGGCATCGA | TTAGCTTCCCAGTG | ATTCATTGCTGGGC | TCATGTAGTCAGTC |
| ACATTGGTTACTAC | ATAAGATGTGCGTT | TCGGATCGTTATGA | CTTACGGTTAATGG |
| AACAATGCTGTTCT | GCGTGTTGCATATC | TTATGCGCTAACGT | CGTTGATTACGTAC |
| TGGGTTAGAATGTA | ACGCTTGGTGCCTT | TGTGTTGAACGCGT | GTCAGGCCTAGTTT |
| TGCCCGATGTTATC | CAGTAATTGTTACG | AGGCTTATCTGCTG | AAGCGCTTAGGTTT |
| ATTCATAGGGTTAC | CGAGAAATTTGCTT | CGTTCCCTAGTGTC | TGGCTGAATGTTGG |
| CTTCATCTTGACGA | TTATAGCGTTCAAG | TGTGGTTATACCAC | CGGTAATTGGATTC |
| ACTATATGGAGGTT | GCTTAAATGCTTCA | GCCCTCTCATCTTC | GTACCAATTTTACC |
| ATAGGTAATGTTCA | TGATTACTGAGGTA | CTGTTAAATAGTGC | CTGTGGATCTCAAT |
| CTACGTGGGTATGT | GCAATATTGCCGTT | CGTCGTAGTTAGTA | ACATTTGCCTCGTG |
| CTTCGGTCACTATA | TTCGGTAGGTTGAC | TGTTGACTACCCTG | AGACTCTGTTGCTA |
| TGTAGCCCTTTAAG | TCCCCTGGGTTCCT | CCTAGCTTCTCTCC | GTGTTAGCTTACCA |
| GAATTTGCGCGTTC | TTCGAAATATAGAT | CAATTTGATTCGAC | TATTTGCCATGCGA |
| AGGTGTTTAGCAAT | CGTATATTGATAAC | TGTGTGTATGAGAA | GCTTCATTAGGTGC |
| CGTTGCTGATTCAC | ACTACCCGGTTTTA | ATCTGTCCTGCCTA | TAGATCAGGGTTTA |
| CATCTTTATGCGCG | TCTTAACTTCGAGC | TAGAGGTTTGTCAC | AGATTTAACTGTCC |
| TAAATTGGTGTGCG | GGCTTGATTAATCA | ATATGCGGGTTTCC | CGATCTGTTGGATG |
| CTCCTGAACTATTC | AAGGGTCCACTTTT | CAATATTGCAATAT | TAAATGGCCCTATT |
| AATCGACTCTCTTC | GTAATAATGTAGTC | GACACTTACTTTCA | TTATCTCGGCACTG |
| TTCAATTTGCAACC | AATTTGTCAGATCG | CATCTTACCATTGC | CAATCCTATGATTG |
| ATATTAGCTCTGCG | TTTTAAGGTGGCCG | GAGTTTGAATTCAG | ATCAAGATAGTTTG |
| GACTTAAGGTTCTA | TTTTCGCACGTGAC | TTCAGATCGTCGTA | ATTTGATTCGAAAA |
| CCTCTTTACATAAA | GGAGTTATAGTTGA | AGCGCCTTCTGTTC | CGAGGTTGTCTTCA |
| GTAACACATTTATG | TTTACAAGTATCCA | ACGGTCTTGACTGT | TATCAGGATCGATT |
| TGATTAATGATCCG | CGGTTCCAACTCTT | GGAAGTCTCGTTGT | TCTAGATGGCATGT |
| CTCTACTGGTGGTG | AGGTGTCTCATATA | CTGATAGGTTCATA | TAAAATGGGTTCTG |
| ATTTTGTGCGGGCG | TACACTCTATGAAT | CATCGTATTGTAGC | GAGATTGAATGTCT |
| CCGGAGATTTCGTT | GGGCCATTAATTTC | ACTGCCTTCGGTGT | TGCTGATTCTCACG |
| CTCTTTTGACAAGC | GTTTCCATACTCAC | CCATTAAGTTATAC | GGATCCATATTGAT |
| TAATTGGATGACAT | GTTGATCTACAACT | GTGTTCGGCCTCTG | TTGTACTCGCTAGC |
| AGTTTCCACGTTCA | GACGAATGTTCTTA | TTGCTGTTACGCGG | TCATTCCCTGTCCG |
| CGTGTTGTGTCAGA | TCCTACCTTAATCG | GTTTCGTGTACAGC | TTCAGGGCTTGGTG |
| AGTAGTTTTGGGAA | TAGGGTGATTACCT | GTTCGCTCCCTACT | CTGATTCATGCGCT |
| TTATGAGGGTCGTG | ATGGAATGGTATTG | AACATGTTAGATTC | GACGCTATTGGCTT |
| TGCGAGATCTTTGC | CCATTTACCTCCGT | CTCACCATTATATG | GTGCTTATCGTACC |
| TAACCTTTCGATCG | TATGCTATTGGAAG | TTGGATTCTAAACG | ATAATGTATGGATG |
| ACTCTGAGATTATA | CGTGGTTGGACCTT | TGAATTGAGTCGGT | CACTCTAAGTTTAA |
| TTCGCCTCCGGCTT | ATACTCTAAAGGTT | CACTCTCTTGAGGT | CAATTTAGTATCAC |
| CCGGTGTTACATTC | ACTATGGGGGTCTT | TCGTTCTATGCGGG | GTCTTCGTAGCCTA |
| TCGGATCATTCGAT | GATTACTCCGTAGT | GCTTCCATTCACCT | CACATTGTCTTAAG |

FIG. 7 (Cont.)

| | | | |
|---|---|---|---|
| GATTCATCTATGGC | AGTGTCTCGCTAAT | TGTTACTCGCCCAT | CAATTATCGTCTTA |
| ATTTCCTCGCCATA | ATGCTTATAGATGA | TGATCATATGGCCT | CTTAAGTCTCTTCC |
| ACGTCTACGTTAAT | GGTTGCGCAGCTTT | AGTTCGTCCTACAT | ATTCTACCGATTGT |
| AGTAAGGTTATCTC | CCAATGTTCAATCT | GTAGAAGTTTATAG | TAGTTGCTTCTCAG |
| CCTTCTATAATGCC | GAAGACTTTTCCAT | TTGGTACTAGAAAT | TATCTCCCTCTTCA |
| GCTCCCGAATCTTT | TGTGTACGGGCTTG | TAGTTCATAATGGC | TTTCCTCTAGACAT |
| TTGTTTCCAAAACC | ACCTATTAGTCTAA | TAGCTGATCTGTCC | TTATGCTATCGTCG |
| TTGAATTGCACGGT | AACTCATCTTTCGA | CAGTGTCGGCCTTT | CCGTATTTCCGTAT |
| GTCTTGGTTCAGAG | TATGTATCCTGGGC | TCTTGGGCACGGTT | GGATTTTTCCTCAG |
| TAACGTGGCTTGTC | AGAGCTTAGAATTT | AGACTTGCTTACTG | GTTGGTCGATCTCT |
| TCCTTGTCTGCGCC | TTAGTAGCTATAGC | GGTATGAAAACTTT | TCTCTCCGTCCTGT |
| ATTGCTGTATGGGA | AGTCGGTTCAATGT | GTCTTGACCGTAAT | ATTCAGCCTTTAAT |
| TTGGATTCAACTAA | CGCCCTATGTTTCG | AATCTTGATGACTA | CTCATTATTCTGGC |
| CCTTTCATACTGGG | GTTACGAAAGTTAT | ATCGCAGTTTATCC | ATACTTCTCACGTT |
| CGAGGCTCTATGTT | CTGCTTGTATCGCA | CCATATTGAATTCG | TTTGCTACGTCACT |
| GTCTACTTTGAACG | ATCGAGAGCTTTCT | TGCTTATACATCAA | CTTTCTCTGACTCG |
| GCAAATATGTGTTC | TTGATCGTCACATG | CATGTGACTTTCAG | GTTTTATACGGTAA |
| GAGTCTAATTTAGA | TCAATGTCTCAATG | ATTGAGAAGTCATT | GTTAGATGTGTTGA |
| TCGGTTTGACATAA | GTTGATGTGTGGCG | AATCCGGATTTGCT | TGAGTGATTTAGTG |
| CGTCTTGCTGGTAG | ATAGCTTCTTACAG | TCTGTCCTGACGTG | TTTACTGAACTTGC |
| TTGATTATAGCCCG | TCTAATCTGTAAAA | ATGTGCAATTGAGT | TAATGGTTGCTTGA |
| TAATCTCACGATTC | TGGGGGTCTATTCA | AAGATGTGCCGTTT | TCGGTATTGGCTTC |
| CTCTGTCCGTGTGG | TGCCTGGTATCTAG | AGAGTTGCTTCTAC | TGCATTAATACTCT |
| ACTCCATTCGATTC | CATCTAGTATGTGA | ATGCTTATATCCAC | TTCTATCTGTCGGA |
| TTGCACGTGATTGA | TGCTATGTAATAGA | ATCATACTAGTATC | GGTATTATGGGTCT |
| CTTCACTATCGAAT | CACTAAGTCATTAT | GGTTCTGAGGTTAC | CTTTCGTGTCTCAA |
| GGCTACATAGTTCT | TTCAACGCTACCTT | GTGTAATTCGCCAT | TTGCTCCGTTGGTA |
| GGTTTTGTGGCACC | CCTATTAAGTGTAC | CGTTCAGAGGCTTT | GATGATGTTAGGTT |
| TTGTGTATAAGAGC | ATGGGTCTCCTTAC | TCGTACTATAAAGT | CTTCATGCGCCTTT |
| CGTGCTAGATTGAT | TTGCACACGCTTCT | TTTGCATCCTAGAA | CTGTATTCCTTGCC |
| CTCGATTCCTGTCG | TGGTGCTAAATCTA | CGGTTTACGTTAGA | TGTAGTAAATCATT |
| TTATCAACCGTCCT | ACTTGCACTGATTG | TCCGTAAGATTCAT | ACTGGGTTATCTCT |
| CTCCTGTGCTAGAT | GGTTTTGAATACGA | GCGATACTTTCTCC | GTCCGCTGGTTTTA |
| CTTGCGTATTAAAA | TTGGCTATCGCCAT | CAAACTTGGTTTAC | ATGATTTGCTACAT |
| CTGTCACTTGTAAG | TGTTAGATAAGAAT | TGTTGCAGATTGCA | TCTTCCCCTTAGAT |
| CATGCGTATGATGT | TAATCACTGATGCT | CGGTTTGATCTCGC | TATTCGTCTGCGAT |
| TTCAGCGCTTCTGA | TGTTTACGAAAATA | AACTCGTAGGATTT | TTCGGTATTCCACT |
| TTTCACCGGGTATA | TGGTAATAAGTCGT | AATTGCTCTAGGTG | CTAGGTTTTACAAT |
| TCAACCTGGTTTCG | TGTAGATGTCTACG | TCATCATTTGGAAG | AGATTTCGTTCATC |
| TGGGGCTCCTAATT | TTGCTACTTAAGCC | TTGCGCTTATCCCA | CCTCATGTTTGATG |
| ATCTATGTGAGAAT | CGACTTCCTTTCAC | AATGTATTCTGAAG | CATGGTTTGTAACT |
| GATGTTTCTCGCGC | TAGCCTTTATCGCC | ACAATTCTTCTTGC | GCTACTTTACTCTG |
| ACACCTTTGTGTGC | ACTAAGCTTTGTCG | AGCTGAATATTTTA | TGCACTTCCCTATT |

FIG. 7 (Cont.)

| | | | |
|---|---|---|---|
| GCTGGCTTTGTGTG | TTCAATGGCCATTT | CTATGTTTCTCCAG | ACCTTATCATGCTT |
| TTAATCTTAGGTAC | TTCTTACCCTTACC | GCCTTTCTCTCTAA | TGTTCTATTGGGCA |
| TTGAAGTCTTTAGG | GTTATTCTAATGGC | TCTCTTTCGACTAA | ACGCTTACTTTGTG |
| GTGATCGGAATTTT | TTCTTTCACCGTGG | GATTTATCGCTCTG | GGTGCTGTCGTTTA |
| TAGCATGTTTTGCA | GGTTCCTTAAGTCT | TATCTTAATGCTGC | CACTTTATAGTTCA |
| TTTCTGTGGGCCGT | CTTCAGATATGTTA | GGTACTTGGTCTTG | TGCTTTTTGGAAGA |
| TCCCGCTCTGTGTT | TTACTTAGGTCCAT | TATCTGTACAGTGT | ATTGCCTGCTTCTG |
| AGCCTTTCGTATAT | CGTCTTGTCCTATA | TAGTTTGAACTGCT | AGGAGTTCGTTATT |
| ACAATTCCTTGCTT | TGGAAGTTGTTTCA | TTAACCTTGTTCGA | ATACTTTTTCCAAG |
| TGTGGCATTTGTGG | ACTTTAGCTCGTAT | CACTGTACTTGCTT | TCGATTGTGTTAGC |
| TAATGTTCTGATGC | ACTAGAGTTTATTC | CGTGTATAATTTGG | TCTCTGGCGGTTTG |
| TCCGTCCTTGTAAT | GCAGTTGTGTGATT | ATGTAACTCTTTCC | CTTCGCATTCTTGA |
| CATTTGTGAGTTGC | GTTTTATGCCACCT | ATGGTCTGTCATGT | GTCGTTTCTTCAAC |
| TATGTGTCCGTCTC | ATGAGATTCGATTT | GTTAGGTTGATGAT | TTCCATTATTCACG |
| AGTGACATGGTTTT | TGCACACTTTATAT | TAGTTTAGTTCGGG | AATGTCGTCTATAT |
| CTGGGTCTCTTGTA | CTATGATCTGTACT | TGTGTTACAACTAT | ATTTGGTATGGGGT |
| TTGTAGAATGATTC | CGCTTAGTTGTCGT | TGTGAGGATTTATC | GTCAAGTTGTTCGT |
| TATTATATGGACTA | TTTTATTAGCGCGA | TTTCGCTAAAATTC | TCGACTTTATACAT |
| CGGTGGTATCTATT | ATCCGTTCTTCCAT | CATAAGTTGTTGTG | TGTCTGTTCCGATC |
| CTTTTTGACTAACC | TCCTGCCGATTTGT | CTTATTGGCATATC | TATACATGTGTCTG |
| ATTACGCTGGTGTT | TATCGCTAGCTCTT | TCGTCTTATGGATA | GTGTGCTAACTTCT |
| TATTTCTAAGAGTG | CGATCCTTATCTTA | TAGAAGTACTCTTT | GTCCATATGCTTTG |
| TTAGTCCTGTCACT | ACTATAAATCCTTT | CTGTTTCCACATTA | TACATTGCTTGTAG |
| ACTGATTTAAGTAT | ATATGTAAGGTGTT | TTGATAGACTGTTG | CCCTTCCTTTCATG |
| CAGCTTTTGGCTTA | GGTCTGGCTCTTCT | CTAATGTTTTGGAG | ACATTTGTACAGTT |
| GGCGTTCTTTCACT | TTTGATCAGTAATG | CTAGCTATTTAATG | GCTTGTTATAACCT |
| GGTATGTTCGTGTC | TAGATTGGTATATA | GGGCTTTTTAGGTG | TTGGTATGGATGTG |
| ATTCTGTTACGTAA | CTGTTACATGTCTA | GGGTTTACTGTCTG | AATGATTTAGTGTA |
| CATGATCAATTTCT | TAATCTTACTTGGC | ATCTCTCATTCTCC | TTTTCGTAAACATG |
| CTATGTTAGTTAAC | CCCCTCTATTTATC | TGTTTACACCATGT | ATGAATTAGCTTCT |
| TCCTTGTCGTAGAT | TCGTATTGTTACAC | CTCTCTTAAGCTTC | CTACATTTGGTGCT |
| ATTGTCGTGATAGT | TCATTCGATCTCGT | CACGATGTTTATTG | ATTGTGGTGAATTC |
| TGATATTAGCACTT | AGATCTGACTTTAT | TATCTGCGTGGTAT | TCTATGAATTAGCT |
| TCGTGGATTGATAT | AGTTTGTTTGAAAC | TTTAGTATCGAATG | TTACTTTCCATCGC |
| TACTTGTTGATACG | AAGTGTGCTTCATT | TGATGATCACTCTT | ATCTGTTGCGTCTC |
| TTGATTGTGGATAA | TTCCTGTTATCAGA | TCTTGAGGTGCTTC | AGCTCGTGTGTTAT |
| AGGGTGTATTTAAT | CTTTGCCCTGTTCA | AATTTGGCAATTAT | TTTCGACGATTATG |
| CGTCGTGTTACTAT | GCTAGTGCTCTCTT | GGCTTATTCAGCTT | TAAGGTTGCTTTGG |
| TAATATCTTAGCGT | CTGCTGGTTAAGTT | GGTATGCTCTGTAT | CGCGTGTTGCTTGT |
| GGAGATCTTTTGGT | ACTGCATTTTTGAG | TTTAAGGGCTTTCA | CATATAGTTGGTAT |
| ATATCCTTCATGCT | ATGATGTTGGTTAC | CAACATGGTTGTTT | TTTCTCACCTATAA |
| CTTAGATCTTAGTG | ACACTTTATACTTA | TTTATGTAGAGAAT | TGTACTTTTAACGC |
| TTATTGTACCACTG | ATGTTTCTAAAGTG | GTGAATGTTCATCT | TTGGTCACTTTCCG |

FIG. 7 (Cont.)

| | | | |
|---|---|---|---|
| GCAGTGCCTTCTTT | TGTGTTGACATCTC | TTAAGTCCGTTTCC | TTATGGCTCTTCCG |
| ATTATCATGTCTAC | TGTTATATAGCTCC | TTTTGCCGTGCAGT | TGCTGATTTATAGC |
| CACCTGTATTTCAT | ACTTAAGTCTTTGA | ATTTCTGTCCAATA | TGGATTTTACAGTC |
| CTATGTTGAAGTTC | GCTGTCTGGATATT | TGAATTTTACGTGG | TTCTCGTCAGTTGG |
| CTGCTGTGCTTATA | CTGTTAATCAGGTT | GGTTAACTTGGATT | TAGATCGTTTGTGC |
| TTTCTGACACCTTG | AAATCTTCCTGATT | TCCATATGTTATGC | TTGCACTTTAAATC |
| TAGCGGCATTTTTG | GTAAAGTGGTGTTT | TACATATTTCTCAA | CTTTACCTGTATAA |
| CATCGGTCTTCTTC | TATCATCCTGTGAT | CTTAGGGCATATTT | TACAACGTTCGTTT |
| GTTACTAATGTGTG | CTTAGTGCCTTTAC | CCCATTGTTTCCGT | CGTTATATACTCAT |
| GATTGATCTAGTCT | AGTTCTCTATATAC | TTGTTGGCCTTCGA | TCCTTTATTGACGG |
| GTAGTTATGATTCG | GGCTAATTTTTGCA | TGTCTGCACCTCTT | TGTGGGTTCTTCAA |
| TTTTCAAGTGGATA | ATTGGCCGTCTTAT | TTACTTGTATAGAC | TGCCTCGTCATTCT |
| TCTATTTCATCAGC | TCTCCTTCTTCCGA | CCTAGAAATTTATT | TGTTACGTTTCAGA |
| GGGCTTCGTTCTGT | CTTTTCAGGCACTT | CTTGATCTATTAAG | ATCTCATACTTGTC |
| TTTGTCCTTACCGC | GTGGTTTAATTGCG | ATTTTTCGTGGGAC | TGTTAGTTCGTCCG |
| CATGTCTCTTTAGC | AGTGATTACTTCCT | CAATCCTGCTTTCT | TACCTTTATAGTCG |
| TGTGTAGTGCCTGT | CTAGTCGTGTTTAA | CTTCATTGTAGATA | ATCTGGATAATTCT |
| TACATATATGTGGT | CATACTTTATCTGC | TGGCTTCAATCTTA | CTATCGTTTTGCCA |
| GGTTCTGTCTGGGT | ATTGTATGATCAAT | ATTGGTAATTCTGG | AACCTTTTTGGCTG |
| GGAGCTTATTGTTA | GTTAATTGGACATT | CTGTTCCTTATACC | ATCTACATGTCTCT |
| TGTGCTTATAGACT | CCTTTGGATATCAT | CACTCTCTTCTTCC | CATCTTTGACATCT |
| GCTATTCTTGGTGA | TAATTCTGGCGCTT | AATTCTTTCTGCAC | GTACTTCCTAACTT |
| GATTATCGTGCCTT | TCGTTATCTCCAAT | AATTACCACTTTGT | CTATATCAATTCTA |
| ATTACTTTCTAGCG | GAATTTTTACTGCC | CTATTTCCCTGTAC | TTAGATGTTTCACA |
| ATTTCGTGGAGTTG | TTGGCCCTGATCTT | TTGTACGTGGATTG | TAGCATTGTCGTTC |
| TTCTTGGGCCTACT | TTGCCGGTCATTTC | CCCGAACTTTTATT | CCTTGTCTGCTCGT |
| CTTTGATCTTCAGC | TGACGGTTTATCCT | CTTTCCAATTAACT | TTAGCCGTTGATTC |
| AGCGATTCTTAGTT | TGGTGCACTATTGT | TTCGCTTCGTACTC | AACTTACTAATGTT |
| CATTCTCATTGTGA | GTCCTACTGTATAT | CTTGTTTGTGAAAG | AGACTTTCTTTACA |
| CTTTCTTCTGAAGA | CCGATACTTATTAT | CTCTCTCCTTCAGT | AGTTCTAAGTCTCT |
| GGCTTTCTAGTGTG | GTTTCCTGCGCTGT | GCTTCGTCGTTGTC | TGGTTTTATAGCGA |
| TATGGAAACTCTTT | TTTAACCTCCTGTA | GGATCTAAGCTTTT | CACTTCGTTCCTTA |
| TGTTAGATGTGGTA | CTTTTTCACTCGGA | TGATATAGTTGTAC | TCATCAGTTACATT |
| TTGCATTGGTCCTC | CTTTAATGATGGAT | CTTACCGTGTACTT | TGCGTTTGTAATAG |
| GCGCGTTTTATCAT | TCTAGTTAACTGTC | TCATTAAATGCTAT | GGATATTAATTCAT |
| CTAGATTGTCTGTC | ATCTTGTTTCGGGA | TGTTTGCCAGTAAT | GAGTCTCCTGTGTT |
| CTAAAGATCCTTTT | GTTAGTAATTTCAC | ATCTTTATGATGAG | AATGTATGGCCTTT |
| TCGTTCTTGAGCTC | GTTTGATAAAAGTT | ACCTCTTTCCTCAT | TGCCAAGTGCTTTT |
| TTATTCAAGTTGCA | TCCATTCAGGTATT | CTTATTTCTAGAGC | ACTCCTTTGTTCCG |
| GCCGTTTACGTTTC | GGGTCTTCTTAGGT | TGTTGGTACTAAGT | GAGTACTTTGATAT |
| TCGTTTACTCTCGA | TCCTTTGCTACAGT | TCCGTTATAGTTAG | CATCTTTCTGTCGA |
| ATCGTTTCCTTGGA | ATTAGGTTTAACTG | AAACTTGATGTTAT | TGGTTGCGGTTATA |
| TATTGCATCTCACT | CTCGATTATTCTGC | ATTCGTGAATTTCA | TTTACTTAACGGAT |

FIG. 7 (Cont.)

| | | | |
|---|---|---|---|
| TTGTGAGTCATGCT | TCTCCTCCGCTCTT | TTGCTAGTTATAAG | TTTTGGGCGAAATT |
| TGTTGATGCCTTGA | ACTTAGATTCGTTA | TTGTCCTATAATCA | TACAGTTCATATGT |
| GTAGTTTTAGCTCC | TCAGGATTTTAGAT | GGGCTCGTTTACTT | GTATAGCCTTGATT |
| ATTCATTTGAACCT | CTCTTCCTAGTGAT | TTATTGAAGCGATT | CTTTGAGCGGTCTT |
| GTCCCTCTTGTTAG | GTATTAAGATGATT | TTGGAGTATACTGT | ATTTGCTTAACTAC |
| CTTTCGTCACTGGT | GATTGTCTTCTGCG | AAGTTACTATCTTG | TTTCGCTTTCCACC |
| AGCTATTAGATTTG | GTTCTACCGTTCTC | GCTGACGTCTTTTC | AAGTATCTTGTAGT |
| TATGGCATAGATTT | CATATCTGAATCTT | TTGTGTCTAACCAT | ACAGTGCTTTTTCA |
| GTTTTGGGGGTTGG | TAGTCAATTAAGTT | GTGTTCTGATGTCG | GTTACCAGATGTTT |
| TTGTAGGTTACTAG | GATTTTGTTGCCAA | CCTTCTAAATCTTA | GTTTGCTTCAAATG |
| GTCTTGCGCGTTTA | CCCGTTATTATAGT | GTGATTTAATACTC | TTTTGCTTACCGGA |
| ACGTATGTTACTGT | GCTTTGTAACTGTG | ATGGCTAGTTGATT | TAATTCATCATCAT |
| TCCTGATATACTTG | ACATTATTTGAGGT | AAGGCTCTTTATGT | CTGTTCTGCCTTCA |
| GTTTTCTAAATGAC | GCTTTTGGCGTTCC | ATCTTTTACGGGAT | GGGTTAATTTATGG |
| AAAGTAGCTTATTT | ATGCGTCTTCTACT | CTGTGTAATTGTCG | ATTGAATTCTGGTA |
| TGTGTGAATGTACT | TTTCTGACATTAGC | TAATTAAGTACCTT | TTTCGCTACTCATA |
| TTCACTGATTGACT | TTGTGGCCTCCTTG | AAGTTTGATTCTCA | TGGTTTTATGAGCC |
| GTTTACTTTGGCGC | ATCTTCAACGTTGT | GATGTTTTCTGGCA | GTATTATCAATCAT |
| AAGGTAATCTGTTT | CTGTTCTCAATCTC | TAGTTCATCTATGA | TTCTCCACTCTAGT |
| ATGAGTAGATTTTG | CACTAGTTTACGTT | AGGTATGTTTCCTC | GTCATTGAGTTTAC |
| TTTTCAACCCTATG | TTCTGCATGCTGAT | TCTTGCTGGCGTTC | TCTGTTTGCAAGTA |
| TCCATTCGTGATAT | AGCACTCTTGTTTA | ACTTGTTATTGCGC | GCTTTTTCGCTGAA |
| TGAATCACTCTGTT | CTGGTAATTTATCA | CCTTGGCACGTTTT | AGCTTTGTTGAGTC |
| TTTGTGGAATAGTC | TTGGGGTCCATGTT | AGTTGTGATTACAT | GTATTTTAACCTGG |
| GTACGTTTTCACCT | CATATGGTCTATTA | TGTAATTGCATTAC | CTAGTTTAGTTCGG |
| TTCTCGATCCGTTC | GTAACGATTTTGTA | CCTTTTGCTAGGTG | TGGCTTCTGTTAAG |
| ATTTATGGTGGTGA | CTGTCGTTATCTCC | ACAGCTCTCTGTTT | GTGATGTCCTTACT |
| CTTAAGCTTATTAA | GTCGTTATCGCATT | GTCTTTGGTGAGGT | TTTTGATCCGAGGT |
| AGATTCTGATGTAT | CTCCTTTTGGCAAT | ACGCATATATATTT | TGAGTTTACGTTCT |
| TTTAAAGGTATGTG | CGTTTTAAATTCCC | GCGATTTTATTGGA | GCTTTTATTGAATC |
| TTGGTTCGCACTAT | ACGTTCATTAAATT | TTGCTACTTCCATA | CTAATTTTAGTCTA |
| TAGTTCTCATAAAT | ACTTGTTTACGCCT | TACGTGGTCATTTA | ATAATGTCGTTTTG |
| ATATTGTACTTCGC | CTCTATTCAATTGC | GTACTTTACATACT | TCTAATTCCGTTGT |
| CTAGCTGTCCTTTC | AGCCTTGTTATGGT | AGCATTGATTTATA | TTACGTTTTGTGGC |
| CTTTATGGCCGTTC | ATGACTCTGTGTCT | TTCGTTGGCGTATA | AGGTTTTTGCTGAT |
| TGGTCTTAACTTCA | TATCTTGAGATTCA | TGTTCATTACACCT | TGGCTTTGTCTCAT |
| CATTCTAGGGTTCT | ATACTGGCTGTTTA | CCTTTAGATTATGA | CTTCCCCGTTTTTC |
| TTTGCATCCACTTG | TTTTCGCTGGTCGG | TTTTCGATCGCTCG | GTTGCTTTTTCCCA |
| GTATGAAGTTTTCG | ATTTCGTGATATGC | ATTGAGCCCTTTTC | CCCTATTGTGTGTT |
| TTTACAGTTCATCA | TCCGTTTCTGATGA | ACATTCTTTCACTA | CATGTTCGTGTATT |
| TTTAGATTCCCAAT | CATATTGCTTTCCC | GTTGTCCTCCTGGT | CTACTCTTTAATTA |
| TTAGCTAGTTTGGA | AACTCTCTTAATTG | GTATTTGTTACCGG | CATTGTATCATTTA |
| TCGTGTCATTAGTA | TGACGTTGACATTT | TGTAAGGTTTCCAT | CGTGTTCTGTGGTT |

FIG. 7 (Cont.)

| | | | |
|---|---|---|---|
| GTTTTCCAGTCTGT | TGCCCTGTTGTCTT | TCCTCATGTTAGTT | TCTACTGTTAATAT |
| GTTATTTGTTCGAG | CGAAGTTTGATTTT | GTGTGTGATTTTGC | TTGTGCGATTTATG |
| AGTAGTTTTCCTTG | TTCTTTAGATGGGT | TTTTTGGTGACCAT | TTTCTATCGTTAAA |
| TCATTTCTGTTCCA | TAGACCTATTTCTT | CTTGCAGTCTTTAT | TTTGTCCTCGGTTC |
| GTATGCATTATTTC | ATTATTTACGTCGT | TATACCTTTTTGAA | TTCTCGTCTAATAT |
| TGTTAGTGGTCTCT | TAGTATTTCGTTCC | GGTTTTATCTCGTC | ATTCCTTCCTTGAT |
| ATGTTGATCCTTAT | GTCACTTTCTTAAT | TTTCCGTATTACTC | CCGCTAAGTTTTTT |
| TCTTTCTCTAATGC | TAGCCTGTATGTTT | ATTTCCTCGTTCGT | CTGATTTATGTTGG |
| TTGGTATTCCTATC | CTTTACTTAGATCT | TTTAGGTATTCTCC | TTTCATAGATGTAT |
| CTTGTGATTCTGTA | TTTAGAGTGTTTAG | TTAGCTCCTTCCTT | TTTCTTGGGACTTC |
| TTATTACTCGGATT | CTTGCCTTTTATGC | AACGTTTTCAATTT | CGTGTGTTTGACTT |
| ATTTGTGGGATTGT | TATTGTTATGTGAA | GCCTATTTAGCTTT | GTCCCTTCTTTTCC |
| TACTTGATGTCCTT | GTCCTTAATTCCTT | CATTTGCTGCTTTC | AGTTATACTTTGGT |
| GTAGGCTCATTTTT | TTTTGGTCATCTAA | TCATCTTTCGAATT | GTGGTAGTTTCTGT |
| CTTTCATTTAGTAG | TGTTTGATCGCATT | TATGTCTTCATACT | TGGGCTTTAGTTAT |
| GGATTCTTTTAAGT | TACTTTAGCGATTT | CTTATCTAGTTCAT | ACCTTGCTTGTTGT |
| ATTTCTTGACTACT | ATAGATTTTCTCAT | TAAGTTCTTTGATC | GTGTAAACTTTCTT |
| TCATGGTATTTGCT | TTATCTTGTATGCC | GTTGTTTGGTGCTA | TTCTGACTGTTGTC |
| CATTTATGTTCCGT | TTCGTGTAGTGTGT | CGTATCATACTTTT | CTGTTGTCTTGAGT |
| TTCGTGTTAATTGC | TCTTCGCTTCGTAT | TTTGCGTTCCTCGT | TTTGCCATACTGTT |
| ATCTAGGTTTGTGT | GCTCCTTGTTACTT | TTGCTGAATTCTAT | TTCCCCATGTTTGT |
| GTATGATTCTCTTA | ACTCTTTTCAGATT | ATGTTTTAACGTTC | TTATCATCTATCTA |
| TCCTGTTTCTTAGA | GTGATCTATGATTT | GCTCTACTATTATT | TAGTTTCTTGCGTC |
| TTCATGTTTCACTC | TAACTGCTATCTTT | ATACTTTTTGGTCA | TTGGGTGTTACTTA |
| CTGGTTATTCCCTT | ACTTTTTAGATGCT | CTCTTTTTCGCGTG | TGTTCTTTGCATAA |
| ACCCTTCTATTTTG | TATTTGTGTTACCA | GCTATATTTTGTAG | CTTTCTCTAAAATT |
| CCGTTTCGCTTTGT | TCTCCGTAATTTGT | GAGTGCTTATTTTC | TGATATAGATTGTT |
| ATGATTCTTTCAGT | TGCCCTTAATTTTC | CATTTGATTTACTC | TTACTCGTGTTATC |
| TTGGTTTGCTGTGA | ACGTATCGTTTTTG | TGTGTCAGATTTTC | AATTTTCTACCATT |
| GTCTGGTATATTGT | GTCAGTGTACTTTT | TGTGTTCGTTTGCA | TGTTTGTTACTCGC |
| ATTGCATCATTTCT | TTGCCTTGTGATTA | TCTTATCGAATTTA | TCCGTACTATATTT |
| TTGGATTTTTGGAC | GGGGATTTTAATTT | TGATATTTTTCGAA | CTACTTTAGTGTCT |
| CCCTTTTTGAACTT | TTTGTTGTCGTGCC | GAACTGTTTGTCTT | TCCTGCTTTATTAA |
| CTCTTAGTGTTTCC | ATATTTTGCCCTTA | TTTTGTAGAATGTC | TTATTCAGGTGTTC |
| TCGTTCCTTTCCGT | TCTTATTGGTCGTA | TGGGATTTTCTTCG | TCAGTCTTTTTGCC |
| TGTTACGGTTTTCG | GCTTAAATTTTGTG | GTATATTGTTGCTG | TTATCCTTTCAACT |
| TTCCTTTTTAGAAC | AGTTGTTGATTATA | TGCTTTCTAATTAC | TGCTTTATCTCTGG |
| TGGTTAGTTTAATC | CATTCTGTATTGTG | TACCATTTATAGTT | CTCCTTCTTTGTAA |
| CTTAGTCTTGTCTC | TTTCATTATGGTAA | GTGGTTCTATGTTG | TCAGTTTCTTGAGT |
| TGTTGTTATCAATG | TGTACTTACTCTGT | CTTTTCTTGTCCGC | CTCACTTCTTGTAT |
| ATTTTTAGATCGTG | ATCTTAACTGCTTT | ATAGATGCTTTATT | TTTCATCGTGTTCG |
| TTGTTTATGGTGGA | TGTTATAACTTCTA | TGTTTTACGTTGAG | TCAGAGTGTTTTAT |
| TACATAGAGTTTTT | GTTTATTCGTATGC | TAGTCCTTGTTTGG | TAGTTTTCGTTACC |

FIG. 7 (Cont.)

TTTTCCTTCGCGTC
CGGTTTTATTACTG
TAATAGTGCTTTTA
GTTGATATGTATAT
CAAGTTGATTTCTT
TTATTGTCTTCACA
AGGTATTTTGTGTG
CCTCTCCTCTTTAT
TTTAGGTTGGTCTA
CGGTCTCTTTGTTC
TGTTATGTAACCTT
CTTTATTCGAGTCT
GGTATACTTTCCTT
CAGCTTGTGTTGTT
TTGCGCTTTCGCTT
TAGTCTATTTGACT
GTCGTTGGTTTTTG
GGTTTATTGATTTA
GTTTTTATGCTATA
TGCTATTTTCGGTT
TATTGTCTTTTCAC
TTGTCCTGGGTTTT
TCTTTTGGCTGTTG
ACTTCGACTTTTTT
TGCTTTTCTTACCT
ATGATCCTTTTTTA
TTTCTATTGTGTGC
TATTTCCTATACTT
GTTTGTTTATTGAG
GGATTGTTTTCTTC
TGTATCCATTTTGT
CCTATTTTCTCGTT
ATTCTTACTGTATT
TTGAGTTTATCTTC
CTTCTTCTCTTCTG
TTGTGTTCTATAAT
GTTTGAAATCTTTT
GTCCTTTGATGTTT
TGTATATTGTTGCT
TTGTCTCGTTGTGT
TCGTACTATTTTTC
CTTTTATTACCTTA
TCAGTCTTGCTTTT

GTGCTTTTCCTTTA
TCATTTCACTTGTT
GATTTTTCTCAGTT
GTATTGGTTTTGCT
TATCCTTTGCTTGT
CTTTTGCTTGCTTG
TTTGTTGCTTGATG
TCTTTGGATTTTCC
ATTTGTGTTTGCTG
TGTACGGTTTTTTA
CCGTAATTATTTTT
TTTTTGCGTAGATT
GTGTTCGTTGTATT
TCTCATTATCTTTG
TGGTGCTTCCTTTT
GTTTTTCAATGCTT
TTGCTTGATTAATT
TATTTTGTCTTGAA
CTTTATTGCTTTAG
GTTCCATTTTCATT
GTTAGTTGTTTACT
TTTCTCTGTAATCT
CCTTTTCCTTGTCT
TTCTTTGAGTGTTA
TTACTGTCTTGCTT
TCCTTATTTTTGGG
TTTGTGTAATTCCT
ATGTATTTTTCGCT
AATACTTTTTGGTT
CCTTTATTCGGTTT
TTCGATCGTTTGTT
GTTTTACTTTTCGG
TTTACTCTGTATTC
TTTAGTCTGTTAGT
TTGTTTTCATCATG
AGTTTTTCCATTTT
ATCGTCTTTTCTTT
ATTGTGTTCTTATT
TTCCGTATTTGTTT
TAGTGTTTTTGTTG
CTTTGCTTGTTTTG
TTTTCTTTCGTTGA
TTGCTTCTATTTGT

TTTTTGGTATTCTG
TATTTTTCGTGTTT
GTTTCGTTATTTTT

FIG. 8

| Gene Name | Forward GSP | Reverse GSP |
|---|---|---|
| ABCF1 | CTGGAGAGTCACGCCCACA | GGCTGACAACGATCACAGCA |
| ACAD9 | CTGGGGCTGACAGGCAACCA | GGCCACCCGCTTCAGTACCA |
| ACTB | CCACACAGGGGAGGTGATAGCA | ACCCACTCCCAGGGAGACCA |
| AGK | CTGGGCACAACCACAGGA | TCAATGGTGGACAGCTGCA |
| ALAS1 | GTGAACCGGCGAGCACA | CCACCTGCCCCAGCACCA |
| AMMECR1L | GTGCACTTAAGGACAGCCGA | CATGGACCCCTACCTCCCA |
| B2M | ACGTCATCCAGCAGAGAATGGA | TGGTTCACACGGCAGGCA |
| C10orf76 | AACACAGGCTTCACAGTGGCAA | CCATCAGGTCCAGTACTGCACA |
| CALM2 | TGGGCAGAATCCCACAGA | ATGGCGAAGTTCTGCAGCA |
| CC2D1B | GGATCTGAAGCCCCAGCA | CTGTGACTCTGTAGGGGCCA |
| CFAP157 | CGGTACCAGCGGAAGTGGGA | CGTGCGCTTGAGGAAGGCCA |
| CIAO1 | CTCGGATCCACAGCAGCCCA | CTCCCCATCATCACTGCAGGA |
| CNOT10 | CCCCTCAGTGCTACCCCA | TTGAAGCCGCCTGGTGGA |
| CNOT4 | GAACCACACAGCAAACCCCA | TGTGAGGGCCTGAAGGGA |
| COG7 | TAACCAGCAGGCCCACCA | GTGAGACTAAAGGCGGGCA |
| DDX31 | CTGGACAAGAGCCATGACCA | TGTAGGAAGAGGCTGTAGTGGA |
| DDX50 | CATCTGCAGAGTGGCCGA | CACTGTGGGCAAGTTGCAGA |
| DHX16 | TCCGTGTACGCAAGGCCA | AGCCACCTCCAGAAGCCA |
| DNAJC14 | TGCATCCTGCTGAGGAAGGAGA | CACGCTGGCATCCAGCCCA |
| EDC3 | CGGGCACCAGTACTCAGCA | CTTGCAGCCAAAGGGCGA |
| EIF2B4 | ATCTGCAATGTAAGCGGGGAGA | GGATCATCCCCAGCTCCGTGA |
| EIF3B | TCAGTCCAAAGCCTCAAAGGA | CCCCTCCTCGCAACTCCA |
| ERCC3 | GAGTGGCTCAAGACCCAGGA | GGGCACCAGACCTCAGCA |
| FCF1 | AGAAAAGAAGGATCCCAGCGCA | GGATGTGGTAAGGTGGGCCCA |
| G6PD | CCATCTGGAACCGGGACA | CTCCATGGCCACCAGACA |
| GAPDH | CTGGGCTACACTGAGCACCA | CCACCCTGTTGCTGTAGCCA |
| GPATCH3 | GATGGCCAACACCCCAGA | ATGAGGGGCTGTCTGAAGCA |
| GUSB | GCAAGACAGTGGGCTGGTGAA | CCCAGTCCCATTCGCCACGA |
| HDAC3 | CCTCAGCATCCGAGGGCA | CGGGCAACATTTCGGACA |
| HMBS | TCTGGAGTCTAGACGGCTCAGA | TACGAGCAGTGATGCCTACCA |
| HPRT1 | ATGACCAGTCAACAGGGGACA | TATACTGCCTGACCAAGGAA |
| HSP90AB1 | CCAGACCCACTCCAACCGCA | AGAGGGGGGATCTCATCAGGA |
| LDHA | AAAATACAGCCCGAACTGCAA | CAAGGACCCACCCATGACA |
| MRM2 | GACCCGAGAACCTCACAGAGA | ATGTCTGGGGTCACGCTGAGA |
| MRPS5 | GAAGCAAGGAAGAGCAGGAGA | CAAGACTGATGCCTCCCCA |
| MTMR14 | GAGAGACTCGGCTGCAGGA | CCGATGGCACCGGAAGGA |
| NACA | CACCCACAACTACCCTAGCCA | AAAGGTGCAAGATGAGAGCCCA |
| NDOR1 | CACCCCTCACGGCTGCAGA | GTGTCTCTGGGAAGGCCAGA |
| NOL7 | CTGTTGCTCGGGCAGCCCA | CTGGGCGCTGGCGAAAGTCA |
| NONO | GATGGAAGCTGCACGCCA | GCCATCTGACCCATCCGA |
| NUBP1 | CGGAGCTCATGTGCCAGGA | GGCTAACGTGGCTGGGGA |

FIG. 8 (Cont.)

| Gene Name | Forward GSP | Reverse GSP |
|---|---|---|
| PGK1 | CTGCTTGGACAATGGAGCCA | GAACATCCTTGCCCAGCAGAGA |
| PIAS1 | CAGTATCCCGCACCCCAA | GAAAAACCGAGACGAGTGTAGGA |
| PIK3R4 | TGGGTCACTGGACCCACCAA | CAAAGGGACACAAATGCCAGCA |
| POLR2A | GCATGGAGATCCCCACCA | CTGGCATCTGACGCAGCA |
| PPIA | GCAGAGGGTTAAGGCGCAGA | TTGCAAAACCTCAAAGCCTCCA |
| PPIH | CTGCACCGGAGAATTCAGGA | GCCATGGAAAGCAGGCCTGGA |
| PRPF38A | CACACTGCGCTACAGGAGGA | CGGGATCTGTGCCGCCGA |
| RBM45 | AAGTTCGCCCGCAGCTCACA | CCAGATGATCGGGACTGAGCA |
| RPL13A | CCACAAAACCAAGCGAGGCCA | TTGTAGGCTTCAGACGCACGA |
| RPL30 | GTGGCCGCAAAGAAGACGA | GATTTCCTCAAAGCTGGGCA |
| RPL5 | AGATCTATGAAGGCCAAGTGGA | TGGCAAGGCCTGCATCCA |
| RPL8 | CTCCCACAACCCTGAGACCAA | GATGGTGGAGGGCTTGCCGA |
| RPLP0 | TCACTGTGCCAGCCCAGA | TGCTGGATGACCAGCCCA |
| RPS19 | GGAAGCTGAAAGTCCCCGA | CCCCAGCGCCACCCCGGA |
| SAP130 | ATACCCACTGGCGGCACA | GACGGTAGACGCTACCCCA |
| SDHA | GGGAAGCGTGTTGCAAGAA | TAGATGGTCTGCAGCGCA |
| SF3A3 | CCAAAGCCTTCCAGCGACA | GGCCCACAAGGAGACAGCA |
| SLC4A1AP | TTGCACCTGGGGAATGGGAGA | CTGAGTGAATGGCCTCAGCCA |
| TBP | CCACGCCAGCTTCGGAGA | CGGCGTTTCGGGCACGAA |
| TFRC | GGCACGAGCAGCTGCAGA | TCCACGAGCAGAATACAGCCA |
| TLK2 | CGATGCTTGGCCTACCGA | GCCCCAGAGGTTGATGCA |
| TMUB2 | CCCCCCTGAGATCTGAGGA | TTCAGGGCACCCACGGTA |
| TRIM39 | TAGACTATGAGGCCGGCACA | TCTTCCGTCCAGCCCGGA |
| TTC31 | CCCTCCAGCCACTTCCCCA | GGTCCTGGGGCTTGAGAGGA |
| TUBB | GCTCTCACAGTGCCGGAA | TGGACATCCGACCACGGA |
| TUBB2A | GAGGAGGAGGGCGAGGACGA | CTAACAGAGGCAAAACTGAGCACCA |
| UBC | CATCCCTCCTGACCAGCAGA | GAGACGGAGCACCAGGTGCA |
| USP39 | GGCACATGTGTCTCCCCA | TCCTCATGGACCCCTGGA |
| VPS33B | GACCGACAAGGCTGCAGGAA | CTCGCCGTCCACACGTGGGA |
| YWHAZ | AAAAAACAGCAGATGGCTCGAGA | TCTTGTCATCACCAGCGGCA |
| ZC3H14 | CCTGCAAAGCCTTCCCCA | CAAGCAGGGAAGTAACGGCA |
| ZKSCAN5 | CATCAGCGCGTCCACACA | GAGTCGAAGATGTCCAGCCA |
| ZNF143 | GCAGGCTGTGGGAAGGCA | GTTGTAAAGGACCGACCGCA |
| ZNF346 | CACTACCTGGGGAAGACCCA | TGCATGGCAGAGGCTGCA |
| ZNF384 | CTTCAGCAGCACACCCGA | GTGGGACTGCAGATTGGAGA |
| A2M | CAGTTCCTGAACACGGAAGGAA | AAACCTCACCACCTGATGGACA |
| ABCA7 | GGGGGACACATTGGCCAGCA | GATGGCATCGGATTGAGGGCA |
| ABCA8 | AGGGCTGAGGAAAGGGGA | GGTCGACGGCTCATCCAGA |
| ABCB1 | TCCGAGCACACCTGGGCA | AGGGCACGAGCTATGGCA |
| ABCC1 | CAACGGGACTCAGGAGCACA | AGCTCATGGGTGACCGCA |
| ABCG2 | GCACTGGCCATAGCAGCA | TACTGAAGCCATGACAGCCA |

FIG. 8 (Cont.)

| Gene Name | Forward GSP | Reverse GSP |
|---|---|---|
| ABI3BP | AGATGGACGCACTGGGCA | GGACAGGTTCCTGGCGAA |
| ACAN | GGGAGGTGTTCTTCGCCA | TGACGATGGGGTAGCGGA |
| ACE | TTCCAGGAGCTGCAGCCA | CTGAAGGGAAGGGCACCA |
| ACHE | TGCCCCACGGCTACGAGA | GCGGGCAAAGTTGGCCCA |
| ACKR1 | TGGCAGAAGCCCTGGCAA | ATCCTTCAGGGAGGGGCA |
| ACKR3 | AGGAGTGGCTGATCGGCA | TGTCCAGCAGCACCGCCA |
| ACP2 | AAGGAGGGGATGCTACAGCA | TTGGCCTCAGCACTCATGAGA |
| ACTN1 | TGATCAGCTGGAGGGCGA | TGGCATCCCGGGTCAGGA |
| ACVR1 | AGCCATTGCCCATCGAGA | TTGGTGCCCACACGGGGA |
| ACVR2A | AGTTACACCTAAGCCACCCTA | ACAAGTACAGGAGGGTAGGCCA |
| ACVR2B | ACGGACAGGTAGGCACGAGA | TGCAGCCTTGCAGCGAGA |
| ADAM10 | AATGCAAACTGAAACCTGGGA | GCTGGGCAGAGAGCTGTGA |
| ADAM12 | CCGCCAGATTCCTACCCA | GGTGGAGGGGAGGAAGCA |
| ADAM15 | CAACCAGCTCCCTGACCACA | GCCGTTCAGAGGGACCAGA |
| ADAM17 | CTGCGAGAGGGAACAGCA | TCAGCATCGACATAGGGCA |
| ADAM19 | CCGCCCTTCTGCAACACA | GCCTCAGCTTGGAAGGGA |
| ADAM22 | GATAGTGGAAGCCACCCCA | GCTCAGGAAAGCAGTTGCCA |
| ADAM8 | GAGCAGACTGCACCCCAA | CAGCCCTGCTGAACACACA |
| ADAM9 | ACCCTTGCTGCGAAGGAA | TACCTCCTGGAAGGAACCGA |
| ADAMTS15 | CGGAAAGAGCTTCCGGGA | TGCCTTGGACACAGACGGA |
| ADAMTSL4 | GGGGAACCTCACTGACCGA | GACCCAGGGGGATCCACA |
| ADGRA2 | CCTCTGGCACAGAACCCCA | GGAAGTGCGTGGTCACCA |
| ADGRA3 | CGTGGCAACAGCTCGACA | GCGCTGAAGACACTGCACA |
| ADGRE1 | TCTTCCTCGCCGGTATACACA | AACAGTATCACAGCCTCCACCA |
| ADGRE2 | CCCTCCGGAACACAAGGA | GAGGAGGCAGTACACCAGGA |
| ADGRE3 | CTGGCCGCCTTCACCTGGA | AACGCCATAGCCGACTGGGA |
| ADGRE5 | GGCAGCACCACCTGCCAA | GGAGCCCACGAAGAGGCA |
| ADGRF1 | AAGACATCGTGACGTGCCAA | AAAGCCTCGATGATCAGGCA |
| ADGRF5 | CCATGCAAGCAGGAGAAGAGCA | TACCTTCAGATCCCAGAGGCA |
| ADGRG1 | GGGTGTGAGACCGTCAGGA | TGGTGACAAGGCAGGCCA |
| ADGRG2 | ACATGGATGGGCCTAGAAGCA | CATCCGGTGAACCATTGGGGA |
| ADGRG6 | CTGGATGGGGCTAGAAGCAA | TGACACCACTAAGGCAGGCA |
| ADGRL2 | TCTCATGGCCCACAGGGAA | TGAAGATGCAGATAGCCAGGCA |
| ADGRL4 | ATCTAAGCCCAGCCGTGGTA | CAACCCTGCAGTGTGACGA |
| ADIPOQ | CCAGGCCGTGATGGCAGA | CCCGGAAAGCCTCGGGGA |
| ADORA1 | CCAAGTCGCTGGCCCTCA | CTTGTGGCAGGACGGGCA |
| ADRA2A | GGTGCTCCGTGCCACGCA | TCTTGAAGGCGCGGCGGA |
| ADRA2C | CCATCAGCCTGGACCGCTA | GACGGCCGAGATGAGCCA |
| ADRB2 | CCACCCACCAGGAAGCCA | TGAAAGACCCTGGAGTAGACGA |
| AEBP1 | TCCCCATTGCCAACGCCA | TCCAGTTGGAGCGAGCCA |
| AGRN | CAGGGTCTCACTGGAGCGAA | ATGGCACCGTCGAAGCCA |

FIG. 8 (Cont.)

| Gene Name | Forward GSP | Reverse GSP |
|---|---|---|
| AGTR1 | CCCGCCTTCGACGCACA | GGCCCAGCCCTATCGGGA |
| AGTR2 | ATAACCCGTGACCAAGTCCTGA | GGAACCCTAAACACACTGCGGA |
| AHSG | AGCTGGCTCACCCCCAGA | CTCCTGAGGGTGACCCCA |
| AKT3 | ATGCAGCCACCATGAAGACA | GACAACCCCTAGGCCCCA |
| ALB | TTGGTGAACAGGCGACCA | TCACGAGCTCAACAAGTGCA |
| ALCAM | ACACGATGAGGCAGACGAGA | ACACCAGCAACAAGGGCA |
| ALK | CAAAGAAGGAGCCACACGACA | CAGCGAAGAGGGCTCTAGGA |
| ALPL | TGCATGAGGCGGTGGAGA | CTCGTTCACCGCCCACCA |
| ALPP | ACAGCCAAGGTGGGACCA | CACAGACGGGTCCAGGGA |
| AMBP | CTGCCAGGGCAACGGGAA | CTCATCACCATCACCAGGGA |
| AMIGO1 | GCAGGTGCAGGTCGAGGA | AGGACCAGGACCACACTAAGGA |
| AMIGO2 | GACTCCATGCCCCTGCAA | CGTTCATCAGCGGAGGCA |
| ANGPT1 | CAACTGGAGCTGATGGACACA | CCAACCTCCCCCATTGACA |
| ANGPTL1 | CAAGCAAAAGAAGCTGGGCA | TGAATAACAGTCCAACCCCCA |
| ANGPTL2 | TCACCACCCTGGACAGAGA | TCCTCGGAACTCAGCCCA |
| ANGPTL4 | GGGACAAGAACTGCGCCA | CCCGCCAGGTCTTCCAGA |
| ANO5 | AAACCACACTGCACCTTCGGAA | ACATCAGGTATCATCCAGGCCA |
| ANO6 | GAAAGCCCAAGACATTGGAGCA | AGTAGTACACTAGGCGGGGGA |
| ANO9 | ATCCAGTACGGCTTCACCACCA | GCACACCGATGGTCTCCAGCA |
| ANP32B | GACTCAGATGCCGAGGTGGA | CTGACTTCATCGTCGTCCTCA |
| ANPEP | GCTACACCCTGAACCCGGA | GGAGAACGAGCCACCACCA |
| ANTXR1 | GGGAGAAAAGGGCTCCACA | TCAGTAGGACCCACAAGGCA |
| APCDD1 | TCAACGGTCAGAGGCCCA | GAGGAGGCACACTGGACCA |
| APLNR | GTTACGCACCACCGGGGA | CCACGGTGGTGGACGAGA |
| APLP1 | CCGAGAAGGCACAGCAGA | TCTGGTCAAGCAGGCCCA |
| APLP2 | CTCGAGGAAGAGCGGGAA | CATCACCAGGCTGATGACGA |
| APOB | CTGACCTGCGCAACGAGA | GAATCTGGGGCAGGCCCA |
| APOD | GCCACCCCAGTTAACCTCACA | GGATCCAGTACGGTGCCGA |
| APOE | AGGAGCAGGCCCAGCAGA | CTTCCACCAGGGGCTCGA |
| APOH | AATGGAGCCGTACGCTATACGA | GGAGGGCAGATGATGGGA |
| AQP1 | CTGGCTACTACCGACCGGA | GTGTGTGATCACCGCGGA |
| AQP2 | CAGCTGTCGTCACTGGCAA | CGAGTGCAGCTCCACCGA |
| AREG | CGGTGTGGGGAAAAGTCCA | AGCAACAGCTGTGAGGATCACA |
| ARSF | GTCGCATCAGTGTCAGGAGGA | TGAGCCTTCCAAACTGACCCA |
| ASIC1 | CATGGTCAAGATCCCCAGCAA | GCCCCGATGAACAGCCCCA |
| ASPN | GGTGCAGCCACACCAGGA | GCAGAGCACAAAGCCAGGA |
| ATM | CCGATGGCAAGGAGAGGA | CACTTCGCTGAGAGAGGGGA |
| ATP1A1 | GGAATGATCCAGGCCCTGGGA | TGATCCAGCGGTCATCCCA |
| ATP1A3 | CGCTCTGAAGAAGGCCGA | CCTGTGACGATGGAGGCA |
| ATP1B1 | CCCCGCCAGGATTAACACA | TTCGGTTCACTGGGCACA |
| ATP1B2 | GAATGTGACCCCCAACGTGGA | TTGATGCGGAGTTTGAAGGCCA |

FIG. 8 (Cont.)

| Gene Name | Forward GSP | Reverse GSP |
|---|---|---|
| ATP1B3 | CAGAGCCTGGCCGAGTGGAA | AAGAGTGCAGCCAGGAACCCA |
| ATP6AP1 | CAGCCCTCTCCCTGGCAGA | CGGGGGAGAAGAAGCTGGCA |
| ATP6V0A2 | GCTTAGCCTGGCTCACGCACA | TCTACCCAGTGGAGGCGTA |
| ATRAID | CTGCCTGAATCAGAAGGGCA | AGCCACGGAAGGTGTTGGCCA |
| ATRN | GAGATTGCACCAGCGGCA | AAGGAGGCCACGTAGGCA |
| AXL | CCCAGCCAGACCCTAAGGA | AGGGGTTGTGGAAGGGCA |
| B3GAT1 | AGATGCGCAGCACCAGGA | ACACCGTCTTCCAGCCGA |
| BACE1 | ATCACCATCCTTCCGCAGCAA | AAGACAACGTAGAAGCCCTCCA |
| BATF | GCCGACAGAGGCAGACACAGAA | CTGTTCAGCACCGACGTGAA |
| BCAM | GGATTACGACGCGGCAGA | GCACGGAGCAGTTCACGA |
| BCAN | GCACACCCGAGGAACAGGA | GGACGCCATCCGACCACA |
| BCHE | TCCTGAGGCTCCAGGGAA | GAGATGTTACCGCCCAAGGA |
| BCL2 | GGGGTGAACTGGGGGAGGA | CTCAGTCATCCACAGGGCGA |
| BCL6 | GTTCAACCGGCCAGCCAA | TAAGCACATGGGCACGGA |
| BDNF | CCAGAAAGTTCGGCCCAA | GCCGGACCCTCATGGACA |
| BGLAP | CCAGGAGGGAGGTGTGTGA | GGGCCGTAGAAGCGCCGA |
| BGN | CGGGCCTACTACAACGGCA | CAGGCGGTCAGTGACGCA |
| BLK | AGGGATGAGCAACCCCGA | CCAGCACCGACTGCAGGA |
| BMP1 | CATTGCCCAAGCCCGCAA | GCCTTCCTCCAGAAGCCA |
| BMP4 | GGGCACCTCATCACACGA | CACCTCAATGGCTAGCCCA |
| BMPR2 | CTGCCACAACCCAATATGCCAA | CAGCCGGGTGTCCTCACCA |
| BSG | CATCCGGGGGCAGCTCTGGA | CTCCAGGGGTGAGCTGGGGA |
| BST1 | CGTGGACCACAGCACCCA | CCTGGAAGCCAGCACCAGA |
| BST2 | CTGCAACAAGAGCTGACCGA | GGGAAGCCATTAGGGCCA |
| BTD | TGGCTGGGAGAATGACCA | CCTCTCATACAAGCGCCCA |
| BTLA | CGACCCTCCAAGGACGAA | CAGGCAGCAGAACAGGCA |
| BTN2A1 | CAGCCCAGGAAAACGGCA | GATATGCACTCCAGCCGGA |
| BTN3A1 | TATCGGACTCTAACTGAGCCCA | TGCGATCCATCCACAGCA |
| BTN3A2 | GAGAGGCGGCTCCGGGGA | AAGCAGCAGCAAGATAGGCA |
| BTN3A3 | AGCCCACTGCCCTGACCA | GGTGGGCAGGGAGAAGCA |
| BVES | AGAGTCCAGCCCATTGAGAGA | ACATCGGTAGAGAGTGGCCCA |
| C11orf24 | GGCACCGGAGCAGGTAGAGA | GGGGCTCAGTGGTGACCA |
| C12orf49 | AACGTCCCTAGCACGAAGCA | CGGCTGCCCGGTTGAGGA |
| C1orf159 | GCTGGAACGCGGACGGGA | AATGGCGCACCCGGGCCA |
| C1QTNF2 | ACAACGGCCAGTACCGCA | GTCACCCTGCTTGAGAGCCA |
| C3 | CCATCACCACGTGGGAGA | CAACAGAGTAGGGTAGCCGCA |
| C4A | GCAGCCTGTGCCCAGCTCAA | TCCTCCCAGCGGAGGTGGGA |
| C4BPA | CCTAGGCCGACAAAAGAGGA | CAGGGCAACATAACGCCTCA |
| C4BPB | GAGGACCACACCTGGGCA | CCACTCCCCATCAACGCA |
| C5AR1 | GGCCTCTACTCACGCTCACGA | GGTGACGATGGCTCCAGGA |
| C6orf120 | ACCCCTCCCACCTGGAGA | CGAACGGGTGCTGCTCGA |

FIG. 8 (Cont.)

| Gene Name | Forward GSP | Reverse GSP |
|---|---|---|
| CA12 | TACTGCACACACATGGACGA | GAATGCCAGCCAGGGCCA |
| CACHD1 | ACCATGAGCCCACAGGAGGA | AGTCTGAGGGGGGGTATCCA |
| CACNA2D1 | GCAGGACATCGCTCAGCA | AGGGAGGCCGTGAAGTCA |
| CACNA2D2 | GCTAGTGCAGAGACCGCGA | GAGCAGCAGTTGCAGGGA |
| CADM1 | AGCCATCGGGAAGCCCCA | ATGAACAGGTTGGGCCCA |
| CADM2 | CCAGAATGGCCCTGACCA | TTGCCAGATATCGACCAAGCA |
| CADM3 | GGCACCTACGGCTGCACA | GAGCATGATGAGCAGCAGGA |
| CADM4 | TGTGGTGAGGGAGGGAGACA | GCGGATACCAGACCCGGCA |
| CALCR | CTGGCTGAGTGTGGAAACCCA | TTGGTCACAAGCACCCGGA |
| CALCRL | AAGAGCCTAAGTTGCCAAAGGA | ATGCCTTCACAGAGCATCCA |
| CALR | GGCACTTGGATCCACCCAGA | GTGCCAGACTTGACCTGCCA |
| CALU | AGAATGGGTAAAGACAGAGCGA | CATAGTCTGAGGGAAGGATCCA |
| CANX | GACGCAGAGAAACCTGAGGA | AATCACAGGTCGCTGCCA |
| CAPNS1 | AAACAGTTCGACACTGACCGA | CACGGAACATGGCGTCCA |
| CASD1 | TGGAAAGGCTGGATGCAA | ATGCAGCAACCAGAACTCGA |
| CAV3 | ACGGCGTGTGGAAGGTGA | CAGAAGGAGATGCAGGCGA |
| CCDC126 | CAGCAGCCAACACCACCA | CAGTGGATGGAGCAGCACA |
| CCDC80 | GAGGACCCAAGGAGAGCACA | TGAGGGAGGTTGGGGCAA |
| CCL1 | GCTGAGGCACTGCCCGTCAA | AGCAAAAGCAGGGCAGAAGGAA |
| CCL13 | CAGATGCACTCAACGTCCCA | ATGACAGCCTTCTGGGGACA |
| CCL17 | GGACCAATGTGGGCCGGGA | CAAAAACGATGGCATCCCTGGA |
| CCL2 | AGGGCTCGCTCAGCCAGA | CTGCTTGGGGTCAGCACAGA |
| CCL22 | GCGCCAACATGGAAGACA | GGTTAGCAACACCACGCCA |
| CCL7 | GAGACCAAACCAGAAACCTCCA | TGAAAGCAGCTGCTGTGAGCA |
| CCR1 | GGTGATCGCCTACACGCA | CCACGGAGAGGAAGGGGA |
| CCR10 | TCTACTGGCTGCGCGCGA | GCCCAGGAAGGCGTAGAGA |
| CCR2 | TACCAACGAGAGCGGTGAA | TAAGATGAGGACGACCAGCA |
| CCR3 | GCTGCATGAACCCGGTGA | GCCCAGGTGCATGAGCAA |
| CCR4 | TGATCATCAGGACCTTGCAGCA | GCTCCACCAGGGTCTCTAGGA |
| CCR5 | GTTTGCGTCTCTCCCAGGAA | CCATGACAAGCAGCGGCA |
| CCR6 | GCATGGACCGGTACATCGCCA | GATGATGACTGACAGCCCCCA |
| CCR7 | GGCCCAGACGGTGGCCAA | TGCGGAACTTGACGCCGA |
| CD101 | TGATGAGCCGTCAGCCGCAA | GCTGGAACTGCCACGTCACA |
| CD109 | GCTCCAAGCCTTCCAACCA | CCCCATCCTCACTGGGAA |
| CD14 | CGCTGCGCAACACAGGAA | GTTCAGGGCGCTGGACCA |
| CD151 | CTGGCGAGACAGTGAGTGGA | CACCACCGTCTTGCAGCA |
| CD160 | GGGAACTACACAGTGACGGGA | GGGCCACAAGGCTGGTGA |
| CD163 | ATGGGAGAAGAGACTGGCCA | GGTCCAGTCCCCTGACCA |
| CD164 | AGCACCCGAACGTGACGA | GGTGACCAGCGGGAGGGA |
| CD177 | CCCCGAATGACCTGCCCCA | TGAGAGACTCCAGGCCCTCA |
| CD180 | TAAGCCACAACAGCCTGACA | AGGGAGGAGACGGGGTGA |

FIG. 8 (Cont.)

| Gene Name | Forward GSP | Reverse GSP |
|---|---|---|
| CD19 | ACCGTGGCAACCTGACCA | CCACAAGGGAACACAGGCA |
| CD1A | GCGGCAAGTGAAGCCCGA | TCCCATCAGCACTGGGCA |
| CD1B | TTGAGATCCAGGGCATAGCA | GGGAAGGCACACATGAAGCA |
| CD1C | GAACAGGAGCAACTGGGCA | TCACTCGACAAGACAGGCCA |
| CD1D | GCACTCAGCCAGGGGACA | GGAACAGCAAGCACGCCA |
| CD1E | GGGAAGTCAGCAGAGGGAGA | GAGGAGGAACAGGAGCAGCA |
| CD2 | CAGCAGGGAACAAAGTCAGCA | GAAAACGAGCAGTGCCACAA |
| CD200 | TGTCTCACCCAAATGGGACCA | TAAAGTCGGTCACAGTCCCCA |
| CD200R1 | GAGGCCAGCCTTCCTGCACA | TCATGAGTGATGGCCACGGTA |
| CD207 | GACCTCAGAGAGTGAGCAGGA | GAATGGCGTGTCATCCACCCA |
| CD209 | CCAGCGGAACTGGCACGA | CAACAGAGGTGAGCCGTCCA |
| CD22 | CTGTGAGAGCGACGCCAA | GAGGGTGCTGAGAGGCGA |
| CD226 | GATCGGGACCCAGCAGGA | GAGAGCAGGAATAGTAGCCAACA |
| CD24 | GGGACATGGGCAGAGCA | GGCCAACCCAGAGTTGGA |
| CD244 | CCAGGAAGTCTGGATCCAGGA | TCTTTGCGGCTCAATCGAGCA |
| CD247 | GAAGTTCAGCAGGAGCGCAGA | CCATCTCAGGGTCCCGGCCA |
| CD27 | ACCCACTGGCCACCCCAA | GGCTCTGCAGGCTCCACA |
| CD274 | GTGGTGCCGACTACAAGCGAA | GGGTAGCCCTCAGCCTGACA |
| CD276 | GCAGATGGCCAACGAGCA | GAGACAGACAGACAGCCCCA |
| CD28 | GGTGAAGCAGTCGCCCCA | TACAACACAGACTTCCACAGCA |
| CD300E | CGAAACCTCAGCACCGGGGA | TCACCCAGAAGACAGCACCCA |
| CD300LF | AGCAGAAAGCAGCCGGGA | CCTTCGGCAAGGAAGCCA |
| CD302 | CTGCACATCAAGACAGGTGA | TACCGTGCTAGCAATCACCA |
| CD33 | AGACGCCAGGAGGAGGGA | GCTCACAGGCCCAGGACA |
| CD34 | GACCTCCAGCTGTGCGGA | GTTCTGTTGGCCAAGACCA |
| CD36 | AACCCAGGACGCTGAGGA | GCAGCTGCCACAGCCAGA |
| CD37 | CTTGTCGGCGACCAACGA | TGTGGCTCTCTGCAGGGA |
| CD38 | CACAGGTCCAGCGGGACA | TGAGCATCACATGGACCACA |
| CD3D | TGGACCTGGGAAAACGCA | CTGGATCCAGCTCCACACA |
| CD3E | CCAAGCCTGTGACACGAGGA | GCGTCTCTGATTCAGGCCA |
| CD3G | CCAAGGACCCTCGAGGGA | CTGAAGCTCTCGACTGGCGA |
| CD4 | CTGCTGAGTGACTCGGGACA | GCCGGCACCTGACACAGA |
| CD40 | TGGACAAGCTGTGAGACCA | CAGCACCAAGAGGATGGCA |
| CD40LG | TCAGAGCTGCAAATACCCACA | GCCAAAGGACGTGAAGCCA |
| CD44 | TCAGTCACAGACCTGCCCAA | TGGACATAGCGGGTGCCA |
| CD46 | GGAGCGGTAAGCCCCCAA | TGGAGCAGCACGACTCCA |
| CD47 | TGCTGCGGATCAGCTCAGCTA | TAAAGTCAGTGGGGACAGTGGA |
| CD48 | GAAAGAGGACAACAGCACCTACA | ACAGACTCGCCAGGTATCACA |
| CD5 | CAGCAGCATCTGTGAAGGCA | GCGTCCAGCACTCGATAGGA |
| CD52 | GGACAAAACGACACCAGCCA | CAACTGAAGCAGAAGAGGTGGA |
| CD53 | AGCGTGGGACTCCATCCA | TCGCATAGCAACCCTCCA |

FIG. 8 (Cont.)

| Gene Name | Forward GSP | Reverse GSP |
|---|---|---|
| CD55 | CATGCCCTAATCCGGGAGA | ACGGGTCACTCCACTGGACA |
| CD58 | CAGAGGCCGGCCCGACGA | GCAGTGCAGCAGGCAGACCA |
| CD59 | ACAACCCGCTTGAGGGAA | AGAAATGGAGTCACCAGCAGA |
| CD6 | GCCACCCTTGGAGGAAGGA | GGGTGATACTGAGGGCCCA |
| CD63 | TCAACGAGAAGGCGATCCA | GCTGCTGCAGCTACCACCA |
| CD68 | CTTCCCCCACGCAGCACA | ACCAGGGCGAGGAGGCCA |
| CD69 | CAATGCCATCAGACAGCCA | AATGACAGCAAGAGTAGCACCA |
| CD7 | TCTCAGGGTCCCAGGACAA | TCCTCTGTCACCAGGACCA |
| CD70 | GCATGGACCAGAGCTGGACA | AGCAGATTCCCACGGCCA |
| CD72 | GCAGCTCCAGCAGACGAA | CTTCCTGACTCTGCGCCA |
| CD74 | CCCCGGAGAGCAAGTGCA | CCTGGCCAGCGAGGAGCA |
| CD79A | GGCAACGAGTCATACCAGCA | CCGCGCAGAACAGGAGGA |
| CD79B | GGACGAGAATCCCCAGCA | ATGGTGAGGGTGGCGAGA |
| CD80 | AGCTGGCACAAACTCGCA | CGCAGAGCCAGGATCACA |
| CD81 | CTATGACCAGGCCCTACAGCA | AGTCAGTGTGCTGGAGCCACA |
| CD82 | TGCAGGAGAACCTGGGCA | GGAATGGACGTGCCGGCA |
| CD83 | CCCCCAATGAAAGGCCCTA | GTGCAGGGCATCCTGTCA |
| CD84 | TACACGTGTACAGCCCAGA | GAACATAGCCAGCACGCTCA |
| CD86 | GAAGAAGCGGCCTCGCAA | CACGCTGGGCTTCATCAGA |
| CD8A | GCCGAGAGAACGAGGGCTA | CTGGCAGGAAGACCGGCA |
| CD8B | GCTGACCTTCGGGAAGGGAA | TGGCCTGGGTAACCGGCACA |
| CD9 | GAAACGCTGAAAGCCATCCA | TGATGGCATCAGGACAGGA |
| CD93 | CCAGCATCCATCACGCCA | CAGGAGTAGGATGGCCACCA |
| CD96 | ACCAGCACAGCCAGAGCA | GCTGCTACAATCACTGGCCA |
| CD99 | AGAAGGGGAAGAGGCCGA | CTCCAGCCACGGCGACCA |
| CDCP1 | CTCTAACTGCAGCCCCACGA | ATGATGAGCCCGAGGGCA |
| CDH1 | GATGCCCCCAATACCCCA | CCAGCACATCCACGGTGA |
| CDH10 | CAGCACAGGCACACTGACCA | TGCAGAGGAGGATGGCGA |
| CDH11 | TCTGAACGCCGGCCTGAGCA | CAATGACCAGGAGAATGACGATGCA |
| CDH13 | CAGGGAAACCACCCATGACGAA | TGAGGGCAGGCTGAAGCGCA |
| CDH15 | CTTCGGACCAGCCTAGCAGA | TGGGTCTGGATCCGGCCA |
| CDH17 | ACTGTCTACCAGGCACACAGA | GCCCACAGTGGGTATCCCA |
| CDH19 | CACAAGCGCTGAGATCAGGA | AAAAGCGTAGGTCTGGAGGGA |
| CDH2 | CTTGAGCCAGCTGCAGCA | GCTGCAGATCGGACCGGA |
| CDH3 | TGACGGTGATCAGGGCCA | GCAGCACCAGCAGGAGGA |
| CDH4 | GGTTGGAGTGGCAGGAACGA | GAGAAACCTGCTGGGCCAGA |
| CDH5 | GCTCCGAGTCCATAGCCGA | GAGCCGTACAGCTCAGCCA |
| CDH6 | CTCCAACAGCTCGCGACA | GTGGTCACTGACTCCAGCGA |
| CDH8 | GTGGACTGGGAGACAAGCAA | TCATCAGCGTCGGTCGCA |
| CDH9 | GACGCAGACCCAAGTGCA | GGCCCCCAGTCACTGAGGTA |
| CDON | CGGTTCGAGTCCCAGGAA | GATGCCCACGGGTGGAGA |

FIG. 8 (Cont.)

| Gene Name | Forward GSP | Reverse GSP |
|---|---|---|
| CDSN | AGCAGCAGCTCCAGTTCCCAA | GCCCCCAGTCAGTGTCAAGGA |
| CEACAM1 | GCAACACCACCCTCAGCA | CAACCAGGGCCACTACTCCA |
| CEACAM6 | CTGGCCTCAATAGGACCACA | GAGCCACCCTGGCCAGCA |
| CEACAM8 | GCCCAGATGCCCCCACCA | GGTGGATTAGAGGCCGCA |
| CELSR1 | CTGTCCAGGAACCGGACACA | TCAGGAGGACGAAGGCCA |
| CELSR2 | TGAGCGGCTACAGCGGAA | TGTGTGGCAGACAGCCCA |
| CELSR3 | GCAGCCTTTCACAGCCAGCCA | AGGGGACGTAGAACAGGGGCA |
| CFH | AGGCGGGTGAGCAAGTGA | GGGCGGATTCACACAGGA |
| CGN | GATCGGGGAGGACTCTAAGCA | AAGTCGGCTCAGTCCTCCAGA |
| CHAT | GCTACAACCCCCAGCCAGA | TCTCAGTAGGCGGCAGCA |
| CHGA | AGGAGGAGGACAACCGGGACA | CAAGGCTGTCCTCCCGGGA |
| CHIT1 | CAGCCCTCTGAACCTGAGCA | GAGGATTGGGATAGAGCCCA |
| CHL1 | AAGCCACAGGGAGCCCCA | GACTGAGGGTCAGGCCCA |
| CHRNA3 | ACCCCTGCCAGGACGGGA | ACAAAGCAGAGAGGGACAGCA |
| CHST10 | CGACTATCCCTCCGGGCA | GGGCATACAGGCGTCGGA |
| CLCA2 | CATAAGCACCCCAGCCCA | GGCCAGCTGGAACTCCCA |
| CLDN12 | CCGGTATGACGGGAGCAGTGA | ATTGACCAGACACTTGGCCA |
| CLEC12A | AACCTCTCCACCACACTGCAA | GCTGGCATTCTGAGCAGCACA |
| CLEC14A | GAGAAGCTGGGAGAGACACCA | GAGGAGTCGAAAGCCTGAGGA |
| CLEC2A | CTGCGGGATGGCAGAGCTGA | ACTCCAAGCCAGTCCCCTGA |
| CLEC2D | GCATGCCCAGAAAGCTGGA | TCAACCTGAGCAAGATCAGCA |
| CLEC4A | TCAGATCCAGAAGGTCAGCGA | CAACGCAGCGCTCATTGGGA |
| CLEC4C | CTGCTGCCCAACCCCTTGGA | CACCACCAGATCAGCCCCCA |
| CLEC5A | TCAACACGCCAGAGAAACTGA | TAGGCCAATGGTCGCACA |
| CLEC9A | GGGATAGCCCAGCACCAGACA | CCTGCAACAACTTGACGCCCA |
| CLIP1 | CAGCCAAAGCCAAGGCCA | CCTGGCGTAACGGGAGGA |
| CLIP2 | AAGGAGAAGCGGCGCCTGGA | CTCCGCTCCTTCCGCAGCA |
| CLMP | AGGCAACGAAGCTGGGAAGGA | TTCGGATTAGCAGCCACACCA |
| CLU | TCATACGAGAAGGCGACGA | CAAGGAGGAGGTGTTGAGCA |
| CMA1 | CGGGCTCAGACACTCTGCAA | TCCTGGGATTGCCCACACA |
| CMKLR1 | ACAGCTGCATGAACCCCA | TAGAGCATTGACCAGGCGA |
| CNGB1 | GGCGCATGCTGAGAAGCA | TCCTGTCATAGCGAGGGCA |
| CNNM2 | GGTCACCGATCCCTACAACGA | TTCGCCGGTGATCATGAAGCA |
| CNNM3 | CCTGAGAACACCGACCTGCA | AGGGCTGCCTTCCACCGGGA |
| CNNM4 | CACTCGGCAGCAGTACCAGA | TCTCGTCCACCACAGGCA |
| CNR2 | TACGCTCAGTGACCAGGTCA | CAGGCAGTGATGGGCAGA |
| CNTFR | AGACCACGACCAGCACCA | TGATGGGGACGCTGACCA |
| CNTN1 | CCGCGTGGTAGCAACCAA | CTACATCTGAAGGAGCCACA |
| CNTN3 | GGAGACAGGGCACCTCTACA | CACCATCAGAACGTAGCACCA |
| CNTNAP1 | TGAGCCGGCCAGTGCCA | CGGGCACAGGCCGACCA |
| CNTNAP2 | CGCCTGGAGCTCTACAGCCA | GCTGGTGCAATGGCCCGA |

FIG. 8 (Cont.)

| Gene Name | Forward GSP | Reverse GSP |
|---|---|---|
| COL10A1 | ATGGAGAGGCTGGCCCAA | GCTATGCCAGCTGGGCCA |
| COL11A1 | GCAGGCCAAGATGGACCA | GACCAGGTGGACCTAAGGGA |
| COL12A1 | CAGAAGCCCCTACAGAGCCA | GTCCCCAATGCTCCAGGA |
| COL14A1 | CCAGGCGTTGGAACCCAA | CCAGGCTGGCCAGAAGGA |
| COL1A1 | CTGGCAAAGAAGGCGGCA | CCAGCAGGACCATCAGCA |
| COL1A2 | GAGGTCCTAGTGGCCCACA | GTGACCAGCGATACCAGGCA |
| COL26A1 | GGTCCAGCGCGTGTACCAGA | ACCGTCACCGTGCGGTAGGA |
| COL2A1 | GGACGAAGCAGCTGGCAA | CAGCCATCCTTCAGGGCA |
| COL3A1 | CAGGGCCTCGAGGTAACAGA | ACACCACCACAGCAAGGACCA |
| COL5A1 | CGGCCCTACTGGTGAACCA | GGGATCCCTCGAAGGCCA |
| COL5A2 | CTGGGCAACGTGGAGAGAGA | CAGGGTCTCCACGATCACCA |
| COL5A3 | AGGGGGAAAAGGGCCACA | CCAATGGGACCAGGGGGA |
| COL6A1 | CCAGGTGAATGAGCCCCA | GGTGGAAGACACCGCGGA |
| COL6A2 | GTGGTGCAGTACAGCCACGA | GCCCGTCCGTGATGACCA |
| COL6A3 | ACAGCGCTGAGACCACCA | CAACTGCCACTCTGGCGA |
| COL6A5 | GAAGAAGCAGCTCCTCCAGCA | GCTTGAACACGTTGCGGGTCA |
| COL6A6 | GAATGCCCAGTGCACCCA | AGGCGTCTGAGAAGCGCA |
| COL7A1 | TCGAGGCGAGAAGGGAGA | TGAGAGACGCGGAGCACA |
| COMP | TGATGCCTGCGACGACGA | CAGCGTTCTCCGGACACA |
| CP | CGCCGGAAATGAGGCCGA | GGCCACATGTGGAGCGTA |
| CPA1 | GGACCTACAGCCAGGGCA | TGATGGTCAGAAGCGCCA |
| CPD | CCTGGGCAGCATGAAGGA | CTGCCCACAAGGAAGGGA |
| CPM | GAAGCCGTCAAAAAGCCTGA | CATGGAGGTTTGCAGAGAGGA |
| CPQ | CAGGGCCATCATGGAGGA | CTGGCTCCAGGCACTCCA |
| CPZ | ACAGCTTCACGGGAGGCA | GGTGCACCGTCTCCACGA |
| CR1 | ATGTGACCCCCACCCAGA | AGTTCACAGCGAGGGGCA |
| CR2 | CCCTGGGCCAGAAAGAGGA | CATGTGAGCACTGGACAGCA |
| CRB2 | CATGGGACTGGGAAGTCAGCA | CCCACCTCCTACAGGATAAGGA |
| CREG1 | CACCATCTCCACGCTGGA | GCAGGTTGCTCACGGAGA |
| CRELD2 | ATCTGCACAGCCTGTGACGA | GCCGCACACTCGTCCACA |
| CRIM1 | CAGAACCCCTCACGCACCCA | CAGAAGGGCAGGACTCAGAGA |
| CRLF1 | CCGCTACCGAGTGGAGGACA | TGCAGCGCACTTGCACGA |
| CRLF2 | CACCAACGCCTCCCAAACCAA | GTATCTCAAAGAGCCCGGGGA |
| CRTAM | GTGCCTAACGTAACCCTGCAA | TCATGGTGGAGCACATGAGTACA |
| CRTAP | GCGAGGGTTCCAGGGAGA | GAGCAGATAGCTGACTGCACA |
| CSF1 | GGAGCACCAGGGATCGGA | CCAGCAAGACCAGGATGACA |
| CSF1R | GAAACCCAGGAGGCTGGAGA | CATCCCAGACCTGCAGCA |
| CSF2 | GAGCCGACCTGCCTACAGA | TTCCGGGGTTGGAGGGCA |
| CSF2RA | GAGCTCCTGGAGTGAAGCCA | GCCGAGGACGATGCCACA |
| CSF2RB | TCCAGAACGCCCACAGCA | CACAGAAGCGGAGGGCCA |
| CSF3R | CACGCCACCCATCACCAA | ACCAGAGTGGGGAGGCCA |

FIG. 8 (Cont.)

| Gene Name | Forward GSP | Reverse GSP |
|---|---|---|
| CSPG4 | AGTACGAGGTCCAGCGGGCA | CGAAGGCCAGCCGCCCTGAA |
| CSPG5 | CTGCGAGTCCATCATCACCGA | GAGCTCAGATGGGGTCCGGA |
| CTLA4 | GCTGAACCTGGCTACCAGGA | GCTGTCAGCCTGCCGAA |
| CTSD | GTGAGGCCATTGTGGACACA | CGCCCTGAATCAGCGGCA |
| CTSG | GCAGGGGAGATCATCGGA | CGCACCAGGAACCCTCCA |
| CTSK | AACCCAACAGGCAAGGCA | GGCTTGCATCAATGGCCA |
| CX3CR1 | CAACTCCATGAACAACCGGA | ATTGCGGAGCACGGGCCA |
| CXADR | CCAAAGAGCCGTACGTCCA | GTGGGAGAGTCGGACTCTGA |
| CXCL13 | GGACCCTCAAGCTGAATGGA | CAGAGCAGGGATAAGGGAAGA |
| CXCL16 | GGACCCATGGGTTCAGGAA | CTGAGTGGACTGCAAGGTGGA |
| CXCL5 | AGCCAGGGCCCATCGCCA | CCTTGGAGCACTGTGGGCCTA |
| CXCR1 | GCTCACCAGTCCCTCCCCAA | CCGACAGGGCCCTGTCTCCA |
| CXCR2 | ATCTACGCCTTCATTGGCCA | GTGCCCTGAAGAAGAGCCA |
| CXCR3 | CAGCTCTGAGGACTGCACCA | AGTGGGGCTCCAGGCAGCCA |
| CXCR4 | GCCAACGTCAGTGAGGCAGA | ACAGGATGACAATACCAGGCA |
| CXCR5 | GAGAACCAAGCAGAAACGCA | GATGTGGTAGGGTGACCAGCA |
| CXCR6 | CAGAGGCCATCGCATACCTGA | GTGAGACCCCAAGGTAAGGGA |
| CYBB | GGACGGCCCAACTGGGA | CACTCCCCGAGGGCCAGA |
| CYP27B1 | CCCCGAAGTCCAGACAGCA | TGACCACCGCCTTCAGCA |
| CYSLTR1 | CTGCCACATGCCATGACA | ATAGACCACACGGAGAGGCA |
| CYTH1 | GCCTGCAAGACCGAGGCTGA | GTAGAAAGGGTCCCTGCTGA |
| DAG1 | GGCTGCTCCCTGAACCAGA | CATGGATCTGCCTCCGGA |
| DBT | GCCTATGTGGGGAAGCCA | TCCATTGCCAGACGGCGA |
| DCBLD1 | GTTCCCTGTCAGACAAGCGA | CTCCCCCAAATCGATCTCCA |
| DCBLD2 | ATGTCAGGGCACCCCACA | GGCCTGGGCTGAGGAGCA |
| DCHS1 | GTCCATGCAGGAGGCACA | CAGGGTCAGGGTCAGCACA |
| DCN | TCTGGCCAACACGCCTCA | GTCCAGGTGGGCAGAAGTCA |
| DCT | AAACTCCAGGTTGGCCCACAA | CAACAGCACAAAAAGACCAACCA |
| DCX | GCCAGCTCTCTACCCCCAA | GTCATCCAAGGACAGAGGCA |
| DDR2 | CGAGATCTGGCCACACGA | CCCAAGACATCCAGCGGA |
| DGCR2 | CACCTGCCATGGAGGGGA | TGCCATCTGGGTCCAGACA |
| DKK3 | GATGGAGCCTTGGACCGA | GGACCTCTCTGGGCAGCA |
| DLL1 | GCTGCACGGATCTCGAGA | TGAAGCCGGAGTAGCCCA |
| DLL4 | GAGGTGCGGACATCCATCGA | CAAAGCCATAAGGGCAGTTGCA |
| DMXL2 | TCGGGGGGTAGGAAAGGACA | ATCTGCATGACTCCAGCCCCA |
| DNER | CACCAACATGCCACGGCA | AATGCGGCTGATGCGGCA |
| DNMT3B | CCCAAGCGCCTCAAGACA | AAGGAAGCGATCCCGGCA |
| DNTT | CTCAGGTTGCCTAGCAGGAA | ACGACGCTCGTAGGGGCA |
| DOCK9 | AGGGAAGCACCCTGGACA | ATCACAGCGAACCACGGA |
| DPEP1 | CCTGCACCAACAAGGCCA | GGGACCCTTGGAACACCA |
| DPP4 | TTGCAGTGGCTCAGGAGGA | CCAACCCAGCCAGTAGTACTCA |

FIG. 8 (Cont.)

| Gene Name | Forward GSP | Reverse GSP |
|---|---|---|
| DPP7 | CCTGACCTTCGCCAGCAA | CCCCAGAAGCTGGTCAGCA |
| DSC2 | AGGGAGAACATGTACGGGGA | CTCATCAGGATCAACCGCA |
| DSG2 | CTGCAGGGAAGCACAGCA | CGCAATGGCACATCAGCA |
| DSP | GACCAAGACATGGCCACCA | CCAGGAAGCGCTGGCCA |
| DYNC2H1 | GGCGCTAAGACCGGACAGA | GAAGGATCAGCACCCGGA |
| EBI3 | CCTGCTCCAAACTCCACCA | GTGACATTGAGCACGTAGGGA |
| ECE1 | CACACGCTCCTCACCCAA | CTTGAAGGCCTCCACGGA |
| EDNRA | AAGCAGCGTCGAGAAGTGGCAA | AGCAGCAGAGGCATGACTGGA |
| EFEMP1 | TCAGAAGCGAGGGGAGCA | CCCAGGACTGCACTGGCA |
| EFNA1 | TCACAGTCCTCAGGCCCA | CACAGTCCAGGCAAGTGGGA |
| EFNA4 | GCCCATCCCCCAGGAGGA | CACAGGGCACAGATGGCA |
| EFNA5 | CATGAGTCAGCCGAGCCA | ATCGCCAGGAGGAACAGTAGGA |
| EFNB1 | CCAGGAGTTCAGCCCCAA | GGCGTCACAGCATTGGGA |
| EFNB2 | CCGCTAAGGACTGCGGACA | CCGGGCTCTGCGGGGGCA |
| EFNB3 | CTGGGAAGGAGAACCTGCCA | CTCCGCCAACACATGGCA |
| EGFR | GGGGTGCAGGAGAGGAGA | TTTGCGGCAGACCAGGCA |
| ELFN1 | GCTACTCCTCCAGCCCCGA | TAGTCCAGGATGTCGTGCAGA |
| ELFN2 | CAGGAGCCGCCAGTCCCCAA | GGTTCAAGGCCCTCAGAGGA |
| EMB | AGAAGCACTCAGATGAGGGGA | TCACTGGCCCAGAGACTCA |
| EMC1 | CGCCCCGAGATCCCAACAGA | ACAAGTGGACTCCAGACCCGA |
| EMILIN1 | ACGGTCCCCTTCGACAGA | TGAGGCTGAAGACGCCCA |
| EMILIN2 | GCAGAGGTTGCAGAGCCA | CTGCCTGACACAGTTCCACA |
| ENG | CCGGGTCTCAAGACCAGGA | CCAGAGTGCAGCAGTGAGCA |
| ENO1 | CAACCCAAAGAGGATCGCCAA | GGCCAGCTTGCACGCCTGAA |
| ENPP1 | CACCGGCTCCTAATAACGGA | GTGAAGGGGCACTGTACCA |
| ENPP3 | TGAGCCATCCCATGCAGAGGA | TGCAGTACCCTAGGCCTCCCA |
| ENPP4 | TTGAGCCCAGTTGCTGCAA | ATTGTCCAGCCTTCATCGGCAA |
| ENTPD1 | CAAGATCCAGGGCAGCGA | AAGACATAGGTGGAGTGGGAGA |
| EPCAM | GAATGGCTCAAAACTTGGGAGA | GACCCCAGCAGTGTTCACA |
| EPDR1 | TGACCAAGCCACCAAGCA | GACCACTCCTGGACGGTGA |
| EPHA1 | ACTGCTTGCCAACCCCCA | GCCGAGTGGAAGTGCAGGA |
| EPHA2 | CTGTGCAGTGGATGGCGA | GCTCAGGGCACTCCAAGCA |
| EPHA3 | GTGAGCCATGCAGCCCAA | GTGATGCTGACCGCAGCA |
| EPHA4 | TCGGACAGCTGCCAGGAA | TGCCCGAGACAGAGACCAGA |
| EPHA5 | TCGAGCACGTACAGCAGCA | GCTGTAGCCACACCGCCA |
| EPHB1 | CAAAATGGTCCAGTACAGGGACA | CTGATGGCCTGCCAAGGTGA |
| EPHB2 | CATGGGCCAGTTCGACCA | GAAAGGAGTCCAGGGAGCCA |
| EPHB3 | CTGAAGGTGGGCTACACCGA | CCCGCAACATGCCCACCA |
| EPHB4 | GCGGCTAAACGACGGACA | GGATGTTGCGAGCAGCCA |
| ERBB2 | TGGCACAGTCTACAAGGGCA | GGAGCCCACACCAGCCA |
| ERBB3 | ATGAACCGGAGGAGAAGGCA | GTACAGGGTGGAGTGGGCA |

FIG. 8 (Cont.)

| Gene Name | Forward GSP | Reverse GSP |
|---|---|---|
| ESAM | TGGCCCAAGAGCTCAGACACA | AGGGCCTGGCTGGAGAGA |
| EVI2A | ATGCCCACGGACATGGAACACA | CTGTTAGCCCACAGACGGGTA |
| EWSR1 | GGAAACGTCCAGCACCGA | CCACGATCCATGAGGCCA |
| EXTL2 | ACACTCATCAGCACCCCAGA | GAATGAGGCTCCAATCAGCA |
| F11R | ACACGGGAAGACACTGGGACA | CAGCACTGCCCGGTTCCCA |
| F13A1 | TCCACCGTGCAGTGGGAA | GTCCAGCTCGCCATACACA |
| F2 | CGGATGCAGAGATCGGCA | GCTTGCCAATGCGCACCA |
| F2R | GCACCTGGCCACGGCAGA | AGCCCAGATGGCCAGACA |
| F2RL3 | GACGGACACAAACTAAGGGATGCCA | GTGAGGGAGAGCCCGTCCCA |
| F3 | GAGTGTGACCTCACCGACGA | CAGAGGCTCCCCAGCAGA |
| F5 | GCAGGGATGCAAACGCCA | TGGGCTCCCAGTAACCCA |
| FABP4 | TGGGCTTTGCCACCAGGA | CATGTACCAGGACACCCCCA |
| FABP7 | CTGGAAGCTGACCAACAGTCA | TTGAATGTGCTGAGAGTCCTGA |
| FAM171A1 | CCCAGCTTCCCTGAACGA | GGACCTGCCATCCAAGGA |
| FAM171A2 | GAGGCAACAGCACCGCAA | AAGAAGTCATCCCGGGAGGA |
| FAM174A | GGAGGGAAGGCCGGGGAA | TCATCCTGACCGTCCTGACCA |
| FAM174B | CCCTCAAGGCAGCCGTGA | CCGACCTGAAGACGCGCA |
| FAP | GTGGCAAGTGGGAGGCCA | CCTGGGCCGTAGCAGACA |
| FAS | TCAGAACTTGGAAGGCCTGCA | CCTTCTTGGCAGGGCACGCA |
| FASLG | GCCTCCACTACCGCTGCCA | CCCAGGCCCAATCCTACCAA |
| FAT1 | GAATTCCACCGAGGCCGA | TCACGACAACGTGGGCCA |
| FAT3 | GGAGATGCACAGCAGCGA | GACAGTCCAGCCCTGAGCA |
| FAT4 | GGCACTCTGGTAGGCACCA | CATTGAGGTCCCGCACCA |
| FBLN2 | GCTACACCATGACGGCCA | GAGGACACTCGAAGCGCA |
| FBN1 | TAACCACCGCTGCCAGCA | GATGTGAGCGCTGAGGCA |
| FBN2 | TGAGCTGTGCCCCAAAGACGA | AAATGCCTGGGCTCTCAAGACA |
| FCAR | CGCATGGCCGTGGCAGGA | CAGCTCGGTTCAGCCACA |
| FCER1A | GGTGGTGATGGAGGGCCA | CTCATAGTCCAGCTGCCACA |
| FCER2 | TGACGACATGGAAGGGCA | CCGAAGGCCAATCCAGGA |
| FCGR1A | CTGCGAGGCAGGAACACA | GGCCAAGCACTTGAAGCTCCA |
| FCGR2A | CTCATCCAAGCCTGTGACCA | TGGGCAGCCTTCACAGGA |
| FCGR2B | CTCATCCAAGCCTGTGACCA | TCAAGGCCACTACAGCAGCA |
| FCGR2C | AGCATCAGCCCCAATGCCCA | CAGCATGGAGAAGGCAGAAACCA |
| FCGR3A | AGCTGGCATGCGGACTGA | TCTCGAGCACCCTGTACCA |
| FCGR3B | CCCGGTGCAGCTAGAAGTCCA | CCCAACAAGCCCCCTGCA |
| FCGRT | GGCCCCAACAGTGACGGA | CGATGACGATTCCCACCA |
| FCRL1 | GAGGACAGGTGATGGAGGGA | TTGGGCGAGACACCGGGA |
| FCRL2 | CTACTCCTGTGAGGCCAACAA | AACAGTCCCCAGAGAACTCCA |
| FCRL3 | CCAGATCTGGAGCATCCAGCA | CTGCTAGCCTCCCCTGCAGA |
| FCRL5 | GCAGTGGCCTCTGACCCCA | TGAGGAAGCCAAGAACAGGGA |
| FCRL6 | CAGGTGGAGAGCAGTGCCCA | TCTCCCCACGGTGAACTCA |

FIG. 8 (Cont.)

| Gene Name | Forward GSP | Reverse GSP |
|---|---|---|
| FEZ1 | AAGCAGAAGGAGCAGCGAGA | TGAAGCGCTTGAGAGGCA |
| FGA | GGGGGCTCCTATGACCCAA | GCGAACAGCCCTGAGGGA |
| FGB | GCTCGTCCAGCCAAAGCA | GTAGGACACAACACCCCCA |
| FGF5 | CCTGGGCTCACGGGGAGA | GAGGAGGAGGCAGAAGAGGA |
| FGFR1 | CTGGACCAGTACTCCCCCA | GCAGCGGCTCATGAGAGA |
| FGFR2 | TCAACGGCAGACACCCCCA | CTCCCAGGGGCTTGCCCA |
| FGFR3 | CGCCAACTGCACACACGA | GCTCGAAAGGCGCCGACA |
| FGFR4 | GACCGGGTGTACACACACCA | ACAGCTCCTCCACCGGGA |
| FGFRL1 | GCCTTGGCGCCAACACCA | CAGGCTAGTGGCCGAGGA |
| FGL2 | TAACTATAATGGCACAGCTGGAGA | TACAGCCCACAGTTCCCAGA |
| FKRP | GACCACCGGCAGGATGTGGA | GGGCCCGAACTTGAGCTCCA |
| FLRT1 | TACAACCGGGGCAGCAGGAA | CTGCTGCCGTTGGAGGGGA |
| FLRT2 | TCCTGACTGGGATGGCAGA | CACGGTGAAGAGAGAGAGCCA |
| FLT1 | TCTGGCACCCCTGTAACCA | CACAACCAAGGTGCTAGCCA |
| FLT3 | TCGCAGAAGCATCGGCAA | TGCACAGCACTTGACCAGGA |
| FLT3LG | GCTCGGGACTCAGTGGGA | CATCTTGGACCCAGCGACA |
| FLT4 | CAACAAGGTGGGCCAGGA | CTTGGCAGCTCAGGAGCA |
| FN1 | GAGGAAATAGCCCTGTCCAGGA | CGGCCAGTGACAGCATACACA |
| FNDC5 | TCCACGTGCAGGCCATCTCCA | AGGACCACGACGATGATCAGCA |
| FOLH1 | ATGCTCCAAGCAGCCACA | TCTCTGCAGCTGCCTGCA |
| FOLR1 | CAGCAACTACAGCCGAGGGA | GCCCCACTCATGGCTGCA |
| FOXA1 | CCTGAAAGGGGACCCCCA | CGGGCAACGTAGAGCCGTA |
| FOXD3 | GTTCAGGGGGCGGCAGCA | GTGGCAGTCGTCCGGCTCA |
| FOXG1 | CTCGCTGGGCAACAACCA | AACTGGTCTGGCCCGCGA |
| FOXJ1 | CTACGCCACCAATCCGCA | GCGTGGCGGAAGTAGCAGA |
| FOXP3 | CATCCTGCCACCTGGAAGAA | CGGAACTCCAGCTCATCCA |
| FPR1 | TGCCACCAAGATCCACAAGCA | GGCCACCACCTGATATGGGGA |
| FPR2 | GCACCGTCTGGCTCAAAGAGA | CGTAAAGCATGGGGTTGAGGCA |
| FRAS1 | AGACACTTCAGTCCCCGGCAA | ATCCCCCCTTCTGGAACCCA |
| FREM2 | TGGACCGCACCAAGAGGCAGA | CGTGGTGCCTCCCACCACA |
| FSTL1 | ATCCAGTGGCTGGAAGCTGA | TCACTGGAGTCCAGGCGA |
| FUT1 | GAAGGGTGTGGTGGGCGACA | CCTCCTGTCCATCGCCAGCA |
| FUT4 | GAACTCGCAGCACCTGGA | GGGAGGAGGCACTTGGGAA |
| FUT5 | ACCCCGACTACATCACCGAGA | TGAAGGAGCGAGGCCGCA |
| FZD4 | TCCCCGCAGTGAAAACCA | ACGAACCCGGTGAGGGCA |
| G6PC | ACCCCCATCCCAAGTCGA | TAGGGGATGACACTGACGGA |
| GABRA2 | GCCAATCAATCGGAAAGGAGA | CACAGTTCTTGCAGGCACAGA |
| GABRB3 | TCGGGAGACCTTGCCCAA | ATACTCCAGAAGGGCCAGGA |
| GAD1 | GCTCTCTGACCACCCCGA | TGACCTGTGCGAACCCCA |
| GAD2 | GTGACGTGGAATCCACACAAGA | TGAAAGAGGTAGGAGGCATGCA |
| GALC | TGAGCCCTCCCACATGCA | CGCCCACAATCCAGGTCA |

FIG. 8 (Cont.)

| Gene Name | Forward GSP | Reverse GSP |
|---|---|---|
| GALNT1 | ATGCCACCACCTAAAAGGCA | GCAGTCTCTAATGCTGGGCA |
| GATA1 | CTGGGAGGCACAGGAGCA | CCCAGTAGGGGTCCAGGGA |
| GATA3 | CTCACTGGAGGACTTCCCCA | AGTGGCTGAAGGGCGAGA |
| GBX2 | CGGCGGCGGTAACTTCGACA | ACCGTCTCGGCCGCGGAGAA |
| GCG | GGACTCCAGGCGTGCCCAA | CCTCGGCCTTTCACCAGCCA |
| GDF15 | CCGTCGCAGTCGGACCAA | GCCCAGGTCTTCCAGCGA |
| GDF3 | AGCCATCCCTGTCCCCAA | AGATGGTCAGTGAGAAGGGACA |
| GFAP | TCGGGAACTCCAGGAGCA | GCATGTTGCTGGACGCCA |
| GFRA1 | GCACAGTCATGACCCCCA | ACGGTCACATCGGAGCCA |
| GFRA2 | GCTTCACAGAGCTCACGACAA | CAGGACAGACAGCACGGTCAA |
| GHRL | TGAGCCCTGAACACCAGAGA | CTAGAGCTCGGGGCTGCA |
| GLG1 | GCAGGAAGCCAAGGAGCA | GATCTGGCTCCAAGCGGA |
| GLMP | GGAGGTAGCCACATTGGGCCA | GAAGGCTCGGACAATGGGTGA |
| GNLY | CGGAGAAACTGCCCAGCA | AGCGAGGAGCCGGCAGA |
| GNPTG | CGAGTGGGAGATCGCCAA | GCTCGGACACATGGGCCA |
| GP1BA | GTGGGGTGCTCCAAGGGCA | TGGCTGTGGTCAGAGCAGCA |
| GP5 | ACTTAGCCCAGCGGCCTGCA | CATCCGCAGGGGAAGACAGA |
| GP9 | CCAGCTGCAGACCCTCGA | TGGGGCTGGCACAGCGGA |
| GPC1 | CTTCAGGCACGCTGGAGA | GGCCATCCCGTTCCAGCA |
| GPC4 | CAACCACAGCAGCTGGCA | GCTCGGAAGGGAGGACCA |
| GPC5 | CAGGCACTCAATCTGGGCA | CAAGGCTTAGTGAGCGCCA |
| GPI | GGGTGTGAGACACACGCCA | CTGGACCGGGATGAGGAA |
| GPM6B | TAAAACAACCGCTTGTGGCCGA | ATCCACACAGATCTGCTCCA |
| GPNMB | AGGGAGCATTCCCACGGA | CCCCAGGGTGAGGTTCACA |
| GPR107 | CCACCGAGGAGGGCACGA | AATGGAACAGCGAGTTTGAGGA |
| GPR132 | TGCCGGGTACTACTACGCCA | GGGCAGCGCTTAAGCCCA |
| GPR174 | CCACTCCTCAGAACCAGTGA | CATAACAACGGACTGGGCCA |
| GPR176 | ATGAGGAAGAGAGTGAGGCCAA | GTGCTCAGGGGTGGGGCA |
| GPR39 | TGCGGCCAAACCCAAGCACGA | GTCGGTGGTGGAGTGCGCA |
| GPR65 | CTGCAACCGGAAAGTCTACCA | ATGCAGCGAATCAGCAACA |
| GPRC5A | TCACGGGCTGGAAGAGACA | CCCAGCCATTGGCAGCCA |
| GREM1 | GCTGCAACAGTCGCACCA | GGGCTTGCAGAAGGAGCA |
| GRIA2 | ATGAGGAACAAGGCAAGGCTGTCAA | TCACGTAAGGGACAGCATGCA |
| GRID1 | GCTGTGACCTCACCAGCCA | CACCACAACTCCAGGGCA |
| GRIK3 | CAAAGCCCTGTCCACACGCA | CCATGCGCTCCACGGTCAGA |
| GRN | CTGCCGAGACAACCGACA | GCGGAAGCCAGCAGGACA |
| GTF3C1 | AGGCACAGCTCAGGCCAA | CAGACAGGTTCCGCACCA |
| GYPA | AAACGGGACACATATGCAGCCA | ATCAGTCGGCGAATACCGTA |
| GZMA | GAGGTGGAAGAGACTCGTGCA | CCCACGAGGGTCTCCGCA |
| GZMB | GCAGGAAGATCGAAAGTGCGAA | GTTACACACAAGAGGGCCTCCA |
| GZMH | GAGGAGATCATCGGGGGCCA | TCTCACTAGGATGCCGCCA |

FIG. 8 (Cont.)

| Gene Name | Forward GSP | Reverse GSP |
|---|---|---|
| GZMM | TCAGGAAGGTCACCGGCCGA | CACCCCACTGCACCCCTGGA |
| HAND1 | AAGAGAACCAGACGCAGGAAGA | GAACTAAACAGGAAGTGCAGCGACA |
| HAND2 | CCAACGTACCCGCCGACA | AAGGCCTCCGCCTCGCCA |
| HAVCR1 | AACCCACGTCACCTATCGGA | CAATATACGCCACTGTCAGACA |
| HAVCR2 | GGCAACGTGGTGCTCAGGA | CCGGCAGCAGTAGATCCCA |
| HEG1 | TGCAAGCGGAAGAGTCCCGAA | TCCACAGTTGAGACCACCA |
| HEPACAM | CCCCGGAGACCGAGGAGA | GGGCAGAGCGGATGGGCA |
| HEPACAM2 | TCACCATGATGCCACCCAA | CCGAGTGCCCCCTTCCACA |
| HES5 | GGGAGGGTGGGTGCCTCCA | GTCGTGCCCACACGCATCCA |
| HFE | CTGGATTGGAGAGCAGCAGAA | AGTGGTCACTGAAGAGGTCACA |
| HHIP | GAAAACAAGTCAGAGGACCAGCA | GAAGAGACGTTGCGAGCCA |
| HHLA2 | GAAGCCAGGAGGAGCAGACA | GCACTGGGACAGCGCTCA |
| HLA-A | CCCCACCCCCATGTCCACCA | AACAGGAAAGATGATTGGGGAGGGA |
| HLA-B | AGGCTGCGTGCAGCGACA | GCTAACAGGGACGCAGACACA |
| HLA-C | GTGCCTTCTGGACAAGAGCA | CAACGATGCCCATGATGGGGA |
| HLA-DOB | CTGAATGGGCAGGAGGAGA | CACAGAAACAGGGCTCAGCA |
| HLA-DPA1 | CTGGGAGGCCCAAGAGCCAA | TATGATGAGGACGGTGCCCA |
| HLA-DPB1 | GTGGAGCACACCAGCCTGGA | CTCCACAGATGATGAGCCCCA |
| HLA-DQA1 | TATGACTGCAAGGTGGAGCA | GAAGCACCAACTGAACGCA |
| HLA-DQA2 | AAGGTGCATCACCATCTACAGGAGA | GTCCCAGAGAAGAGGTGAGAGAAGA |
| HLA-DQB1 | CCAGCCTCCAGAGCCCCA | TGACGGATGATAAGGCCCA |
| HLA-DQB2 | GCGGAGCATCGAGGACTGGA | CCGCTGCAAGGTCGTGCGCA |
| HLA-DRA | GAGAGAGCCCAACGTCCTCA | GGAGATAGTGGAACTTGCGGA |
| HLA-DRB1 | ACAAGCCCTCTCACAGTGGAA | GATGAACAGCCCGGCCCCA |
| HLA-DRB5 | GTCCACAGGCCTGATTCAGAA | CCCCGACTCCACTCAGCA |
| HLA-E | CGCCAGGGACACCGCACAGA | AGCTCGCAGCCATGCATCCA |
| HLA-F | GACCGAGTGGCCCTGAGGAA | CTGGTGATACCCGCGGAGGA |
| HMCN1 | GGGGGACCAGACTCCCAGA | CACCTCCTCCACAGGAGGCA |
| HNF4A | GCTCGGAGCCACCAAGAGA | GCAGCTCCTGGAAGGGCA |
| HNRNPK | TCTCCCATCAAAGGACGTGCA | ATCCCACTGGGCGTCCGCGA |
| HP | GCTGACCAAGACCAATGCA | GGTACTTAGACATGCCAGCACA |
| HPX | CCAAGCCACGTGGACAGA | AGGTACAAGCCGGGACCA |
| HSD11B1 | CTGAAGCAGAGCAATGGAAGCA | ATGGAGGAGAAGAACCCATCCA |
| HSPG2 | GCAGAAGCGAGTCCCAGGGA | TCACGGTGTGGAAATGGCCCA |
| HTR1D | CAGTGCCCTGGAACGCAA | AGCAGGAGTCCCGGCAGA |
| HTR2B | CACCGGAAAAGGTGGCAA | AAGAAGGGACACCACATAAGCA |
| HYAL2 | CGGGGTACACCACAAGCA | CGCAGCTGGGGTTCACCA |
| IBSP | TGAATACGAGGGGGAGTACGA | GCCGGATGCAAAGCCAGA |
| ICAM1 | CAAGAACCAGACCCGGGA | GACACTTGAGCTCGGGCA |
| ICAM2 | CACAAACACTCAGCCCCGAA | GAGCAGGACAGATGTCACGA |
| ICAM3 | GTCCAGCTCACGAGGCAA | CGATAGTCACCACGCCCA |

FIG. 8 (Cont.)

| Gene Name | Forward GSP | Reverse GSP |
|---|---|---|
| ICAM5 | TACCTGCCCAAGTCACCAGA | CGCATTGGTGGCCACACA |
| ICOS | AAGGGGGGCAAATACTCTGCGA | GTAACCAGAACTTCAGCTGGCA |
| ICOSLG | AGCCGCTACCGGAACCGA | TGACGTTGAACAAGCGCA |
| IDO1 | GAAAGGCAACCCCCAGCTA | CTGGAGGAACTGAGCAGCA |
| IFI30 | CATGCACGCCAACGCCCA | AACTGGCAGACAAGGGTAAGGA |
| IFNAR1 | CCGCAGCCGCAGGTGGAA | GAAAAAGTCACATTCCCGACAGA |
| IFNAR2 | CCCGGAGTCCGAGGAGGA | TCTCACAGGGCCCACTCA |
| IFNG | CTGACTTGAATGTCCAACGCA | GGGATGCTCTTCGACCTCGA |
| IFNGR1 | AAAATACTCACGCAGAAGGAAGA | TCAGTTGTAACACCCCACACA |
| IGDCC4 | CTACCCGGACCTCCAGCCA | CAGAGGAGGAGACCGGGGA |
| IGF1R | CCAGGAACAACGGGGAGA | CCAGCTGTTGGAGCCGCA |
| IGF2 | CCGTGGCATCGTTGAGGA | GAACTTGCCCACGGGGTA |
| IGF2R | GACGACGGGCAGATGCACAA | GTAGAGCAACAGGGCCAGCA |
| IGFBP3 | CAAGTTCCACCCCCTCCA | CCGCTTGGACTCGGAGGA |
| IGLON5 | GACTGCTGAGCAGCGGCA | CCAGGGATCCTGGGCGCA |
| IGSF1 | GAGGCTCAGAGACAGACGGA | GGAACGGGCAGTTCCACA |
| IGSF3 | GGTTCTCAACCGCACCAGCA | AAGGTGGCGTCACGGCTCAA |
| IGSF8 | GGTGGAGCGACCAGAGGA | GTCGGCATGCTGCACCCA |
| IL10RA | CAGCTGCAGTGACCTGGGAA | CAGGCTAGAGATGAGGGGCA |
| IL10RB | AAAGCTGGGGAATGGAGTGA | GCAAGGCGAAGCAGCCGA |
| IL12RB1 | AGGCCAAGGCCACCAGGA | TGGTTCAGGCCAGGACCA |
| IL12RB2 | CTGCTCCAACTGGCCACA | GGGAGCACCGTCCAGGGA |
| IL13RA1 | CCCGAGGGAGCCAGCTCA | GTGCTACACTGGGACCCCA |
| IL13RA2 | AACAAGGGCATTGAAGCGAA | ATGCATGATCCAAGCCCTCA |
| IL17A | GCTGCATCAACGCTGATGGGA | GCCGGAAGGAGTTGGGGCA |
| IL17D | TCGCCCTGGGCCTACAGA | GACGGTGGGCATGTAGACA |
| IL17RA | GGCCGTCAGAAGCAGGAGA | GGCCTCTTGAAGTCCGGGA |
| IL17RB | GTGGCAAGAGCGAGGGCA | GGGGCAGACACTGAGAGCA |
| IL17RD | CTCCACTGCGCTACCGGGA | GTCTTGGTCCAGGCCCCCA |
| IL18R1 | GGCTGATATCCCAGGCCA | TCACTAGGCACACTACTGCCA |
| IL1R1 | CGTTGCAGGAGACGGAGGA | TCAGCCACATTCATCACGA |
| IL1R2 | CCCCGCATCAACCTGACA | TAGTGCAGACGTAGGTGCCA |
| IL1RAP | CGGGACCTTGAGGAGCCAA | GGCCGGAACCACAGCACA |
| IL1RL2 | GGACTTCACGGAGCAGTCACA | TGTGTGCTGCAGCAGCTGGA |
| IL21R | CCGGCCTGGATATGGACA | GTGGCGGAGGAATGACCA |
| IL26 | GCTGAGTGGGGTGAAGGGAA | AGACAGAGTGACTAACAGCAACCCA |
| IL27RA | AGAGGTCCCAAGGCACCA | CAGCTCACAGGGACCCCA |
| IL2RA | CACGGGAAGACAAGGTGGA | TGTTGTGACGAGGCAGGAA |
| IL2RB | GTCCTGAAGTGTAACACCCCA | GCGAGATCTCAGGTGCCA |
| IL2RG | CCGGACTGACTGGGACCACA | ACCACGGCTTCCAATGCA |
| IL3RA | CAACAGGCGTCAACAGTACGA | GAGAACCGCTGGAGAGTCGA |

FIG. 8 (Cont.)

| Gene Name | Forward GSP | Reverse GSP |
|---|---|---|
| IL4R | AGGAGGAGGAGGAGGTAGAGGA | TCCCAGGGCATGTGAGCA |
| IL5RA | AGCAAAGACACACTGGGGAGA | TCAATGGCGTGAAGGGCA |
| IL6R | TCCACCCCCATGCAGGCA | GGAGCGTTCCGAAGGCCA |
| IL6ST | GCGCTGTGGAGACGCGGA | AAACAAGGCTTGCACTAGCCA |
| IL7R | TAATAGCTCAGGGGAGATGGA | ATCGGGGAGACTGGGCCA |
| INHBE | GACCAAGGAGGAGGCGCCAA | GACTTCTCACCCCTCAAGCCA |
| INS | GCAGGTGGGGCAGGTGGA | TCCAGCTGGTAGAGGGAGCA |
| INSR | CGGTCAACGAGTCAGCCA | TGGACACCACTCCCAGGA |
| ISG20 | GGGTCACCCCTCAGCACA | CTTCAGGTCATGACCCACCA |
| ISL1 | CAGCAAAAGCGCAGGAAGAGAGA | CCAGCTACAGGACAGGCCAA |
| ISLR | GACAACGAGGTGCAGCCA | GCCTCAGGGTTCCCAGCA |
| ITFG1 | CCAACTCAGCCAATCCGCACA | TTCTCCAGATGGACGGGGA |
| ITGA1 | CAGGTGGGGATGGTAAGACA | TACGGCCACATCTCGGGA |
| ITGA10 | CAGAACCTGACTGAACCCCCA | CCCAAGGTGGCACCTCACCA |
| ITGA11 | GCTTGTTCCCCATCCACGGGA | TGCCCCAGATGTTACAGGA |
| ITGA2 | AGAGTTGCCCCGAGCACA | GGCTTCAAGGGCAGGGCTA |
| ITGA2B | GATGGACGCAGCCAACGA | CCCAGCTCACACAGCACCA |
| ITGA3 | CAGGCCATCATCCCCACA | GGATGGGGCACTCTAGCCA |
| ITGA4 | CGGAGCCAGCATACTACCGAA | CTGCATTGAGGTCCACAGCA |
| ITGA5 | GGGACTCAACTGCACCACCA | AAGCAGAGCTGCGGCTTGGA |
| ITGA6 | GGCTGCCAAATGCAGGCA | AAGCATCAAGATCCCAGCGA |
| ITGA7 | CATGCAGTCTGAGCGGGA | TGAGGAAGGCAGAGCCCA |
| ITGA8 | CAAAGAGGAGGAGGTTGGACCA | CCCGGGCAGAGAAAGGCCA |
| ITGA9 | GATGGCTGACGTGGCCAA | CGCTTCACATGGGCCACA |
| ITGAE | CTCATGCCCACAGAGGGAGA | CTCAGTGTAGCGGTCCAGGA |
| ITGAL | TGGCAGAGGTGTCCCGAA | ATGGAGGGGCTTCAGGCA |
| ITGAM | CTCGAGTACGTGCCACACCA | CAGCAGGGTGAACACGGA |
| ITGAV | GCAAGGTGAGCGGGACCA | CAAGCACTGAGCAACTCCACA |
| ITGAX | GAGGGACCTGCCTGTCAGCA | TCTGAGGAGCACCGAAGGGA |
| ITGB1 | ACCAAGGTAGAAAGTCGGGACA | CAATTCCAGCAACCACACCA |
| ITGB2 | TGAGCGCTACAACGGCCA | GCATACGTTGCAGCGGCA |
| ITGB3 | GGGGAGCCCTACATGACGA | CGGCAAGGCCAATGAGCA |
| ITGB4 | CGGAGGACCAGAAGGGCAA | GCACACACACTGTCCGCA |
| ITGB5 | TGGCCAGATCTGCAGCGA | TCCCAGAGTGGAGCAGCA |
| ITGB6 | ATCCCTCCTGCAGCGGAA | TCCAGCCGCTCCTGCACA |
| ITGB7 | ATGCGAGAGACACCGGGA | AGATAGGGGCCAAGGCCA |
| ITGB8 | TTCAGCAGCAGCCCAGCA | GTTCACAGAAGCGGCCGA |
| ITIH2 | AGAAGCCAGAGGCCAGCA | AGAAAGCTGTAGAGCTGAGGCA |
| ITM2B | GTGGACTGCAAGGACCCAGA | AGCTGGGGCATCTGCAGA |
| ITPRIP | CGCAAGGTGCCTGAGGCCA | GGTAGGCTGGTCTGAGGGGA |
| JAG1 | GGTGCCAAGTGCCAGGAA | GCAAGGTCGAGGGCCACA |

FIG. 8 (Cont.)

| Gene Name | Forward GSP | Reverse GSP |
|---|---|---|
| JAG2 | CTGCGACCAGTACGGCAA | CCGGGGTAGGGGACACA |
| JAM2 | TGACAAGAAGTGATGCGGGGA | ATGATGGAACTGCTGGAGCCA |
| JAM3 | CAGGTGTGAGGAGCAGGAGA | CCAACGTGATCAGGGCCA |
| JAML | GCCCGGAAGAGCCTCGAA | TATCAGAACAGGGAGCAGCA |
| KCNA3 | CGAGCTGGCCGAACGACA | GCAATCCCAGCTCCCGCA |
| KDR | GAGCCCAGTCAGAGACCCA | GGAAACAGGTGAGGTAGGCAGA |
| KEL | AAGAGGCTGTTACGGCACCA | CACCACGTGCACAGCGGA |
| KIAA1324L | TCCCAGTTCCAACAAGCCA | ATGCTCCGTACACAGAGGGCA |
| KIR2DL1 | ACCCCCGACACCTGCACA | GAGCACCAGCGATGAAGGA |
| KIR2DL3 | CAACGGAACATTCCAGGCCGA | AAACAAGCAGTGGGTCACTCGA |
| KIR2DS4 | CTGCCTGCTGGAGAGAAAACACA | GCAGCCTCAGGTAGACTAGGA |
| KIR3DL1 | CCAAGGTTCAGGCAGGAGAGA | GACCTTGCGCACTGCAGGGA |
| KIRREL1 | GGAAAGAGCAGCCAAAATCCCAA | TGGGTAGAAAATGTGACCACAGGGA |
| KIT | GTGGATGGCACCTGAAAGCA | AGGGCTGAGCATCCGGAA |
| KITLG | CAAAACTGAAGGGATCTGCAGGA | GCAAAACATCCATCCCGGGGA |
| KLRB1 | CCCACAGACTCAGGCCCA | TGCCAAGGTGAACCCTGACA |
| KLRC1 | AAACCCAAAGAGGCAGCAACGA | ACTATCGTTACCACAGAGGCCA |
| KLRC2 | GGTTTACTGCCACCTCCAGAGA | TAACACAGTGGCCATCAGGA |
| KLRD1 | CAGCATTTACTCCAGGACCCA | GAGAAGCACAGAGATGCCGA |
| KLRF1 | AAAGAAAAGGAGTTCTGCCCAA | AGGATCAAGGAGATCAAAGTCA |
| KLRG1 | CAGGAAATGAGCCTGCTCCAA | GGCACCGCATGTCTGCACAA |
| KLRK1 | GTCTCGACACAGCTGGGAGA | GCTACAGCGATGAAGCAGCA |
| KNG1 | CCGTGGGGAAGAGGAGCA | CACAGCCGAGGCAGTCGTA |
| KRT1 | CTGGAGAATGTGCCCCGA | CCGCCACCTCCAGAACCA |
| KRT10 | GGAGCCTCGTGACTACAGCAA | CTCCAGGTCAGCCTTGGTCA |
| KRT14 | AGGCCCCCCGTGTGGACACA | GAGGGGGTGAGGGTGAAGCA |
| KRT18 | GGCTCGGAAGAACCGAGA | TCCAGGTCGATCTCCAAGGA |
| KRT20 | AACTCCAGTCCCATCTCAGCA | CATCAGTTGGGCCTCCAGAGA |
| KRT5 | GTCCCAGATGCAGACGCA | TTGCGGAGGTCATCGCCA |
| KRT8 | GGCTGGAGTCTGGGATGCAGA | TGGAGCCCAGGCTGTAGCTGA |
| L1CAM | GGAGAGGATGTTCCGGCA | GAGGATGAGCAGGACGAGGA |
| LAG3 | GTGCCCAACGCTCTGGGAGA | AAGCCAAAGGCTCCAGTCACCA |
| LAIR1 | GCCGTCGGACAACAGTCA | TCTGGCGATGGAGGCAGA |
| LAIR2 | CCGCCTGGAGAGGGAGGA | GGAAGTCACTGTGCTCAGACCA |
| LAMA1 | CAGTGACACCTGTGACCCCA | GGCTGTGAGGACAGGCACA |
| LAMA2 | GTGGAGCTCACTGATGGGCA | AGCGTTGGCAGGCCACCA |
| LAMA3 | ACTCGGTGGCAGTCACCA | TGGCAGGTGGGAAGGGGA |
| LAMA4 | CCTGGACCCTGAGGACACA | AGTGGCCAGTTCCAGGCA |
| LAMA5 | ACGCGCAGAGCAACCACA | CAGAGCGAGTCATGGCGA |
| LAMB1 | GCCAGTGCGACAAAGCCA | GCAAGATGGCCCGAAGGA |
| LAMB2 | TCACACAGGGGGTGAGCA | GGCCTTCAGGACAGGGACA |

FIG. 8 (Cont.)

| Gene Name | Forward GSP | Reverse GSP |
|---|---|---|
| LAMB3 | CCGACACTGATGCAGCCA | TGGTCTGGGACAGCACCA |
| LAMC1 | TCACGTGACTGGCCAGGA | GCGCTCACAGTGCTGACCA |
| LAMC2 | CAGAGCTGGAAGAGAGGGCA | TGTAGCAGCCTGGGGGCA |
| LAMP1 | GAGCACGTCCGTGTCACGAA | GTCCAGCAGACACTCCTCCA |
| LAMP2 | TGCAGCTGAACATCACTCAGGA | GAGCAGTGTGAGAACGGCA |
| LAMP3 | GCCTCCAGTTGTCAGCCCA | TGATTGACACCTTAGGCGGA |
| LDLR | CAGCACACAACCACCCGA | AGCACGATGGGGAGGACA |
| LEFTY1 | AGGAGGGAGGCAGGACCA | CTCCTTGGCACGAGCGCA |
| LEPR | CTGTGGACAGAGCAAGCACA | TAAGCACTGAGTGACTGCACGA |
| LGALS3BP | ACCTCCCCACCATCCAGA | CGAAGAGCCCTTCGCAGA |
| LGR5 | ACATGCTCACGGGAGTCTCCA | TCACAGAGAACCCACGCTCCA |
| LIFR | GAAGCTGGAGGGACTGCACA | CTGCCCCTCCTACAGGGTCA |
| LILRA1 | CACCCTCAGCCCATCACA | GCAGAATCCCGAGGACCA |
| LILRA2 | CACCAAGCTCAGCAGAACCA | AGGGGGTCACTGGGGAGA |
| LILRA4 | CCACGGTGACCTCAGGAGAGA | ATCTCAGACGCAACGGGGGA |
| LILRA5 | CTGTGACCCCCAGCCACA | GAAGGTGTGAGGCAGTCCCA |
| LILRB1 | GACATCGACGTCAGGGCA | GAGTGTCCATCTCCACCCCA |
| LILRB2 | CCTGAACTCCCAGCCCCA | CCGGCTGCACTGAGAGTGA |
| LILRB3 | CCAGCTGCTGACGTCCAGGAA | TTCACCGGGGCATACGTCA |
| LILRB4 | CTACAGGGTCAGTCCCCCA | CTGACGCCAGTGTTGGAGGA |
| LIPG | CTGGTCTACACCGAGGAGGA | TGCGGGGTTGAGACAGGTA |
| LMAN2 | ACACGCCCGACGAGGAGA | GATGCCCAGGAGAGCGCA |
| LMAN2L | CACAGCCATTGTCCGCAA | TGATGGAGGAGGTGCCGA |
| LNPEP | GAACTCAGCCTACACCCGAA | CATGTGACCTGAAGAGCCTGA |
| LOX | CGGCATGGTGGGCGACGA | GCCACCAGGTCTGGGAGA |
| LOXL4 | ATGGACTGGCCCTACGGA | TCAGCCACCTTGGAGCCA |
| LPAR5 | CGAAAGGTCCGCCGTCACCA | GGGCGGAATCCTGGGGACA |
| LRFN1 | CAGTTCACCACCGCTGGGGA | AACGATGAAGACGAGGACCGA |
| LRP1 | AGGGCTTCCAGCACCAACGGA | CGTCCAGTAGGCCTCCCACA |
| LRP10 | CTCACTGCCCCTAGAGCCA | CATCTTCCAGGGCCAGGA |
| LRP11 | GCAGCCTACTCCACAGGAGGA | TTGCGGTCCAGGCCCAGA |
| LRP12 | TCAAGGACAAGGGCTTAGACAACCA | GCTCACAGGGGCCATCTCGA |
| LRP1B | TGGTCAGGCACACAGTGTGAA | ACGAGAGGCACAATGATGGCA |
| LRP2 | GGGAGTGCACAGAGAGCGA | GCCTGGCAGTATGCACCA |
| LRP4 | GTGCCAACCTCAACGGCA | CCAGGTTCTGCCACAGCA |
| LRP5 | GAGGAAGTCAGCCTGGAGGA | GTGGACTGGGCATGAGCA |
| LRRC15 | GCCTAGGTTAGGGACGGACA | GGGACATGGACGCTTGGAACA |
| LRRC25 | ATGTTTGTGGGCCAGCCAGCA | GCCTGGCCCAGTGACTGCA |
| LRRC32 | ACTCAGCTGCTGCGGCAA | GCACGTGGCTCAGGGACA |
| LRRC4B | CCGAGCTCAAATGCCGCA | GCGTGCCGTCATGCAGGA |
| LRRN1 | AGAATGTCCAAGGGGCAGACA | TCATGGACATCGACTGGGA |

FIG. 8 (Cont.)

| Gene Name | Forward GSP | Reverse GSP |
|---|---|---|
| LRRN4CL | GGTCCGCAGAGCCGAACTGA | GGATGTCGGCCCCCTCGA |
| LSAMP | ATGAGTGCAAAGCTGCCAACGA | ACTCAAAGTCAGGTGCAGGCA |
| LTA | GTATCCAGGGCTGCAGGAA | CTGAGGACTAGGTGGGGGA |
| LTB4R | GCCCCAGGAAACAAAGATTCCCA | CTTGTCAGAACAGAGTTGGACCA |
| LTBP1 | CGGAGCCAGAAGTGGCAA | GAGACAGCTGGGGTTGACCA |
| LTBP3 | GTGAACGAGTGCGAGGCA | GTTCAGGTCCACGCACGA |
| LTBR | AGCCACTGCCCCCAGAGA | GCGGACGCCTCTTGAGCA |
| LTF | GCCTCGATGGCAAACGGA | ATCCGAGACACCACGGCA |
| LTK | GAGTGCCTAAGACCCCCACA | GAGGGGCTTGAGGCCAGA |
| LUM | CTGCCCTGAAAGCTACCCAA | ATCTAGAATGAGCCACTGCAGA |
| LY6K | CTCCCAGCGAACGGACGA | CGCTGCACAACCAGCGGA |
| LY75 | AAAGCAGACAGACGTTGCAGA | TGAAGGAGCGCCTGCACA |
| LY9 | CTGAGGTGCACAAGCCCA | GTGACATATGGAGTGACGGGA |
| LYPD3 | CCACCAGGACCGCAGCAA | CCAACAGAAGGGCTGCCA |
| LYVE1 | AGGCGAACCAGCAGCTGA | ATCAGGACACCCACCCCA |
| M6PR | TGCTGGAGGACTGGACTGCTA | GTTGCCAGCTTCCCGGCACA |
| MAF | TGCCGCTTCAAGAGGGTGCA | CTCTCGCGCACCAGCCTGGA |
| MAFA | CTCAGGGGCCATCAGTGGGA | GGCGCGCCTTCCACTCCGA |
| MAN2B2 | GAAAGGCCATCGAGGGGA | TGCAGCACAGCCTCCAGA |
| MAP2 | ACCCCGACGACTCAGCAA | AGCAGTGACATCCTCAGCCA |
| MAP3K12 | CCCTGGACATCAGGGAGCA | CTTGCTCTCGCCTGAGCA |
| MARCKS | CCAGCGGAGGCGGCAGA | CAAAACCAGTACCTGGCACCA |
| MARCO | CCAGAAGGGAGACCAGGGA | GTAACCCAGCATGCGGCA |
| MBP | CCCTGCCCCAGAAGTCACA | GGTGTGCGAGGCGTCACA |
| MCAM | ACGTCAACGGCACGGCAA | GACCAGCTCCAGGAAGAGGA |
| MCOLN1 | CTCGCTCATCAATGGGGACGA | TGAGCGCGATGAAGAGGCTGA |
| MDGA1 | CTGCAGTGGACTCAGAGGGA | CGGGAGGCCATGTCACCA |
| MEGF8 | GCCGCAACTGCTCCACGGAA | GCCTCCGACAGCTGAACCCA |
| MELTF | CTCCACTCCCGAGATCCAGA | GGACTTGGCTGACACGCA |
| MERTK | CAGGTTGAAGCAGCCCGA | GGTTCCGAACGTCAGGCA |
| MET | TGGCCACGGGACAACACA | AAGTGCCACCAGCCATAGGA |
| MFAP3 | AACTGGATGGCAGAAGCAGA | TAGGGTGACAGAGTAGGAGGCA |
| MFAP3L | GATGACCAAGAGGGTGGACA | AGCTCGGTGGACGTGACA |
| MFAP4 | GGTCAGCGCAGAGGAGGA | GTGGCAGCTGCGGAACCA |
| MFAP5 | ATTCGCCAGCCAAAGTAGGA | GCAGCAAGAAACAGCAGCA |
| MFGE8 | GTGACAGGCATCATCACCCA | GTCCCAGTTGCCAGGGAA |
| MFSD4B | TTGAGCAACATTGGCAGCCTGA | TTCTCCCAGGGAAGCACCA |
| MIA3 | CACAGGCTGTCAGCTGCAGA | CAGCACGAGCTTTGAGCCA |
| MICA | CGAGGCCTCAGAGGGCAA | TTCCCATCAGGCAGGACA |
| MICB | GAGCCACAACACCCAGCA | CACCAGCGCCTTCCCAGA |
| MILR1 | CCAGGGACCGTGGAGACACA | TGTGGAAACACACGGCCTGGA |

FIG. 8 (Cont.)

| Gene Name | Forward GSP | Reverse GSP |
|---|---|---|
| MIOX | CGGGATGTATCAGCCCCA | GTGTGCCAGGGGTAGAAGGA |
| MIXL1 | ACTGCCTGCCCGAACCAA | GTGTTCCTCCCATGAGTCCA |
| MME | CATAGGACACGAAATCACCCA | ACCTGCCAGGTCCCAGGA |
| MMGT1 | CCAAATACTGTGCAGCCGCAGAA | TCAAGCCACTGAGAAGCCACA |
| MMP13 | CTGAGAGGCTCCGAGAAATGCA | ACCCACATCAGGAACCCCGCA |
| MMRN1 | ATGTCCCAGGTGGGAAAGGA | CGGCCCACTGTATCCAGGA |
| MOXD1 | CACGAGTGCTATCACCCCAA | CCAGCCTCAATCACCCCA |
| MPIG6B | ACCTGGACCAGGAACCGA | CTGCATAGATGGTGGAGGCA |
| MPL | CTAGGGTGGAGACCGCCA | GTCTGGAAGTGAGGGCCACA |
| MPPED1 | TGCTCAACACGGTGCAGA | CACAGTGCATACGGACGCA |
| MPZ | GCCAGGAAAGGACGCGTCGAA | ATCCTTGCGAGACTCCCCCA |
| MPZL1 | TCCACTACTCCCAAGGGCAA | GTGTCCAGGCTGGACAACGA |
| MPZL2 | CAGGTGAAGAACCCACCTGA | GCCAGAGCCAGGAAGTGGA |
| MR1 | ACCTATCAGGCGTGGGCA | TGACAAGGACAATGGACCCA |
| MRC1 | GACGACTCCCGAACCCAA | TCCACCCAGAGCTCGACA |
| MRC2 | TACCATGGCAGCTGTCCCCA | AGGATAGACAGGACGGCCCCA |
| MRGPRF | TCAACCACGTCATCCTGGCCA | CCCTGAGCGGCTCCCACA |
| MS4A1 | AGAGCCAATGAAAGGCCCTA | CCCCAGAGAGGGTACCACACA |
| MS4A2 | CTCATCCCCACCACTGCA | TACAGAGCAGACAACTGTTCCA |
| MSLN | GGAAGGGGCCAGCTAGACA | CGGGCCTTGGGATAGAGGA |
| MSR1 | GGAAGCCAACCTCATGGACACA | CCATGTCCCTGGACTGAGGAA |
| MST1R | TGAGAGCTGCCAGCACGA | CCAGTGCAGCCACAAGCA |
| MUC1 | GTCCACGACGTGGAGACACA | CGGCACTGACAGACAGCCA |
| MUC16 | CAAATGGCCAGCACAATCCCCA | GCTCCCAGGCTGGTAGCCA |
| MUC4 | CTTGAGCCTCACGACGCA | AGAGCGCGATCACCGAGA |
| MXRA5 | CCACTGTGCGGGAGATAGCA | GCAGAACCACACCCTCGGGA |
| MXRA8 | CCAGGCCCAGACCCCACA | GCGGCCAGGAGGACAGTGA |
| MYH1 | TTACCCGAACCCAGGCCA | CAGGGCCAGTGCTTCACA |
| MYH10 | CAAGAACCGCCTGCAGCA | CGGCATAGCGAGCAGAGA |
| MYH11 | GAAAGCAACGTGCCCTGGCA | CATCTCTGGAGGCACGGGCA |
| MYH6 | GGCAGAGATCGAGCGGAA | TCTGCAGCGAGTCCACCA |
| MYH7 | TGCCACCCTGGAGACCAA | TCCTCCTGCTCCAGCACA |
| MYH9 | GCCCAAGCAGCTGAAGGA | ATCCTTCCACAGCTCCGAGA |
| MYL3 | AGGACACAGGCACCTATGAGGA | GTGGCCAGCACGTGGCGA |
| MYOCD | AAAGCGGAGAAATGCCAGCAGA | AGCCGAGGGCTTGGTGAGGA |
| MYOD1 | CCAGTGCACTCCGGTCCCAA | AAAAGTGGTCCTGAACCGGGAA |
| MYOF | AGATGAGCCTCCTCCTGAGAGA | AGAAGGTCACCCACCGGA |
| NAGPA | GCCCCTCTAACTGCAGCCA | ATGCCAGCCAAGGGGACA |
| NANOG | CCACCAGTCCCAAAGGCA | ACACACAGCTGGGTGGAAGA |
| NCAM1 | GGCAGTGAGTCAGAGGCCA | CATCACACACAATCACGGCA |
| NCAM2 | GCTCTCCAGAACCCGCCA | TGGCCCTGCAGACATAAGGA |

FIG. 8 (Cont.)

| Gene Name | Forward GSP | Reverse GSP |
|---|---|---|
| NCLN | GCTGACAAGCGGGACCCAGA | AGAGGAGGCTGAAGTGCTGGA |
| NCR1 | CACCAGCCTTGCACCTGAAGA | CTGGGCAGTGTGATCCCAGA |
| NCR2 | AGACAAGCCCCTGAGTCTCCA | CTCTTGGCTACGAGGAGTCCA |
| NCR3 | GCACATCCGGGACGTGCGA | CTTTCTCCACCACCAGCCGA |
| NCR3LG1 | GCCTTGCGAGACAACCCA | GCTGGAGGAGGTTCCCAGA |
| NCSTN | CCGAGAGCAGTGCCAGGA | AATCGTGCAGTAGAACGCACA |
| NECTIN1 | CAACTGGTACCTGCAGCGGA | CCTCCACACCCTTGGGGA |
| NECTIN2 | CCTGGTCCCATGGAACCA | CCGCCGTGAGATGAGGGA |
| NECTIN3 | CAGATTTGCTAGAGGAAGGCGA | ATCCAACCTGCTCCACACAGA |
| NEFH | GCCTCCTACCAGGAAGCCA | GGGAGTCCTTCTGGAAGCGA |
| NEFL | TCACCAGCGTGGGAAGCA | GGCTGGTGTAGTAGGACGGGA |
| NEGR1 | ACCAACGTGACACAGGAGCA | GTTAAGAGGCAGGCTCGCA |
| NELL1 | GCCACTCACTTGCCCCAA | TGCAGGGAGATCCAGCCA |
| NEO1 | CAATCCGTTCGAAATACCCCCA | TTCAATGGGTGGGAAGGGCGA |
| NEU1 | CTCCAACCCAGCACATCCAGA | CCTCCAGGGTTGCCAGGGA |
| NEUROD1 | ACACGAACCGTCCGCCGA | ATGGGGATCTCGCAGCGA |
| NEUROG2 | CTGGGAAGAGATGATGGTGGCA | TCGGCGTTAAAGAGAAAGGGGAGGA |
| NFASC | CGGGACACCCAGATCAGCA | ACCATCGCAGTGTGGGGA |
| NFATC4 | CTCTGCCTCGGTCTGAGGA | AATCCGGGCCTTGGACCA |
| NGFR | GCTACCAGCCCGAGCACA | ACTGCACAGACTCTCCACGA |
| NID2 | GGGAGCAGAGCCTGAGACGA | TGGCACGGGGATTCACCA |
| NKX2-2 | ACGCCGGCAAGAAGCGAA | GGCGGATGAGGCTGGCCA |
| NLGN1 | AATACCAGACGACCCCCAGA | TGACGGTCAGCCCAGTCA |
| NLGN2 | CACCAATGGGTGGCACCA | TGACCACGGCACTGAGCA |
| NLGN4X | TCGCTGCAGGCACACGACACA | GCAAAGGCTGCATCCCCGTCA |
| NMUR1 | GCACCTGGCCTTCCAGCA | TCTGAGGCGATGGCAGCA |
| NOMO3 | GAGATCCACGGGAAGGCA | GGGGCCAACACTGTAGGCA |
| NOS3 | GTGCTGCGGGATCAGCAA | CTGACGCTCCTGCAAGGA |
| NOTCH1 | CACAGGACCCAACTGCGAGA | CACAGGCACACTCGTAGCCA |
| NOTCH2 | CCCATTGATCGACGGCCA | CCTCCTCGGAGAGAAGCCA |
| NOTCH3 | TGCAACCCGGTGTACGAGA | CTGGCACAATCCAGCCCA |
| NPC1 | CCTCTGACTCCGGAAGGCA | TGGTGCCATGGCCAAGGA |
| NPHS2 | CAAAGACAAGCCAAAGTGCGGA | ATCGAAGCTGAACGGCAGCA |
| NPPA | CCTGGACCGGGGAAGTCA | CGCAGGCTCCGAGGGGCA |
| NPR1 | CTGGACCCAGAGCAAGGACA | TCCACGTGGAAGACCCCA |
| NPR2 | GGTCAACGCCATGCACCA | AGGCCAACAACCCCAGCA |
| NPR3 | CATGGCATGACCAGTGGAGA | GTGACTGTCTGGAGGGACGA |
| NPTN | TGTCAGCGCTCCTAAAGCA | GGTGGGGGTAGCCAACTGA |
| NPTX2 | AGGACGGAGAGAAGCTGGGCA | TGGCATCAAACCTACCCCCCA |
| NPY1R | AGTACAGGTCCAGTGAAACCAA | GCTGTGAGGTGGCAGAGCA |
| NRCAM | CTGTCATGGACCCCAGGCGA | TGTTCACTGCCATCACGCGGA |

FIG. 8 (Cont.)

| Gene Name | Forward GSP | Reverse GSP |
|---|---|---|
| NRP1 | GGTGGGAAGCACCGAGAGA | CGCGTGGAGAGAGCTGGA |
| NRP2 | ACCGAAGAGGAGGCCACA | CACAGGGCTCCTCGAGGA |
| NT5E | CGTGCACCGCTACGGCCA | GAGAGGGTCATAACTGGGCA |
| NTM | TAGCCTCACCTGCATAGCAA | GCCACGTCATTGGAGGCA |
| NTN3 | CGACCCGCGACGGGCACA | GCAGGCTCACGAAGACCA |
| NTNG1 | ACTGCCAGAACGGAGGGA | GCCAGAGTCGGAGCCGCA |
| NTRK1 | ACTGAAGGAGGCGTCCGAGA | CCCTCGGTGCAGACGCCGAA |
| NTRK2 | CGAGAGCCCCACATGAGGA | GAATGTCCAGGTAGACCGGAGA |
| NTRK3 | AGACCTGGCCACCAGGAA | TCAGGAGGCATCCAGCGA |
| NTSR1 | TCTTCTACGTCAGCTCCACCA | TCCTCCTGCGCCGCCACA |
| NUP107 | GAGGCAGAGGTGACACGGA | AATGAGCTAGGAGTTCGAGGGA |
| NUP210 | TCCTCCACATCGACCCCA | TCTGAGGGACGCTGACCA |
| NXPH4 | CACCAAGAGGAAGCCGTCCA | TTGCCGGTCACCAGCAGCGA |
| OAS3 | AGCTACAGCAATGCGGGCGA | ACCAGTGCTTCACCAGCCGGA |
| OGN | CACCTTCCTCTACTTGGACCA | CTTCAATGCGGTCCCGGA |
| OLFM1 | CCATCCTCAAGACCCGCA | TGGCGTACACGGCCCACA |
| OLFML2A | CAACCAGCAGGAAGGCCA | GCTCGTTGAGGAACGGCA |
| OLFML2B | GCGGACCTGAGCACACAGA | CGAACAGCAGCCTGGGGA |
| OLFML3 | CCTGGCAGCTGATGAGGA | GACGACATAGAGGGTCCCACA |
| OLIG2 | CATGGATGGCCTCCGCGA | CGCTTCATCTCCTCCAGCGA |
| OLR1 | TGAAGGACCAGCCTGATGAGA | AGGAGGTCAGACACCTGGGA |
| OPCML | GGAACACCAATGCCAGCA | AAGAGGGTCCCTGATAGCCA |
| ORM1 | CGTGGGAGGCCAAGAGCA | GCATAGACAGACAGCCCCCA |
| OSCAR | CAGTACCGCCACTCCGCGCA | CAGCACGTAGGGCGCGGA |
| OSMR | AACCCAGTAGAGGCACCACA | TCTCGGTCGGGGGAGGCA |
| OSTM1 | CTTCGGCAGCAGTCCGCACA | TCCGGGGGCAGCGACAGA |
| OTX2 | TTCCCGGACCAGGGGCCA | TAAAACCCAAGCTTGAAGCTCCA |
| P2RX7 | GGGCCTGCATCACCACCTCA | GGAATCCACATCCAGCGCCA |
| P2RY10 | AAGGGATCAGTGAGAGGCAGA | ACTTGCAAGGCACAGGCA |
| P2RY11 | ACATAGCCCAGGCCACAGCA | GGGGCAGTGTCGGCAGCA |
| P2RY8 | GCTGTTGCGCACGGAGGA | TGTTGAGGCAGCTGAGACA |
| P3H1 | GCTGGGGCAAGAAGGCAA | CGATGGCAGTGCGGCACA |
| PANX1 | GAAGAACTCACTGCAGAGCGA | ATGTCAAGGTCACGCGCA |
| PARM1 | AGACCACCACCACCTTTCCCA | TAGGTAGGCTGCAACTCCA |
| PCDH1 | CCTGCCCCTCAACTACCCA | GCAGCTGGATGGAAGGCA |
| PCDH15 | TCCAGAGGCAGTGACCAGCA | CAAAACCACCAAGATGGCAGGA |
| PCDH17 | CCTCCCCTCAACTCCACCA | GGATCCTGGGCGAGCACA |
| PCDH18 | CCAGCAGCAGCATCCACA | CCGATCCACCTCACTGCA |
| PCDH19 | TGTGACCATCTGCAGCCCCAA | CACGGAAGGCTTGGTGGGCA |
| PCDH20 | CAGCGAGGAGAGAGGCCAA | CCAACACTGTGAGGGCCA |
| PCDH7 | CACATCCCACTCACCCAGGA | ATGCCAGCAACCACGCCA |

FIG. 8 (Cont.)

| Gene Name | Forward GSP | Reverse GSP |
|---|---|---|
| PCDH9 | AGTCCTGACCTGGCCAAGCA | GGGAACTGCACTCTGAGGCA |
| PDCD1 | CCTGAAGGAGGACCCCTCA | GCTCAGGGACACAGGGCA |
| PDCD1LG2 | CCACACCGTGAAAGAGCCA | TAGTCCCAGGCGACCCCA |
| PDE6B | GAGACGACCCGGAAGGAGA | CTCCCAGAACTCAGCAGCCA |
| PDGFRA | TGGGTACCGGATGGCCAA | CAGGCAGCAGATTCTCCACA |
| PDGFRB | TCAGCTACCAGGTGGCCAA | CAGAGCAGGATCCCGAAGGA |
| PEAR1 | CCCCTGATCCATGACCGA | GGATGCCGTACTGGAGGCA |
| PECAM1 | GACTCACCTGGCCCAGGA | TGCCACTGTGCTCCACCA |
| PI16 | TCCTCCAAGTCCCTGCCCAA | TCCAGCCAACACCAGAGGA |
| PIEZO1 | CAAGTACATCCGTGCCCCCAA | TCCTGCAGCTCGATGACCCA |
| PIGT | CTGGTGAACCTGCCGACA | GTGGAAGGTTCGGGTGAGGA |
| PILRA | CAGCACAAGGCCGCCTTCCA | TGTGTCCAGCTCAACTCGGCA |
| PKHD1L1 | AAGGTGACTGCCCAGCCA | ACCGAAGGCTGCTGAGGA |
| PLA2G3 | TGCGGAGGCTTCAGCAGA | CCTGGGTTAGCTGCAGGCA |
| PLA2G6 | GGCCAAGGAACTGGGCAA | CCCAGAGGGCGTTGACCA |
| PLA2R1 | GAGCCGGTGCAGTACACACA | GGCTGCTTGCACAAGGACA |
| PLAT | CCATCCAGCCGCTGCACA | GCGGCCATCGTTCAGACA |
| PLAU | GGTGATCAGCGCCACACA | AACGGATCTTCAGCAAGGCA |
| PLAUR | CAGGACCCTGAGCTATCGGA | CGAGGTAACGGCTTCGGGAA |
| PLBD1 | GGCAAGAGGTGGGCAGACA | GGAACATTGTAGGAGGGCCA |
| PLPP1 | AGGCAGACTGCGGCCTCA | CAAACAGCATGCAGTACATGGA |
| PLPP3 | CAAAGTCCAGGAAGCCAGGAA | CTATGCAGCAGGCCACCA |
| PLTP | GAGGTCCAGCTGTCCAGCA | TGGGATCAGAGCCAGCGA |
| PLVAP | ATCAGAAACTCAGCCCTGGACA | CTCCAGGCTAGCTGGGTCGA |
| PLXDC1 | CAGAATCTCGGCGAAGGAGCA | ATGCTGCAGGCAGGTCGGCA |
| PLXNA1 | TGACGGTCACAGGCACCA | CACAGGGTTGGCCACAGA |
| PLXNA2 | GCCCCGATGATCACCCCAGA | TGTACTTGATGGCCAGGGGGA |
| PLXNA3 | AGGCTCAACTCACTGGCCCA | CTCTCGTAGCGGCTGAGGGA |
| PLXNA4 | GGAGGGACCCAAGTGACCA | TGTCCACCTGCACCGACA |
| PLXNB1 | CCAAACTGCCATGCCCCA | CAGTCAGTGGCTCCACCGA |
| PLXNB2 | CCCACGATGCCAACGAGA | CAGGGCCTCATACACGCA |
| PLXNB3 | TGAAAGCCACCGAGGAGCCA | GGTACTTGACGGCGATGGGGA |
| PLXNC1 | GCGAGCTCCGGAAAGAGA | GAAGCCACCTGACTCAGGGA |
| PLXND1 | GGGAATCTCCGACCCCGACA | GTCGATGAAGGCCTGCGCGA |
| PMCH | TCTGCCACTGAATCTGGCTA | CTTGCCAACAAGGTCGGTA |
| PMEL | CATGGGTACCACACTGGCAGA | GGACCTTCAGGCTCAGGGA |
| PMEPA1 | GCAACACGAAGCTTCCAGAACCA | CACAACAGCCATGGAATCAGGCA |
| PODXL | GCCGAGCAGTCAAAGCCA | GTACACATCCTTGGCAGGGA |
| PODXL2 | GCATATGCCTCCCAGAGAGGA | GGGATCCATTCACAGGGAGCA |
| POMC | AGGCCGACCTGGAGCACA | GCGTCTGGCTCTTCTCGGA |
| PON1 | GTGAACCATCCAGATGCCAA | TAAAAGTGCTCAGGTCCCACA |

FIG. 8 (Cont.)

| Gene Name | Forward GSP | Reverse GSP |
|---|---|---|
| POSTN | CAGCAAACCACCTTCACGGA | TTAAGGAGGCGCTGATCCA |
| POU3F4 | TGCACAGGGCCGCAAGCGCA | AGGAGATCTCCTGCGCGGCA |
| POU4F2 | CGCGCTGGCCAACCTCAAGA | CTCGAGCCATGCCTGCAGGA |
| POU5F1 | AGGAGCTAGGGAAAGAAAACCTGGA | CCCAAACTCCCCTGCCCCCA |
| PPY | CAATGCCACACCAGAGCAGA | CCCACTCCGAGAAGGCCA |
| PRELP | CCTGGAGAACGTGCCACA | TCATGAGGTCCAGCGGGA |
| PRF1 | ATCTCCAACTACGGCACCCA | GGCCTTGGCTTCGGCAGA |
| PRG2 | GGAGGTGCTACAGGGGCAA | AGCGACCCGAGCCTGTGA |
| PRNP | CAGTCAGTGGAACAAGCCGA | CCCAGCATGTAGCCGCCA |
| PROCR | CTCGGTATGAACTGCGGGAA | GATGCCTACAGCCACACCA |
| PROM1 | GACCAAAGAGGCGTTGGAGA | ATGGATGCACCAAGCACAGA |
| PROM2 | GAGGAGGTGACTCAGCGCA | TGCACCATGCCAGGCAGA |
| PROX1 | GCCGAAGCGAGAAGGCAA | GAGGTGGGAAGACCTGAGGA |
| PRSS23 | GTGAGCCCTCCTGCTAAGCA | ACATCCTCACATAGACCCCAGA |
| PRSS35 | GGAATCAGCCCAACGATCAAGA | GGATTCGTCGGACACACTGCA |
| PTAFR | CCAACACAGTGCCCGACA | CCGTGCACACCATCCACA |
| PTCRA | CACAGGCCTGGTGCTCAAGA | TGTGACGCAGGGGAGGTAGA |
| PTGDR | CAGCAAAAAGCCCACCCAGGA | CGTCTCCACGGACAGCAGAA |
| PTGDR2 | GCCACAGCAACACCAGCA | TGCGGCAGCCCACCACGA |
| PTGER2 | GAGGAGACGGACCACCTCA | CAGGAGGCCTAAGGATGGCA |
| PTGER3 | GGGCCAGTACACCGTCCA | GGTGGCCAGGTTGCAGGA |
| PTGFRN | CTGGCAGAAGGAGGCAGAGA | GACAGGACAGGAGCCCGA |
| PTGIR | GCGCACCGGAGAGGACGA | GCGTAGAAGCGGAAGGCA |
| PTK7 | CCCCTCAGCACCAAGCAGA | TGAGGCCCAGGGCAGACA |
| PTPRA | AGTCAGGGAACCACCCCA | CTGCACCACCTTGTAGCAGA |
| PTPRB | AAGTCACAGCGGAGAGCAGA | CCACGTGATGGCCAAGGA |
| PTPRC | CACCAGCTGGCCAGACCA | GTGCGCCCAACACCAGCA |
| PTPRD | GGGAGCATGGAGAGGAGCA | ACCCAGGCCTTGAGGGGA |
| PTPRF | AGACCCTGCCACGAGCAA | GTAACGTGTGCCTGCCGA |
| PTPRG | GATCCCAAGAGGCCCGAA | GAGAAGGATGAGGCACACGA |
| PTPRJ | CAGCGAATGGCACAGAAGGA | ATGACAGCGCGAGGCTCA |
| PTPRK | CAAGAGAGAAGCCGGAGCCA | CCCACAGTGAACGGGGCA |
| PTPRM | CGATGGGGAGAGCAGCAA | GTGGACACAACTGGGCAGGA |
| PTPRQ | GGCCAGAGGACAACAAGCCA | AGGAACCCCATGCTCTGGCCA |
| PTPRS | CAGTTCACAGACTGGCCGGA | CCACGCCTTCATACCGCA |
| PTPRZ1 | GGAGGAGTGACGGCAGGAA | TCAGGCAATGCTGCACCA |
| PTTG1IP | GGCCGACGCCGTACTGGA | AACTCCCCAGCGTGCAGA |
| PVR | AGCAACCCAGAGCCCACA | TGGCGAGCTCCTAGGGCA |
| PXDN | CTGTGACGCCTCAGGACAGA | CAGTCAGGTGGGCCACGA |
| QSOX1 | CGCTAGCCACTTCGAGCA | ACGTCCCACACGGGCACA |
| QSOX2 | CCAGGGGTGAGGAAGAGGAGA | GGCTGGAGAAGTCAACCCCGA |

FIG. 8 (Cont.)

| Gene Name | Forward GSP | Reverse GSP |
|---|---|---|
| RAB5C | TCCAGGAAGCACAAGCCTA | GGTTTCGGCCTGGAGCACCA |
| RAET1G | CCACCCTCAGTCCCTGCA | GCGAGTCACGTGTCCACCAGA |
| RAMP3 | CACCGGCATCCACAGGCA | CCAGGCCAGCCATGGCGA |
| RCVRN | CCCAGCATGTGTTCCGCA | CCGTCCACGTCGTAGAGGGA |
| RECK | TATCAACTCTGACAGCCCGA | GTCCAGAGCAAGTGCAAGGCA |
| RELL1 | AAGTCCAGAGAGAGCAGACCA | GTTGCCGGCACCTCCCCA |
| REPS1 | TCATCCCAGCGGTGGGAA | CTGACCACACTGCATCACCA |
| RET | CTGCTTCCCTGAGGAGGAGA | AGAGGAGTAGCTGACCGGGA |
| RETN | GTGCCAGAGCGTCACCTCCA | GTGGTCTCGGCGCGCACA |
| RHBDF2 | TCACAGGCAACCTCGCCA | AGCCGAAGATGTGGGCGA |
| RIN2 | CTGACAGCAAACCCCCGA | TGACGCAGGGAGGCAGGA |
| RLBP1 | CTTCATCCGCGCACGGAA | AGCATGACCACTCGGCCA |
| RNF13 | TATCGGAATCCCGCTCACA | CCATTAGGCTGCAACTGGACCA |
| RNF130 | AAGATCAGCCCTCGGCGA | AGGGCACTGAGGAGGCCA |
| RNF149 | TACGGGAACATCACCTTGCCCA | ACACCACAGACTGACCGCTGA |
| ROBO1 | GGATACGGATGCGCCAGA | CATGGACCCCGTGACAGA |
| ROR1 | CTGAAGACTGCCCACCCAGA | TGGGCTGGCACTGAGGGA |
| ROR2 | TGACACACAGAACGCCCCAGA | GGCCTCGTCCACCTGCAGA |
| RORC | GGAGCCTGTGTAGCCAGCA | AAGCGGCTTGGACCACGA |
| RPN1 | CAGCCGCAGAAGCCAGGA | GGTGGAGATGTCCCGGGA |
| RPN2 | GAGGAGACTGTGCTGGCAACA | CGAGTTCATCCAGGCGAGCA |
| RRAD | CACGACGGCAAGCAGGCA | AACCGAGAGGTCGTGGCA |
| RTN4R | AGGCCAGGCTGTTCACGCAA | GCTGCAGGTGAGGCTGGGTA |
| RUNX1 | GTCCACAGTCCACGGTACACA | CTCAGGCTGGGCACGACGAA |
| RYK | GCCAGACTCCCTACGTGGACA | CTCTGGATCTAAGGCCCAGCA |
| RYR2 | CTACACGCAGTCAGAAACGGAA | GACGGCGACGTTGAAGCCGA |
| S100A8 | CCGTCTACAGGGATGACCTGA | ACCAGAATGAGGAACTCCTGGA |
| S1PR1 | ACTCCGGCACCAACCCCA | AGAGTCTCCGCTCGGGCA |
| S1PR2 | CTGCCTCTCTACGCCAAGCA | CGTGGCTTGAGCGGACCA |
| S1PR3 | GTCCATGGCACTGCTGCGGA | ATGACCGGGTTCATGGCGGA |
| S1PR4 | CGTCGAGGCTCACTCCGGA | TGGACAGGGGCTCCCGCA |
| S1PR5 | CTGCGGGGACCACCTCGA | GCCAGTCCCAGGAAGGGA |
| SCARA5 | AATGGCTCAGGTCCGCACGA | CCTCCTCCACACCGCGGA |
| SCARB1 | CGGTCACGGGAATCCCCA | TGGCAGATGACAGGGACCA |
| SCARF2 | CGGGACCTCCAGGGGCGA | GCCAAGCCCCCGCCGGGA |
| SCN2B | TGCCACCCTCAACGTCCTCA | TCTCAGCATCACCGACACA |
| SCN4B | CGGCGAGATGGCTGGGCA | CCGGAAGTGGAGGTCCTCGA |
| SCNN1D | GGAACCGCCTCAAGACGA | CCGTCACACAGGGTGACCA |
| SDC1 | TGCTGAGGATGGAGCCTCCA | CAGGCTCCACGGCCACTACA |
| SDC2 | ATGTACCTTGACAACAGCTCCA | TCATCAGCTCCCGAGCCA |
| SDK1 | TCAGCTCAAGTGGAAGCCCCA | ATTCTGCCCCGTGCAGGACGA |

FIG. 8 (Cont.)

| Gene Name | Forward GSP | Reverse GSP |
| --- | --- | --- |
| SDK2 | GGTACAGCTCTGCCATCGCCA | CTCACGCCCGGCTTCAGGA |
| SECISBP2L | TCCATTTGACACACCCCCA | TGTGAGGCCCATTCCAGGTCA |
| SEL1L | AGCTGAAGCCAGCCCAGA | GTTCCCAACAGCAGCGCA |
| SELE | GGGACAACGAGAAGCCCA | TCCTCACAGCTGAAGGCACA |
| SELL | CAAGGAGGACTGCGTGGAGA | CATGACCAGGGCTGGCAAGA |
| SELP | CTGCACAAACAGCATGCCA | CGTAGAAGCCACCGCTCCA |
| SELPLG | TCCCATGGCAGCCAGCAA | CCTCACCCCCATCAGGCA |
| SEMA3A | GGCAATTCCAGAGGCGAA | AACCCATGTTCCACCGCA |
| SEMA3C | ACGGACAAATGGTCCCCA | AGTGGCTGAATGCCCCCA |
| SEMA4A | TGGACAGCCAGGACCAGA | CTCTCAATGGGGAGGCCA |
| SEMA4B | GTAGCCAGCTACTGCCCAGA | AGCAGCACGGCCAGCACA |
| SEMA4C | GGCCCTGTCCTGAACCAGA | GCCGAGTTGGAGAAGGCA |
| SEMA4D | GCGTGTTGAAGGCCGAGA | CAGGCACTGGTACACCCCA |
| SEMA4F | GGACACCTCCACCGAGCA | GCTCTGGAGACGGCCACA |
| SEMA4G | GCCTGAGCACAGTGGCAA | AGGATGAGGCAGAGGCCA |
| SEMA5A | GCAACAACCCCGAACCCA | GGGGACCAGCAAGACCACA |
| SEMA6B | GGCTTAGGGGACTGCACAGGA | CACGGAGGCCCACGAACCA |
| SEMA7A | ACAAGGAGAACGTGGAGCAGA | CAGTGCTGAGCCTCGCGGA |
| SERPINA1 | GAGGACTTCCACGTGGACCA | GCAGCACCCAGCTGGACA |
| SERPINA3 | GAGGAAGCCTTCACCAGCAA | CAAGCACAGCCTTATGGACCA |
| SERPINB2 | TCAGCGCACACCTGTACAGA | TCCAGCAGCTCCAAGCCA |
| SERPINE2 | GTCGACAAGTGCCCCCAA | TCGGCAGTGCAATCAGCA |
| SERPINF1 | AAGCTCGCCAGGTCCACA | AACAGCCTTAGGGTCCGACA |
| SERPING1 | CAGCACCAGACAGTGCTGGAA | CGAAGAGGAAGGGCTGCTGCA |
| SERPINI1 | CAAAATGTAGCCGTGGCCAA | GAGGGCCAGATAAGTGGCA |
| SEZ6L2 | AGGTCCCGAGGAACGACA | AGCCTAGCAGCTCGTAGCCA |
| SFTPB | AGAATGGCTGCCGCGAGA | CAACACAGGCCTGGAGCA |
| SFTPC | TTCCAGGCCAAGCCCGCA | TAGAGCGGCACCTCGCCA |
| SFTPD | GCACACAGGCTGGTGGACA | CAGTCCTCTGACCCGCCA |
| SGCB | AGAAGGCTGTTGAGAGAAGGA | AATGCGAATCACGGCCCA |
| SGCD | GAAGCCACCTGCAGGACAGA | CCCATTGGCGCAGACGCA |
| SGCE | ATGTGCTGCCGACGGGAA | AAGCGTTGACAGGGGCCA |
| SGCZ | TGAGAGCCAGTGAAGATGGCA | GCGTCTCCACAGAGTGCCCA |
| SIDT2 | GCAGAGTCGAGGGAGCACA | ACACCAGGAAGGACCCGA |
| SIGLEC1 | CTGGCGTCTACACCTGCCAA | GGCATCCTCCAGCAGGACA |
| SIGLEC10 | CATCCTGCAGCTGCCAGA | GATGATCAGGGCCAGGCA |
| SIGLEC12 | GGAAGGGGGATTCAGGGA | CCCCTGTTCACAGGCCCA |
| SIGLEC5 | CTGGAGGGGAACAGCAGCCA | GACAGATACAGAGCAGGGCCA |
| SIGLEC6 | CCAGGACCACAGCACCAA | GGGGAAGCCCTGGAACCA |
| SIGLEC7 | AGCCAGACTGACTCTGACCCA | TTCCTCCTGCACTGCCCAA |
| SIGLEC8 | GGGGAGGGACCTGGTGGGA | GGCGGGGGAGGCCTCAGGA |

FIG. 8 (Cont.)

| Gene Name | Forward GSP | Reverse GSP |
|---|---|---|
| SIGLEC9 | GGCCCAACATCCTCATCCCA | GACACGGAGGTCCCTATCCA |
| SIRPA | AGCCCACCCGAAGGAGCA | CCGCCATCAGTAGGGCCA |
| SIRPB1 | GGAGACTCACAGGAGTGGCA | GGGATCAGGGACGTCATAGCA |
| SIRPG | GCATCCGCAGCACAGCCA | CAAGTTGGCAGTCCCACGA |
| SLAMF1 | AGGAGAACGGGACCTGCA | GTGAGGGACAGGAGGTGGGA |
| SLAMF6 | ATGGGAGGCCTTGGGAAACACA | ATCTTCGCAAAGCTTCTGGGCA |
| SLAMF7 | AAGCAGCCAATGAGTCCCA | CAGAGCTTCCTGGCAAGGA |
| SLAMF8 | GGCGACGGGAGACAACCA | CAGCATCAGGAGCAGCGA |
| SLC12A6 | AGAGCGAGACAGAGAGGCACA | GTCCGGACGCATGTTAAGCA |
| SLC12A7 | GACACCGTCCGCGACACCA | GTTGTCGTCCACCTGGGCCA |
| SLC12A9 | GGACCCTGTACAGCCGCA | CCGGAGATTCGCAGCAGA |
| SLC14A1 | GATAATCCATGGACAGGGGGCA | CGACTCCAAGATAGGCCGTGA |
| SLC17A6 | CAAATTCAACTGGGACCCGGAA | CTGTTGGCTGCCAGCCGAGA |
| SLC17A7 | AAGCACAAGACTCGGGAGGA | TGTCGTCACTGCCAGCCA |
| SLC1A3 | GACAAGCGCGTCACCAGA | CCGCGATGATGAGCGTGA |
| SLC22A16 | ATGGACAAGGTCGGGAGGAGA | GTCCACAGAGAACGGCGCCA |
| SLC23A2 | GCCAGCTCATTGGGACCA | CGGATCCGGGGATACCAGA |
| SLC26A5 | GGAACCGGTGGGAAGACACA | CAATCACAATGGCCGACAGCA |
| SLC29A1 | CAGAGACCGCAGGAGCCA | TGCCCGGAACAGGAAGGA |
| SLC29A2 | GCTCCACCAGTCCTGGGAA | TCTGGGGCACGTGGCACA |
| SLC29A4 | GGGTGATCTGGGCCGACA | GAAGACCACACGCAGGCA |
| SLC2A1 | CTCCACGAGCATCTTCGAGA | CAGGGTAGCTGCTCCAGCA |
| SLC2A2 | AAATTGGGCCAGGCCCGA | AAGGCCAGGAGCACTCCA |
| SLC2A4 | CCTGGGGACGCTCAACCA | AGAAGGGCAGCAGGACCA |
| SLC32A1 | CGTGGTGGTGAGTGGCAA | AGTGGGCCAGAGTGCACA |
| SLC38A1 | TGACAACGTGCAGTCCGA | AGGTAACCACGGTATGACGACA |
| SLC39A10 | CCAGTGGCACCACAAGCA | GCACCAATTGCGAGCCCA |
| SLC39A14 | GAAGCTGCAGAACGGGGA | GCGGACACCTTTCAGCCA |
| SLC39A6 | CAGCGCTACTCTCGGGAGGA | AGCAGCACCAATTGCTAGGCCA |
| SLC3A2 | CTGCTCAGCACCCAGCCA | CGTAGGGGAAGCGGAGCA |
| SLC44A1 | TAGGTACGGTGGCAAAAGGA | TCAGCACACATCGTGCACA |
| SLC46A1 | CGGGCCCAGGGTTATGCCAA | TAAGATGTCCTGGGCCCCA |
| SLC4A1 | TCACGTCGCTCAGCGGCA | CGTGGACTTCACCACCCA |
| SLC4A7 | TGAACCTCCAAACCCCAGCAA | GATGACCACAAGCTGACCCCA |
| SLC6A6 | CCTGGAATCGACCACCCA | AGGCGGGTGATGTCAGGA |
| SLC7A5 | CCCTGGCCATCATCGGCA | TCCAGAAGGAGACGGCGA |
| SLC8A1 | CCATCTACCACGCAGCCA | CGATACAGCAGCACCCCCA |
| SLC8B1 | GATCTCCCGAAGCCACACAGA | CAGGTAGAAGAGGAGCAGGCA |
| SLC9A1 | GATGCTGCTCCGGAGGCAGA | GGTCGATGGTGATGACAGGCA |
| SLCO2A1 | CCCCGCATAGCTACCACCA | GGGGTAGACTTCGGCCACA |
| SLCO3A1 | CCCGAAGGTCACCAAGCA | CCAGACAAGCACACGGGA |

FIG. 8 (Cont.)

| Gene Name | Forward GSP | Reverse GSP |
|---|---|---|
| SLCO4A1 | TCGGCTGGGTGATCGACA | CACCTTGTACAGGAGCCCCA |
| SLCO4C1 | TCCGAAGAGAAGCTCCGGTCA | CAATACCTTGCGTGACGGCCA |
| SLIT2 | TGGACCGCTGAGGAGCAA | ACACCTCGTACAGCCGCA |
| SLIT3 | CAGGTGGCCACTGACAAGGA | AGCGTCACCAGCTCCACA |
| SLITRK2 | GCTAGAAAAGCAGGCCACACCA | GACTAGGCCTGCGCTGGGAA |
| SLITRK3 | GGCATCCAAATGCAATGCCACA | CTCATACACATGACCCACGGGA |
| SLITRK4 | TCCGGAGCACCCTTAGCTA | TCACAACAATCCCGTCGCTCA |
| SLITRK6 | CCCCCGGGCATCTCGACA | TTGTTGCAGGAGTGGTGACCA |
| SMAD2 | GAGCAGAATACCGAAGGCAGA | GCAACGCACTGAAGGGGA |
| SMO | GGCCTTCTCTAAGCGGCA | TGCCACAGGGGTGACAGA |
| SMPD3 | GGGTACATCGCCTGCACA | GTTGGCTGCGCTGGACGA |
| SMPDL3B | CTCGAGTACCAGCTGACCGA | CAATGTCCACCTGGCGCA |
| SMTN | CCTCAGAACCGACGCCAGA | ACCTCCACCAGGGGCACA |
| SORCS1 | ACCCTGAACCACCCAAGCAACA | CAAGCACCCCACTGCTCTCAA |
| SORCS2 | GAACCTTACACTGACCGGGGA | TTGAGGCCAATGACAGGAACCA |
| SORL1 | CAGTGGGTCCCAGATGGAGA | CCCTGAGGGCAGTCACACA |
| SORT1 | AGCCGAATGCCGTAGGCA | GATGCCTCCAGAATCCAGGA |
| SOX17 | GAGGTGGACCGCACGGAA | AGCTGGCGTCGGACACCA |
| SOX2 | ACATGAACGGCTCGCCCA | CCTCGGACTTGACCACCGA |
| SOX7 | AACACTCCTGGCCACCCA | TGGCCGTGGCATCAGCCA |
| SPANXC | GGCCAACGAGATGATGCCGGA | ACGTTCCTCCTGTAGCGAACCA |
| SPN | GTCTCCAACGACCTCCACCA | CGCCACAGCAGGAGCAGA |
| SPPL2A | GCACAACCAAGGACTACTGCA | GGCAGCTTCCCCATGGAA |
| SPPL2B | CATCACGCCCTTCCTGACCAA | CAAAATGTCTCCGAAACCCAGGA |
| SRPRA | AGCATGGTGGCCGCACCA | CTGCCGTGTCCACCAGCA |
| SSR1 | CCCATGGGCGGACGACCA | CTAGGAGTTGATGAAGGCCA |
| SSR2 | GCACCTGGACAGGGAGGAA | CGATGGAGGGAAGGGTCA |
| SST | GGACCCCAGACTCCGTCA | GATCTTCAGGTTCCAGGGCA |
| ST3GAL1 | CAACTGGCTGCAAGGGCA | CAAGTCCACCTCATCGCAGA |
| ST3GAL4 | CAAACTGCTGAGCCTGCCAA | CACAGAGGTGGAGGGCCA |
| ST6GAL1 | CCTCCCATCCAAGCGCAA | TCATAGAGCAGCGGGTGGTA |
| STAB1 | GGCCTATGGCATCGACCA | CCTGTGACCCCTCAGGACA |
| STAT4 | GGTACAACGTGTCAACCAACGA | TAAGACCACGACCAACGTACGA |
| STAT6 | GACCGTGGAAAGGGACCA | TGGAGGAATCAGGGGCCA |
| STEAP4 | GAGGCACAAAATACCGTCGA | GAATCACTGAGCCAGGCTGA |
| STIM1 | CTGCCCTCAACATAGACCCCA | GCTGCCGAACACTGCTCTGCA |
| STS | CCCTTGCCTGAGGACAGGA | TCTGAGGGTGCCAGCGCA |
| SUCNR1 | GTGCACCCTCCCCATGCTGA | TAAAACCCAAATGGCCAAGGAGA |
| SUCO | TGGGCAGCGGTGAACAGGAA | CTGCGCTGCCGATAAAGAGCA |
| SUSD1 | CCACGCCTCAGACTGAGGA | CTTTGGAGGGCCAGGGGA |
| SUSD2 | GCTGAGCTTCACCGAGCA | CAGGCAGCAGGACGGACA |

FIG. 8 (Cont.)

| Gene Name | Forward GSP | Reverse GSP |
|---|---|---|
| SUSD5 | AAGCGAGGGCATGACCCA | GCCCTCAGTCTCGGAAGCA |
| SV2A | CGTGACAGGGACGGGCGAA | ACAGTCAACACGTCCAGCGCA |
| SYT17 | GACCGGGGTCAAACGCAA | AATCAGCGCCTTCCACCA |
| TACSTD2 | CGGTATCGTCCCAGACCCAA | AGGAGACCCTGAGGCCAGGA |
| TAGLN | GCAGCTTGGCAGTGACCAA | CTGCCCATCTGAAGGCCA |
| TAT | CCATCCCTGGACTCCGGCCA | CTAACCGCTCCGTGAACTCCA |
| TBX21 | GGACTGAGATTGCCCCCA | GAGGAGCTGTCACCACTGGA |
| TBXA2R | GATGGCTCAGCTCCTGGGGA | TCCAGGTGGCCACGCGCA |
| TBXT | CATGTGAAGCAGCAAGGCCCA | CCAGTCACCACTGGCTGCCA |
| TCTN2 | CACGTTGCAATGAGAGGCAA | CGGATGCTCAGGTGAGCA |
| TEK | AGAAGCGGCCTAGGACAGAACA | GGTCCCAGGTGTACAGCACA |
| TENM1 | AAGTCCAGCCTAGGGCAGCA | TGACCTCGGCTGCTGAACACA |
| TENM2 | GCGACCTGGTCACACTAGGCA | AGTCCTGCCGTTGACCAGCA |
| TF | CCGAAGACTGCATCGCCA | CTGCCAAGACAGGCACCA |
| TFPI | GTATGGTGGATGCCTGGGCAA | GTTGATTGCGGAGTCAGGGA |
| TFPI2 | CGGTGGGTGTCACCGGAA | TTGGTGCGCAGAAGCCCA |
| TGFB1 | TGCTTCAGCTCCACGGAGA | CCGAGGCAGAAGTTGGCA |
| TGFBR2 | AGCCCAGTGTGTGGCAGA | TAGGGAGCCGTCTTCAGGA |
| TGFBR3 | TCCTGCTCAACTCCCCACA | TGGACCACAGAACCCTCAGACA |
| TH | GTGCAGCCCTACCAAGACCA | CGCTGGATGCGTGAGGCA |
| THBD | GCAGCGCTGTGTCAACACA | GCTGGCACTGGTACTCGCA |
| THBS1 | ACTCGTGCCCAATCCCGA | TAACCTACAGCGAGTCCAGGA |
| THSD1 | CCTCAGAGTCGAGGTGCCCA | TTCCTCAAGGGCTGCCCCA |
| THSD4 | GGAACAACCGGCCGGCAGA | CCGCTCCCACACTCGATGGA |
| THSD7A | CAGCATCTGTGCCCAGAGCA | GACACCACACTGTTCGGGAAGA |
| THY1 | GACCCGTGAGACAAAGAAGCA | TGAAGGCGGATAAGTAGAGGA |
| TIE1 | GGCCCTCTCAGACTCCGAGA | GCCACCTGCACCTCCACA |
| TIGIT | AGGAGGAATGGAGCCCCA | GTCATGCAGCTCGGCACA |
| TIMP1 | CCGGGGCTTCACCAAGACCTA | TGGCTCCCGAGGCAGGCA |
| TLL1 | CCATGAGGCACTGGGAAAAGCA | CCTCGCCGACCTACATAGGA |
| TLL2 | TCGGATGCCTCAGTGCAGA | TCCCCAAACTGGGCGTGGGAA |
| TLR1 | GCTGGAACCCATTCCGCA | GCTGCCCTTAAGTTAGCCCA |
| TLR2 | GCAGCAAGCACTGGCCAA | CCGTGAGCAGGATCAGCA |
| TLR3 | CACAGGCCAGGAATGGAGA | AGGCTTGGGACCAAGGCA |
| TLR4 | TGGATCAAGGACCAGAGGCA | TGCAGCCAGCAAGAAGCA |
| TLR6 | CGTCACCATCGGTGCCACCA | TTCCTGGCCCTGCGCCGA |
| TLR9 | TGGCAGACTGGGTGTACAACGA | GCGGCTGCCATAGACCGA |
| TM2D1 | CGAGGACCTCAAAGTGGGACA | AAAAAGAGACAATGCGACTGCCA |
| TM2D3 | CTGCACGGTGCGGGACCA | CCAGGCCACCGAAGCTGA |
| TM9SF1 | CCGGCAGATTGGAGGCGA | CCGTCAGAAGCAGCAGGA |
| TM9SF3 | GAAATCTGTCAGGTCAGCCCAA | ACAGGATAACCAGCACCAGCA |

FIG. 8 (Cont.)

| Gene Name | Forward GSP | Reverse GSP |
|---|---|---|
| TMCO3 | TCCATCGAACCCATCCGCGA | GAAAACTCGCTGACCTGGGCA |
| TMED4 | GAAGGACCCCGACGGCAA | CATGCTCCCCAACCTGGA |
| TMED7 | GGGTGCAGGCTGCTCGCA | GTCAGGAAGCTCGAAGGTGA |
| TMED9 | AAGCAGCGGGAGGAGTACCA | TGAACCTGCCCTCGGAGCCA |
| TMEFF1 | CGGCGGCAAAGGCAAGAGCA | TACAAGCAGCCCTTCTGAGA |
| TMEM131L | CCGCCCTACCTCACAAGCA | GGGGTTGATGGGGCAGCA |
| TMEM132A | CCTGTGAGAGTGGGGGAGGA | GTCCTCACACACCCAGCGGA |
| TMEM132E | CCTACCCCATCCCACAGCCA | AGCTGCTGCCCCCACCTCCA |
| TMEM231 | CCTGAGGCTGCAGCAGAAGCA | CCTCTCCTGGTAGGCAGCAA |
| TMEM25 | ATCGACCAGGATGGGCCA | CTTCCACCCGGGTAGCCA |
| TMEM87A | AAACTTGGCAAGATGCACCA | ATCTCTCCAGTAGCAGGCAGA |
| TMEM87B | GCAACACTGGACTGTCAACCCA | ATCACGCCTTCAACAGCTGCA |
| TMEM8A | CCTCCGTCTACGCCTACACCA | AGGGCCCCAGCATGTTCCACA |
| TMEM9 | GCGAGTGCAGGTACGAGGA | CGGATCAGAGGGTCCACCA |
| TMIGD2 | CAGGGACGGCTCTCCTGGCA | CAGCCTCCTCCAACTCAGGAA |
| TMPRSS5 | GGGAGTCAGGACCCTCTCCA | TCCAGTGTACCCACCCCACA |
| TMX3 | CTGCGGCTCTGCGCCACA | TGGCCACACCATGGCGCA |
| TMX4 | TTGCAGGATGCGGAGGAGGAA | CTCTCCTCATCCACACCAGCA |
| TNC | AGGGGTACAGTGGGACAGCA | GCCCTTCCAGTGGAACCA |
| TNFRSF10B | AATAGCATGTGACACAGGACAGCCA | AGGGCAGAAGCATGAAAGGACACCA |
| TNFRSF10C | CACAGCTTCAAGGGGGAGGA | TGCACGGGTTACAGGCTCCA |
| TNFRSF11A | CTGCACAGGCTGCCGGAA | AGCCTCCCATCAGCCCCA |
| TNFRSF11B | AGAAAGTGGGAGCAGAAGACA | ACAAACTGAGCAGCTTCAGGA |
| TNFRSF12A | ACGATGCCGCAGGAGAGAGA | ATCAGCGCCACAGCTGGGCA |
| TNFRSF13C | AGCCCCTGGACAAGGTCA | CCAGGAGGAGGCCAGGCA |
| TNFRSF14 | TGCAAGGAGGACGAGTACCCA | AGGCCATTGAGGTGGGCA |
| TNFRSF17 | CTGCATCAAGAGCAAACCGA | GCACTCAAAGCAGCTGGCA |
| TNFRSF18 | CAGGAGGGAGAGAGAGACACA | GCACTGCACACCCACGGACA |
| TNFRSF1A | AAGAGGGGGAGCTTGAAGGA | TGAAGGTGGAACTGGGCA |
| TNFRSF21 | AGAAGTCCAGCACGCCCA | TCCGGATACTGCACACCACA |
| TNFRSF25 | CCTTGGACAGCGCCCACA | ATGTCACCTGCGGGCAGA |
| TNFRSF4 | GCCCAGAACCTCACAGGGA | GGAGCAGGTACAGGGCCA |
| TNFRSF8 | CTGCATCACCCACAGCCGCA | CTCCCATCATGGGCGCCAGA |
| TNFRSF9 | TGGGACGAAGGAGAGGGA | GCAGTCGACGTCAGCGCA |
| TNFSF10 | GACCCAGCCTGGGACAGA | CGTAAGTTACAGCCACACAGAGA |
| TNFSF13 | CAGAGGTGATGTGGCAACCA | CTTCTCGAGACACCACCTGA |
| TNFSF14 | ACCCCGCTACCCCGAGGA | ACCGGGTACCATCACGCA |
| TNFSF18 | GGCCAAGTGGCTCCCAATGCA | TCTATGGTGTCCCCAACATGCA |
| TNFSF9 | GCAGCCCACCTGGACAGA | GGAGGTCAGCAGCAGGGA |
| TNXB | GCAATGAGGCCCTGCACA | GTCCCGATCACGGGCAGA |
| TPBG | ACAGAGGTAGTGCAGGGCAA | GGTCACAGTCCAGGTCAGCA |

FIG. 8 (Cont.)

| Gene Name | Forward GSP | Reverse GSP |
|---|---|---|
| TPSAB1 | TGGCGCCTACACGGGAGA | GTGCCATTCACCTTGCACA |
| TREM1 | CCAAGCTCCACCCAAGTCAA | GACCTCAGCGTGACAGCAA |
| TREML2 | GCCAGGGACCCAGGAGGA | CTGGTGCTGAGGTCCCCAGA |
| TRHR | CAGGTCACCAAGATGCTGGCA | AGCTTTCTGAAGGCTGCACGGA |
| TRIL | TGCCCCCAACATGGCCAGAA | GCAGAGATCACCAAACCAGTGGA |
| TRPV2 | ACTGGGCTTCATGGGAGCAGA | GAGGAGCTGGACGGGCACA |
| TSHR | GCCCAGTACGCAGACTCTGAA | CCAGCTGCTGCAGAGTCACA |
| TSPAN7 | TGAGGACTTACACGGACGCTA | CTGCACACCACAGCAGCTCA |
| TSPAN8 | GTGGCGACAGGTATCCTAGGA | ATCAGCAGCTCCATTGACCA |
| TTYH2 | CGGCTCACAGTCCCCCGA | CGGAGACAGGGGCGTTGGA |
| TTYH3 | CCCGCACACCTGGCAGCAA | ACAGCTGTACAGGCTGGGCA |
| TUBB3 | TGAGGAGTATCCCGACCGCA | CACCAGCTGGTGGATGGACA |
| TXNDC15 | GGCAGCAGAAGAGGCCAA | GTCCTCAGCTTCCCCAGGAA |
| TYR | AATGGAACGCCCGAGGGA | CTACATCAGCTGAAGAGGGGA |
| TYRO3 | GCATGCTGGCAGAGGACA | CCAGCCACTTGACAGGCA |
| TYRP1 | GCACCGAGGATGGGCCAA | AACTTCCAAGCACTGAGCGA |
| UGT8 | ACCAGAGTACAGGCAAAAGGCA | TCGATTGACAGGGTGACCA |
| ULBP2 | CAGCTGGAGAATTACACACCCA | AAAGAGGAGGAAGATCTGCCCA |
| ULBP3 | CTGAGAGAGGTGGGGCAGA | CGAAGCTGAACTGCCAAGA |
| UMOD | CCAGGACAGATGCCCACA | CCGGAACATCTGGACGGA |
| UNC5A | CCACAACCTGCGCCTATCCA | GCAAGTACCGCTGCGTGCCA |
| UNC5B | TCCCACTGTCCATCCGCCAGA | AGCTTCCCAGAGGTCCAGGA |
| UNC5C | CAGCCTGTGAACATCAAGGCA | CTGAGACGTCATGCAGGGCA |
| USP9Y | CTCCAGAGGAACAAGGGCAA | GCAAAACAGGAACCACCCA |
| VAMP5 | GCAGCAGCGTTCAGACCAA | CAATCAGGATGATGAGCAGGA |
| VASN | CAGTGAAGGAAGCTCCCGGA | GGGGCCAAGACTAGAGTCACACA |
| VCAM1 | CCAGTTGAAGGATGCGGGA | AGAGCACGAGAAGCTCAGGA |
| VCAN | GGGCACAGACCACTGAGCA | CGGCAGCAGCTTCTCCAGA |
| VDAC1 | GGGTACAAGCGGGAGCACA | GGCCAGCCAGCCCTCGTA |
| VEGFC | ACAAGACCTGCCCCACCA | CCACAGCTGGCAGGCCGA |
| VIPR1 | GAACCCCAAATACCGGCA | GGCTTGGAAGCTGGAGGA |
| VNN1 | AATGTACCCAAGGAGCCTGAGA | CCTCATGCCCATAGCCCA |
| VNN2 | CCGTGTCAAGACCCCCACAGA | GGACATGTGGAGTCACGGGA |
| VSIG10 | CCAGCTGTCGGATGGCAA | AGCGTCACATTGCCCCCA |
| VSIR | CGAGGCCAAAGTCAGGCA | AGGGACAGGGTCCAGGGA |
| VSTM1 | CAGAGCTCGGCAGAAAACGA | TGCAGCTGAAGATGGCGA |
| VSTM4 | CTCCCAGAAAAGGCGGAAGGA | CATAGTACTGCACCACCCGGA |
| VTN | CTGCCACCTGTGAACCCA | CCCAGCCAGTACTGAGCGA |
| VWF | ACTGCAGCTCAGCCCCAA | CAAGACACTGCTCCTCCAGGA |
| WNT11 | CGGGACACAAGACAGGCA | GGCAGGTGACGTAGCAGCA |
| WNT5A | ACAAGACGTCGGAGGGCA | TGCACTTGACGTAGCAGCA |

FIG. 8 (Cont.)

| Gene Name | Forward GSP | Reverse GSP |
|---|---|---|
| WNT5B | ACAAGACCTCGGAGGGCA | CGAAGCAGCACCAGTGGA |
| YBX1 | AGGGGCCCTCCTCGCCAA | TTGAAGTTGCGGCGGTACCGA |
| ZDHHC5 | GCAACGGGAAGCTGAGAGGCA | TCGTTCCTGGAGAGAGGCCA |
| ZFP42 | AGACCACGTCTGTGCGGA | TGGATGCGCACGTGCGTA |
| ZIC1 | CGCCAGCTCTGGCTACGAA | GTGGACTGCGGAGGAGGA |
| ZNF205 | CGGAAGAGCTTCAGCCACCA | AAGTCCGAGCGGCGGGTGAA |
| ZP4 | CTGGTCCAACAACCAACAACATGGA | GAGTGGCAGGGAACGTGACA |

MULTIPLEX PREPARATION OF BARCODED GENE SPECIFIC DNA FRAGMENTS

CROSS-REFERENCE TO RELATED APPLICATIONS

This application is a continuation of U.S. application Ser. No. 17/587,500 filed on Jan. 28, 2022, which application is a continuation of U.S. application Ser. No. 16/543,211 filed on Aug. 16, 2019, which application, pursuant to 35 U.S.C. § 119(e), claims priority to U.S. Provisional Application Ser. No. 62/765,124 filed on Aug. 17, 2018, and U.S. Provisional Application Ser. No. 62/799,448 filed Jan. 31, 2019, the disclosures of which applications are herein incorporated by reference.

INCORPORATION-BY-REFERENCE OF MATERIAL ELECTRONICALLY SUBMITTED

A Sequence Listing is provided herewith as a Sequence Listing XML, "CLCT-005DIVCON_SEQ_LIST" created on Apr. 5, 2023, and having a size of 9,362,580 bytes. The contents of the Sequence Listing XML are incorporated by reference herein in their entirety.

INTRODUCTION

Multiplex polymerase chains reactions (multiplex PCR) include the simultaneous amplification of many DNA sequences in one reaction. Applications of multiplex PCR include, but are not limited to, the identification of mutations, gene deletions, and polymorphisms and the production or quantitation of amplicons for high throughput sequencing and genotyping. Multiplex reactions may include two or more target sequences with primer pairs or one template selectively amplified with primers designed to target specific regions. Additionally, such reactions may include multiple templates with regions multiplied by multiple primer pairs.

During multiplex PCR, proper amplification requires optimal conditions. It is important to maintain controlled cycling and annealing temperatures and fine-tuned relative concentrations of primers, buffers, dNTP's, Taq DNA polymerase, template and other PCR reagents. Common problems associated with multiplex PCR include: i) mis-priming due to nonspecific primer binding to non-target templates; and ii) the formation of unwanted side products due to the presence of multiple primer pairs. In conjunction with several other sensitive procedural variables, these issues may lead to cross hybridization, and uneven or no amplification of some target sequences. Unwanted multiplex PCR side products form in the presence of multiple primer pairs. These side products may include homodimers, formed by inter-molecular base pairing between two similar primers, and heterodimers, formed from inter-molecular interactions between sense and antisense primers. Another undesirable occurrence is the formation of hairpins and fold-back structures from intra-molecular interactions.

Furthermore, the technological problems with design of PCR primers and assay optimization are compounded in the analysis of small nucleic acid samples from large numbers of biological samples, like small amounts of clinical samples and in single cells. One of the best strategies of processing large numbers of biological samples is labeling of target nucleic acids (e.g. mRNAs) present in every sample with unique sample-specific barcodes, where the barcodes are employed to denote the source of each particular sample. These sample-specific barcodes can be used for deconvolution of the final multiplex profiling data and assigning these data to specific originating samples. Current RNA barcode labelling technologies are based on the mixing together of biological samples, e.g., from single cells, with universal (not gene-specific) sample-specific barcoded primers (e.g. oligo dT), e.g., present in a micro well or in a single droplet. The plurality (i.e., more than one) of barcoded oligo dT primers are commonly synthesized on the surface of beads using combinatorial phosphoramidite chemistry with one specific barcode labeled oligo dT primer per bead. In another strategy, the barcoded primers with unique barcodes are synthesized separately, optionally immobilized on the beads or encapsulated in a matrix (e.g. acrylamide) and deposited in a separate compartment (e.g., microwell). Each oligo dT primer with a sample-specific barcode (e.g., attached to the single bead) is annealed to the conservative polyA+ mRNA portion and extended by reverse transcriptase. As a result, the oligo dT-extended first strand cDNA molecules derived from one sample are labeled with a sample-specific barcode, and these cDNA molecules may then be mixed together with other barcode labeled cDNAs derived from other samples (e.g., cDNAs derived from 10,000 cells in the current 10×Genomics platform), where the resultant pooled mixture may then be amplified as a pool and analyzed for sequence and composition using next generation sequencing (NGS) protocols.

To date, known barcode labelling strategies can only be used in multiplex targeted PCR assays with a combination of forward gene-specific primers, which allow one to amplify and analyze only the 3-end of RNA molecules. Unfortunately, non-coding 3-end portions of mRNAs are highly promiscuous in different cell types and disease states. As a result, the design of gene-specific primers for the amplification of 3-ends of mRNA molecules is highly problematic and there are significant obstacles to using this strategy for expression profiling in different disease states, e.g., for profiling different cancer cell types. Furthermore, the barcoded oligo dT primers cannot be directly applied for conventional multiplex PCR assay, employing two gene-specific primers (forward and reverse), as the barcoded domain of the oligo dT primers are not physically connected with any gene-specific primer or amplified products. Importantly, multiplex targeted PCR assay commonly employs set of hundreds-thousands of gene-specific primers. Therefore, it is technologically challenging to label such a plurality of primers with, e.g., 10,000 different sample-specific barcodes, and deliver each barcoded primer pool to different samples or cells.

In some instances, the multiplex PCR primers may also incorporate unique molecular identifiers (UMI), the highly complex (usually random) sequences which allow one to label each nucleic acid molecule used in the assay with molecule-specific identifiers. The UMIs are useful in identification and elimination of PCR duplicate biases introduced during multiplex amplification steps.

Although genome-wide analysis of nucleic acid compositions can be achieved by many known technologies, multiplex PCR is a unique technology which can be designed for analysis of hundreds or thousands of distinct nucleic acid molecules or their fragments. The complexity and composition of a nucleic acid pool which needs to be amplified and analyzed in such multiplex targeted PCR assays is dependent on specific application. As a result, reduction in complexity of analyzed nucleic acids provides dramatic improvement in the sensitivity and specificity of the assay for many critical applications, including single-cell analyses and clinical diagnostics. Combination of multiplex PCR assays with sample-specific barcodes is the next frontier in reducing cost and quality of the analysis of multiple biological samples for clinical and experimental research applications.

SUMMARY

Methods of preparing a plurality of sample-barcoded anchor-domain-flanked gene specific deoxyribonucleic acid (DNA) fragments from a template nucleic acid, e.g., ribonucleic acid (RNA), sample are provided. Aspects of the methods include employing a set of gene specific primer pairs, wherein each pair of gene specific primers is made up of a forward primer and a reverse primer, at least one of which includes a sample barcode domain. The methods find use in a variety of different applications, including high-throughput sequencing, e.g., expression profiling, applications, including of small biological samples, e.g., single-cells.

BRIEF DESCRIPTION OF THE FIGURES

FIG. 7 shows Table 1 which provides examples of suitable sequences for 18 nt long barcode domains. The sequences in each vertical column from left to right are set forth in the following SEQ ID NO's: (i) 85-2104 (ii) 2105-4125 (iii) 4126-6106 (iv) 6107-8084.

FIG. 8 shows Table 2 which provides sequences of forward and reverse gene specific primers of gene specific primer pairs. The sequences are set forth in the following SEQ ID Nos: Forward: 8085-9444; Reverse: 9445-10640.

DEFINITIONS

Figure 1:
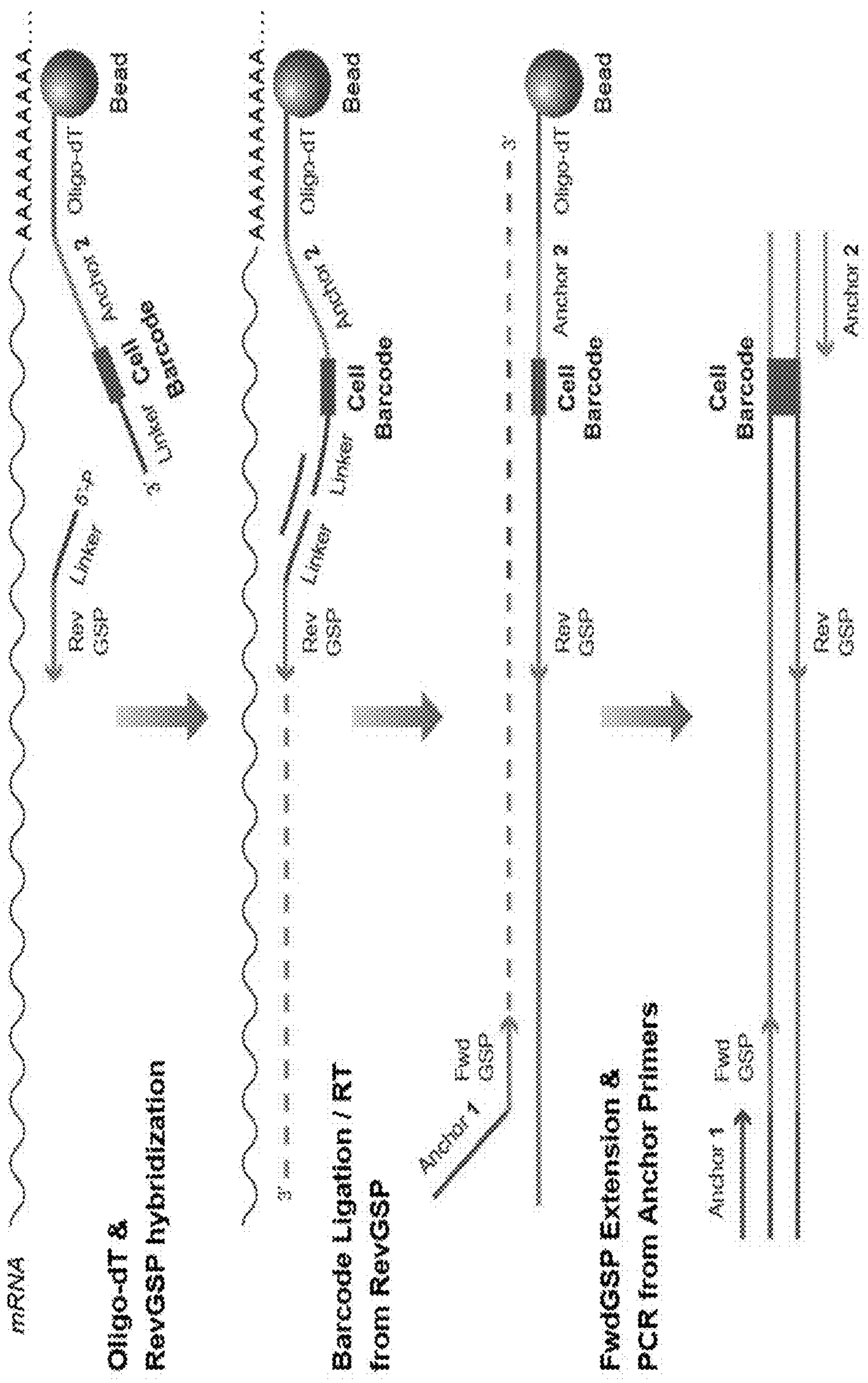
FIG. 1 provides a schematic diagram of a method of preparing a plurality of sample-barcoded anchor-domain-flanked gene specific deoxyribonucleic acid (DNA) fragments in accordance with an embodiment of the invention.

As used herein, the term “hybridization conditions” means conditions in which a primer, or other polynucleotide, specifically hybridizes to a region of a target nucleic acid with which the primer or other polynucleotide shares some complementarity. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, “Overview of principles of hybridization and the strategy of nucleic acid probe assays,” Elsevier (1993).

The terms “complementary” and “complementarity” as used herein refer to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, “complementary” refers to a nucleotide sequence that is at least partially complementary. The term “complementary” may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%).

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score-100, wordlength=12, or can be varied (e.g., wordlength=5 or wordlength=20).

A "domain" refers to a stretch or length of a nucleic acid made up of a plurality of nucleotides, where the stretch or length provides a defined function to the nucleic acid. Examples of domains include Barcoded Unique Molecular Identifier (BUMI) domains, primer binding domains, hybridization domains, barcode domains (such as source barcode domains), unique molecular identifier (UMI) domains, Next Generation Sequencing (NGS) adaptor domains, NGS indexing domains, etc. In some instances, the terms "domain" and "region" may be used interchangeably, including e.g., where immune receptor chain domains/regions are described, such as e.g., immune receptor constant domains/regions. While the length of a given domain may vary, in some instances the length ranges from 2 to 100 nucleotides (nt), such as 5 to 50 nt, e.g., 5 to 30 nt.

By "primer extension product composition" is meant a nucleic acid composition that includes nucleic acids that are primer extension products. Primer extension products are deoxyribonucleic acids that include a primer domain at the 5' end covalently bonded to a synthesized domain at the 3' end, which synthesized domain is a domain of base residues added by a polymerase mediated reaction to the 3' end of the primer domain in a sequence that is dictated by a template nucleic acid to which the primer domain is hybridized during production of the primer extension product. Primer extension product compositions may include double stranded nucleic acids that include a template nucleic acid strand hybridized to a primer extension product strand, e.g., as described above. The length of the primer extension products and/or double stranded nucleic acids that incorporate the same in the primer extension product compositions may vary, wherein in some instances the nucleic acids have a length ranging from 50 to 1000 nt, such as 60 to 400 nt and including 70 to 250 nt. The number of distinct nucleic acids that differ from each other by sequence in the primer extension product compositions produced via methods of the invention may also vary, ranging in some instances from 10 to 25,000, such as 100 to 20,000 and including 1,000 to 10,000, 10,000 to 20,000, 15,000 to 20,000 and 15,000 to 19,000.

DETAILED DESCRIPTION

Methods of preparing a plurality of sample-barcoded anchor-domain-flanked gene specific deoxyribonucleic acid (DNA) fragments from a template nucleic acid, e.g., ribonucleic acid (RNA), sample are provided. Aspects of the methods include employing a set of gene specific primer pairs, wherein each pair of gene specific primers is made up of a forward primer and a reverse primer, at least one of which includes a sample barcode domain. The methods find use in a variety of different applications, including high-throughput sequencing, e.g., expression profiling, applications, including of small biological samples, e.g., single-cells.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various aspects of the invention, embodiments of various methods will be discussed first in greater detail, followed by a review of various applications in which the methods find use as well as kits that find use in various embodiments of the invention.

Methods

As summarized above, methods of preparing a plurality of sample-barcoded anchor-domain-flanked gene specific deoxyribonucleic acid (DNA) fragments from a ribonucleic acid (RNA) sample are provided. Before describing the methods further, the product nucleic acids prepared the methods is now described first in greater detail.

Sample-Barcoded Anchor-Domain-Flanked Gene Specific DNA Fragments

By "sample-barcoded anchor-domain-flanked gene specific deoxyribonucleic acid (DNA) fragment" is meant a DNA that includes an anchor domain on each side of a gene specific domain. As the gene specific domain is flanked by anchor domains, the DNA fragments prepared by methods of the invention include a first anchor domain located at a first end of the DNA fragment and a second anchor domain located at a second end of the DNA.

By gene specific domain is meant a region of the dsDNA fragment the includes a sequence found in template nucleic acid, such as a template mRNA. While the length of the gene specific domain may vary, in some instances the gene-specific domain ranges in length from 50 to 500 nt, such as 60 to 300 nt.

In addition to the gene specific domains, as described above, the DNA fragments have anchor domains on either side of the gene specific domain. Anchor domains are domains that are employed in nucleic acid amplification, such as polymerase chain reaction (PCR), steps of the methods, where they serve as primer binding sites for the primers employed in such amplification steps. Where the amplification employed is PCR, the anchor domains may also be referred to as PCR primer binding domains. The length of the anchor domains may vary, as desired. In some instances, the anchor domains of each primer pair range in length from 10 to 50 nt, such as 10 to 30 nt, e.g., 10 to 24, including 12 to 20 nt. Where desired, the anchor domains may include PCR suppression sequences. PCR suppression sequences are sequences configured to suppress the formation of non-target DNA during PCR amplification reactions, e.g., via the production of pan-like structures. Such sequences, when present, may vary in length, ranging in some instances from 5 to 25 nt, such as 7 to 21, including 7 to 20 nt. PCR suppression sequences of interest include, but are not limited to, those sequences described in U.S. Pat. No. 5,565,340; the disclosure of which is herein incorporated by references. An example of forward and reverse anchor domains that include PCR suppression sequences are: AGCACCGACCAGCAGACA (SEQ ID NO:01) and AGACACGACCAGCCACGA (SEQ ID NO:02).

As summarized above, the DNA fragments are also "sample-barcoded", by which is meant that they include a barcode domain that denotes, i.e., indicates or provides information about (such that it may be used to determine), the specific sample, e.g., cell, from which the fragment has been produced. Barcode domains include unique, specific sequences. While the length of a given barcode domain may vary, in some instances the length ranges from 6 to 30 nt, such as 8 to 20 nt, and including 12 to 18 nt. Examples of suitable sequences for 18 nt long barcode domains are provided in Table 1 in FIG. 7.

In addition to the gene-specific, barcode and anchor domains, the fragments produced by methods of the invention may further include a unique molecular index (i.e., unique molecular identifier or UMI) domain. UMI domains have sequences configured for labeling of the each in the plurality of RNA molecules (and extended cDNA product) present in the hybridization mix with different molecule-specific indexes. UMI domains are stretches of random or semi-random nucleotides. While the lengths of UMI domains may vary, in some instances the length of a UMI domain ranges from 8 to 20 nt, which in a given assay provides for complexity of different unique sequences of 10,000 or more different UMIs. In some instances, using at least 10,000 unique indexes is sufficient to label each template molecule with the same sequence with a unique index, i.e., UMI. By analyzing the number of the indexes, e.g., via NGS, the number of each unique template molecule with the same sequence employed in multiplex PCR assay can be calculated. In some instances, the UMI domain may be combined with the barcode domain, e.g., where the UMI nucleotides are interspersed with the barcode nucleotides in a BUMI domain, e.g., as described in United States Patent Application Publication No. US20150072344, the disclosure of which is herein incorporated by reference.

Also present in the DNA fragments produced by methods of the invention may be ligated linker domains. Ligated linker domains are domains having sequences found in first and second linker domains employed in methods of the invention, e.g., as described in greater detail below. In the ligated linker domain, the sequences of the first and second linker domains are joined to each other, such that the sequence of one of the linker domains begins at the end of the other linker domain. The length of the ligated linker domain may vary, and in some instances ranges 15 to 60 nt, such as 20 to 50 nt, and including 24 to 40 nt. While not required, in some cases the ligated linker domain has a sequence with a GC-content in the range 50% to 80%.

As indicated above, the methods are methods of preparing a plurality of sample-barcoded anchor-domain-flanked gene specific DNA fragments from a template nucleic acid sample, e.g., a template ribonucleic acid (template RNA) sample. More specifically the methods are multiplex methods of preparing a plurality of sample-barcoded anchor-domain-flanked gene specific deoxyribonucleic acid DNA fragments from a template nucleic acid, e.g., RNA, sample, such that each DNA fragment of the plurality is produced at the same time from the RNA sample, e.g., each DNA fragment is produced simultaneously from the source RNA sample. The number of distinct DNA fragments prepared in a given method may vary, where in some instances the number in the plurality ranges from 10 to 25,000, such as 100 to 20,000 and including 1,000 to 10,000, 10,000 to 20,000, 15,000 to 20,000 and 15,000 to 19,000.

Among the DNA fragments of the plurality that are produced from a single sample by methods of the invention, a given DNA fragment is considered to be distinct from another DNA fragment if the gene-specific domains of the two fragments differ from each other by sequence. While the gene-specific domains of the DNA fragments in a given plurality may all differ from each other, e.g., because they include coding sequences of different genes, the DNA fragments will also include common domains, i.e., domains that are identical to each other (i.e., domains having sequences that do not differ from each other), where these domains are the flanking anchor domains, the barcode domains and the ligation linker domains. When employed, the DNA fragments may further differ with respect to additional domains, such as distinct UMI domains, such that the UMI domains of the DNA fragments have different sequences, i.e., they are not common or identical.

As indicated above, during a given protocol a plurality of DNA fragments produced from one sample may be combined, i.e., pooled, with one or more additional pluralities produced from one or more additional samples. In such pooled compositions, each plurality of the pooled composition will have a distinct barcode domain, such that the barcode domain of a first plurality of the composition will have a sequence that differs from every other barcode domain of every other plurality in the pooled composition. In a given pooled composition, each barcode domain has a sequence that is significantly different from that of any other barcode domain in the pooled composition, with a difference of at least 1 nucleotide, such as 2 nucleotides and including 3 or more nucleotide differences in the whole set of barcodes employed in the assay. In this way each plurality of the pooled composition will have a distinct identifying barcode domain. The number of different barcode domains in such pooled compositions is the same as the number of different pluralities in the pooled composition, where the number represents the number of different samples that is employed to make the pooled composition. The number of different barcodes present in a given pooled composition depends on number of samples being analyzed in a given assay. In some instances, the number ranges from 10 to 1,000,000, such as 100 to 100,000, and including 1,000 to 10,000. For example, currently for analysis of single-cell samples, the number of barcodes may be 10,000 or more, but for analysis of clinical samples the number of barcodes may not exceed 1,000.

Gene Specific Primers

As summarized above, in embodiments of the invention a set of gene specific primers, i.e., a collection of gene specific primer pairs of known sequence, is employed. While the number of primer pairs in a given set may vary, as desired, in some instances the number of primer pairs in a given set is 10 or more, such as 20 or more, 30 or more, 40 or more, 50 or more, 60 or more, 70 or more, 80 or more, 90 or more, 100 or more, 125 or more, 250 or more, 500 or more, including 1000 or more, 200 or more, 5000 or more, 8000 or more, 10,000 or more 15,000 or more, 18,000 or more and 20,000 or more. In some instances, the number of gene specific primer pairs that is present in the set is 25,000 or less, such as 20,000 or less. As such, in some embodiments the number of gene specific primer pairs in the set that is employed in the methods ranges from 10 to 25,000, such as 50 to 20,000, including 1,000 to 10,000, e.g., 2,500 to 8,500, and 10,000 to 20,000, e.g., 15,000 to 19,000.

Gene specific primer pairs present in a given set of the invention are made up of a forward primer and a reverse primer, wherein the forward and reverse primers of each primer pair include gene specific domains, where these gene specific domains may be experimentally validated as suitable for use in a multiplex amplification assay. By "experimentally validated as suitable for use in a multiplex amplification assay" is meant that the set of primers for each target gene in a given set has been experimentally tested in a multiplex amplification assay, such as described in U.S. patent application Ser. No. 15/133,184 published as US-2016-0376664-A1 and U.S. application Ser. No. 15/914,895 published as US-2018-0245164-A1 (the disclosures of which are herein incorporated by reference), and the best performing primer set is selected based on parameters, e.g., one or more functional parameters, e.g., as described in greater detail below. While the multiplex amplification assay employed to experimentally validate a set of primers may vary, in some instances the protocol employed includes a first step of, for each target gene selected from the genome-wide set of human or mouse genes, selecting a region that is conservative for different mRNA isoforms, following which a set of forward and reverse PCR primers which are complementary and specific for the selected gene region are designed. The primers may be designed using any convenient algorithm and/or software tool, e.g., such as the Primer3 algorithm, Primer Design Tool from NCI, etc. The melting temperature of the selected primers may vary, ranging in some instances from 60° C. to 80° C., such as 65° C. to 80° C. Furthermore, the primers may be selected that lack significant secondary structures, or self-complementarity (e.g., primers may be selected with less than 4-bp complementary regions) and cross-complementarity to each other of less than 10 nt complementarity region. The length of the selected PCR primers may vary, and in some instances ranges from 15 to 25 nt, such as 16 to 24 nt, with GC-content of between 45% to 85%, such as 50% to 75%. In order to avoid primer/dimer formation in a multiplex RT-PCR assay, the selected primers in some embodiments are designed with the nucleotide A at the 3'-end and biased GCA-rich composition with reduced percentage of T nucleotides, where in some instances the percentage of T is 20% or less, such as 15% or less, including 10% or less, down to 0%. Following primer design, homology searching for similar PCR primer binding domain(s) in other RNA species (such as available in GeneBank), e.g., via BLAST or Thermo-Blast algorithm, is performed in order to select primers specific only to the target region of interest. Next, the resultant primer set is ranked based on the distance between primers with the preferred size of amplicons, e.g., which ranges in some instances between 60 to 250 base pairs (bp). Following this ranking, a set of at least 1 primer pair, such as 3 or more, e.g., 5 or more, up to 12 or more, but in some instances not exceeding 12 primer pairs, is synthesized and functionally validated in a multiplex Reverse Transcription (RT)-PCR-NGS (next generation sequencing) assay, e.g., using the protocol disclosed in the Experimental section, below. In some embodiments, e.g., those specific for mutation profiling in clinically actionable or cancer driver genes, a complete set of PCR primers is designed and validated which allows one to amplify a set of overlapping amplicons that cover the complete mRNA sequence from the 5' to the 3'-end. Primers present in sets of gene specific primers of the invention may be experimentally validated using any convenient protocol. In some instances, the experimentally validated gene specific domains are validated in a multiplex amplification assay with a synthetic control template mix which mimics the natural target template sequences and includes binding sites for the whole set of gene-specific primer pairs and/or a universal natural template mix derived from multiple different mammalian tissues or cell types. Specifically, as a template for multiplex RT-PCR assay, a set (usually between 3 to 6) of natural total universal RNAs, e.g., including a mix of several RNAs isolated from human or mouse cell lines or tissue samples (e.g., available from Takara-Clontech, Agilent, Qiagen, Origene, etc.) may be employed as a natural nucleic acid control. In addition (or alternatively) to the set of the natural control template nucleic acids, a mix of the synthetic control template nucleic acids, e.g., one that has been synthesized on the surface of custom microarrays (e.g., Custom Array or Agilent) and designed for each target amplicon, may be employed. In such synthetic control templates, the templates include the sequence of the both PCR primer-binding site domains and the full-length or truncated in the middle cDNA region between PCR primers that corresponds to the primer extension domain. In some functional validation assays, two synthetic template concentrations (e.g., 10-fold difference) may be employed to measure expression level (number of specific reads) in a manner that is not dependent on the amount of starting universal RNA template. The length of synthetic control templates may vary, ranging in some instances from 100 to 200, such as 110 to 180, including 120 to 160 nt. The amplification products generated in the multiplex RT-PCR assays may be quantitatively analyzed by sequence analysis using conventional NGS instruments (e.g., available from Illumina, Thermo-Fisher, Nanopore and other commercial vendors). The NGS data generated for different templates and experimental conditions may be scaled to the same number of total reads (usually total 10,000,000 reads), aligned with the sequences of PCR primer domain and downstream extended domain sequences for each target amplicon. The number of specific reads corresponding to each target amplicon may be measured as the number of correctly aligned sequences for each PCR primer pair and downstream extended domain sequences. In addition, for each primer pair, the number of non-specific (off-target) reads for the amplicons may be calculated which has correct the PCR primer domain but different, non-target extended domain sequences. The set of PCR primer pairs designed for each target gene may then be ranked using the set of criteria described below. The highest rank PCR primer pair for each target gene is first selected based on the highest number of specific reads (e.g., 100 or more, such as 500 or more and including 1,000 specific reads) and minimum number of non-specific reads (e.g., 2-fold less than number of specific reads, but not exceeding 5,000, or such as 2,000 reads) measured across all universal RNAs and control synthetic template. Next, the highest activity PCR primer set may be selected from among other primers that demonstrate a common pattern of expression among different natural universal RNAs used in the assay. Common pattern of expression between different primers sets indicates that they target the same conservative cDNA region, rather than a unique target region specific for particular mRNA isoform(s). In some embodiments, human PCR primers are selected that effectively amplified target regions from human but not from the mouse universal RNAs. In other embodiments, e.g., those specific for detection of clinically actionable mutations, not one but a complete set of PCR primers are selected which amplify amplicons overlapping the whole mRNA/cDNA sequence. In some embodiments, specific activity of primers is assayed at thermocycling extension temperatures of both 60° C. and 65° C. Using these two different conditions enables the identification of primer pairs that demonstrate similar (e.g., less than 2-fold difference) specific activity across several control templates and universal RNAs. In some instances, if a PCR primer set with high specific activity in both control synthetic template (e.g., less than 500 reads) and in all universal RNAs (e.g., less than 100 reads) for any target gene is not identified, a new candidate PCR primer set for the failed gene(s) is designed and validation protocol repeated until a suitable set is found. As a result of functional validation experiments, one can select at least one PCR primer set for each target gene of interest that has high sensitivity and selectivity, e.g., for at least 90%, such as 95% or more target genes of interest.

Each pair of gene specific primers are configured to hybridize to a target nucleic acid sequence for which they are specific at locations that are separated by a known or predetermined distance, i.e., a template distance. The length of the template distance may vary, ranging in some instances from 50 to 750 bp, such as 60 to 500 bp, including 60 to 300 bp, e.g., 70 to 250 bp. As such, the product nucleic acid produced from the gene specific primers may have a central domain, i.e., extension domain, complementary to the template nucleic acid from which it is produced (that is, identical to the reverse-complement sequence of the template nucleic acid from which it is produced) that varies in length, ranging in some instances from 50 to 750 nt, such as 60 to 500 nt, including 60 to 400 nt, e.g., 60 to 300 nt, including 80 to 200 nt.

A given gene specific primer may include a multiplex experimentally validated gene specific domain, e.g., as described above. The length of the gene specific domain may vary, so long as the domain serves to specifically hybridize to a target nucleic acid under hybridization conditions of interest. An example of such hybridization conditions is hybridization at 50° C. or higher and 0.1×SSC (15 mM sodium chloride/1.5 mM sodium citrate). In some embodiments, these hybridization conditions may be defined by length and nucleotide sequence of the gene-specific domains of the PCR primers, composition of PCR buffer, properties of DNA polymerase and conditions used in the primer extension step. Furthermore, hybridization conditions could be compatible with primer extension conditions, e.g., where both hybridization and extension step performed in DNA polymerase reaction buffer (e.g. 1×HF or 1×GC buffer from Thermo-Fisher). In another embodiment, where the hybridization step and primer extension step are separate steps in the protocol, the hybridization buffers could contain additional components for increasing hybridization rate (e.g., CTAB, PEG, high salt concentration (e.g., 1M or more), etc.), lysing the cells, denaturing proteins, stabilizing RNA, protein (detergents, guanidium salts, urea, PMSF, 2-mercapoethanol, etc.). If reverse barcoded primers are hybridized with target template RNA composition in cell extracts (e.g., single cells), the hybridization buffer could be optimized by highly denaturing conditions to stabilize the RNA. Furthermore, the reverse barcoded primers may be longer (such as 25-80 nt, such as 30 to 70 nt) than regular PCR primers to facilitate highly specific and stable interaction with target RNAs at elevated temperatures (e.g., 50° C. to 80° C.). Furthermore, the use of stringent hybridization conditions and the removal of non-binding primers permits the formation of specific complexes between reverse gene specific primers and target RNAs. Therefore, the specificity of extension of reverse barcoded primers could be significantly defined by hybridization rather than follow-up primer extension step specificity. Primer extensions temperatures may vary, ranging in some instances from 50 to 75, such as 60 to 72° C. As disclosed in Experimental section below, in one of the embodiments a primer extension step is employed in which extension occurs between 60 and 65° C. using Phusion II DNA polymerase, HF or GC buffer reagents available from Thermo-Fisher. Both the length and the specific nucleotide sequence of the PCR primers define the hybridization condition at the primer extension step. In some embodiments, the length and specific sequence of the gene specific domains of the PCR primers is selected in order to provide efficient binding and extension at 60 and 65° C. under the PCR conditions used in the primer extension step. Such conditions may provide or high efficiency and specificity of the primer extension in PCR reaction conditions. In some embodiments, the primer length and sequence may be adjusted to perform an extension step at 68° C. or even 72° C.

To control efficiency and specificity of primer extension step, the length of the gene specific domain of the forward and reverse primers may vary. In some instances, the length ranges from 10 to 80 nt, such as 15 to 75 nt, e.g., 10 to 50 nt, such as 10 to 30 nt, including 14 to 22 nt or 16 to 24 nt. The gene specific domain of the forward and reverse primers may vary length. In some instances, the gene specific domain of the forward domains is shorter than the gene specific domain of the reverse primers. For example, in some instance the length of the gene specific domain in the forward primers ranges from 15 to 30 nt, such as 18 to 25 nt, while the length of the gene specific domain in the reverse primers ranges from 25 to 80 nt, such as 30 to 70 nt, including 30 to 50 nt. Each primer of the gene specific primer set may include only a gene specific domain, or may include one or more additional domains as desired, e.g., anchor domains, NGS adaptor domains, labels or label domains, etc., e.g., as described below. In some embodiments where additional domains are present, each primer pair may include primers ranging in length from 10 to 150 nt, such as 10 to 100 nt, including 10 to 75 nt, such as from 15 to 60 nt, including from 24 to 45 nt.

Where desired, the gene-specific primer domain of each primer is GCA- and/or GCT-rich. By GCA- and/or GCT-rich is meant that the gene-specific primer domain has a substantial portion of G, C, A- and/or G, C, T nucleotides. While the number of such nucleotides in a gene specific primer domain may vary, in some instance the number of such sequences ranges from 75% to 100%, such as 85% to 100%. As the gene specific primer domains of such embodiments are GCA- and/or GCT-rich, the GC content of the gene specific primer domains is also high. While the GC content may vary, in some instances the GC content ranges from 40 to 90%, such as 45 to 85%, including 50 to 85%, e.g., 50 to 80%.

Depending on the specific application for which the set is configured, the set of gene specific primers may be configured to target a wide range of mammalian genes, and pathogenic genes from a wide range of pathogenic organisms, such as viruses, bacteria, fungi, etc. which could be present in the human or mammalian bodies. Of interest in certain applications are human, mammalian species commonly used as a model organisms to study human diseases, such as mouse, rat, or monkey, and pathogenic organisms associated with human diseases. To be analyzed in accordance with embodiments of the invention, the targeted genes may be present in the mammalian cells or fluids. In some embodiments, the targeted genes are may be protein coding, or may express non-coding RNAs, micro RNAs, mitochondrial RNAs, regulatory RNAs, etc. In some instances, the set of genes selected is genome-wide, such that it covers all genes present in the genome of an organism. In other embodiments, the genes are selected from the genes that could be transcribed or expressed in the organism and present in the biological samples in the form of RNA. The genome-wide set of genes specific for human, model and pathogenic organisms is of special interest in some instances and may be used to develop a set of genome-wide targeted RNA expression assays based on the disclosed multiplex PCR assay. Genome-wide sets of PCR primers may vary in number, and in some instances are configured to assay 18,000 or more, such as 20,000 or more and 25,000 or more, such as 30,000 or more genes. Additional sets of PCR primers may be configured based on a genome-wide set of genes from a wide range of viral, bacterial and eukaryotic pathogenic organisms. In another embodiment, the set of gene specific primers may be configured to produce primer extension products from a subset of specific genes selected from the genome-wide set of genes. One of these subsets is the set of cancer associated genes, that is, the genes that have been shown to be associated with initiation, development, diagnostic, treatment of cancer. Such genes could be implicated in, or be diagnostic of, or otherwise of interest in, the study and/or treatment of cancer, i.e., any of various malignant neoplasms characterized by the proliferation of anaplastic cells that tend to invade surrounding tissue and metastasize to new body sites. As such, cancer associated genes that may be represented in a given set of gene specific primers include, but are not limited to: cancer hallmark genes, pan-cancer driver genes, pathway and signaling network genes, drug metabolism genes, extracellular proteome genes, drug target genes (including those of FDA approved and/or clinical trial targets), cell lineage genes, immunity mechanisms & immunotherapy markers, immunotherapy drug target genes, known biomarkers, epigenetics genes, etc.

In another embodiment, the subset of the cancer associated genes is employed in developing of Cancer Clinically Actionable 26 assay for profiling all clinically actionable mutations in the set of 26 human genes (ABL1, AKT1, ALK, BRAF, CDK4, CDK6, CDKN2A, EGFR, ERBB2, FGFR1, FGFR2, FLT3, KDR, KIT, KRA, MET, NRAS, PDGFRA, PIK3CA, PIK3R1, PTCH1, PTEN, PTPN11, RET, ROS1, SMO). This assay includes the additional set of multiplex PCR primers designed and validated to amplify the set of overlapping amplicons that cover the whole mRNA sequence of the target genes.

In another embodiment, the multiplex PCR assay is designed for analysis of a subset of cell-specific, tissue-specific or state-specific genes. These genes encode marker products (e.g. proteins, peptides or RNAs) that are specifically expressed in different cell types (e.g. markers for T, B, NK, stromal, cancer, epithelial, neuronal, etc. cells), different tissues or different cell states, e.g. marker products induced by treatment (e.g. drugs) or changes in conditions (e.g. heat shock), disease states (e.g. cancer, infection), or natural biological processes (e.g. differentiation, apoptosis, aging, etc.). The development of multiplex PCR assay, based on the set of gene-specific primers specific for the marker genes, may be employed in the development of prognostic and predictive clinical diagnostic tools, profiling different cell types and their phenotypes in normal and disease states. For a marker gene analysis assay, the set of gene specific primer pairs includes primers configured to produce primer extension products for 10 or more genes listed in Table 2 (FIG. 8). As such, the set of gene specific primers employed in a given method may represent at least some of the genes listed in Table 2(FIG. 8), such that the set may include primer pairs that correspond to at least some of the genes listed in Table 2(FIG. 8).

A primer pair is considered to correspond to a given gene if the primers of the pair specifically hybridize to sequences of the gene. It is understood based on the current prior-art knowledge, the selected primer pair sequences could include all or only portion of the primer sequences (e.g. disclosed in the Table 2(FIG. 8)), so long as they provide for the desired gene specificity. Modification in the specific sequences of the PCR primers, such as mutations, deletion, extensions, using nucleotide analogs, etc., may be present so long as the functionality of the primers in the primer extension step is maintained. The number of genes from Table 2(FIG. 8) represented in the set of gene specific primers may vary, ranging from 10 to 10,000, including 25 to 10,000, 50 to 10,000, 100 to 10,000, where in some instances the number is 150 or more, such as 200 or more, 250 or more, 500 or more, 1,000 or more, up to and including all of the genes listed in Table 2. In some instances, the set of gene specific primers includes primer pairs having gene specific sequences listed in Table 2(FIG. 8). The number of gene specific primer pairs having gene specific sequences listed in Table 2(FIG. 8) that may be present in a given set of gene specific primers may vary, where in some instances the number ranges from 10 to 10,000, including 25 to 10,000, 50 to 10,000, 100 to 10,000, where in some instances the number is 150 or more, such as 200 or more, 250 or more, 500 or more, 1,000 or more, up to and including all of the primer pairs listed in Table 2. Subsets of the genes listed in Table 2 that may be employed in a given assay may vary. Specific subsets of interest that may be employed in a given assay include but are not limited to: cell-specific markers, disease-specific markers, tissue-specific markers, or any specific set of genes selected based on specific functions, expression, or association with human diseases, and the like. Essentially any combination of primers, including all the primers, identified by the sequence identifiers provided in Table 2(FIG. 8) may be assembled to form a set or subset of primer pairs of the present disclosure.

Sets and subsets of primer pairs may be configured to include or exclude multiple primer pairs for a particular gene. For example, a set or subset of primer pairs may include no or essentially no two or more primer pairs that target the same gene. Correspondingly, a set or subset of primer pairs may include two or more different primer pairs that target the same gene. Where two or more primer pairs for a particular gene are included in a set or subset, the primer pairs may or may not share the same forward primer or the same reverse primer. For example, in some instances, two primer pairs for a single gene may include the same forward primer but have different reverse primers, the same reverse primer but have different forward primers, or have different forward primers and different reverse primers.

As described above, in some instances, a set or subset of primer pairs may be configured such that no two primer pairs target the same gene, i.e., there is only one primer pair for each gene included in the set or subset. In some instances, the number of different primer pairs targeting the same gene may be low, including but not limited to e.g., 10 or less primer pairs targeting each gene of the set or subset, such as 5 or less, 4 or less, 3 or less or no more than 2 primer pairs targeting each gene of the genes of a set or subset. In some instances, 10% or less of the genes of a set or subset may be targeted by more than one primer pair, including 8% or less, 7% or less, 5% or less, 3% or less, 2% or less and 1% or less.

In some instances, the methods include selecting the set of gene specific primers from a provided master library of gene specific primers, e.g., choosing a subset of primer pairs from an initial collection of primer pairs. For example, the methods may include selecting a subset of primer pairs (and thereby identify the primer pairs of a set of gene specific primers to be employed in methods of the invention, such as described above) that correspond to genes from Table 2, where the number of primer pairs in the selected subset may vary, ranging in some instances from 10 to 10,000, including 25 to 10,000, 50 to 10,000, 100 to 10,000, where in some instances the number is 150 or more, such as 200 or more, 250 or more, 500 or more, 1,000 or more.

The disparate primer pairs of a given set are present in substantially the same, if not the same amount. As such, in some instances, the copy number of any given primer pair in a set does not vary from the copy number of any other primer pair of the set by a value of 100% or less, such as 50% or less. A given primer pair may be present in a set in any desired amount, where in some instances the amount ranges from 1% to 1000%, such as 5% to 500%, or 10% to 500%. The final concentration of each primer in the primer extension step may vary, and in some instances ranges from 0.01 to 50 nM, such as 0.01 to 20 nM, or 0.01 to 10 nM, where examples of specific concentrations of interest include 0.01 nM, 0.1 nM, 1 nM, 2 nM, 5 nM, 10 nM, 20 nM and 50 nM.

The sets of gene specific primers, e.g., as described above, are non-naturally occurring compositions. In some instances, the sets of gene specific primers include domains or regions that are not naturally occurring sequences and/or are not naturally joined to the gene specific primer domains in naturally occurring nucleic acids. For example, the gene specific domains may be joined to one or more synthetic domains, e.g., universal primer binding site domains, indexing domains, barcode domains, adaptor domains, anchor domain, linker domain, etc. In some instance the gene specific primers may include one or more moieties that are not present in naturally occurring nucleic acids, e.g., label moieties (e.g., directly detectable labels, such as fluorescent labels, indirectly detectable labels, e.g., components of a signal producing system, etc.), non-naturally occurring nucleotides, etc.

Depending on the particular protocol, the forward and reverse primers of the pairs of the sets of gene specific primers may be used together or separately. As such, a given method may include using the forward and reverse primer subsets of a given set separately, such as in methods where a template composition is first contacted with a subset of the reverse primers of a set, and then contacted with a subset of the forward primers of the set. Alternatively, a given method may include contacting a template both the forward and reverse primer subsets of a given set of gene specific primers at the same time.

The methods of the invention are characterized by employing a set of gene specific primer pairs, wherein each pair of gene specific primers is made up of a forward primer and a reverse primer and at least one of the forward and reverse primers includes, at some time during the method, a sample barcode domain. In some instances, the methods are characterized by employing: a sample-barcoded donor nucleic acid that includes an anchor domain and a sample barcode domain, wherein the sample-barcoded donor nucleic acid is employed in conjunction with a set of gene specific primer pairs, wherein each pair of gene specific primers is made up of a forward primer and a reverse primer and the methods include transferring at least the sample barcode domain to one of the forward and reverse primers. In other instances, the methods are characterized by employing a set of gene specific primers in which the reverse primers include a sample barcode domain.

Sample-Barcoded Donor Nucleic Acid Mediated Protocols

A sample-barcoded donor nucleic acid is an initial nucleic acid from which the sample barcoded domain of the DNA fragments is derived. In other words, the sample-barcoded donor nucleic acid serves as the source of the barcode domain of the final sample barcoded DNA fragments. Since the sample-barcoded donor nucleic acid serves as the source of the sample barcode domain, the sample barcode domain does not need to be incorporated into any of the gene specific primers employed to produce gene specific fragments from a template nucleic acid sample. A sample-barcoded donor nucleic acid includes a sample barcode domain and an anchor domain, e.g., as described above. In addition, a give sample-barcoded donor nucleic acid may include a linker domain and/or a UMI domain, e.g., as described above.

In some instances, the donor nucleic acid includes a capture domain. In some such instances, the sample-barcoded donor nucleic acid includes a template, e.g., an RNA, template-binding or capture domain, an anchor domain, and a barcode domain, and optionally a linker domain and/or a UMI domain. The template-binding domain is the sequence necessary for binding barcoded oligonucleotide to template, like DNA or RNA. Examples of template-binding domains include but are not limited to oligo dT sequences, e.g., for binding to polyA tails of mRNA molecules with number of dT nucleotides between 15 to 35, random oligonucleotides with a length of randomly synthesized A, T, G or C between 6 to 30 nucleotides, or semi-random oligonucleotides with length between 6 to 18 nucleotides designed against conservative regions in target templates, e.g. stretches of the nucleotides coding triplets for the most abundant amino acids, splicing sites, etc. Where the target RNA template molecule is mRNA, the RNA binding domain may be a poly dT sequence that hybridizes to the mRNA polyA tail. The length of the RNA binding domain may vary, and in some instances ranges from 10 to 40 nt, such as 15 to 35 nt, including 20 to 30 nt. The linker domain is a domain having a sequence configured for binding and/or ligation with linker domain present in another component of the assay, such as a gene specific primer, e.g., as described below. While the length of a given linker domain may vary, in some instances the length ranges from 5 to 30 nt, such as 10 to 25 nt, including 12 to 20 nt. There are no special requirements for nucleotide composition or sequence of the linker domain, but in some instances the linker domain is selected with GC-content in the range 50% to 80% without significant secondary structure within the domain or with other domains present in the oligonucleotide. In addition to the RNA binding domain, the anchor domain, barcode domain and linker domain, the donor nucleic acid may also include a UMI domain, e.g., as described above. In such instances, a given assay may employ a plurality of donor nucleic acids that have common RNA binding, anchor, barcode and linker domains but distinct UMI domains that differ from each other in terms of sequence. In such instances, the number of different donor nucleic acids that differ from each other in terms of their UMI domains, and in some instances solely in terms of their UMI domains, employed with a given RNA sample may vary, and in some instances may range from 1,000 to 20,000, such as 5,000 to 10,000.

The donor nucleic acids employed in methods of the invention may be in solution or bound to the surface of a solid phase, as desired. When bound to a surface of a solid phase (i.e., solid support), the donor nucleic acids may be covalently bound or non-covalently bound. The solid phase may vary, where examples of solid phases include, but are not limited to, beads, wells, plates, etc., e.g., made of a suitable solid phase material, such as a polymeric material, where the surface is configured to provide the desired bond to the donor nucleic acids.

In the sample barcoded donor nucleic acids employed in methods of the invention, the order of the different domains may vary. Accordingly, in some embodiments a sample-barcoded donor nucleic acid may have the structure: 3'-linker 1-sample barcode domain-anchor 2 domain-RNA binding domain-5'. In yet other embodiments, the sample-barcoded donor nucleic acid comprises the structure: 3'-RNA binding domain-anchor 1 domain-sample barcode domain-linker 1 domain-5'. These various donor nucleic acids and the protocols in which they find use are further described below.

With respect to donor nucleic acid mediated embodiments, in some instances, additional domains present among a given pair of forward and reverse gene specific primers are a linker and anchor domains. In some instances, the forward gene specific primer includes an anchor domain and the reverse gene specific primer includes a linker domain. In such instances, the forward primers may have the structure 5'-anchor 1-forward gene specific primer (GSP) domain-3' and the reverse primers have the structure: 3'-reverse GSP domain-linker 2-5'. In other instances, the forward gene specific primer includes a linker domain and the reverse gene specific primer includes an anchor domain. In such instances, the forward primers may have the structure: 3'-forward GSP domain-linker 2-5'; and the reverse primers may have the structure 5'-anchor 2-reverse GSP domain-3'.

In some instances, a reverse GSP mediated barcoding protocol is employed. In these embodiments, a sample-specific barcode is ligated to a plurality of different gene-specific primers hybridized to template nucleic acids, e.g., template RNAs, such as template mRNAs, where the GSPs may or may not be extended in a first round primer extension reaction, such as a first round of cDNA synthesis (i.e., a reverse transcription), at the time of ligation. As a result, the reverse GSPs and/or their primer extension, e.g., first strand cDNA, products include a sample-specific barcode domain which originates from the donor nucleic acid. In other words, the sample-specific barcodes are transferred from an initial sample barcoded donor nucleic acids to reverse gene-specific primers that are hybridized to template nucleic acids, such as RNA template molecules, e.g., mRNA. Accordingly, these embodiments may be characterized in that the reverse GSPs are employed in the first strand synthesis step and the sample barcode domain and anchor domain of the donor nucleic acid is ligated to the reverse GSPs such that these domains are incorporated into the first strand synthesis products. A schematic illustration of an embodiment of this protocol is illustrated in FIG. 1.

In the embodiment illustrated in FIG. 1, a sample barcode initially present in a donor nucleic acid is transferred to a reverse GSP during first strand cDNA synthesis from an mRNA template. As shown in FIG. 1, the sample-barcoded donor nucleic acid has the structure: 3-linker 1-sample barcode domain-anchor 2 domain-RNA binding domain-5'. The 5' end of the donor nucleic acid is bonded to a solid support, and specifically a bead. Also, as illustrated, the reverse GSPs include the structure: 3'-reverse GSP domain-linker 2-5'. In the first step of the protocol illustrated in FIG. 1, the donor nucleic acids and Rev GSPs are combined with the sample ribonucleic acids, e.g., an mRNA sample obtained from a single cell, under hybridization conditions such that the donor nucleic acids bind to the polyA tails of the mRNAs and the GSPs bind to their complementary domains of the mRNAs. Where desired, the resultant mRNA template/GSP/RT Primer complexes may be purified from any excess of unbound gene-specific primers and donor nucleic acids. In the illustrated embodiment shown in FIG. 1, the resultant complexes are immobilized on beads and can be purified from any excess of non-hybridized gene-specific primers using a convenient washing protocol, such as washing protocols known in the art. Alternatively, any excess of unbound oligonucleotides may be removed using other purification protocols, such as but not limited to: nuclease treatment, chromatography, size-dependent binding to specific matrix, e.g. AMPure beads, etc.

Following hybridization of the GSPs and the donor nucleic acids to the mRNAs of the sample, the linker 1 and linker 2 domains of hybridized sample-barcoded donor nucleic acids and GSPs are ligated to produce sample-barcoded reverse primers, e.g., as illustrated in FIG. 1. To provide for sufficient proximity of the ends of the linker domains, a ligation linker may be employed. The ligation linker is an oligonucleotide that includes a first domain complementary to the linker 1 domain of the donor nucleic acid and a second domain complementary to the linker 2 domain of the donor nucleic acid. When employed, the length of the ligated linker may vary, and in some instances ranges 15 to 60 nt, such as 20 to 50 nt, and including 24 to 40 nt. While not required, in some cases the ligation linker domain has a sequence with a GC-content in the range 50% to 80%. The linker 1 and linker 2 domains may be ligated to each other using any convenient DNA ligase, where DNA ligases that may be employed include, but are not limited to: DNA ligases, e.g., Ampligase® Thermostable DNA Ligase, CircLigase-DNA Ligase, *E. coli* DNA ligase, T3 DNA ligase, T4 DNA ligase, T7 DNA ligase, Taq DNA ligase, and the like.

In the embodiment illustrated in FIG. 1, following ligation to produce sample-barcoded reverse GSPs, the methods include reverse transcribing first strand cDNA molecules from the sample-barcoded reverse primers. Reverse transcription may be accomplished by contacting the template RNA/sample-barcoded reverse GSP complexes with a reverse transcriptase under reverse transcription conditions, e.g., as described in greater detail below. Reverse transcription results in the production of a population of GSP primer extension products having a sample barcode domain and an anchor domain at their 5' ends. Where desired, the donor nucleic acids may include a linker domain at the 3'-end that provides for ligation to the linker of the gene-specific primer but that cannot be extended by a reverse transcriptase, e.g., during the first strand cDNA synthesis step.

Following production of the population GSP primer extension products, e.g., first strand cDNA molecules, as well as any desired purification or enrichment, e.g., to remove unhybridized GSPs, the resultant first strand cDNA molecules may be contacted with a population of forward GSPs, where the forward GSPs have an anchor domain at their 5' ends and a gene-specific domain at their 3' ends. Contact occurs under polymerase mediated primer extension reaction conditions, e.g., as described in further detail below, to produce forward GSP primed primer extension products, e.g., forward GSP primed second strand cDNA molecules. The resultant primer extension products may then be amplified, e.g., using universal primers that bind to the anchor domains, which results in production of a plurality of sample-barcoded anchor-domain-flanked double-stranded gene specific DNA fragments, e.g., as illustrated in FIG. 1. The resultant population of sample-barcoded anchor-domain-flanked double-stranded gene-specific DNA fragments may be further processed, e.g., further amplified, e.g., to add sequencing adaptors, etc., such as described in greater detail below.

In a variation of the protocol illustrated in FIG. 1, the sample barcode domain that is ligated to GSPs is not initially present in a donor nucleic acid that includes a capture domain, such as a RNA binding domain, but instead in a sample barcode donor nucleic acid which lacks a capture, e.g., RNA, binding domain. In such instances the donor nucleic acid may still include an anchor domain positioned 5' of the sample barcode domain. In such instances, the sample barcode donor nucleic acid may be ligated to the GSPs at any convenient time, e.g., following hybridization of the GSPs to the template RNA, prior to GSP hybridization to template RNA, etc.

Figure 2:
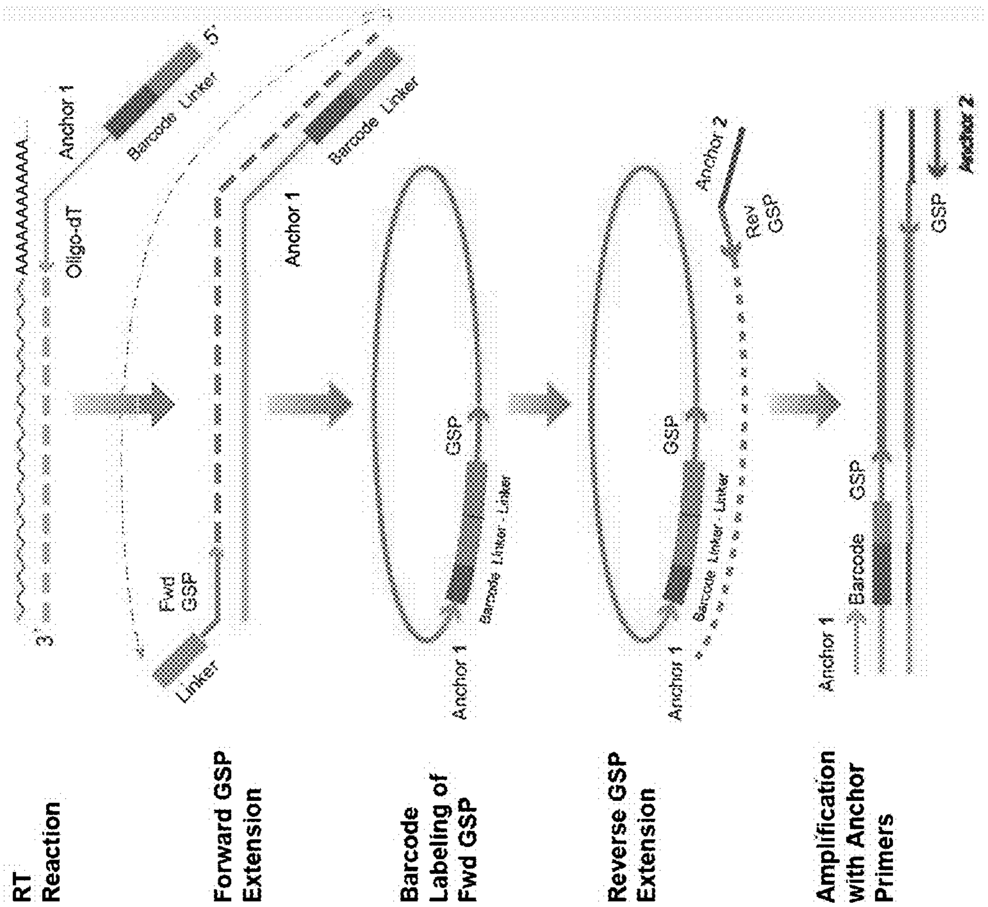
FIG. 2 provides a schematic diagram of a method of preparing a plurality of sample-barcoded anchor-domain-flanked gene specific DNA fragments in accordance with another embodiment of the invention.

In another embodiment where a donor nucleic acid is employed, a circular nucleic acid intermediate molecule is produced to transfer a sample barcode and anchor domain to a gene-specific primer. In examples of this embodiment, a forward GSP primed primer extension product, i.e., forward GSP primed second strand cDNA molecule, is circularized to transfer a sample barcode domain from an initial sample barcoded donor nucleic acid to the forward GSP, e.g., as illustrated in FIG. 2. As shown in the protocol illustrated in FIG. 2, the sample-barcoded donor nucleic acid comprises the structure: 3'-RNA binding domain-anchor 1 domain-sample barcode domain-linker 1 domain-5'. The RNA-binding domain may vary as desired, where examples of such domains include oligo dT domains, random sequence domains, and semi-random sequence domains which may be configured to interact and bind to conservative or common regions in RNA, e.g. polyA, short random sequences (e.g., N6) or short conservative sequences (e.g., nucleotide triplets coding the most abundant amino acids). The anchor 1, sample barcode and linker 1 domains may be as described above. Also, as described above, the donor nucleic acid may include a UMI domain, e.g., linked to the barcode domain, such as described above.

As illustrated in FIG. 2, the donor nucleic acid is employed to prime first strand cDNA synthesis, e.g., by contacting the RNA sample with the sample-barcoded donor nucleic acid under conditions sufficient to reverse transcribe first strand cDNA molecules from the RNA source, e.g., as reviewed in greater detail below. The resultant first strand cDNA molecules (i.e., donor nucleic acid primed primer extension products) are then contacted with a population of forward GSPs, where the forward GSPs include a linker domain and have the structure: 3'-forward GSP domain-linker 2-5'. Contact of the first strand cDNA molecule with the forward GSPs occurs under polymerase mediated primer extension reaction conditions sufficient to produce second strand cDNA molecules comprising a 5' linker 2 domain and a 3' linker 1 domain flanking a forward GSP primed domain, e.g., as illustrated in FIG. 2.

Following forward GSP mediated second strand cDNA synthesis, the flanking linker 1 and linker 2 domains are ligated to produce a circular intermediate, e.g., as illustrated in FIG. 2. To provide for sufficient proximity of the ends of the linker domains, a ligation linker may be employed. As reviewed above, the ligation linker is an oligonucleotide that includes a first domain complementary to the linker 1 domain of the RT primer and a second domain complementary to the linker 2 domain of the donor nucleic acid. When employed, the length of the ligated linker may vary, and in some instances ranges 15 to 60 nt, such as 20 to 50 nt, and including 24 to 40 nt. While not required, in some cases the ligation linker domain has a sequence with a GC-content in the range 50% to 80%. The linker 1 and linker 2 domains may be ligated to each other using any convenient DNA ligase, where DNA ligases that may be employed include, but are not limited to: DNA ligases, e.g., Ampligase® Thermostable DNA Ligase, CircLigase-DNA Ligase, *E. coli* DNA ligase, T3 DNA ligase, T4 DNA ligase, T7 DNA ligase, Taq DNA ligase, RNA ligase, and the like. As result of this ligation step and consequent circularization of the second strand cDNA molecule, the anchor and sample barcode domains from the initial donor nucleic acid are ligated 5' of the forward GSP. The resultant circularized second strand cDNA molecules are then contacted with the reverse GSPs under primer extension reaction conditions, e.g., as described in greater detail below. The reverse GSPs have the structure: 5'-anchor 2-reverse GSP domain-3' and contact under primer extension reaction conditions produces reverse GSP primed primer extensions products that include an anchor domain at their 5' ends. The resultant primer extension products may then be amplified, e.g., using universal primers that bind to the anchor domains, which results in production of a plurality of sample-barcoded anchor-domain-flanked double-stranded gene specific DNA fragments, e.g., as illustrated in FIG. 2. The resultant population of sample-barcoded anchor-domain-flanked double-stranded gene-specific DNA fragments may be further processed, e.g., further amplified, e.g., to add sequencing adaptors, etc., such as described in greater detail below.

Sample Barcoded GSP Mediated Protocols

As summarized above, embodiments of the methods employ gene specific primers that include a sample barcode domain. Specifically, in such embodiments at least one of the forward or reverse primers of the set of gene specific primers includes a sample barcode domain. In some instances, the reverse gene specific primers of the set, i.e., the reverse gene specific primer subset, include a sample barcode domain. In some instances, the forward gene specific primers of the set, i.e., the forward gene specific primer subset, include a sample barcode domain. Within the a given subset, while the gene specific domain will vary, the sample barcode domain is the same. In some instances, both the forward gene specific primers and the reverse gene specific primers include a barcode domain. In some instances, the barcode domain is 5' of the gene specific domain. In some instances where an anchor domain is also present, the anchor domain is 5' of the sample barcode domain. Other domains such as described above, e.g., UMI domain, etc., may also be present as desired. The length of the selected PCR primers may vary, in some embodiments the reverse barcoded primer is longer than forward primer. Reverse barcoded primer involving in stringent hybridization step with target RNA template composition could have the size in the range between 16 to 120 nt, such as 20 to 80 nt, including 25 to 60 nt, and 30 to 50 nt. Forward gene specific primers in some instances ranges from 16 to 25 nt, such as 18 to 24 nt.

The sample barcode containing gene specific primers employed in these embodiments may be prepared using any convenient protocol, including nucleic acid synthesis protocols, which protocols may or may not include a ligation step, e.g., as described in the working exemplification below. In some embodiments, the sample specific barcodes are attached to set of gene specific primers via a ligation reaction, such as mediated by DNA ligase activity. In ligation reactions, two oligonucleotides are ligated to each other using enzymes having ligation activity, such as DNA-ligases, Circligase, RNA-ligases, etc. The sample-specific barcodes may be ligated directly to the gene-specific primers using single-strand ligases, e.g., Circligase, RNA ligase, etc. In another embodiment, the sample barcodes may be ligated to the gene-specific primers via formation of double-stranded intermediate products and DNA ligases like T4 DNA ligase, Tth DNA ligase, Taq DNA ligase, etc., may be employed. The double-stranded intermediate products may be formed by using oligonucleotides complementary to the 5'-end of gene-specific primers and 3'-end of barcoded oligonucleotides. In order to simplify the ligation reaction composition, specific sequences may be provided at the both 5'-ends and 3'-ends of ligated molecules, e.g., linker domains disclosed in the current application. If both gene-specific primers and barcoded oligonucleotides have linker domains, adding oligonucleotide complementary to both linker domains will form double-stranded intermediates. These double-stranded intermediates with nick between two linker domains may then be ligated by DNA ligase. The linker domains of gene-specific primers may be phosphorylated. The labelling of gene-specific primers with sample-specific barcodes could be performed under gene-specific primer extension conditions, including adding reagents necessary for ligase activity, e.g. NAD, ATP, etc. In another embodiment, the barcode labeling conditions could be different from gene-specific primer extension conditions and use reaction buffer compositions specific for a particular DNA or RNA ligase. If all oligonucleotides are present in solution (e.g., in the wells of microtiter plates), the ligase-mediated barcoding reaction could be easily scaled-up for labeling sets of thousands of gene specific primers with hundreds of different unique sample-specific barcodes (in a separate wells).

Significantly larger scale (up to several millions) sample barcoded primers may be achieved if barcoded oligonucleotides are attached to the bead surface. Synthesis of barcoded oligonucleotides on the bead surface using combinatorial chemistry (pool and split synthesis approach) is well known in art technology and commonly applied for single-cell analysis. For the most single-cell RNA expression profiling assays developed so far, the oligonucleotides with structure: 5'-Anchor-Barcode-oligo dT-3' are synthesized on the beads, wherein the barcode is a combinatorial barcode unique for each bead and the oligo dT domain is a universal sequence used to prime cDNA synthesis from polyA tail of all mRNAs present in biological sample. The current invention uniquely allows the combination of known-in-art combinatorial bead-based barcode synthesis technology with DNA ligation assay for barcode labelling and immobilization of thousands of gene specific primers for each bead. The barcoded gene specific primers immobilized on the beads will be a unique experimental tool for high-throughput single-cell targeted expression profiling of hundreds-thousands of gene targets. As opposed to genome-wide barcode labeling of cDNAs using oligo dT-barcode strategy, the targeted labeling of subset of target transcripts address the main limitation (cost, throughput, quality of data) of current single-cell analysis technologies.

In another pool-split chemical synthesis embodiment, the thousands of gene-specific primers are synthesized on bead surface using conventional phosphoramidite chemistry in the 3'-to-5' direction. Furthermore, all bead-immobilized gene specific primers are mixed together and split for several (e.g., hundreds-thousands) compartments wherein each compartment comprises the same pool of gene specific primers. Each gene specific primer set immobilized on beads in each compartment is used in the next step of barcode synthesis wherein unique sample specific barcode will be synthesized in each compartment. As a result of this pool-split chemical synthesis strategy, the hundreds-thousands of sets of gene specific primers will be encoded with specific barcodes. The barcoded gene specific primer sets could be released from the beads and used in the disclosed primer extension assay.

Figure 3:
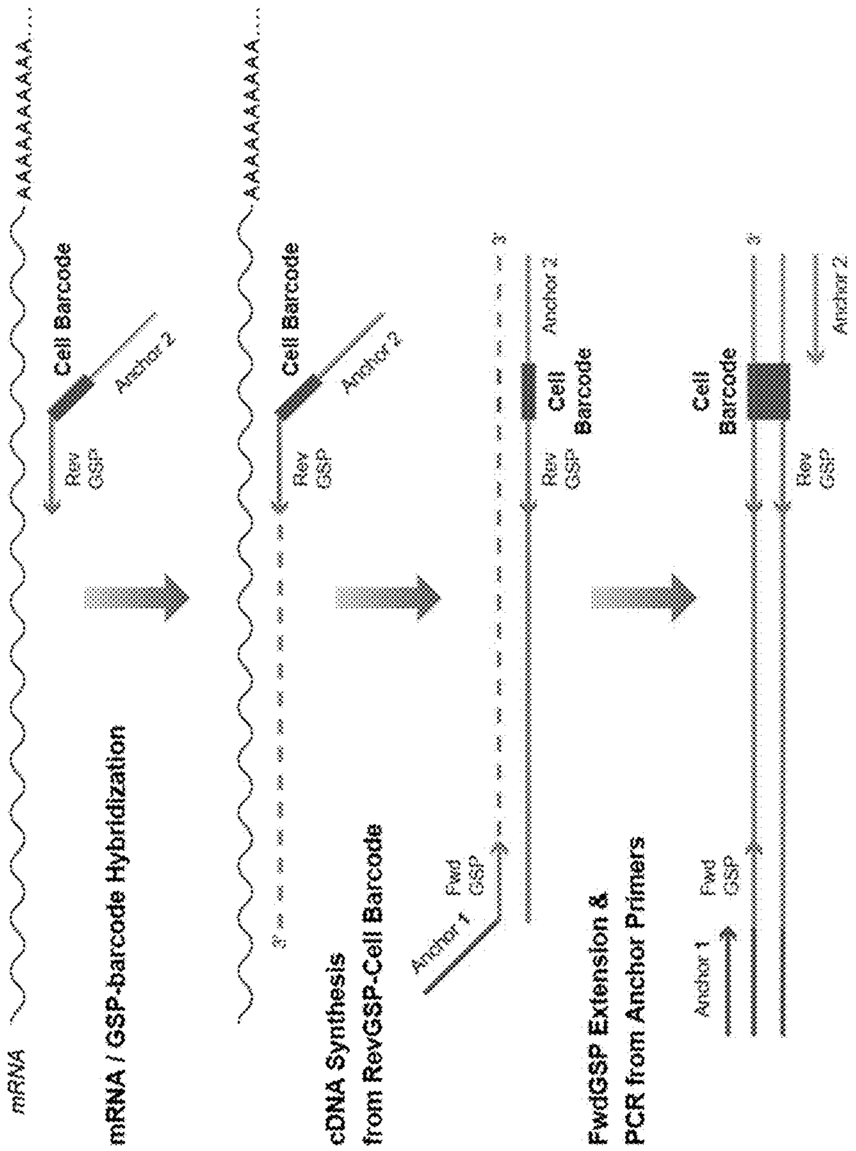
FIG. 3 provides a schematic diagram of a method of preparing a plurality of sample-barcoded anchor-domain-flanked gene specific DNA fragments using reverse primers that include a barcode domain in accordance with an embodiment of the invention.

A schematic illustration of an embodiment a protocol employed sample barcoded reverse gene specific primers is illustrated in FIG. 3. In the embodiment illustrated in FIG. 3, reverse gene specific primers are employed that include a 3' reverse gene specific primer domain (denoted RevGSP), a sample barcode domain (denoted as Cell Barcode) positioned 5' of the gene specific primer domain, and 5' anchor domain (denoted Anchor 2) that is 5' of the sample barcode domain. In the first step of the protocol illustrated in FIG. 3, the reverse gene specific primers are combined with the sample ribonucleic acids, e.g., an mRNA sample obtained from a single cell, under hybridization conditions such that the reverse gene specific primers bind to their complementary domains of the mRNAs. Where desired, the resultant mRNA template/GSP complexes of the resultant hybrid composition may be purified from any excess of unbound gene-specific primers, e.g., using any convenient protocol. For example, any excess of unbound oligonucleotides may be removed using purification protocols, such as but not limited to: nuclease treatment (e.g., exonuclease I treatment), chromatography, size-dependent binding to specific matrix, e.g. AMPure beads, etc.

In the embodiment illustrated in FIG. 3, following hybridization of the sample barcode domain anchor domain comprising reverse gene specific primers to mRNAs of the sample, the methods include reverse transcribing first strand cDNA molecules from the sample-barcoded reverse primers. Reverse transcription may be accomplished by contacting the template RNA/sample-barcoded reverse GSP complexes with a reverse transcriptase under reverse transcription conditions, e.g., as described in greater detail below. Reverse transcription results in the production of a population GSP primer extension products having a sample barcode domain and an anchor domain at their 5' ends.

As illustrated in FIG. 3, following production of the population GSP primer extension products, e.g., first strand cDNA molecules, as well as any desired purification or enrichment, e.g., to remove unhybridized GSPs, the resultant first strand cDNA molecules may be contacted with a population of forward GSPs, where the forward GSPs have an anchor domain at their 5' ends and a gene-specific domain at their 3' ends. Contact occurs under polymerase mediated primer extension reaction conditions, e.g., as described in further detail below, to produce forward GSP primed primer extension products, e.g., forward GSP primed second strand cDNA molecules. Following any desired purification step, e.g., to remove unbound forward GSPs, the resultant primer extension products may then be amplified, e.g., using universal primers that bind to the anchor domains, which results in production of a plurality of sample-barcoded anchor-domain-flanked double-stranded gene specific DNA fragments, e.g., as illustrated in FIG. 3. The resultant population of sample-barcoded anchor-domain-flanked double-stranded gene-specific DNA fragments may be further processed, e.g., further amplified, e.g., to add sequencing adaptors, etc., such as described in greater detail below.

Figure 4:
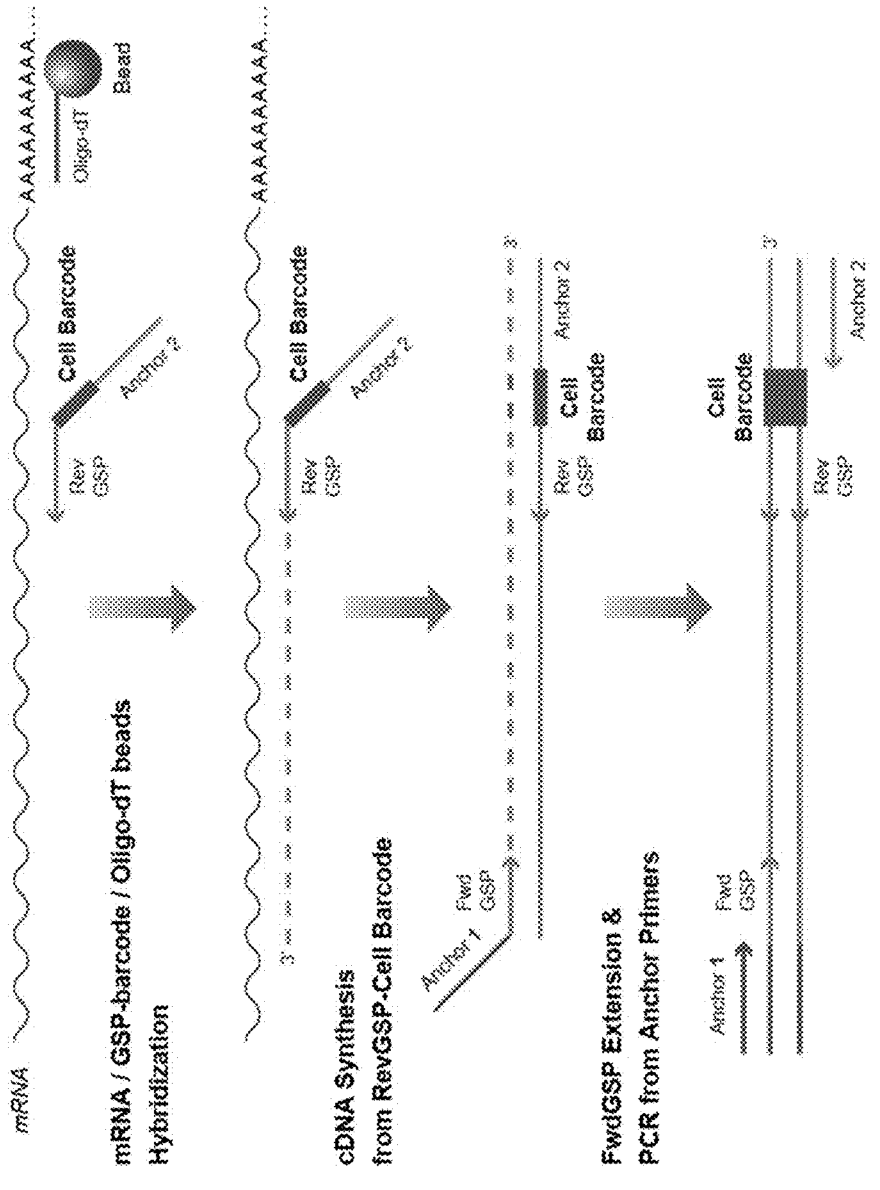
FIG. 4 provides a schematic diagram of a method of preparing a plurality of sample-barcoded anchor-domain-flanked gene specific DNA fragments using bead linked reverse primers that include a barcode domain in accordance with an embodiment of the invention.

In the embodiment illustrated in FIG. 4, reverse gene specific primers as employed in the protocol described for FIG. 3 are employed in conjunction with oligo-dT beads, such as described above. In the first step of the protocol illustrated in FIG. 4, the reverse gene specific primers and oligo-dT beads are combined with the sample ribonucleic acids, e.g., an mRNA sample obtained from a single cell, under hybridization conditions such that the reverse gene specific primers bind to their complementary domains of the mRNAs and the oligo-dT labels of the beads bind to the polyA tails of the mRNAs. Where desired, the resultant mRNA template/GSP/bead complexes of the resultant hybrid composition may be purified from any excess of unbound gene-specific primers, e.g., using any convenient protocol. In the illustrated embodiment shown in FIG. 4, the resultant complexes are immobilized on beads and can be purified from any excess of non-hybridized gene-specific primers using a convenient washing protocol, such as washing protocols known in the art.

In the embodiment illustrated in FIG. 4, following hybridization of the sample barcode domain anchor domain comprises reverse gene specific primers to mRNAs of the sample, the methods include reverse transcribing first strand cDNA molecules from the sample-barcoded reverse primers. Reverse transcription may be accomplished by contacting the template RNA/sample-barcoded reverse GSP complexes with a reverse transcriptase under reverse transcription conditions, e.g., as described in greater detail below. Reverse transcription results in the production of a population GSP primer extension products having a sample barcode domain and an anchor domain at their 5' ends.

As illustrated in FIG. 4, following production of the population GSP primer extension products, e.g., first strand cDNA molecules, as well as any desired purification or enrichment, e.g., to remove unhybridized GSPs, the resultant first strand cDNA molecules may be contacted with a population of forward GSPs, where the forward GSPs have an anchor domain at their 5' ends and a gene-specific domain at their 3' ends. Contact occurs under polymerase mediated primer extension reaction conditions, e.g., as described in further detail below, to produce forward GSP primed primer extension products, e.g., forward GSP primed second strand cDNA molecules. The resultant primer extension products may then be amplified, e.g., using universal primers that bind to the anchor domains, which results in production of a plurality of sample-barcoded anchor-domain-flanked double-stranded gene specific DNA fragments, e.g., as illustrated in FIG. 4. The resultant population of sample-barcoded anchor-domain-flanked double-stranded gene-specific DNA fragments may be further processed, e.g., further amplified, e.g., to add sequencing adaptors, etc., such as described in greater detail below.

In some instances, the sample barcoded reverse primers are linked to a solid support. The solid support may vary, where examples of solid supports include beads, wells, plates, etc., e.g., made of a suitable solid phase material, such as a polymeric material, where the surface is configured to provide the desired bond to the reverse primers. In some instances, the reverse gene specific primer is linked to the solid support by a cleavable linker, i.e., a linker that may be broken in response to an applied stimulus. In such instances, any convenient cleavable linker may be employed. Examples of cleavable linkers that may be employed include, but are not limited to, thermal-labile linkers, enzymatically-labile linkers, light-labile linkers, etc.

In some instances, the linker is a thermal labile linker that includes a thermally-labile blocking moiety. A thermally-labile blocking moiety is a moiety that may be cleaved when the temperature of the primer is raised above a certain threshold value. While the threshold value may vary, in some instances the threshold value is 60° C. or higher, such as 75° C. or higher, including 90° C. or higher. Examples of thermally labile moieties that may be employed in accordance with the invention include, but are not limited to, those described in U.S. Pat. Nos. 8,133,669 and 8,361,753; the disclosures of which are herein incorporated by reference. In some instances, the thermally labile blocking moiety is a 3' blocking moiety, such as but not limited to: O-phenoxyacetyl; O-methoxyacetyl; O-acetyl; O-(p-toluene)sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl.

In some instances, the linker is an enzymatically-labile linker. An enzymatically-labile linker includes a moiety that may be cleaved by exposing the linker to a suitable enzyme that cleaves the moiety. Examples of enzymatically-labile moieties of interest include those having a linkage group cleavable by a hydrolase enzyme. Examples of hydrolase enzymes of interest include, but are not limited to: esterases, phosphatases, peptidases, penicillin amidases, glycosidases and phosphorylases, kinases, etc. Hydrolase susceptible linkages and hydrolase enzymes are further described in U.S. Patent Application Publication No. 20050164182 and U.S. Pat. No. 7,078,499; the disclosures of which are herein incorporated by reference.

In some instances, the linker is a chemically-labile linker that includes a chemically-labile moiety. A chemically-labile is a moiety that may be cleaved by exposing the linker to a chemical agent that cleaves the moiety. The chemically-labile moiety may be reactive with the functional group of a chemical agent (e.g., an azido-containing modifiable group that is reactive with an alkynyl-containing reagent or a phosphine reagent, or vice versa, or a disulfide that is reactive with a reducing agent such as tris(2-carboxyethyl) phosphine (TCEP) or DTT). A variety of functional group chemistries and chemical agent stimuli suitable for modifying them may be utilized in the subject methods. Functional group chemistries and chemical agents of interest include, but are not limited to, click chemistry groups and reagents (e.g., as described by Sharpless et al., (2001), "Click Chemistry: Diverse Chemical Function from a Few Good Reactions", Angewandte Chemie International Edition 40 (11): 2004-2021), Staudinger ligation groups and reagents (e.g., as described by Bertozzi et al., (2000), "Cell Surface Engineering by a Modified Staudinger Reaction", Science 287 (5460): 2007), and other bioconjugation groups and reagents (e.g., as described by Hermanson, Bioconjugate Techniques, Second Edition, Academic Press, 2008). In certain embodiments, the chemically-labile blocking moiety includes a functional group selected from an azido, a phosphine (e.g., a triaryl phosphine or a trialkyl phosphine or mixtures thereof), a dithiol, an active ester, an alkynyl, a protected amino, a protected hydroxy, a protected thiol, a hydrazine, and a disulfide.

In some instances, the cleavable linker is a light-labile linker that includes a light-labile moiety, which is a moiety that may be cleaved by exposing the linker to light at a wavelength that cleaves the moiety from the linker. Examples of light-labile moieties of interest include cleavable by light of a certain wavelength that cleaves a photocleavable group in the linkage group. Any convenient photocleavable groups may find use. Cleavable groups and linkers may include photocleavable groups comprising covalent bonds that break upon exposure to light of a certain wavelength. Suitable photocleavable groups and linkers for use in the subject MCIPs include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., achieving >90% yield in 5-10 minutes using a 365 nm peak lamp at 1-5 mW/cm2. In some embodiments, the modifiable group is a photocleavable group such as a nitro-aryl group, e.g., a nitro-indole group or a nitro-benzyl group, including but not limited to: 2-nitroveratryloxycarbonyl, α-carboxy-2-nitrobenzyl, 1-(2-nitrophenyl)ethyl, 1-(4,5-dimethoxy-2-nitrophenyl)ethyl and 5-carboxymethoxy-2-nitrobenzyl. Nitro-indole groups of interest include, e.g., a 3-nitro-indole, a 4-nitro indole, a 5-nitro indole, a 6-nitro-indole or a 7-nitro-indole group, where the indole ring may be further substituted at any suitable position, e.g., with a methyl group or a halo group (e.g., a bromo or chloro), e.g., at the 3-, 5- or 7-position. In certain embodiments, the nitro-aryl group is a 7-nitro indolyl group. In certain instances, the 7-nitro indolyl group is further substituted with a substituent that increases the photoactivity of the group, e.g., substituted with a bromo at the 5-position. Any convenient photochemistry of nitroaryl groups may be adapted for use. In certain embodiments, the linker includes a photocleavable group, such as a nitrobenzyl protecting group or a nitro-indolyl group.

Figure 5:
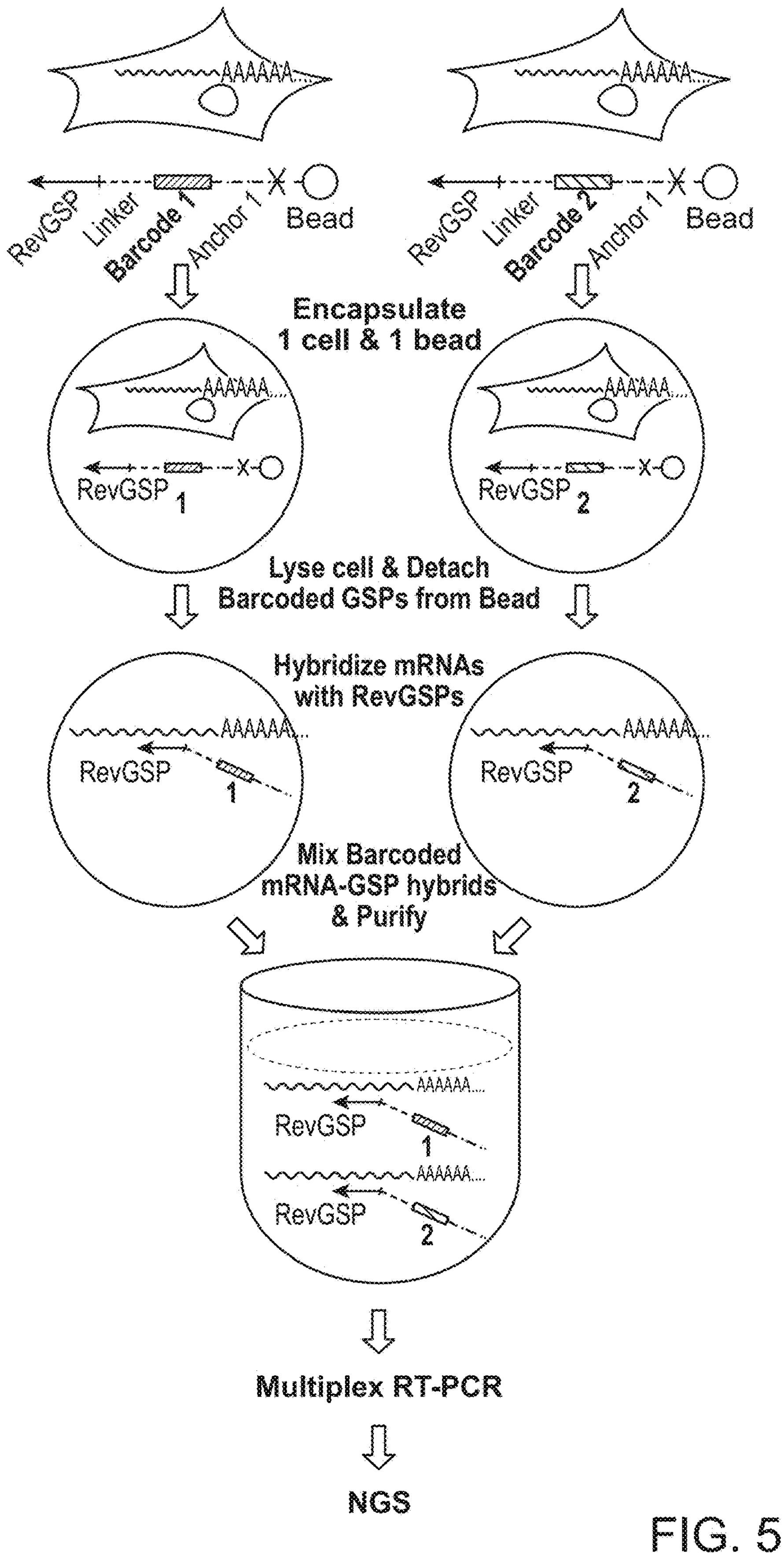
FIG. 5 provides a schematic diagram of a method of preparing a plurality of sample-barcoded anchor-domain-flanked gene specific DNA fragments using bead linked sample barcode domain comprising reverse primers in a droplet mediated protocol in accordance with an embodiment of the invention.

An example of a protocol that employs sample barcoded reverse gene specific primers linked to a solid support by a cleavable linker is illustrated in FIG. 5. In the protocol illustrated in FIG. 5, template ribonucleic acids from two cells are employed, where the protocol employs a pooling step and sample barcodes to match the results to the cellular source. As illustrated in FIG. 5, reverse gene specific primers are employed that include a 3' reverse gene specific primer domain (denoted RevGSP), a non-cleavable linker domain (denoted Linker) that is 5' of the RevGSP, a sample barcode domain (denoted as Barcode 1 or Barcode 2) positioned 5' of the non-cleavable linker, a 5' anchor domain (denoted Anchor 1) that is 5' of the sample barcode domain, and a bead linked to the 5' end of the Anchor 1 domain by a cleavable linker (shown as an X).

In the first step of the protocol illustrated in FIG. 5, the sample barcoded reverse gene specific primers that include the Barcode 1 sample barcode are combined with a first cell and encapsulated in a first droplet, e.g., as described below. The sample barcoded reverse gene specific primers that include the Barcode 2 sample barcode are combined with a second cell and encapsulated in a second droplet. The cells in the first and second droplets are then lysed and the beads are removed from the reverse primers by cleaving the cleavable linker. In each of the first and second droplets, the resultant cleaved reverse primers are maintained with the liberated mRNAs obtained from the lysed cells under hybridization conditions such that the reverse gene specific primers bind to their complementary domains of the mRNAs.

As illustrated in FIG. 5, the first and second droplets containing the resultant hybrid composition of the mRNA template/GSP complexes are then combined or pooled into a single composition. Following this pooling step, excess unbound gene-specific primers are removed from the combined composition so that the combined hybrid compositions can be purified from any excess of unbound gene-specific primers, e.g., using any convenient protocol. For example, any excess of unbound oligonucleotides may be removed using purification protocols, such as but not limited to: nuclease treatment (e.g., exonuclease I treatment), chromatography, size-dependent binding to specific matrix, e.g. AMPure beads, etc.

In the embodiment illustrated in FIG. 5, following purification, the methods include reverse transcribing first strand cDNA molecules from the sample-barcoded reverse primers. As reviewed above, reverse transcription may be accomplished by contacting the template RNA/sample-barcoded reverse GSP complexes with a reverse transcriptase under reverse transcription conditions, e.g., as described in greater detail below. Reverse transcription results in the production of a population GSP primer extension products having a sample barcode domain and an anchor domain at their 5' ends.

Following production of the population GSP primer extension products, e.g., first strand cDNA molecules, as well as any desired purification or enrichment, e.g., to remove unhybridized GSPs, the resultant first strand cDNA molecules may be contacted with a population of forward GSPs, where the forward GSPs have an anchor domain at their 5' ends and a gene-specific domain at their 3' ends. Contact occurs under polymerase mediated primer extension reaction conditions, e.g., as described in further detail below, to produce forward GSP primed primer extension products, e.g., forward GSP primed second strand cDNA molecules. Following any desired purification, e.g., to remove unbound forward GSPs, the resultant primer extension products may then be amplified, e.g., using universal primers that bind to the anchor domains, which results in production of a plurality of sample-barcoded anchor-domain-flanked double-stranded gene specific DNA fragments. The resultant population of sample-barcoded anchor-domain-flanked double-stranded gene-specific DNA fragments may be further processed, e.g., further amplified, e.g., to add sequencing adaptors, etc., such as described in greater detail below, e.g., for performing NGS.

In some instances where the sample barcoded reverse primers are bound to a solid support, such as a bead, by a cleavable linker (e.g., as described above), the solid support may further include a specific binding pair member, e.g., that includes a specific binding domain that specifically binds to a marker of a cell of interest. Specific binding domains of interest include, but are not limited to, antibody binding agents, proteins, peptides, haptens, nucleic acids, etc. The term “antibody binding agent” as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'2 fragments. Also within the scope of the term “antibody binding agent” are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. The marker of the cell of interest may be any convenient marker, such as a cell surface protein or structure having an epitope to which the specific binding domain may specifically bind. In such instances, the bead linked sample barcoded reverse primers may include one or more additional domains of interest, such as bead identifying domains (bead barcodes), antibody identifying domains (antibody barcodes), etc.

Figure 6:
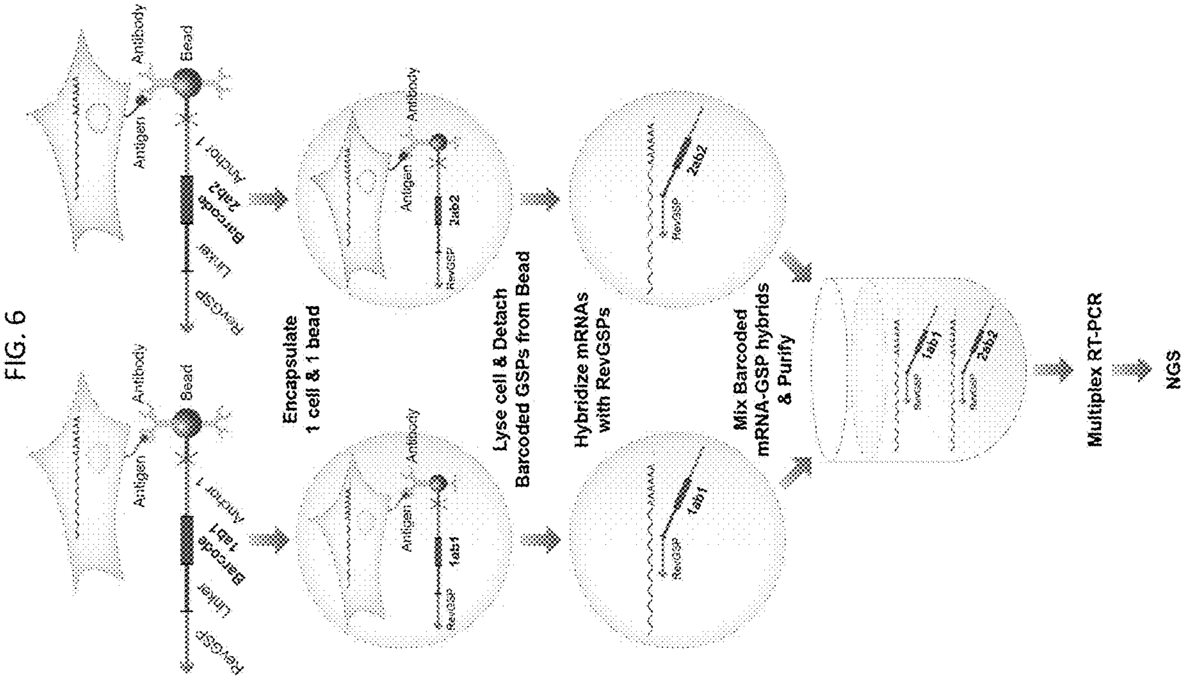
FIG. 6 provides a schematic diagram of a method of preparing a plurality of sample-barcoded anchor-domain-flanked gene specific deoxyribonucleic acid (DNA) fragments using specific binding member bead linked sample barcode domain comprising reverse primers in a droplet mediated protocol in accordance with an embodiment of the invention.

An example of a protocol that employs sample barcoded reverse gene specific primers linked to a solid support by a cleavable linker, where the support includes a cell specific binding domain, is illustrated in FIG. 6. In the protocol illustrated in FIG. 6, template ribonucleic acids from two cells are employed, where the protocol employs a pooling step and sample barcodes are employed to match the results to the cellular source and antibody employed. As illustrated in FIG. 6, reverse gene specific primers are employed that include a 3' reverse gene specific primer domain (denoted RevGSP), a non-cleavable linker domain (denoted Linker) that is 5' of the RevGSP, a sample barcode domain (denoted as Barcode 1 or Barcode 2) positioned 5' of the non-cleavable linker, an antibody barcode domain (denoted ab1 or ab2) positioned 5' of the sample barcode domain, a 5' anchor domain (denoted Anchor 1) that is 5' of the sample barcode domain, a bead linked to the 5' end of the Anchor 1 domain by a cleavable linker (shown as an X) and an antibody on the bead that specifically binds to a cell surface antigen.

In the first step of the protocol illustrated in FIG. 6, the sample barcoded reverse gene specific primers that include the Barcode 1 sample barcode and ab1 barcode (collectively denoted 1ab1) are combined with a first cell under conditions sufficient for the antibody on the bead to specifically bind to the antigen on the cell, and the resultant binding complex is encapsulated in a first droplet. The sample barcoded reverse gene specific primers that include the Barcode 2 sample barcode and ab2 barcode (collectively denoted 2ab2) are combined with a second cell under conditions sufficient for the antibody on the bead to specifically bind to the antigen on the cell, and the resultant binding complex is encapsulated in a second droplet. The cells in the first and second droplets are then lysed and the beads are removed from the reverse primers by cleaving the cleavable linker. In each of the first and second droplets, the resultant cleaved reverse primers are maintained with the liberated mRNAs obtained from the lysed cells under hybridization conditions such that the reverse gene specific primers bind to their complementary domains of the mRNAs.

As illustrated in FIG. 6, the first and second droplets containing the resultant hybrid composition of the mRNA template/GSP complexes are then combined or pooled into a single composition. Following this pooling step, excess unbound gene-specific primers are removed from the combined composition so that the combined hybrid compositions can be purified from any excess of unbound gene-specific primers, e.g., using any convenient protocol. For example, any excess of unbound oligonucleotides may be removed using purification protocols, such as but not limited to: nuclease treatment (e.g., exonuclease I treatment), chromatography, size-dependent binding to specific matrix, e.g. AMPure beads, etc.

In the embodiment illustrated in FIG. 6, following purification, the methods include reverse transcribing first strand cDNA molecules from the sample-barcoded reverse primers. As reviewed above, reverse transcription may be accomplished by contacting the template RNA/sample-barcoded reverse GSP complexes with a reverse transcriptase under reverse transcription conditions, e.g., as described in greater detail below. Reverse transcription results in the production of a population GSP primer extension products having a sample barcode domain and an anchor domain at their 5' ends.

Following production of the population GSP primer extension products, e.g., first strand cDNA molecules, as well as any desired purification or enrichment, e.g., to remove unhybridized GSPs, the resultant first strand cDNA molecules may be contacted with a population of forward GSPs, where the forward GSPs have an anchor domain at their 5' ends and a gene-specific domain at their 3' ends. Contact occurs under polymerase mediated primer extension reaction conditions, e.g., as described in further detail below, to produce forward GSP primed primer extension products, e.g., forward GSP primed second strand cDNA molecules. Following any desired purification, e.g., to remove unbound forward GSPs, the resultant primer extension products may then be amplified, e.g., using universal primers that bind to the anchor domains, which results in production of a plurality of sample-barcoded anchor-domain-flanked double-stranded gene specific DNA fragments. The resultant population of sample-barcoded anchor-domain-flanked double-stranded gene-specific DNA fragments may be further processed, e.g., further amplified, e.g., to add sequencing adaptors, etc., such as described in greater detail below, e.g., for performing NGS.

Template Nucleic Acids

Components of the subject reaction mixtures may include one or more template nucleic acids. Such template nucleic acids provide the template from which template nucleic acid-mediated primer extension reactions and other nucleic acid production reactions may be performed. Nucleic acid templates may be added to a reaction mixture, e.g., through direct addition of the nucleic acid template, through lysing one or more cells containing the nucleic acid template, and the like, or one or more nucleic acid templates may be generated during the reaction, e.g., as an intermediate product of a prior nucleic acid production reaction. Essentially any nucleic acid template may find use in the subject methods, including e.g., RNA template nucleic acid and DNA template nucleic acids. RNA template nucleic acids may vary and may include e.g., messenger RNA (mRNA) templates, and the like. In addition, various types of DNA templates may be employed, including but not limited to e.g., genomic DNA templates, mtDNA templates, synthetic DNA templates, etc.

According to certain embodiments, the template nucleic acids are template ribonucleic acids (template RNA). Template RNAs may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

According to certain embodiments, the template nucleic acids are template deoxyribonucleic acids (template DNA). A template DNA may be any type of DNA of interest to a practitioner of the subject methods, including but not limited to genomic DNA or fragments thereof, complementary DNA (or "cDNA", synthesized from any RNA or DNA of interest), recombinant DNA (e.g., plasmid DNA), or the like.

The number of distinct template nucleic acids of differing sequence in a given template nucleic acid composition may vary. While the number of distinct template nucleic acids in a given template nucleic acid composition may vary, in some instances the number of distinct template nucleic acids in a given template nucleic acid composition ranges from 1 to $10^6$, such as 1 to $10^7$, including 1 to $10^5$.

The template nucleic acid composition employed in such methods may be any suitable nucleic acid sample. The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 fg/μL to 10 μg/μL, such as from 1 μg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL.

Template nucleic acid components are nucleic acid samples that contain one or more types of template nucleic acids, as described in more detail below. Template nucleic acid components may be derived from cellular samples including cellular samples that contain a single cell or a population of cells containing, e.g., two or more cells. Cellular samples may be derived from a variety of sources including but not limited to e.g., a cellular tissue, a biopsy, a blood sample, a cell culture, etc. Additionally, cellular samples may be derived from specific organs, tissues, tumors, neoplasms, or the like. Furthermore, cells from any population can be the source of a cellular sample used in the subject methods, such as a population of prokaryotic or eukaryotic single celled organisms including bacteria or yeast.

As such, in some instances, the source of an RNA sample utilized in the subject methods may be a mammalian cellular sample, such as a rodent (e.g., mouse or rat) cellular sample, a non-human primate cellular sample, a human cellular sample, or the like. In some instances, a mammalian cellular sample may be mammalian blood sample, including but not limited to e.g., a rodent (e.g., mouse or rat) blood sample, a non-human primate blood sample, a human blood sample, or the like.

In some instances, the template nucleic acid component is from a single cell. A template nucleic acid component from a single cell is a nucleic acid composition, e.g., a composition of one or more distinct nucleic acids, such as ribonucleic acids or deoxyribonucleic acids that originate or are derived from a single cell. As used herein, a "single cell" refers to one cell. Single cells useful as the source of template nucleic acids, e.g., RNAs or DNAs, can be obtained from an organism or tissue of interest, or from a biopsy, blood sample, or cell culture, etc. Additionally, cells from specific organs, tissues, tumors, neoplasms, or the like can be obtained and used in the methods described herein. In some instances, the template nucleic acid component is obtained from a portion of a single cell. Single cell portions of interest include, but are not limited to: organelles, exosomes or more broadly nucleic acids contained within, or associated with, a protein and or lipid bearing membrane.

Template nucleic acids of template nucleic acid components employed in embodiments of the invention may contain a plurality of distinct template nucleic acids of differing sequence. Template nucleic acids (e.g., a template RNA, a template DNA, or the like) may be polymers of any length. While the length of the polymers may vary, in some instances the polymers are 10 nt or longer, 20 nt or longer, 50 nt or longer, 100 nt or longer, 500 nt or longer, 1000 nt or longer, 2000 nt or longer, 3000 nt or longer, 4000 nt or longer, 5000 nt or longer or more nt. In certain aspects, template nucleic acids are polymers, where the number of bases on a polymer may vary, and in some instances is 10 nt or less, 20 nt or less, 50 nt or less, 100 nt or less, 500 nt or less, 1000 nt or less, 2000 nt or less, 3000 nt or less, 4000 nt or less, or 5000 nt or less, 10,000 nt or less, 25,000 nt or less, 50,000 nt or less, 75,000 nt or less, 100,000 nt or less.

Single cells, for use in the herein described methods relating thereto, may be obtained by any convenient method. For example, in some instances, single cells may be obtained through limiting dilution of cellular sample. In some instances, the present methods may include a step of obtaining single cells. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example, a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm. Such methods are further described in greater detail below.

In some instances, single cells may be obtained by sorting a cellular sample using a cell sorter instrument. By "cell sorter" as used herein is meant any instrument that allows for the sorting of individual cells into an appropriate vessel for downstream processes, such as those processes of library preparation as described herein. Useful cell sorters include flow cytometers, such as those instruments utilized in fluorescence activated cell sorting (FACS). Flow cytometry is a well-known methodology using multi-parameter data for identifying and distinguishing between different particle (e.g., cell) types i.e., particles that vary from one another terms of label (wavelength, intensity), size, etc., in a fluid medium. In flow cytometrically analyzing a sample, an aliquot of the sample is first introduced into the flow path of the flow cytometer. When in the flow path, the cells in the sample are passed substantially one at a time through one or more sensing regions, where each of the cells is exposed separately individually to a source of light at a single wavelength (or in some instances two or more distinct sources of light) and measurements of scatter and/or fluorescent parameters, as desired, are separately recorded for each cell. The data recorded for each cell is analyzed in real time or stored in a data storage and analysis means, such as a computer, for later analysis, as desired.

Cells sorted using a flow cytometer may be sorted into a common vessel (i.e., a single tube), or may be separately sorted into individual vessels. For example, in some instances, cells may be sorted into individual wells of a multi-well plate, as described below.

Useful cell sorters also include multi-well-based systems that do not employ flow cytometry. Such multi-well based systems include essentially any system where cells may be deposited into individual wells of a multi-well container by any convenient means, including e.g., through the use of Poisson distribution (i.e., limiting dilution) statistics, individual placement of cells (e.g., through manual cell picking or dispensing using a robotic arm or pipettor). In some instances, useful multi-well systems include a multi-well wafer or chip, where cells are deposited into the wells or the wafer/chip and individually identified by a microscopic analysis system. In some instances, an automated microscopic analysis system may be employed in conjunction with a multi-well wafer/chip to automatically identify individual cells to be subjected to downstream analyses, including library preparation, as described herein.

In some instances, one or more cells may be sorted into or otherwise transferred to an appropriate reaction vessel. Reaction components may be added to reaction vessels, including e.g., components for preparing a template nucleic acid component, components for generating a product double stranded cDNA, components for one or more library preparation reactions, etc.

The wells of a multi-well device can be designed such that a single well includes a single cell or a single droplet. An individual cell or droplet may also be isolated in any other suitable container, e.g., microfluidic chamber, droplet, nanowell, tube, etc. Any convenient method for manipulating single cells or droplets may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells or droplets can be deposited in wells of a plate according to Poisson statistics (e.g., such that approximately 10%, 20%, 30% or 40% or more of the wells contain a single cell or droplet—which number can be defined by adjusting the number of cells or droplets in a given unit volume of fluid that is to be dispensed into the containers). In some instances, a suitable reaction vessel comprises a droplet (e.g., a microdroplet). Individual cells or droplets can, for example, be individually selected based on features detectable by microscopic observation, such as location, morphology, the presence of a reporter gene (e.g., expression), the presence of a bound antibody (e.g., antibody labelling), FISH, the presence of an RNA (e.g., intracellular RNA labelling), or qPCR.

Following obtainment of a desired cell population or single cells, e.g., as described above, nucleic acids can be released from the cells by lysing the cells. Lysis can be achieved by, for example, heating or freeze-thaw of the cells, or by the use of detergents or other chemical methods, or by a combination of these. However, any suitable lysis method can be used. In some instances, a mild lysis procedure can advantageously be used to prevent the release of nuclear chromatin, thereby avoiding genomic contamination of a cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kuimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313).

Calibration Control Template Composition

In some instances, preparation of the target nucleic acid template composition includes combining an initial nucleic acid composition, e.g., as described above, with a calibration control template composition, e.g., to produce a target nucleic acid template composition that is spiked with a control template mixture, which mixture may be made up of synthetic nucleic acids, naturally occurring nucleic acids or a combination thereof. As to structural requirements, the calibration control template nucleic acids at least include an amplicon structure with two primer binding sites which mimic natural target template nucleic acid. In some embodiments, the control template mix is a synthetic control template mix that includes calibration control template nucleic acids having sequences that mimic, but are different from, the sequences of target template nucleic acids. For example, a calibration control template nucleic acid could have one, two, or more point mutations downstream of primer binding sites. These mutations may be identified by downstream NGS analysis allowing one to uniquely identify and differentiate sample specific and control template nucleic acids from each other. Other types of control template modifications (e.g., deletions, insertions, etc.) could be employed, as desired. Furthermore, the calibration control templates may mimic natural target nucleic acid template structures. For example, synthetic gene or gene fragments with several point mutations could be synthesized under the control of a T7 promoter, and T7 transcripts which mimic the natural template target mRNA sequences and structures could be synthesized in vitro and spiked to into a cell extract or purified RNA at any known concentration. Moreover, the set of calibration standards designed against the same target mRNA with different mutations could be spiked into target template compositions at different amounts (e.g. at 1, 10, 100, 1000 copies per cell). The spiked calibration controls could be employed as internal calibration standards in primer extension assays which allow one to calculate the actual concentration of natural target mRNA template. Moreover, the spiked calibration standards may be employed as universal standards to do quality control of target mRNAs in biological samples. For example, if cells are apoptotic, non-functional or damaged, the calibration standards spiked into a single-cell analysis would allow one to reveal these defect cells with degraded or missing template RNAs. The calibration control nucleic acid templates could be spiked directly into a cell, cell extract, cell fractions, purified cells or at any step of the primer extension and multiplex PCR protocol. In one embodiment, the control nucleic acid templates are spiked into cells, cell extracts or purified RNA. For example, in single-cell analysis, the control RNA templates could be mixed with lysis/hybridization buffer prior to droplet formation in 10×Genomics, Mission Bio or BioRad single-cell analysis platforms. In other embodiments, the control template compositions could be spiked into cell lysates by pipet (e.g., ink-jet printer) or immobilized on beads together with barcoded gene specific primers. Calibration control templates could be designed and developed for single gene or gene sets including genome-wide set. For example, a mix of calibration control RNAs could be developed for a set of housekeeping genes. The housekeeping calibration control RNAs would allow one to compare the content and quality of target template RNAs in the single-cells or multiplex analysis of plurality of clinical samples. The set of cell specific marker calibration control RNAs may allow one to perform QC and identify specific cell types. Genome-wide set of calibration control RNAs could be employed to perform quantitative analysis of expression of all genes in any cell or biological sample. In another embodiment, the calibration control RNAs designed against pathogens (e.g. viruses, bacterial species, etc.) may be employed as a unique tool to perform quantitative expression analysis of pathogenic genes in the background of human transcripts in clinical samples. Calibration control templates as internal calibration standards are unique tool for analysis plurality of biological samples in parallel. Combination of barcoded gene specific primers and calibration control nucleic acid templates allows one to combine samples together at the early stage of the protocol and perform powerful multiplex analysis of hundreds of samples or thousands of single cells in parallel in single test tube.

Primer Extension Reaction Conditions

As reviewed above, aspects of the methods include contacting primers, e.g., oligo dT primers and/or GSPs, such as described above, with a nucleic acid template composition, which may be made up of an initial nucleic acid sample or be primer extension products, under primer extension reaction conditions. By "primer extension reaction conditions" is meant reaction conditions that permit polymerase-mediated extension of a 3' end of a nucleic acid strand, i.e., primer, hybridized to a template nucleic acid. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner.

The concentration of primers in the primer extension reaction mixture produced upon combination of the template nucleic acid and primers may vary, as desired. The amount of target template nucleic acid that is combined with the primers and other reagents, e.g., as described below, to produce a primer extension reaction mixture may vary. In some instances, the target nucleic acid template composition is combined into the reaction mixture such that the final concentration of nucleic acid in the reaction mixture ranges from 1 fg/μL to 10 μg/μL, such as from 1 μg/μL to 5 μg/μL, such as from 0.1 ng/μL to 50 ng/μL, such as from 0.5 ng/μL to 20 ng/μL, including from 1 ng/μL to 10 ng/μL.

In producing the primer extension reaction mixture, the primers and target template nucleic acid composition are combined with a number of additional reagents (e.g., to increase specificity, uniformity, yield, etc. of extension products), which may vary as desired. A variety of polymerases may be employed when practicing the subject methods. Reference to a particular polymerase, such as those exemplified below, will be understood to include functional variants thereof unless indicated otherwise. Examples of useful polymerases include DNA polymerases, e.g., where the template nucleic acid is DNA. In some instances, DNA polymerases of interest include, but are not limited to: thermostable DNA polymerases, such as may be obtained from a variety of bacterial species, including *Thermus aquaticus* (Taq), *Thermus thermophilus* (Tth), *Thermus filiformis, Thermus flavus, Thermococcus literalis*, and *Pyrococcus furiosus* (Pfu) or modified and mutated versions of these DNA polymerases (e.g. Phusion DNA polymerase, Q5 DNA polymerase, etc.). Alternatively, where the target template nucleic acid composition is made up of RNA, the polymerase may be a reverse transcriptase (RT), where examples of reverse transcriptases include Moloney Murine Leukemia Virus reverse transcriptase (MMLV RT), e.g., SuprScript II, SuperScript III, MaxiScript reverse transcriptase (Thermo-Fsher), SMARTScribe™ reverse transcriptase (Takara), AMV reverse transcriptase, *Bombyx mori* reverse transcriptase (e.g., *Bombyx mori* R2 non-LTR element reverse transcriptase), etc. In one embodiment, the enzymes with DNA polymerase activity are designed for hot-start primer extension reaction, e.g., used as a complex with specific antibody or chemical compound which blocks enzymatic activity at low temperature but fully releases the activity at reaction conditions. For example, in some instances a hot-start reverse transcriptase composition, e.g. complex between MMLV RT and Therma-Stop RT reagent (Thermagenix) is employed.

Primer extension reaction mixtures also include dNTPs. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.05 to 10 mM, such as from 0.1 to 2 mM, including 0.2 to 1 mM. According to one embodiment, at least one type of nucleotide added to the reaction mixture is a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

In addition to the template nucleic acid, primers, the polymerase, and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, CA)), betaine, single-stranded binding proteins (e.g., T4 Gene 32, cold shock protein A (CspA), recA protein, and/or the like) DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions.

The primer extension reaction mixture can have a pH suitable for the primer extension reaction. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the product nucleic acid may vary according to factors such as the particular polymerase employed, the melting temperatures of any optional primers employed, etc. According to one embodiment, the primer extension reaction conditions include bringing the reaction mixture to a temperature ranging from 4 to 72° C., such as from 16 to 70° C., e.g., 37 to 65° C., such as 60° C. to 65° C. The temperature of the reaction mixture may be maintained for a sufficient period of time for polymerase mediated, template directed primer extension to occur. While the period of time may vary, in some instances the period of time ranges from 5 to 60 minutes, such as 15 to 45 minutes, e.g., 30 minutes.

In a given primer extension reaction condition, where desired, hybridization complexes of template and primer may be purified, e.g., via separation from excess of non-bound primers, e.g., by nuclease treatment or binding to solid support, e.g., such as beads, e.g., as described above. In this way, excess of primers, such as oligo dT primers and/or gene-specific primers, may be removed in order to achieve a high specificity of primer extension reaction from the target template sequences.

As reviewed above, the barcode labelling step, i.e., where a barcode domain is transferred from an initial donor nucleic acid to a gene-specific primer, may be performed before, after or at the same time as a primer extension step. Transfer is mediated by a ligation reaction, where in some instances linker domains and a linker oligonucleotide are employed to enhance ligation results. Where ligation occurs at the same time as primer extension, primer extension conditions as described may be employed, where reagents necessary for ligase activity, e.g. NAD, ATP, etc., are included. Alternatively, ligation may be carried out in a step separate from primer extension.

Where desired, the primer extension reaction conditions may include one or more temperature cycling steps. For example, in some instances, the primer extension product composition is produced by a method that includes first contacting the target nucleic acid template composition with a first primer subset that includes for example the forward primers of the set of primer pairs under primer extension reaction conditions to produce a forward primer extension product composition; increasing the temperature to denature the resultant product and template strands and inactivate any additional enzymatic activity (e.g., exonuclease I activity added after extension step to degrade PCR primers) present in the forward primer extension product composition (where the elevated temperature may vary, ranging in some instances from 90 to 100° C., such as 95° C.) and then contacting the resultant denatured forward primer extension product composition with a second primer subset that includes the reverse primers of the set of primer pairs under primer extension reaction conditions to produce the desired primer extension product composition. Where desired, the primer extension products and template nucleic acids may be separated from any free forward primers prior to contact with the set of reverse primers. The extended DNA products after the first and second extension steps may be purified from the excess of the primers using any convenient protocol, including primer digestion with exonucleases (exonuclease I) or purification, such as Magnetic beads or spin columns, etc.

Amplification

As reviewed above, in some instances primer extension products are amplified, where amplicons are produced from the primer extension products. The term "amplicon" is employed in its conventional sense to refer to a piece of DNA that is the product of artificial amplification or replication events, e.g., as produced using various methods including polymerase chain reactions (PCR), ligase chain reactions (LCR), etc. Where primer extension products are amplified, the primer extension products, e.g., as described above, may include additional domains that are employed in subsequent amplification steps to produce a desired amplicon composition. For example, as illustrated in FIGS. 1 to 4, flanking anchor domains are provided in the primer extension products, where the flanking anchor domains include universal priming sites which may be employed in PCR amplification.

As such, embodiments of the methods may include combining a primer extension product composition with universal forward and reverse primers under amplification conditions sufficient to produce a desired product barcoded amplicon composition. The forward and reverse universal primers may be configured to bind to the common forward and reverse anchor domains and thereby nucleic acids present in the primer extension product compositions. The universal forward and reverse primers may vary in length, ranging in some instances from 10 to 75 nt, such as 15 to 60 nt.

In some instances, the universal forward and reverse primers include one or more additional domains, such as but not limited to: an indexing domain, a clustering domain, a Next Generation Sequencing (NGS) adaptor domain (i.e., high-throughput sequencing (HTS) adaptor domain), etc. Alternatively, these domains may be introduced during one or more subsequent steps, such as one or more subsequent amplification reactions, e.g., as described in greater detail below. The amplification reaction mixture will include, in addition to the primer extension product composition and universal forward and reverse primers, other reagents, as desired, such polymerase, dNTPs, buffering agents, etc., e.g., as described above.

Amplification conditions may vary. In some instances, the reaction mixture is subjected to polymerase chain reaction (PCR) conditions. PCR conditions include a plurality of reaction cycles, where each reaction cycle includes: (1) a denaturation step, (2) an annealing step, and (3) a polymerization step. The number of reaction cycles will vary depending on the application being performed, and may be 1 or more, including 2 or more, 3 or more, four or more, and in some instances may be 15 or more, such as 20 or more and including 30 or more, where the number of different cycles will typically range from about 12 to 24. The denaturation step includes heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture may be raised to, and maintained at, a temperature ranging from 85 to 100° C., such as from 90 to 98° C. and including 94 to 98° C. for a period of time ranging from 3 to 120 sec, such as 5 to 30 sec. Following denaturation, the reaction mixture will be subjected to conditions sufficient for primer annealing to template DNA present in the mixture. The temperature to which the reaction mixture is lowered to achieve these conditions may be chosen to provide optimal efficiency and specificity, and in some instances ranges from about 50 to 75° C., such as 60 to 74° C. and including 68 to 72° C. Annealing conditions may be maintained for a sufficient period of time, e.g., ranging from 10 sec to 30 min, such as from 10 sec to 5 min. Following annealing of primer to template DNA or during annealing of primer to template DNA, the reaction mixture may be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture may be raised to or maintained at a temperature ranging from 65 to 75, such as from about 68 to 72° C. and maintained for a period of time ranging from 15 sec to 20 min, such as from 20 sec to 5 min. In some embodiments, the annealing stage could be avoided, and protocol could include only denaturation and polymerization steps as described above. The above cycles of denaturation, annealing and polymerization may be performed using an automated device, typically known as a thermal cycler. Thermal cyclers that may be employed are described in U.S. Pat. Nos. 5,612,473; 5,602,756; 5,538,871; and 5,475,610, the disclosures of which are herein incorporated by reference.

The product amplicon composition of this first amplification reaction will include amplicons corresponding to the gene specific domains that are present in the initial target nucleic acid composition and are bounded by primer pairs present in the employed set of gene specific primers and barcode sequence from one side of the amplicon. In some instances, the number of distinct amplicons of differing sequence in this initial amplicon composition ranges from 10 to 19,000, 10 to 15,000, 10 to 10,000, and 10 to 8,000, such as 25 to 18,500, 25 to 12,000, 25 to 8,000, and 25 to 7,500, including 50 to 15,000, 50 to 10,000 and 50 to 5,000, where in some instances the number of distinct amplicons present in this initial amplicon composition is 25 or more, including 50 or more, such as 100 or more, 250 or more, 500 or more, 1,000 or more, 1,500 or more, 2,500 or more, 5,000 or more, 7,500 or more, 8,500 or more, 10,000 or more, 15,000 or more, 18,000 or more. In some instances, this initial amplicon composition includes sequences found in at least a subset of the genes listed in Table 2, e.g., a subset of 10 to 5,000, such as 20 to 5,000, 50 to 5,000, 100 to 5,000, such as 100 to 5,000, including 100 to 4,000, 100 to 3,000, and 100 to 2,000 of the genes listed in Table 2, or in some instances the amplicon composition includes sequences found in all of the genes listed in Table 2. A subject amplicon composition may include or exclude multiple different product amplicons corresponding to same gene as amplified by two or more different primer pairs directed to the gene. The multiple product amplicons making up the amplicon composition may vary in length, ranging in length in some instances from 50 to 1000, such as 60 to 500, including 70 to 250 nt.

The sample barcoded initial product amplicon composition may be employed in a variety of different applications, including evaluation of the expression profile of the sample from which the template target nucleic acid was obtained. In such instances, the expression profile may be obtained from the amplicon composition using any convenient protocol, such as but not limited to differential gene expression analysis, array-based gene expression analysis, NGS sequencing, etc.

For example, the barcoded amplicon composition may be employed in hybridization assays in which a nucleic acid array that displays "probe" nucleic acids for each of the genes to be assayed/profiled in the profile to be generated is employed. In these assays, the amplicon composition is first prepared from the initial target nucleic acid sample being assayed as described above, where preparation may include labeling of the target nucleic acids with a label, e.g., a member of signal producing system. Following amplicon production, e.g., as described above, the sample is contacted with the array under hybridization conditions, whereby complexes are formed between target nucleic acids that are complementary to probe sequences attached to the array surface. The presence of hybridized complexes is then detected, either qualitatively or quantitatively. The detection and quantification of different barcodes could be achieved in the follow-up hybridization steps with labeled targets complementary to barcode domains of the amplicons. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptome), may be both qualitative and quantitative.

Alternatively, non-array-based methods for quantifying the levels of one or more nucleic acids in a sample may be employed, including quantitative PCR, real-time quantitative PCR, and the like. (For general details concerning real-time PCR see Real-Time PCR: An Essential Guide, K. Edwards et al., eds., Horizon Bioscience, Norwich, U.K. (2004)).

In some embodiments, the method further includes sequencing the multiple barcoded product amplicons, e.g., by using a Next Generation Sequencing (NGS) protocol. In such instances, if not already present, the methods may include modifying the initial amplicon composition to include one or more components employed in a given NGS protocol, e.g., sequencing platform adaptor constructs, indexing domains, clustering domains, etc.

By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the NovaSeq™, NexSeq™, HiSeq™, MiSeq™ and/or Genome Analyzer™ sequencing systems); Thermo Fisher (e.g., Ion Torrent™ (such as the Ion PGM™ and/or Ion Proton™ sequencing systems) and Life Technologies™ (such as a SOLID sequencing system)): Pacific Biosciences (e.g., the PACBIO RS II sequencing system); Roche (e.g., the 454 GS FLX+ and/or GS Junior sequencing systems); Oxford Nanopore technologies (e.g., MinION™, GridION™, PrometION™ sequencing systems) or any other sequencing platform of interest.

In certain aspects, the sequencing platform adapter construct includes a nucleic acid domain selected from: a domain (e.g., a "capture site" or "capture sequence") that specifically binds to a surface-attached sequencing platform oligonucleotide (e.g., the P5/i5 or P7/i7 oligonucleotides attached to the surface of a flow cell in an Illumina® sequencing system); where the construct may include one or more additional domains, such as but not limited to: a sequencing primer binding domain or clustering domain (e.g., a domain to which the Read 1 or Read 2 primers of the Illumina® platform may bind); a indexing domain (e.g., a domain that uniquely identifies the sample source of the nucleic acid being sequenced to enable sample multiplexing by marking every molecule from a given sample with a specific index or "tag"); a barcode sequencing primer binding domain (a domain to which a primer used for sequencing a barcode binds); a unique molecular identification domain (e.g., a molecular index tag, such as a randomized tag of 4, 6, or other number of nucleotides) for uniquely marking molecules of interest to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

The sequencing platform adapter constructs may include nucleic acid domains (e.g., "sequencing adapters") of any length and sequence suitable for the sequencing platform of interest. In certain aspects, the nucleic acid domains are from 4 to 200 nucleotides in length. For example, the nucleic acid domains may be from 4 to 100 nucleotides in length, such as from 6 to 75, from 8 to 50, or from 10 to 40 nucleotides in length. According to certain embodiments, the sequencing platform adapter construct includes a nucleic acid domain that is from 2 to 8 nucleotides in length, such as from 9 to 15, from 16-22, from 23-29, or from 30-36 nucleotides in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGACCACCGA-3') (SEQ ID NO:03), P7 (5'-CAAGCAGAAGACGGCATACGAGAT-3')(SEQ ID NO:04), Read 1 primer (5'-ACACTCTTTCCCTACACGACGCTCTTCCGATCT-3') (SEQ ID NO:05) and Read 2 primer (5'-GTGACTGGAGTTCAGACGTGTGCTCTTCCGATCT-3') (SEQ ID NO:06) domains employed on the Illumina®-based sequencing platforms. Other example nucleic acid domains include the A adapter (5'-CCATCTCATCCCTGCGTGTCTCCGACTCAG-3')(SEQ ID NO:07) and P1 adapter (5'-CCTCTCTATGGGCAGTCGGTGAT-3')(SEQ ID NO:08) domains employed on the Ion Torrent™-based sequencing platforms.

The nucleotide sequences of nucleic acid domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the template switch oligonucleotide (and optionally, a first strand synthesis primer, amplification primers, and/or the like) may be designed to include all or a portion of one or more nucleic acid domains in a configuration that enables sequencing the nucleic acid insert (corresponding to the template nucleic acid) on the platform of interest.

The sequencing adaptors may be added to the amplicons of the initial amplicon composition using any convenient protocol, where suitable protocols that may be employed include, but are not limited to: amplification protocols, ligation protocols, etc. In some instances, amplification protocols are employed. In such instances, the initial amplicon composition may be combined with forward and reverse sequencing adaptor primers that include one or more sequencing adaptor domains, e.g., as described above, as well as domains that bind to universal primer sites found in all of the amplicons in the composition, e.g., the forward and reverse anchor domains, such as described above. As reviewed above, amplification conditions may include the addition of forward and reverse sequencing adaptor primers configured to bind to the common forward and reverse anchor domains and thereby amplify all or a desired portion of the product nucleic acid, dNTPs, and a polymerase suitable for effecting the amplification (e.g., a thermostable polymerase for polymerase chain reaction), where examples of such conditions are further described above. The forward and reverse sequencing adaptor primers employed in these embodiments may vary in length, ranging in length in some instances from 20 to 60 nt, such as 25 to 50 nt. Addition of NGS sequencing adaptors results in the production of a composition which is configured for sequencing by an NGS sequencing protocol, i.e., an NGS library.

In certain aspects, the methods of the present disclosure further include subjecting the NGS library to NGS protocol, e.g., as described above. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS system employed. Protocols for performing next generation sequencing, including methods of processing the sequencing data, e.g., to count and tally sequences and assemble transcriptome data therefrom, are further described in published United States Patent Application 20150344938, the disclosure of which is herein incorporated by reference.

Pooling

Where desired, a given workflow may include a pooling step where a product composition, e.g., made up of synthesized first strand cDNAs or synthesized double stranded cDNAs, is combined or pooled with product compositions obtained from one or more additional samples, e.g., cells. The number of different product compositions produced from different samples, e.g., cells, that are combined or pooled in such embodiments may vary, where the number ranges in some instances from 2 to 50,000, such as 3 to 25,000, including 4 to 20,000 such as 5 to 10,000, where in some instances the number ranges from 100 to 10,000, such as 1,000 to 5,000. Prior to or after pooling, the product composition(s) can be amplified, e.g., by polymerase chain reaction (PCR), such as described above.

Template Switch

In some embodiments, the primer reaction extension conditions using RNA template could incorporate a template switching oligonucleotide, e.g., with optional sample-specific barcode domain and anchor domain. Template switch is described in U.S. Pat. Nos. 5,962,271 and 5,962,272, as well as Published PCT application Publication No. WO2015/027135; the disclosures of which are herein incorporated by reference. Under the primer extension conditions, the template switching oligonucleotide could be employed by reverse transcriptase as a second template in the primer extension reaction. As a result of this extension reaction, the sample-specific barcode sequences of the template switch oligonucleotide will be incorporated to the 3'-end of the synthesized cDNA. In another embodiment, in addition to template switching oligonucleotide the extension reaction could also include a set of gene-specific oligonucleotides complementary to the target regions of RNA templates. This set of gene-specific oligonucleotides is designed as complementary sequences to the gene-specific portion of forward gene-specific primers and with the sequences or modification at the 3'-end which block extension of these oligonucleotides by reverse transcriptase. Under this disclosed condition, the RNase H activity of reverse transcriptase (or RNAse H enzyme which could be added externally), will degrade the RNA target region complementary to the gene-specific oligonucleotide, thus generating target RNA template truncated at the sites selected for design of forward gene-specific primers. Using of target RNA templates specifically truncated at the sites of forward gene-specific primers will allow to add at this site the sample-specific barcode encoded by template switching oligonucleotide by extension of reverse gene-specific primers with reverse transcriptase. Therefore, the extension reaction composition comprising target RNAs, barcoded template switching oligonucleotides, oligonucleotides complementary to gene-specific portion of forward gene-specific primers and reverse gene-specific primers allow to specifically extend and barcode the target amplicon regions in a single reaction step catalyzed by reverse transcriptase.

Utility

The subject methods find use in a variety of applications, including expression profiling or transcriptome determination applications, where a sample is evaluated to obtain an expression profile of the sample. By "expression profile" is meant the expression level of a gene of interest in a sample, which may be a single cell or a combination of multiple cells (e.g., as determined by quantitating the level of an RNA or protein encoded by the gene of interest), or a set of expression levels of a plurality (e.g., 2 or more) of genes of interest. In certain aspects, the expression profile includes expression level data for 1, 2 or more, 5 or more, 10 or more, 20 or more, 50 or more, 100 or more, 200 or more, 300 or more, 400 or more, 500 or more, 1,000 or more, 5,000 or more, 10,000 or more, 15,000 or more, e.g., 18,000 or more genes of interest. According to one embodiment, the expression profile includes expression level data of from 50 to 8000 genes of interest, e.g., from 1000 to 5000 genes of interest. In some embodiments, the expression profile includes expression level data of from 50 to 19,000 genes of interest, e.g., from 1000 to 18,000 genes of interest. In certain aspects, the methods may be employed detecting and/or quantitating the expression of all or substantially all of the cancer associated genes transcribed in a target cell. In a preferred embodiment, the methods are described for profiling all known cell and tissue marker genes, as listed in Table 2. In certain aspects, the methods may be employed detecting and/or quantitating the expression of all or substantially all of the genes transcribed by an organism, e.g., a mammal, such as a human or mouse, in a target cell. The terms "expression" and "gene expression" include transcription and/or translation of nucleic acid material. For example, gene expression profiling may include detecting and/or quantitating one or more of any RNA species transcribed from the genomic DNA of the target cell, including pre-mRNAs, mRNAs, non-coding RNAs, microRNAs, small RNAs, regulatory RNAs, and any combination thereof.

Expression levels of an expressed sequence are optionally normalized by reference or comparison to the expression level(s) of one or more control expressed genes, including but not limited to, ACTB, GAPDH, HPRT-1, RPL25, RPS30, and combinations thereof. These "normalization genes" have expression levels that are relatively constant among target cells in the cellular sample.

In some instances, quantitative analysis of gene expression using set of calibration control template composition is performed. Internal calibration control templates which mimic but differ from natural target RNAs and spiked into cell or cell lysates at specific amount may be effectively used for truly quantitative expression analysis. The calibration control RNAs could be developed for the set of genes (e.g. cell marker genes) or for genome-wide set of transcripts. In order to address the reproducibility of the profiling assay for multiple biological samples (e.g. thousands of single cells), embodiments of the invention uniquely employ the strategy of using barcoded reverse gene specific primers. Target template RNAs (e.g., present in cell extracts) hybridized with barcoded reverse gene specific primers could be combined for the all follow-up steps. The strategy of barcoding and combining target RNAs at early (hybridization) stage allows for significantly reduced cost of the assay, eliminates sample-to-sample profiling variability due to differences in experimental assay conditions, etc. The developed protocol which addresses sample-to-sample and batch effect variability has significant utility in biomarker discovery in clinical samples (e.g., whole blood).

According to certain embodiments, the expression profile includes "binary" or "qualitative" information regarding the expression of each gene of interest in a target cell. That is, in such embodiments, for each gene of interest, the expression profile only includes information that the gene is expressed or not expressed (e.g., above an established threshold level) in the sample being analyzed, e.g., tissue, cell, etc. In other embodiments, the expression profile includes quantitative information regarding the level of expression (e.g., based on rate of transcription, rate of splicing and/or RNA abundance) of one or more genes of interest. A qualitative and/or quantitative expression profile from the sample may be compared to, e.g., a comparable expression profile generated from other samples and/or one or more reference profiles from cells known to have a particular biological phenotype or condition (e.g., a disease condition, such as a tumor cell; or treatment condition, such as a cell treated with an agent, e.g., a drug). When the profiles being compared are quantitative expression profiles, the comparison may include determining a fold-difference between one or more genes in the expression profile of a target cell and the corresponding genes in the expression profile(s) of one or more different target cells in the cellular sample, or the corresponding genes in a reference cell or cellular sample. Alternatively, or additionally, the expression profile may include information regarding the relative expression levels of different genes in a single target cell. In certain aspects, the fold difference in intercellular expression levels or intracellular expression levels can be determined to be 0.1 or more, 0.5 fold or more, 1 fold or more, 1.5 fold or more, 2 fold or more, 2.5 fold or more, 3 fold or more, 4 fold or more, 5 fold or more, 6 fold or more, 7 fold or more, 8 fold or more, 9 fold or more, or more than 10 fold or more, for example.

In some instances, the methods may be employed to determine the transcriptome of a sample. The term “transcriptome” is employed in its conventional sense to refer to the set of all messenger RNA molecules in one cell or a population of cells. In some instances, a transcriptome includes the amount or concentration of each RNA molecule in addition to the molecular identities. The methods described herein may be employed in detecting and/or quantitating the expression of all genes or substantially all genes of the transcriptome of an organism, e.g., a mammalian organism, such as a human or a mouse, for a particular target cell or a population of cells.

Expression profiles obtained using methods of the invention may be employed in a variety of applications. For example, an expression profile may be indicative of the biological condition of the sample or host from which the sample is obtained, including but not limited to a disease condition (e.g., a cancerous condition, metastatic potential, an epithelial mesenchymal transition (EMT) characteristic, and/or any other disease condition of interest), the condition of the cell in response to treatment with any physical action (e.g., heat shock, hypoxia, normoxia, hydrodynamic stress, radiation, and/or the like), the condition of the cell in response to treatment with chemical compounds (e.g., drugs, cytotoxic agents, nutrients, salts, and/or the like) or biological extracts or entities (e.g., viruses, bacteria, other cell types, growth factors, biologics, and/or the like), and/or any other biological condition of interest (e.g. immune response, senescence, inflammation, motility, and/or the like).

Embodiments of the invention find further application in tumor microenvironment analysis applications. Transcriptome data obtained, e.g., as described above, may be employed to determine the cellular constitution of a tumor sample, e.g., to provide an evaluation of the types of cells present in a tumor sample, such as infiltrating hematopoietic cells, tumor cells and bulk tissue cells. For example, transcriptome data may be employed to assess whether a tumor sample does not include infiltrating immune cells, including those of the adaptive and/or innate immune system, such as but not limited to: T, B, natural killer, monocyte, granulocytes, neutrophils, basophils, platelets, and their myeloid and lymphoid progenitor cells, hematopoietic stem cells, and the like. Such information may be used, e.g., in therapy determination applications, for example where the presence of infiltrating immune cells indicates that a patient will be responsive to immunotherapy while the absence of infiltrating immune cells indicates that a patient will not be responsive to immunotherapy. As such, aspects of the invention include methods of therapy determination, where a patient tumor sample is evaluated to assess the tumor microenvironment. Aspects of the invention may further include making a determination to employ an immunotherapy protocol is made if the tumor microenvironment includes infiltrating tumor cells and a determination is made to employ a non-immunotherapy treatment regimen if the tumor microenvironment lacks infiltrating immune cells.

Methods as described here also find use in large-scale profiling of single-cell phenotypes derived from model system (e.g., cultivated cells, organoid cultures, 3D cultures, etc.), model organisms (e.g., mice, rat, monkey, etc.) and clinical samples derived from normal or pathological conditions (e.g., blood, biopsy, sputum, saliva, etc.). Currently, there is a substantial need for comprehensive characterization of different cell types present in normal and pathological conditions. The disclosed methods and compositions provide an improved technological platform for large-scale discovery of key cellular markers for developing novel diagnostic and prognostic tools.

Transcriptome data, e.g., produced as described above, also finds use in other non-clinical applications, such as predictive and prognostic biomarker discovery applications, evaluation of cancer immunoediting mechanism applications, drug target discovery, and the like.

Compositions

Aspects of the invention further include various compositions. Compositions of the invention may include, e.g., one or more of any of the reaction mixture components described above with respect to the subject methods, where the reaction mixtures may be present in a nucleic acid amplification device, such as in a container of such a device. For example, the compositions may include one or more of a target nucleic acid template (e.g., genomic DNA sample, cDNA sample, RNA sample, etc.), individual cells or group of cells, a polymerase (e.g., a thermostable polymerase), ligase, a set of gene specific primers, barcoded oligonucleotides (e.g., donor nucleic acids), primers for cDNA synthesis, dNTPs, NAD, ATP, a salt, a metal cofactor, one or more nuclease inhibitors (e.g., an RNase inhibitor), one or more enzyme-stabilizing components (e.g., DTT), or any other desired reaction mixture component(s). Composition may vary for the different steps of the disclosed methods. For example, for cDNA synthesis steps the compositions may include only reagents necessary for reverse transcription and for the subsequent ligation step the composition may employ a different buffer, oligonucleotides and enzymes (DNA ligase) components. Some components of composition (e.g., barcoded oligonucleotides), may be immobilized on a solid surface (e.g., plate wall, beads, etc.). Also provided are compositions that include a primer extension product composition, and barcoded primer extension product composition, e.g., as described above. Also provided are barcoded amplicon compositions and NGS libraries, such as described above.

In certain embodiments disclosed in the application, the different compositions are physically separated from each other, e.g., they are present or deposited in different wells or plate or in microdroplets. For example, compositions comprising a plurality of single barcoded oligonucleotides immobilized on bead and single cell sample could be present in each microdroplet. In other embodiments, the plurality of barcoded compositions (e.g., hybridization complexes between target RNAs and barcoded reverse gene specific primers or barcoded primer extension product compositions) are mixed together and used as a mix of different compositions in all follow-up steps. In such instances, the different compositions may include the common components necessary to perform hybridization, enzymatic modification, e.g., primer extension, purification, etc. steps and unique components which are specific for each biological sample, e.g., individual cells, purified nucleic acid from each sample, and sample-specific barcoded oligonucleotide, as described in a more details above.

The subject compositions may be present in any suitable environment. According to one embodiment, the compositions are present in reaction tubes (e.g., a 0.2 mL tube, a 0.5 mL tube, a 1.5 mL tube, or the like) or a well. In certain aspects, the compositions are present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular hybridization or enzymatic reaction to occur. According to certain embodiments, the composition is present in a thin-walled polypropylene tube, or a plate having thin-walled polypropylene wells. Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

In another embodiment, the different compositions are present or delivered to microwells of microplates with well sizes dimensioned to accommodate individual cells, where the dimensions may be configured to accommodate on average no more than 2 cells, such as no more than 1 cell. Examples of such wells are those found in the plates of the Rhapsody instrument (Becton, Dickinson and Company), the ICELL8 instrument (Takara Bio USA), etc. where such instruments employ plates having approximately 10,000 wells and a deposition protocol for individual cells and single beads.

In another embodiment, the different compositions are present in microdroplets. For example, emulsion PCR may be employed. For emulsion PCR, an emulsion PCR reaction (e.g., in a droplet, droplet microreactor) is created with a "water in oil" mix to generate thousands or millions of micron-sized aqueous compartments. Sources of nucleic acids (e.g., cells, nucleic acid libraries, optionally coupled to solid supports. e.g., beads) are mixed in a limiting dilution prior to emulsification or directly into the emulsion mix. The combination of compartment size and limiting dilution of the nucleic acid sources is used to generate compartments containing, on average, just one source of nucleic acid (e.g., cell, or sample nucleic acid(s), such as cellular nucleic acid—e.g., RNA combined with a solid support, such that the nucleic acids may be stably associated with the solid support (e.g., bead) etc.). Depending on the size of the aqueous compartments generated during the emulsification step, up to 3×109 individual amplification reactions per μl can be conducted simultaneously in the same container, e.g., tube, well, or other suitable container. The average size of a compartment in an emulsion ranges from sub-micron in diameter to over 100 microns, depending on the emulsification conditions. Protocols that may be employed include those that allow one to deliver individual cells with unique barcoded beads and reagents necessary for reverse transcription step into separate microdroplets. Such microdroplet technologies include the Chromium instrument (10× Genomics), the ddSeq instrument (Bio-Rad), etc. Microdroplets that include compositions as described above may also be generated and delivered to separate compartments or to oil (to form water-oil droplets) using conventional technologies, e.g., FACS, ink-jet deposition, etc.

Kits

Aspects of the present disclosure also include kits. The kits may include, e.g., one or more of any of the reaction mixture components described above with respect to the subject methods. For example, the kits may include one or more of: a set of gene specific primers, barcoded oligonucleotides (e.g., donor nucleic acids, e.g., immobilized on the beads), a polymerase (e.g., a thermostable polymerase, a reverse transcriptase, or the like), ligase (e.g. DNA ligase), dNTPs, a salt, a metal cofactor, NAD, ATP, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s), such as solid supports. e.g., tubes, beads, microfluidic chips, etc.

Components of the kits may be present in separate containers, or multiple components may be present in a single container. For example, the individual barcoded oligonucleotides could be provided pre-aliquoted in separate wells or attached/encapsulated with different beads, and mixture of all beads is provided as kit components. In certain embodiments, it may be convenient to provide the components in a lyophilized form, so that they are ready to use and can be stored conveniently at room temperature.

In addition to the above-mentioned components, a subject kit may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

I. Barcoding Via Reverse Gene Specific Primer Extension

The objective of this experiment is to demonstrate performance of expression profiling in sorted cells or cell mixes using a set of gene specific primers pairs, i.e., the 1.3K Cell-Tissue Marker primer set (1.3K hCTM) as detailed Table 2 using the protocol illustrated in FIG. 1.

A. Hybridization of Gene-Specific Primers and Sample-Barcoded Donor Nucleic Acid to mRNA Sample Individual cells are isolated using a microfluidic cartridge or sorting technology. Each of the individual cells (or cell samples) are mixed with TLC lysis buffer (Qiagen)(e.g. 5-μl for single cell), RevGSP-L1 primers (1.3K human Cell Marker primer set, Table 2) and a set of T30-Anc2-BC-UMI-L2 donor nucleic acids immobilized on beads (ChemGenes) (where each set of donor nucleic acids for each cell varies only by the UMI domain and each cell contacted with its own unique set of donor nucleic acids that differs from any other set used with the any other cell by the BC domain). The donor nucleic acids and RevGSP-L1 Primers are hybridized to the cellular RNA at 50° C. for 30 min. The structures of the donor nucleic acid and RevGSP primers employed in this step are provided below:

```
RevGSP-L1 Primer:
                                                 (SEQ ID NO: 09)
                L1 domain
3'<RevGSP-AGCACCGACCAGCACCp-5'

T30-Anc2-UMI-BC-L2:
                                                 (SEQ ID NO: 10)
                  L2 domain             Anchor 2 domain
3'GCCAGCACGCCACCA-(UMI-BC)AGACACGACCAGCCACGA(INVT30)-Bead
```

An example of a T30-Anc2-UMI-BC-L2 donor nucleic acid showing an exemplary UMI8 domain (unique molecular identifier of 8 residues in length) and a BC14 domain (sample barcode of 14 residues in length) is provided below:

```
                                                                         (SEQ ID NO: 11)
  T30VN                                   Anc2      UMI8       BC14            L2
TTTTTTTTTTTTTTTTTTTTTTTTTTTTTTVNAGCACCGACCAGCAVVNVVNVVGCCCAGGAAGAACGAACCACCGCACGACCG
```

Beads with immobilized mRNA, dT30-Anc2-BC-UMI and RevGSP-L2 primers produced from different cells/samples are then pooled together and washed with TCW buffer (Qiagen).

B. Ligation of Gene Specific Primers to Donor Nucleic Acids

The double-stranded complexes formed between polyA+ mRNA, T30-Anc2-UMI-BC-L2 donor nucleic acid and RevGSP-L1 Primer as shown in FIG. 1 are then contacted under hybridization conditions with a complementary ligation linker oligonucleotide (L1-L2) having the following sequence:

```
                                   (SEQ ID NO: 12)
A-TCGTGGCTGGTCGTGG--CGGTCGTGCGGTGGT-3'dT
                 L1-L2
```

Specifically, beads with immobilized complex between polyA+ mRNA and T30-Anc2-UMI-BC-L2 and Rev-GSP-L1 as described above are mixed with 10-μl of Multiplex Reverse Transcription master mix (DriverMap kit, Cellecta, Inc. Mountain View, CA), where the mix includes the L1-L2 ligation linker (20 nM), Ampligase (Epicentre, 1/250 dilution) and NAD (1 mM) as well as all reagents required for reverse transcription. The resultant reaction mixture is incubated at 50° C. for 30 min. The beads are treated with 1-μl of ExoI (20 units/μl, New England Biolabs) at 37° C., 30 min, and washed with TCW buffer.

As a result, the L1 and L2 domains of the RT and RevGSP primers are brought together as shown in FIG. 1 and also illustrated in the following structure:

```
                                                                   (SEQ ID NOs: 12, 13 and 14)
3'             L1         5' 3'    L2                                T30-Anc2-BC-UMI       5'
<RevGSP-AGCACCGACCAGCACCp GCCAGCACGCCACCA-(BC14-UMI8)-AGACACGACCAGCCACGA(NVT30)-Bead
      A-TCGTGGCTGGTCGTGG--CGGTCGTGCGGTGGT-3'dT <Anc2
                       L1-L2
```

The Ampligase catalyzes ligation between the L1 and L2 domains resulting in the BC14, UMI8 and Anc2 domains being transferred to the reverse gene specific primer, such that the reverse gene specific primer is labeled with BC14-UMI8-Anc2 domains necessary for barcoding and amplification of gene specific extension products as described in the following steps. First strand cDNA is also synthesized in this step, as illustrated in FIG. 1.

C. Forward (FWD) GSP Extension-Second Strand cDNA Production

Resultant barcoded first strand cDNA products immobilized on beads produced in Step B, above, are subjected to a second round of extension to produce second strand cDNA. For this step, Anchor 1-Fwd GSP primers (1.3K hCTM primers) are employed, having the structure:

```
                                   (SEQ ID NO: 15)
         Anchor 1
   5' AGCAGCACCGACCAGCAGACA-Fwd GSP-3'
```

In this step, the barcoded cDNA products immobilized on beads produced in Step B, above, are combined with 10-μl of Extension master mix (DriverMap kit, Cellecta, Inc., Mountain View, CA) that includes 1 nM of each Anchor 1-Fwd GSP primer and DNA polymerase at 64° C. for 30 min, followed by treatment with 1-μl of ExoI (20 units/ul, New England Biolabs) at 37° C. for 30 min. The beads are then washed with TCW buffer.

D. 1st PCR

Anchored DNA fragments produced in Step C are amplified in 50-μl of Multiplex DNA polymerase reaction mix (DriverMap kit) with universal anchor PCR primers (Fwd-Anc1 and Rev-Anc2) as shown below for 14-20 cycles.

```
PCR primers for 1st PCR Step:
Fwd-Anc1
                                   (SEQ ID NO: 16)
AGCAGCACCGACCAGCAGACA

Rev-Anc2
                                   (SEQ ID NO: 17)
ACGAGCACCGACCAGCACAGA
```

This first round of PCR results in production of sample-barcoded anchor-domain-flanked double-stranded gene specific DNA fragments having the following structure:

```
                                                                                  (SEQ ID NOS: 18 and 19)
       Anc1         Fwd                L2             L1
AGCAGCACCGACCAGCAGACA-GSP>sDNA--GSP-ACCACCGCACGACCGCCACGACCAGCCACGA-(BC14-UMI8)-TCTGTGCTGGTCGGTGCTCGT
TCGTCGTGGCTGGTCGTCTGT-GSP>asDNA-GSP-TGGTGGCGTGCTGGCGGTGCTGGTCGGTGCT-(BC14-UMI8)-AGACACGACCAGCCACGAGCA
                                Rev                                                  Anc2
```

The resultant adaptor containing sample-barcoded anchor-domain-flanked double-stranded gene specific DNA fragments are analyzed by gel (if necessary, combined at equal amount based on the smear analysis (180-400 bp range) for several samples), and purified using 1.8V of AMPpure magnetic beads (Beckman Coulter). The purified cDNA products are quantitated by Qubit fluorescence measurement, and diluted to 10 nM (2 ng/μl) for next-generation sequencing using NextSeq500 Illumina platform.

II. Variations of Example 1 Protocol

A. In a variation of the protocol described in Example I, only RevGSP-L1 primers are hybridized with polyA+ mRNA in solution following which the resultant hybridization complexes are purified. The purified hybridization complexes are then combined T30-Anc2-UMI-BC-L2 donor nucleic acids or a variant thereof lacking the T30 domain in the presence of the L1-L2 ligation linker under ligation conditions to join the BC-UMI domains to the RevGSP-L1 primers.

B. In a second variation of the protocol described in Example I, RevGSP-L1 primers are hybridized with polyA+ mRNA in conjunction with oligo dT immobilized on beads or test tubes following which the resultant hybridization complexes are purified. The purified hybridization complexes are then combined Anc2-UMI-BC-L2 in the presence of the L1-L2 ligation linker under ligation conditions to join the BC-UMI domains to the RevGSP-L1 primers.

E. $2_{nd}$ PCR

2-μl aliquot of the 1st PCR amplicon product produced in Step D, above, is added to multiplex DNA polymerase reaction mix (50-μl) and amplified using P7-Anc1 and P5-Anc2 PCR primers with different indexes, as shown below:

```
2nd PCR amplification primers:
P7-Anc1
                                          (SEQ ID NO: 20)
          P7                    Anc1
AGCAGAAGACGGCATACGAGATAGCAGCACCGACCAGCAGACA

P5-Anc2
                                          (SEQ ID NO: 21)
          P5                     Anc2
ACGGCGACCACCGAGATCTACAC ACGAGCACCGACCAGCACAGA
```

The reaction mixture is amplified for 7 cycles, treated with ExoI (0.5 μl) at 37° C. for 30 min. The resultant adaptor containing sample-barcoded anchor-domain-flanked double-stranded gene specific DNA fragments have the following structure:

```
                                                         (SEQ ID NOs: 22 and 23)
       Anc1         Fwd                L2             L1
P7-AGCAGCACCGACCAGCAGACA-GSP>sDNA--GSP-ACCACCGCACGACCGCCACGACCAGCCACGA-(BC14-UMI8)-
TCTGTGCTGGTCGGTGCTCGT-P5
P7-TCGTCGTGGCTGGTCGTCTGT-GSP>asDNA-GSP-TGGTGGCGTGCTGGCGGTGCTGGTCGGTGCT-(BC14-UMI8)-

                                      Rev
AGACACGACCAGCCACGAGCA-P5
     Anc2
```

III. Barcoding Via Circular Intermediate

A. First Strand cDNA Synthesis.

50 ng of total RNA (human Brain RNA, Thermo-Fisher) is mixed with a set of T25-Anc1-UMI-BC-L2 donor nucleic acids that differ from each other with respect to the UMI domain at a 1 μM final concentration. Each of the T25-Anc1-UMI-BC-L2 donor nucleic acids is an oligo dT primer configured for cDNA synthesis, where the primers include a sample specific barcode domain (BC14), universal molecular index domain (UMI8), a ligation linker domain (L2), anchor domain (Anc1) and template binding domain (oligo dT25VN). The T25-Anc1-UMI-BC-L2 donor nucleic acids have the following structure:

```
                                        (SEQ ID NO: 24)
L2             BC14          UMI8       Anc1          dT25VN
CGGTCGTGCGGTGGTTCGGCTTCCTGGGCBBNBBNBBTGTCTGCTGGTCGGTGCTTTTTTTTTTTTTTTTTTTTTTTTTVN
```

The resultant reaction mixture is treated at 72° C. for 2 min, cooled to 4° C. and reverse transcribed in 1×RT reaction buffer using Maxima reverse transcriptase (Thermo-Fisher) at 50° C. for 30 min in 10-μl reaction mix (Thermo-Fisher), following which RT is inactivated at 95° C. for 5 min. The resultant first strand cDNA product composition is combined with a second first strand cDNA product composition prepared from 50 ng human universal RNA (Agilent Technologies) from a second set of T25-Anc1-UMI-BC-L2 RT primers having a BC domain different from that used with the human Brain RNA. The resultant pooled samples are purified using RNA/DNA micro isolation kit (Qiagen) using manufacturer protocol and eluted in 14-μl of water.

B. Forward Gene-Specific Primer Extension Second Strand cDNA Synthesis and Ligation Step.

14 μl of the first strand cDNA composition produced as described in Step A, above, is mixed with 11 μl of Multiplex DNA polymerase master reaction mix (DriverMap kit, Cellecta) that includes the pool of L-1 Forward 1.3K CTM GSP primers (Table 2) (final concentration 1 nM of each primer). The L-1 Forward gene specific primers (L-1 Fwd GSPs) have the following structure:

```
L1-Fwd GSP
                             (SEQ ID NO: 25)
  L1
CCACGACCAGCCACGA-FWd GSP
```

Hybridized L1-Fwd GSPs are extended for 1 cycle at 64° C. extension temperature (30 min), treated with 1-μl of ExoI (New England BioLabs) for 30 min at 37° C., and 95° C. for 5 min.

The resultant forward gene specific primer extension product composition (i.e., second strand cDNA composition) is then mixed with DNA ligation master mix (5-μl) that includes DNA polymerase master mix with L1-L2 ligation linker oligonucleoptide (20 nM) complementary to the both ends of the forward primer driven second strand cDNA and 1×buffer with AmpliTaq DNA ligase (10 units, Epicentre), 1 mM NAD (Sigma). The L1-L2 ligation linker has the following structure:

```
                                       (SEQ ID NO: 26)
ATCGTGGCTGGTCGTGGCGGTCGTGCGGTGGTA/3InvdT/
```

Combination of the forward gene specific primer extension product (second strand cDNA) composition with the L1-L2 linker results in production of a circular nucleic acid loop intermediate made up of the second strand cDNA whose ends are held together by the L1-L2 linker, as illustrated below:

The resultant reaction mixture is ligated for 5 cycles: (95° C. for 20 sec, 65° C. for 1 min). Ligated circle products are purified by AMPpure beads (1.8×volume, Beckman Coulter) according to manufacturer's protocol. In the course of ligation of the above circular intermediate by DNA ligase (between L1 and L2 linker domains), the universal primer binding domain (Anc1), unique molecular index domain (UMI8) and sample barcode domain (BC14) are transferred to the forward gene specific domain in the final single-stranded circular structure, as illustrated in FIG. 2.

C. Reverse Gene Specific Primer Extension Step

The ligated second strand circular cDNA composition produced is Step B, above, is then subjected to a reverse gene specific primer (RevGSP) round of extension with 5-μl of DNA polymerase master mix that includes 1.3K CTM reverse gene specific primers which include a second anchor domain, i.e., Anc2. The Anc2-Rev GSPs have the following structure:

```
Anc2-Rev GSP
                                   (SEQ ID NO: 29)
      Anc2
ACGAGCACCGACCAGCACAGA-Rev GSP
```

For this step, the same conditions as employed for the first forward gene-specific primer extension step are used, and the resultant product is treated with 1-μl of ExoI at 37° C. for 30 min, and 95° C. for 5 min.

D. First PCR

Anchored cDNA fragments produced in Step C, above, are then amplified in 100-μl of Multiplex DNA polymerase reaction mix (DriverMap kit, Cellecta) with universal anchor PCR primers (Anc1 and Anc2) for 16 PCR cycles (98° C. for 10 sec, 72° C. for 20 sec). The universal anchor PCR primers have the following structures:

```
Anc1
                              (SEQ ID NO: 30)
AGCAGCACCGACCAGCAGACA

Anc2
                              (SEQ ID NO: 31)
ACGAGCACCGACCAGCACAGA
```

This first PCR results in the production of sample-barcoded anchor-domain-flanked double-stranded gene specific deoxyribonucleic acid (DNA) fragments having the structure:

```
Amplicon Structure after 1st PCR step.
                                (SEQ ID NOs: 32 and 33)
             Anc1>                            L2-L1
AGCAGCACCGACCAGCAGACA-(UMI8-BC14)-ACCACCGCACGACCGC

             Fwd
CACGACCAGCCACGA-GSP>SDNA--GSP-TCTGTGCTGGTCGGTGCTCG

T
```

```
                                                  (SEQ ID NOs: 26, 27 and 28)
             Anc1                          L2      3' 5'    L1        Fwd
Loop-sDNA-A25--AGCACCGACCAGCAGACA-(UMI8-BC14)-ACCACCGCACGACCG pCCACGACCAGCCACGA-GSP>sDNA-Loop
                                        3'dT-TGGTGGCGTGCTGGC--GGTGCTGGTCGGTGCT-A
                                                     L1-L2linker
```

-continued

```
TCGTCGTGGCTGGTCGTCTGT-(UMI8-BC14)-TGGTGGCGTGCTGGCG
                                 MB-Ind

GTGCTGGTCGGTGCT-GSP>ASDNA-GSP-AGACACGACCAGCCACGAGC
                                     Rev        <Anc2

A
```

E. Second PCR

A 5-μl aliquot of the first PCR product produced as described in Step D, above, is combined with Multiplex DNA polymerase reaction mix (100-μl) and amplified using forward and reverse PCR primers (P7-Anc and P5-Anc2) for 8 cycles. The forward and reverse PCR primers (P7-Anc1 and P5-Anc2) primers have the following structure:

```
P7-Anc1
                                         (SEQ ID NO: 34)
AGCAGAAGACGGCATACGAGATAGCAGCACCGACCAGCAGACA

P5-Anc2
                                         (SEQ ID NO: 35)
ACGGCGACCACCGAGATCTACACACGAGCACCGACCAGCACAGA
```

The resultant amplicon composition is treated with ExoI (1-μl) at 37° C. for 30 min. This first PCR results in the production of sequencing adaptor containing sample-barcoded anchor-domain-flanked double-stranded gene specific deoxyribonucleic acid (DNA) fragments having the structure:

```
Amplicon structure after second PCR step.
                                   (SEQ ID NOs: 36 and 37)
P7                                      Anc1
AGCAGAAGACGGCATACGAGATAGCAGCAGCACCGACCAGCAGACA-

                              L2-L1                    Fwd
(UMI8-BC14)ACCACCGCACGACCGCCACGACCAGCCACGA-GSP>

sDNA-

TCGTCTTCYGCCGTATGCTCTATCGTCGTCGTGGCTGGTCGTCTGT-

(UMI8-BC14)TGGTGGCGTGCTGGCGGTGCTGGTCGGTGCT-GSP>

asDNA

--sDNA-GSP-TCTGTGCTGGYCGGTGCTCGTCGTGTGTAGATCTCG

GTGGTCGCCGT

-asDNA-GSP-AGACACGACCAGCCACGAGCAGCACACATCTAGAGC
         Rev    Anc2

CACCAGCGGCA
        P5
```

The resultant adaptor containing sample-barcoded anchor-domain-flanked double-stranded gene specific deoxyribonucleic acid (DNA) fragments are analyzed by gel and combined at equal amount based on the smear analysis (220-480 bp range) and purified using AMPpure magnetic beads (1.8×volume, Beckman Coulter) according to the manufacturer's protocol.

The purified adaptor containing sample-barcoded anchor-domain-flanked double-stranded gene specific deoxyribonucleic acid (DNA) fragments are quantitated by OD260 measurement, and diluted to 10 nM (2.2 ng/μl) for next-generation sequencing in NextSeq500 Illumina platform using the following program: Read 1: RevSS-SeqDNA>34cycles; Ind 1:RevSS-SeqInd>14cycles; Ind 2: FwdSS-SeqMB>8cycles; Read 2: FwdSS-SeqDNA>34cycles. The sequencing primers have the following structure:

```
FwdSS-SeqDNA
                              (SEQ ID NO: 38)
ACGACCGCCACGACCAGCCACGA

FwdSS-SeqMB
                              (SEQ ID NO: 39)
ACGAGATAGCAGCACCGACCAGCAGACA

RevSS-SeqDNA
                              (SEQ ID NO: 40)
ACTACACACGAGCACCGACCAGCACAGA

RevSS-SeqInd
                              (SEQ ID NO: 41)
TGGTCGTGGCGGTCGTGCGGTGGT
```

IV. Protocol Employing Sample Barcoded Reverse Gene Specific Primer

A. Design of Barcoded Reverse Gene Specific Primers.

```
                              (SEQ ID NO: 42, 43, and 84)
3'            L2       5'3'  L1
 RevGSP-ACCGACCAGCACCp GCCAGCACGCCA-(Barcode)-AGACA

Anchor 2        5'
CGACCAGCCACGAGCA-X-Bead

     A-TGGCTGGTCGTGG--CGGTCGTGCGGT-3'dT
                Link1s
```

Barcoded oligonucleotides with minimum structure linker 5'-Anchor 2-Barcode-Linker L1-3' are ligated to reverse gene specific primer set (RevGSP) with minimum structure 5'-phosphate-Linker L2-RevGSP-3' using complementary to linker L1 and linker L2 oligonucleotide Link1s and DNA ligase under ligation conditions.

The DNA ligation reaction attaches barcoded anchor oligonucleotides to reverse gene specific primers. As a result of the ligation reaction, the set of reverse gene specific primers is labeled with specific barcode. The set of barcoded reverse gene specific primers is purified from non-ligated products and used in the disclosed primer extension assay. The same set of gene specific primers could be labeled with plurality of different barcodes using the same protocol. In another embodiment, the same protocol could be used for barcoding set of forward gene specific primers.

Barcode-Anchor oligonucleotides are attached to the solid surface (e.g. beads) through linker X (e.g. X could be a cleavable linker). Furthermore, the different binding moiety (e.g. antibodies) may be attached to the beads to provide binding of the antibody-bead-barcoded GSP complex to specific cell types through antigen-antibody interactions.

Importantly, each barcode could have a complex structure as described in the application in more detail. These complex composite barcodes could have several domains, including but not limited to:

1) Sample barcode—specific sequence (usually from 8-14 nt) attached to a set of gene-specific primers, to label all extension products derived from target RNA sample.
2) UMI—complex random, semi-random (usually 8-12 nt), or set of unique specific sequences which allow to label each molecule used in disclosed primer extension assay with unique sequence/barcode. UMI could be added to RevGSP-Linker 2 set between RevGSP and linker L2.

3) Bead barcode—specific sequence (10-16 nt) unique for each bead if gene-specific primers are attached to the beads. In some embodiments, e.g. for single cell analysis applications (e.g. if only one biological sample used in the assay) bead barcode could be sample barcode.

4) Antibody barcode—specific sequence unique for each specific antibody immobilized to the beads.

Linker L1, linker L2 and complementary Link1s could be designed with variety of different sequences with minimum length of 4 nt each.

Examples of Anchor2-Barcode-Linker 1 Oligonucleotides Used in Ligation Reaction:

Barcodes are underlined

```
Anc2-BC1-L1
                                    (SEQ ID NO: 44)
ACGAGCACCGACCAGCACAGAGAACAAACACCGCACGACCG

Anc2-BC2-L1
                                    (SEQ ID NO: 45)
ACGAGCACCGACCAGCACAGAGGCGAAACACCGCACGACCG

Anc2-BC3-L1
                                    (SEQ ID NO: 46)
ACGAGCACCGACCAGCACAGAGCAAAAGGACCGCACGACCG
```

Example of Bead-Barcoded Oligonucleotide Conjugates (Synthesized by Chemgenes, Inc.) Used in Ligation Reaction.

In the diagram below: T25—is oligo dT (25 nt) moiety used for binding to the beads and purification of hybridization complexes between target RNA and barcoded reverse gene specific primers; PClinker—photocleavable linker, or SSlinker—bisulfite linker cleaved by sulfite ions (e.g. DTT treatment) used for detachment of reverse barcoded gene specific primers from the beads; Anchor2—binding site for universal amplification primer; UMI—Unique molecular index; Barcode—sample-specific 6 nt barcode (underlined); Linker L2-sequence necessary for ligation of barcodes with gene specific primer set.

```
ChemB-T25-PC1-Anc2-BC-L2
                                              (SEQ ID NO: 48)
                                        Anchor 2   UMI
Bead-linker-T25-PClinker-AGCACCGACCAGCACAGAVVNVVNV

 Barcode Linker L2
VCATCAGACCGCACGACCG-3'

ChemB-T25-SS-Anc2-BC-L2
                                              (SEQ ID NO: 50)
                                        Anchor 2   UMI
Bead-linker-T25-SSlinker-AGCACCGACCAGCACAGAVVNVVNV

 Barcode Linker L2
VCAGCATGACCGCACGACCG-3'
```

Example of Final Barcoded Reverse Gene Specific Primer Structure Employed in the Assay

```
                                    (SEQ ID NO: 51)
3'          L2-L1
RevGSP-ACCGACCAGCACCGCCAGGACGCCA-(Barcode)-

  Anchor2           5'
AGACACGACCAGCCACGAGGA
```

wherein, L2-L1 linker sequence generated by ligation of L1 and L2 linkers, Barcode—complex barcode, as described in a more details above, Anchor2—universal primer binding site. A similar structure could be generated for barcoded forward gene specific primer set and employed in the disclosed assay:

```
                                          (SEQ ID NO: 52)
3'          L2-L1
FwdGSP-ACCGACCAGCACCGCCAGGACGCCA-(Barcode)-ACAG

Anchor1          5'
ACGACCAGCCACGACGA
```

In some embodiments, the barcoded reverse gene specific primer composition could be synthesized by combinatorial (pool and split) chemical synthesis without DNA ligation step. In this embodiment, L2-L1 linker will be missing in the final structure.

B. High-throughput Synthetic Template and Calibration Control Template Oligonucleotide Synthesis Oligonucleotide libraries consisting of complex mixtures of oligonucleotides ranging in length from 150-250 base pairs were manufactured by Agilent Technologies under contract. Oligonucleotide design comprises full-length (or truncated in the middle) sequences of all amplicons flanked by gene specific primers, surrounding amplicon RNA sequences (for amplicons shorter than 200 bp) and two-point mutations downstream (4 nt) from the 3'-end of the each forward and reverse primer. In some embodiments, the oligonucleotides comprise the sequence of T7 promoter upstream of the forward primer binding site in order to generate sense synthetic template RNA that mimic natural target RNAs surrounding amplicon domains. Oligonucleotides were synthesized in spatially distinct locations using standard phosphoramidite chemistry on a silylated 6.625×6 inch wafer using an automated tool designed by Agilent Technologies. The solid support used in synthesis was a flat, non-porous silane coated glass rather than a locally curved, porous surface traditionally used. The coupling steps used inkjet-printing technologies to deliver the appropriate amount of activator and phosphoramidite monomer to specific spatial locations on the solid support under anhydrous conditions. Oxidation and detritylation reactions were performed in dedicated flowcells using novel mechanical operations and fluid management steps to eliminate the depurination side reaction limiting synthesis of long oligonucleotides. After deprotection and release, oligonucleotides were recovered and concentrated by lyophilization in 2 mL tubes. Each Oligo Library yields 10 pmol of nucleic acid material equally divided among up to 55,000 user-defined, unique sequences. In another embodiment, the synthetic templates were synthesized using conventional phosphoramidate chemistry and mixed together at approximately equal concentration by IDT and MWG-Operon companies.

C. Calibration Control RNA Template Synthesis by Gene Assembly

The calibration control genes which mimic natural genes were synthesized by GeneScript Technologies using modified Gibson gene assembly protocol. In one embodiment, the calibration control genes comprising T7 promoter, full-length target mRNA sequences including amplicon domain with at least 1-2 point mutation downstream of primer binding site, and polyA (approximately 50 nt) were synthesized and cloned in the GeneScript vector, and clones were validated by Sanger sequencing. To generate a set of calibration control templates, plasmid DNA clones corresponding to the set of control genes were mixed together (or used separately), digested by NotI restriction enzyme at a site located downstream of polyA site. Furthermore, the linearized plasmids were used as templates for RNA synthesis using T7 RNA polymerase and the manufacturer's protocol (MonsterScript kit, Epicentre Technologies).

D. High-throughput Gene Specific Primer Validation

Multiplex PCR primers with cognate target sequences were screened en masse. In some embodiments, the set of barcoded reverse gene specific primers (with the structure shown above) was first hybridized to control natural or synthetic template RNAs. Furthermore, the hybrids between target mRNA and barcoded reverse gene specific hybrids were combined together, purified and used as mix in the follow-up primer extension and amplification steps. In preferred embodiments, the hybridization step was performed with RNA sample and barcoded reverse gene specific primers in solution (e.g. primers released from beads). As discussed in a more detail above, the selection of primers with high hybridization efficiency and stability of target mRNA-primer complexes is the critical step which defines the overall performance of the assay and cross-talk between different samples. Moreover, using the barcoded reverse primers in the first step of protocol allows all samples to be combined together and therefore allows scale-up of the assay for analysis of hundreds-thousands of samples in single test tube format.

In another embodiment, the natural or synthetic template RNAs are reverse transcribed e.g., from random primer and synthesized cDNAs used as templates for the extension step, using barcoded forward gene specific primers and follow-up amplification steps.

In both protocols, uniformity of amplification, including primer efficiency, primer specificity and dynamic range (minimum 100-fold) were determined from multiplex reaction kinetic data. In order to reliably measure expression of different genes, the panel of 15 different human universal RNA from different commercial sources (Agilent, Clontech, BioChain, Qiagen, etc.) and synthetic template RNA were used as templates for cDNA synthesis. Non-specific primer activities were measured by yield of non-targeted products from human universal RNAs and negative control templates (human genomic DNA and mouse universal RNAs). The protocol for testing primer performance was repeated several times with sets of 3-5 PCR primer pairs per gene until the primers with high specific and low non-specific activity were selected. Finally, functionally validated primers were selected as experimentally validated primers for use in sets of experimental validated gene specific primers.

E. Multiplex RT-PCR Assay

1. Design of Primers for Anchor Addition, First and Second PCR Steps

Design of Barcoded Forward and Barcoded Reverse gene specific primers with anchor1 (Fwd-anchor1-GSP primers) and anchor2 (Rev-anchor2-GSP primers) with 3'-extended suppression portions for primer extension steps and universal PCR primers (F-MP1GAC and R-MP2CAG) to amplify anchored cDNA fragments by PCR.

Sequences that are underlined are the common PCR suppression portions, and those in italics and bold are unique sequences for forward or reverse primers, respectively. GSP is the gene-specific primer domain. The BC-Link is Barcode-Linker domain, which comprises the composite barcode as described in more details above and could be present in only reverse (preferred embodiment), only in forward or in both reverse and forward primers (SEQ ID NOS: 53 to 56).

```
F-MP1GAC
AGCAGCACCGACCAGCAGAC
   AGCACCGACCAGCAGACA(BC-Link)FwdGSP>

    Fwd-Anc1-GSP                      cDNA          Rev-Anc2-GSP
                                         <RevGSP(Link-BC)AGACACGACCAGCCACGA
                                                        GACACGACCAGCCACGAGCA
                                                               R-MP2CAG
```

For simplicity, the structures below show the design of primers and amplification products only for the preferred embodiment of using barcoded reverse and non-barcoded forward gene specific primer set:

```
                                              (SEQ ID NOS: 57 to 60)
          F-MP1GAC
      AGCAGCACCGACCAGCAGAC
         AGCACCGACCAGCAGACA-FwdGSP>

           Fwd-Anc1-GSP           cDNA          Rev-Anc2-GSP
                                     <RevGSP(BC-Link)AGACACGACCAGCCACGA
                                                     GACACGACCAGCCACGAGCA
                                                                 R-MP2CAG
```

The resultant structure of amplified cDNA products after the two sequential primer extension steps using Barcoded Rev-anchor2-GSPs and Fwd-anchor1-GSPs and a first PCR step using universal F-MP1GAC and R-MP2CAG primers is shown below:

```
                                  (SEQ ID NO: 61 and 62)
                                        (60-250 nt)
AGCAGCACCGACCAGCAGACA-FwdGSP-cDNA-RevGSP-Link-BC-

TCTGTGCTGGTCGGTGCTCGT

TCGTCGTGGCTGGTCGTCTGT-FwdGSP-cDNA-RevGSP-Link-BC-

AGACACGACCAGCCACGAGCA
```

The first PCR amplified cDNA products were then subjected to a second round of PCR to add Illumina P7, P5 sequencing adaptors. PCR primers for the second PCR step comprise anchor 1 and anchor 2 binding domains, indexing (highlighted in red) domains (optional domains, can be used if experiment requires to combine the different samples together for NGS step) and P5 or P7 sequences necessary for cluster formation in Illumina NGS instrument, as illustrated below:

Set of Forward Indexing Primers for $2^{nd}$ PCR step:

(SEQ ID NOS: 63-68)

FP7-A1Ind-A
AGCAGAAGACGGCATACGAGATATACGACAGCAGCAGCACCGACCAGCAG
ACA

FP7-A1Ind-B
AGCAGAAGACGGCATACGAGATACTGATGAGCAGCAGCACCGACCAGCAG
ACA

FP7-A1Ind-C
AGCAGAAGACGGCATACGAGATAGCATCAAGCAGCAGCACCGACCAGCAG
ACA

FP7-A1Ind-D
AGCAGAAGACGGCATACGAGATAAGTCGTAGCAGCAGCACCGACCAGCAG
ACA

FP7-A1Ind-E
AGCAGAAGACGGCATACGAGATATCGCATAGCAGCAGCACCGACCAGCAG
ACA

FP7-A1Ind-F
AGCAGAAGACCGCATACGAGATACATAGCAGCAGCAGCACCGACCAGCAG
ACA

Set of Reverse Indexing Primers for $2^{nd}$ PCR step:

(SEQ ID NOS: 69-74)

RP5-A2Ind-A
ACGGCGACCACCGAGATCTACACATACGACACGACGAGCACCGACCAGCA
CAGA

RP5-A2Ind-B
ACGGCGACCACCGAGATCTACACACTGATGACGACGAGCACCGACCAGCA
CAGA

RP5-A2Ind-C
ACGGCGACCACCGAGATCTACACAGCATCAACGACGAGCACCGACCAGCA
CAGA

RP5-A2Ind-D
ACGGCGACCACCGAGATCTACACAAGTCGTACGACGAGCACCGACCAGCA
CAGA

RP5-A2Ind-E
ACGGCGACCACCGAGATCTACACATCGCATACGACGAGCACCGACCAGCA
CAGA

RP5-A2Ind-F
ACGGCGACCACCGAGATCTACACACATAGCACGACGAGCACCGACCAGCA
CAGA

Set of Forward and Reverse Non-indexing Primers for $2^{nd}$ PCR step:

(SEQ ID NOS: 75-76)

Fp7-A1
AGCAGAAGACGGCATACGAGATAGCAGCAGCACCGACCAGCAGACA

RP5-A2
ACGGCGACCACCGAGATCTACACACGACGAGCACCGACCAGCACAGA

After a second PCR step with Forward and Reverse indexing primers the final amplicon structure, flanked with P7 and P5 Illumina's adaptor sequences and ready for NGS, is shown below:

(SEQ ID NOS: 77-78)

P7(Ind)*AGC*AGCACCGACCAGCA*GACA*-FwdGSP-cDNA-RevGSP
(LinkBC)TCTGTGCTGGTCGGTGCTCGT(Ind)P5

P7(Ind)TCGTCGTGGCTGGTCGTCTGT-FwdGSP-cDNA-RevGSP
(LinkBC)AGACACGACCAGCCACGAGCA(Ind)P5

The sequences of primers for NGS sequencing (e.g. Illumina NextSeq500 platform) of cDNA inserts, barcode domain and indexes are provided below:

SeqDRAlink-Rev
(SEQ ID NO: 79)
TGGCGTGCTGGCGGTGCTGGTCGGT

SeqDNA-Fwd
(SEQ ID NO: 80)
AGCAGCAGCACCGACCAGCAGACA

SeqBarcode-Fwd
(SEQ ID NO: 81)
ACCGACCAGCACCGCCAGCACGCCA

Optional sequencing primers:

SeqIND-Fwd
(SEQ ID NO: 82)
TCTGTGCTGGTCGGTGCTCGTCGT

SeqIND-Rev
(SEQ ID NO: 82)
TGTCTGCTGGTCGGTGCTGCTGCT

SeqDNA-Rev
(SEQ ID NO: 83)
ACGACGAGCACCGACCAGCACAGA

An example protocol for NGS sequencing of amplified cDNA products in Next Seq500 machine using 150-nt sequencing kit is shown below:

Read 1: SeqDNAlink-Rev>81 cycles
Ind 1: SeqIND-Rev>6 cycles
Ind 2: SeqBarcode-Fwd>38 cycles
Read 2: SeqDNA-Fwd>35 cycles The read number for SeqBarcode-Fwd primer could depend on the design of the specific barcode domain cassette. The read cycle number 38 was selected for reading complex sample barcode domain with the structure: Antibody barcode(6)-Sample barcode(6)-Bead barcode(14)-UMI(12).

F. Protocol for Multiplex RT-PCR amplification of target genes for expression profiling or mutation analysis starting from total RNA (1 ng-50 ng) mixed with calibration control RNA templates and using barcoded forward gene specific primer set.

Step 1. Total RNAs (mixed with synthetic calibration control RNA templates in a separate wells) was converted to cDNA in 10-μl of reaction mix using random primer (N6, 5 uM), 1×GC buffer, dNTP (500 uM) and Maxima Reverse Transcriptase (10 units, Thermo-Fisher) at $50^{4}$C for 30 min.

Step 2. cDNA was primed (adding universal anchors 1 and barcodes) using a mix of Barcoded Forward-anchor1-GSP primers (5 nM final concentration for each primer) in 20-ul reaction mix comprising 1×GC buffer, dNTP (250 uM) and Phusion II (4 units, Thermo-Fisher) for 1 cycles at (98° C. for 1 min, 64° C. for 30 min).

Step 3. Barcoded cDNA products after first primer extension step were combined together and purified using an equal volume of AMPure magnetic beads (Beckman-Coulter) using manufacturer's protocol. Eluted cDNA (20 ul) was treated with exonuclease I (20 units, New England BioLabs) at 37° C. for 30-min.

Step 4. The Barcoded DNA products generated in step 3, were further extended (add universal anchor 2) using mix of Reverse-ancho2-GSPs in 25-ul reaction mix comprising 1×GC buffer, dNTP (250 uM) and Phusion II (5 units, Thermo-Fisher) for 1 cycles at (98° C. for 1 min, 64° C. for 30 min) and treated with exonuclease I (20 units) at 37° C. for 30-min.

Step 5. 1st PCR step. Whole volume (25-µl) of barcoded anchored cDNA fragments (from Step 4) were amplified in 75-µl reaction mix comprising 1×HF Buffer, dNTP (200 uM), universal PCR primers F-MP1GAC and R-MP2CAG and Phusion II (15 units, Thermo-Fisher) for 8-20 cycles (50 ng-1 ug of starting RNA, respectively) at (98° C. for 10 sec, 72° C. for 20 sec).

Step 6. 2nd PCR step. 5-pi aliquot of 1st PCR was amplified in 100-µl of PCR mix comprising 1×HF Buffer, dNTP (200 µM), indexed (specific for the each of several samples) or non-indexed (only for one sample) forward and reverse PCR primers and Phusion II (20 units, Thermo-Fisher) for 7 cycles at (98° C. for 10 sec, 72° C. for 20 sec).

Step 7. The amplified PCR products were analyzed in 3.5% agarose-1×TAE gel to optimize the cycle number and finally digested with exonuclease I (20 units, New England Biolabs), incubated and 37° C. for 30 min, inactivated at 65° C. for 15 min and purified by Qia PCR column. Purified PCR products were quantitated by Qubit (Thermo-Fisher) and if necessary different samples were mixed together (at an equal amount), diluted to 10 nM and sequenced in NextSeq500 using Illumina paired-end protocol and reagents for 150 cycles.

G. Protocol for Multiplex RT-PCR Amplification of Target Genes for Expression Profiling or Mutation Analysis in Single Cells Using Barcoded Reverse Gene Specific Primer Set.

Step 1. Individual cells (5,000-10,000) were deposited by FACS in a separate wells (or as a separate droplets in oil) or partitioned in microdroplets using a microfluidics instrument (MissionBio) together with the barcoded reverse gene specific primer set immobilized on beads through photo-cleavable linkers (ChemB-T25-PCI-Anc2-BC-L2, ChemGenes, see structure above) in 1×TCL lysis-hybridization buffer (Qiagen) together with calibration control RNA template set.

Step 2. Barcoded reverse gene specific primers were released from beads by UV365 nm treatment (20 watts) for 5 minutes and hybridized with target RNA templates (present in lysates in a separate compartments) at 60° C. for 30 min. The hybridized complexes between the target RNA and the barcoded reverse gene specific primers were combined together (after removal of the oil phase for microdroplets) and purified bound to oligo dT25-beads by washing the beads three times in 1×SSC buffer. The purified target RNA-Barcoded reverse gene specific primer complexes were treated with thermosensitive exonuclease I (20 units, New England BioLabs) in 20-µl of 1×GC buffer at 37° C. for 30-min, 50° C. for 5 min. In an alternative protocol, the hybridized complexes between the target RNA and the barcoded reverse gene specific primers were combined together (after removal of the oil phase for microdroplets), purified using RNA/DNA micro kit (Qiagen) and treated with thermosensitive exonuclease I.

Step 3. Reverse primer extension step. RNA was converted to cDNA from barcoded reverse gene specific primers (hybridized to target RNA in Step 2) in 40-µl of reaction mix comprising 1×GC buffer, dNTP (500 uM), ThermaStop-RT (80 units, ThermaGenix) and Maxima Reverse Transcriptase (400 units, Thermo-Fisher) at 55° C. for 30 min.

Step 4. Forward primer extension step. Barcoded cDNA (generated in Step 3) was primed using a mix of Forward-anchor1-GSP primers (5 nM final concentration for the each primer) in 50-ul reaction mix comprising 1×GC buffer, dNTP (250 uM) and Phusion II (10 units, Thermo-Fisher) for 1 cycles at (98° C. for 1 min, 64° C. for 30 min) and treated with exonuclease I (20 units) at 37° C. for 30-min.

Step 5. 1st PCR step. The whole volume (50-µl) of barcoded anchored cDNA fragments (from Step 4) was amplified in 100-µl reaction mix comprising 1×HF Buffer, dNTP (200 uM), universal PCR primers F-MP1GAC and R-MP2CAG and Phusion II (20 units, Thermo-Fisher) for 14 cycles at (98° C. for 10 sec, 72° C. for 20 sec).

Step 6. 2nd PCR step. A 5-µl aliquot of 1st PCR was amplified in 100-µl of PCR mix comprising 1×HF Buffer, dNTP (200 µM), indexed (specific for the each of several samples) or non-indexed (only for one sample) Fwd and Rev PCR primers and Phusion II (20 units, Thermo-Fisher) for 7 cycles at (98° C. for 10 sec, 72° C. for 20 sec).

Step 7. The amplified PCR products were analyzed in 3.5% agarose-1×TAE gel to optimize the cycle number and finally digested with exonuclease I (20 units, New England Biolabs), incubated and 37° C. for 30 min, inactivated at 65° C. for 15 min and purified by AMPure beads (1.5× volume) using manufacturer's protocol (Beckman-Coulter). Purified PCR products were quantitated by Qubit (Thermo-Fisher) and if necessary different samples were mixed together (at equal amount), diluted to 10 nM and sequenced in NextSeq500 using Illumina paired-end protocol and reagents for 150 cycles.

H. Next Generation Sequencing Applications

Recently developed targeted approaches reduce NGS data complexity and generate qualitative sequencing information by measurement of a subset of targets per technical replicate with minimal sample usage. Nonetheless, targeted approaches reported thus far have limited clinical utility due to several scientific challenges, such as a priori determining which genetic markers have the most clinical significance and identifying key genetic variants that are correlated with a specific drug response. Furthermore, technical limitations due to skewed or inaccurate quantitative representation of clinical targets and inter-library variation confound their utility in the clinical setting.

For example, cancer is a complex multigenic disease characterized by diverse genetic and epigenetic alterations. A comprehensive catalog of all types of variants in cancer opens novel and unique opportunities for understanding the mechanism of cancer onset or progression and facilitates a more personalized approach to clinical care, including improved risk stratification and treatment selection. Next-generation sequencing (NGS) is now a major driver in translational and genetic research, providing a powerful way to study DNA or RNA from clinical specimens. For example, transcriptome profiling can unambiguously define a unique gene expression signature for each tumor that may prove useful for both disease classification and prognosis. Unfortunately, both the cost and the complexity of whole genome DNA sequencing or transcriptome RNA-sequencing data sets impede the use of these methodologies in routine molecular diagnostic testing.

Predesigned targeted gene panels disclosed in the current invention contain essential genes associated with human disease or phenotype(s), selected from publications, open access databases/resources, and expert curation. By focusing on the genes most likely to be involved in cellular processes and disease, these targeted RNA-Seq panels conserve sequencing next-generation sequencing (NGS) resources and minimize data analysis considerations. Predesigned panels will be unique experimental tools for clinical research on various diseases, such as cancer, signaling pathways, markers of cell lineage, differentiation, and activation. Examples below illustrate several assays we developed for clinical research applications.

1. Cell Marker Panel Assay for Profiling Cell Composition

The human Cell Marker Assay is a targeted multiplex RT-PCR panel that enables gene signature-based inference and quantitative evaluation of multiple unique immune and stromal cell types. The Cell Marker Assay provides a cost-effective strategy for quantitative analysis of cell composition in a wide range of clinical samples based on analysis of all well-characterized cell specific biomarkers.

The cell marker gene sets summarize and characterize gene signatures for 64 distinct cell types, spanning multiple adaptive and innate immunity cells, hematopoietic progenitors, epithelial cells, and extracellular matrix cells derived from thousands of published gene expression signatures. To generate our compendium of gene-specific signatures for human cell types, we used data from ENCODE, FANTOM, ImmGen, and the Human Primary Cells Atlas (HPCA). Also, we collected gene expression profiles from the Blueprint project, from which we annotated 144 samples from 28 cell types, and the IRIS project, from which we annotated 95 samples from 13 cell types. We collected and curated gene expression profiles from ~2,310 samples of pure cell types and annotated 64 distinct cell types and cell subsets.

The Human Cell Marker 1.3K targeted panel measures the expression level of 1,285 human protein-coding genes by combining highly multiplexed RT-PCR amplification with the depth and precision of NGS quantitation. The Cell Marker 1.3K panel also includes a set of 85 housekeeping genes with constant expression between different cell types. The Cell Marker 1.3K panel employs computationally-predicted set of PCR primers for multiplex PCR which are functionally (i.e., experimentally) validated, e.g., as described above. The unique multiplex primer design minimizes primer dimerization and cross-reactivity while enhancing specificity of hybridization and efficacy in primer extension steps. The set of calibration control RNA templates was developed for all housekeeping and 1285 cell marker genes, and is mixed with sample template RNA to be used as internal standards for calibration and QC of all RNA samples employed in the assay. It is an easy-to-run, one-tube assay that can be run directly from cell extract or total RNA (10 pg-50 ng) isolated from cells, tissues, or blood. In this embodiment, the RNA template compositions from different samples are hybridized with set of barcoded reverse gene specific primers, the RNA-primer hybrids are combined together in single-test tube, purified from non-bind primers, and used for follow-up primer extension and amplification steps. The multiplex single-tube assay provides robust, quantitative, and reproducible measurements of each expressed gene in the set of biological samples over as much as 5-orders of magnitude differences in expression level.

In another embodiment, the reverse gene specific primer set is immobilized to barcoded beads (one specific barcode per bead) through a cleavable linker. The barcoded bead-gene specific primer conjugates are mixed with the set of individual cells from a cell sample together with calibration control RNAs. One bead-one cell compositions are then isolated in separate compartments by FACS, aliquoting or microdroplet technology. The hybridization of detached barcoded gene specific primers with target mRNAs in solution, combining of all samples together, extension of purified of RNA-gene specific primer hybrids and follow up RT-PCR-NGS protocol allows a high level of multiplexing in analysis of thousands of individual cells. Moreover, single cell analysis combined with calibration control templates allows quality control analysis of each individual cell, plus normalization and calibration of the single cell data.

As to utility, the generated normalized quantitative single cell data could be used to accurately profile the specific cell composition in a wide range of clinical samples, including blood, tissue, biological fluids, organoids, isolated cells, organs, etc. in normal, treated, and disease states. The comprehensive set of cell type specific markers included in the assay allows robust and cost-effective cell typing analysis even at the scale of hundreds of thousands of individual cells. Moreover, Cell Marker 1.3K assay provides a cost-effective strategy for the discovery of novel diagnostic and prognostic cell types and cell specific biomarkers in xenograft, fine needle aspirate (FNA), biopsy, blood, and circulating tumor cell (CTC) clinical samples. Currently, an extended panel of cell markers based on the most recent public data are in development to address specific disease areas.

2. Blood Biomarker Diagnostic Panel

There is ample evidence that development of novel prognostic and predictive biomarkers is a critical step for selecting patients predisposed to respond to existing and novel (e.g. immunotherapy) treatments and their combinations. The Blood Biomarker 10K assay (BB10K) allows one to dissect immunological response mechanisms and discover novel prognostic and predictive immune response gene signatures.

The BB10K assay was developed to quantitatively profile expression of 10,000 key immunity genes expressed in different types of blood cells, using, in the preferred embodiment, single-cell multiplex RT-PCR amplification from total RNA followed by NGS sequencing. The individual cells (10K-100K) from peripheral blood mononuclear cell (PBMC) samples were mixed with cell type-specific antibody-bead-barcoded reverse gene specific primer conjugate and sorted by FACS or microfluidic technologies in separate droplets (compartments) for cell-specific barcoding of target mRNAs directly in cell lysates. Furthermore, each specific bead-antibody conjugate could be optically encoded to facilitate isolation and analysis e.g. by FACS specific single cell-bead conjugates. No mRNA enrichment, beta-globin depletion, or other processing are required. Up to 100 PBMC clinical samples could be run and combined together in the assay to provide a high level of multiplexing and significantly reduce sample-to-sample variation and batch effect issues. Furthermore, the built-in internal calibration standards allow calibration and adjusting of digital HT sequencing data depending on the level of intrinsic noise and quality of samples. The BB10K assay provides quantitative expression data of immune-related genes with 1,000-fold dynamic range and sensitivity down to 10 copies of RNA per cell in whole cell lysate or cell fractions (e.g. nucleus) from frozen PBMC clinical samples. Up to 100 PBMC clinical samples could be run and combined together (after hybridization step) in the assay to provide high level of multiplexing and significantly reduce sample-to-sample variation and batch effect issues.

The BB10K panel includes more than 100 experimentally validated core gene signatures (e.g., based on immunity HallMark database, Broad Institute) which correlate with a wide range of pathological conditions (cancer, cardiovascular, infection, acute pain, etc.), and predict efficacy of immunotherapy in several cancer types, including melanoma, colorectal, breast, and lung cancers after stimulation in vitro or in vivo by drugs, physical treatment, biologics or chemical compounds (heat shock, LPS, bacterial antigens, etc.). Furthermore, the core signatures were expanded by developing a computational functional interaction network model to predict key nodes in pathways specific for antigen presentation and recognition, inhibition and activation of immune cells. The BB10K panel also includes a set of TCR and BCR genes (variable regions) and housekeeping genes with constant expression between different blood cell types. The set of calibration control RNA templates was developed for all housekeeping and 1000 different blood cell type-specific genes in order to use as internal standards for calibration and QC of all cells employed in the assay.

Single cell expression profiling in all main blood cell types with the BB10K gene panel enables researchers to discover prognostic and predictive immune response biomarker signatures. The predictive signatures have the potential to stratify patients with a wide range of clinical indications for responses to the growing number of therapeutic treatments.

Notwithstanding the appended claims, the disclosure is also defined by the following clauses:

1. A method of preparing a plurality of sample-barcoded anchor-domain-flanked gene specific deoxyribonucleic acid (DNA) fragments from a template ribonucleic acid (RNA) sample, the method comprising:
   - employing a set of gene specific primer (GSP) pairs to produce the plurality of sample-barcoded anchor-domain-flanked gene specific DNA fragments from the template RNA sample, wherein each pair of gene specific primers (GSPs) is made up of an anchor domain comprising forward primer and an anchor domain comprising reverse primer, at least one of which comprises a sample barcode domain.

2. The method according to Clause 1, wherein each pair of the set of GSPs is made up of a forward primer comprising an anchor domain and a reverse primer comprising an anchor domain and a sample barcode domain.

3. The method according to Clause 2, wherein the method comprises contacting the template RNA sample with the reverse primers of the set to produce a hybrid composition comprising RNA/anchored sample barcoded reverse primer hybrids.

4. The method according to Clause 2, wherein the reverse primers are linked to a solid support.

5. The method according to Clause 4, wherein the solid support is a bead.

6. The method according to Clauses 4 and 5, wherein the reverse primers are linked to the solid support by a cleavable linker.

7. The method according to any of Clauses 3 to 6, wherein the method comprises removing unbound reverse primers from the hybrid composition to produce a hybrid enriched composition.

8. The method according to Clause 7, wherein the method comprises contacting the hybrid enriched composition with the forward primers of the set under primer extension reaction conditions to produce the plurality of sample-barcoded anchor-domain-flanked gene specific DNA fragments from the template RNA.

9. The method according to Clause 1, wherein the method comprises employing a sample-barcoded donor nucleic acid comprising an anchor domain and a sample barcode domain to produce the set of GSPs.

10. The method according to Clause 9, wherein the sample-barcoded donor nucleic acid comprises an RNA capture domain.

11. The method according to Clause 10, wherein the sample-barcoded donor nucleic acid further comprises a first linker, either the forward primers or the reverse primers comprise a second linker and the method further comprises ligating the first and second linkers.

12. The method according to any of Clauses 9 to 11, wherein the sample-barcoded donor nucleic acid comprises the structure: 3'-linker 1-sample barcode domain-anchor 2 domain-RNA binding domain-5'.

13. The method according to Clause 12, wherein the reverse primers comprise the structure: 3'-reverse GSP domain-linker 2-5'; and the forward primers comprise the structure 5'-anchor 1-forward GSP domain-3'.

14. The method according to Clause 13, wherein the method comprises:
   - contacting the template RNA sample with the sample-barcoded donor nucleic acid and the reverse primers under hybridization conditions;
   - ligating the linker 1 and linker 2 domains of hybrid sample-barcoded donor nucleic acid and reverse primers to produce sample-barcoded reverse primers;
   - reverse transcribing first strand complementary DNA (cDNA) molecules from the sample-barcoded reverse primers; and
   - contacting the first strand cDNA molecules with the forward primers under polymerase mediated primer extension reaction conditions to produce the plurality of sample-barcoded anchor-domain-flanked gene specific DNA fragments from the RNA sample.

15. The method according to any of Clauses 9 to 11, wherein the sample-barcoded donor nucleic acid comprises the structure: 3'-RNA binding domain-anchor 1 domain-sample barcode domain-linker 1 domain-5'.

16. The method according to Clause 15, wherein the forward primers comprise the structure: 3'-forward GSP domain-linker 2-5'; and the reverse primers comprise the structure 5'-anchor 2-reverse GSP domain-3'.

17. The method according to Clause 16, wherein the method comprises:
   - contacting the template RNA sample with the sample-barcoded donor nucleic acid under conditions sufficient to reverse transcribe first strand cDNA molecules from the template RNA sample;
   - contacting the first strand cDNA molecules with the forward primers under polymerase mediated primer extension reaction conditions sufficient to produce second strand cDNA molecules comprising a 5' linker 2 domain and a 3' linker 1 domain;
   - ligating the 5' linker 1 domain to the 3' linker 2 domain to circularize the second strand cDNA molecules; and
   - contacting the circularized second strand cDNA molecules with the reverse primers to produce the plurality of sample-barcoded anchor-domain-flanked gene specific DNA fragments from the template RNA sample.

18. The method according to any of the preceding clauses, wherein the forward and reverse primers of each primer pair comprise gene specific (GSP) domains that are experimentally validated as suitable for use in a multiplex amplification assay.

19. The method according to any of the preceding clauses, wherein the forward and reverse primers of each primer pair are separated by a template distance of 60 to 300 nt.

20. The method according to any of the preceding clauses, wherein the template ribonucleic acid sample comprises messenger ribonucleic acids (mRNAs).

21. The method according to any of the preceding clauses, wherein the template RNA sample is obtained from a single cell.
22. The method according to Clause 21, wherein the method comprises obtaining the template RNA sample by isolating the single cell and then lysing the isolated single cell to produce the RNA sample.
23. The method according any of the preceding clauses, wherein the GSP domain of each forward primer ranges in length from 18 to 25 nt.
24. The method according any of the preceding clauses, wherein the GSP domain of each reverse primer ranges in length from 30 to 70 nt.
25. The method according to any of the preceding clauses, wherein the flanking anchor domains comprise a universal priming site and the method further comprises amplifying the primer extension products comprising the anchor domains with universal forward and reverse primers having sequences complementary to the universal priming sites under amplification conditions sufficient to produce a barcoded amplicon composition comprising multiple product amplicons.
26. The method according to Clause 25, wherein the universal forward and reverse primers further comprise Next-Generation Sequencing (NGS) adaptor domains.
27. The method according to Clause 26, wherein the method further comprises adding NGS adaptor domains to the multiple product amplicons of the barcoded amplicon composition
28. The method according Clause 27, wherein the NGS adaptor domains are added to the multiple product amplicons of the barcoded amplicon composition via an amplification protocol.
29. The method according to any of Clauses 25 to 28, wherein the method further comprises sequencing the multiple product amplicons.
30. The method according to Clause 29, wherein the multiple product amplicons are sequenced using an NGS protocol.
31. The method according to any of the preceding clauses, wherein the method is performed in a well.
32. The method according to any of Clauses 1 to 30, wherein the method is performed in a droplet.
33. The method according to Clause 32, wherein the droplet is produced using a microfluidics protocol.
34. The method according to Clause 32, wherein the droplet is producing using a fluorescence activated cell sorter (FACS) protocol.
35. The method according to any of the preceding clauses, wherein the method comprises a pooling step.
36. The method according to any of the preceding clauses, wherein the method comprises employing a calibration ribonucleic acid composition.
37. A method of preparing a plurality of sample-barcoded anchor-domain-flanked gene specific DNA fragments from a template RNA sample, the method comprising:
- contacting the template RNA sample with reverse primers of a set of GSPs, wherein the reverse primers comprise an anchor domain and a sample barcode domain, to produce a hybrid composition comprising RNA/anchored sample barcoded reverse primer hybrids;
- removing unbound reverse primers from the hybrid composition to produce a hybrid enriched composition;
- reverse transcribing the hybrid enriched composition to produce a cDNA composition; and
- contacting the cDNA composition with forward primers of the set, wherein the forward primers comprise an anchor domain, under primer extension reaction conditions to produce the plurality of sample-barcoded anchor-domain-flanked gene specific DNA fragments from the template RNA sample.

38. The method according to Clause 37, wherein the reverse primers further comprise a UMI domain.
39. The method according to Clause 37, wherein the reverse primers are linked to a solid support.
40. The method according to Clause 39, wherein the solid support is a bead.
41. The method according to Clauses 39 and 40, wherein the reverse primers are linked to the solid support by a cleavable linker.
42. The method according to Clause 41, wherein the method further comprises cleaving the cleavable linker.
43. The method according to any of Clauses 39 to 42, wherein the solid support further comprises specific binding pair member.
44. The method according to Clause 43, wherein the specific binding pair member specifically binds to a cell surface marker.
45. The method according to any of Clauses 39 to 44, wherein the reverse primers further comprise a solid support barcode domain.
46. The method according to any of Clauses 37 to 45, wherein the template RNA sample is obtained from a single cell.
47. The method according to Clause 46, wherein the method comprises obtaining the template RNA sample by isolating the single cell and then lysing the isolated single cell to produce the template RNA sample.
48. The method according to Clause 47, wherein the cell is isolated and lysed in a well.
49. The method according to Clause 47, wherein the cell is isolated and lysed in a droplet.
50. The method according to Clause 49, wherein the droplet is produced using a microfluidics protocol.
51. The method according to Clause 49, wherein the droplet is producing using a fluorescence activated cell sorter (FACS) protocol.
52. The method according to any of Clauses 37 to 51, wherein the method comprises a pooling step.
53. The method according to Clause 52, wherein the pooling step comprises pooling the enriched hybrid composition with at least one additional enriched hybrid composition produced form at least one additional template RNA sample.
54. The method according to any of Clauses 37 to 53, wherein the method comprises employing a calibration ribonucleic acid composition.
55. The method according to any of Clauses 37 to 54, wherein the method further comprises removing non-extended forward primers from the plurality of sample-barcoded anchor-domain-flanked gene specific DNA fragments.
56. The method according any of Clauses 37 to 55, wherein the GSP domain of each forward primer ranges in length from 18 to 25 nt.
57. The method according any of Clauses 37 to 56, wherein the GSP domain of each reverse primer ranges in length from 30 to 70 nt.
58. The method according to any of Clauses 37 to 57, wherein the flanking anchor domains comprise a universal priming site and the method further comprises amplifying the primer extension products comprising the anchor domains with universal forward and reverse primers having sequences complementary to the universal priming sites under amplification conditions sufficient to produce a barcoded amplicon composition comprising multiple product amplicons.

59. The method according to Clause 58, wherein the universal forward and reverse primers further comprise Next-Generation Sequencing (NGS) adaptor domains.

60. The method according to Clause 59, wherein the method further comprises adding NGS adaptor domains to the multiple product amplicons of the barcoded amplicon composition 61. The method according Clause 60, wherein the NGS adaptor domains are added to the multiple product amplicons of the barcoded amplicon composition via an amplification protocol.

62. The method according to any of Clauses 58 to 61, wherein the method further comprises sequencing the multiple product amplicons.

63. The method according to Clause 62, wherein the multiple product amplicons are sequenced using an NGS protocol.

64. A system comprising:

nucleic acid amplification device;

a sample-barcoded donor nucleic acid comprising a RNA binding domain, an anchor domain and a sample barcode domain; and a set of GSPs wherein each pair of GSPs is made up of a forward primer and a reverse primer.

65. The system according to Clause 64, wherein the sample-barcoded donor nucleic acid further comprises a first linker and either the forward primers or the reverse primers comprise a second linker.

66. The system according to Clause 65, wherein the sample-barcoded donor nucleic acid comprises the structure: 3'-linker 1-sample barcode domain-anchor 2 domain-RNA binding domain-5'.

67. The system according to Clause 66, wherein the reverse primers comprise the structure: 3'-reverse GSP domain-linker 2-5'; and the forward primers comprise the structure 5'-anchor 1-forward GSP domain-3'.

68. The system according to Clause 67, wherein the sample-barcoded donor nucleic acid comprises the structure: 3'-RNA binding domain-anchor 1 domain-sample barcode domain-linker 1 domain-5'.

69. The system according to Clause 68, wherein the forward primers comprise the structure: 3'-forward GSP domain-linker 2-5'; and the reverse primers comprise the structure 5'-anchor 2-reverse GSP domain-3'.

70. The system according to any of Clauses 64 to 69, wherein the forward and reverse primers of each primer pair comprise GSP domains that are experimentally validated as suitable for use in a multiplex amplification assay.

71. The system according to any of Clauses 64 to 70, wherein the forward and reverse primers are separated by a template distance of 60 to 300 nt.

72. The system according to any of Clauses 64 to 71, wherein the system further comprises a RNA sample.

73. The system according to Clause 72, wherein the RNA sample is from a single cell.

74. The system according to any of Clauses 64 to 73, wherein the device is a thermal cycler.

75. A system comprising:

nucleic acid amplification device; and a set of GSPs wherein each pair of GSPs is made up of a forward primer and a reverse primer comprising a sample barcode domain.

76. The system according to Clause 75, wherein the forward and reverse primers of each primer pair comprise GSP domains that are experimentally validated as suitable for use in a multiplex amplification assay.

77. The system according to any of Clauses 75 to 76, wherein the forward and reverse primers are separated by a template distance of 60 to 300 nt.

78. The system according to any of Clauses 75 to 77, wherein the reverse primers are linked to a solid support.

79. The system according to Clause 78, wherein the solid support is a bead.

80. The system according to any of Clauses 78 to 79, wherein the reverse primers are linked to the solid support by a cleavable linker.

81. The system according to any of Clauses 78 to 80, wherein the solid support further comprises specific binding pair member.

82. The system according to Clause 81, wherein the specific binding pair member specifically binds to a cell surface marker.

83. The system according to any of Clauses 78 to 82, wherein reverse primers further comprise a solid support barcode domain.

84. The system according to any of Clauses 75 to 83, wherein the system further comprises a RNA sample.

85. The system according to Clause 84, wherein the RNA sample is from a single cell.

86. The system according to any of Clauses 75 to 85, wherein the device is a thermal cycler.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to “at least one of A, B, and C, etc.” is used, in general such a construction is intended in the sense one having skill in the art would understand the convention (e.g., “a system having at least one of A, B, and C” would include but not be limited to systems that have A alone, B alone, C alone, A and B together, A and C together, B and C together, and/or A, B, and C together, etc.). In those instances where a convention analogous to “at least one of A, B, or C, etc.” is used, in general such a construction is intended in the sense one having skill in the art would understand the convention (e.g., “a system having at least one of A, B, or C” would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase “A or B” will be understood to include the possibilities of “A” or “B” or “A and B.”

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase “means for” or the exact phrase “step for” is recited at the beginning of such limitation in the claim; if such exact phrase is not used in a limitation in the claim, then 35 U.S.C. § 112 (f) or 35 U.S.C. § 112(6) is not invoked.

SEQUENCE LISTING

The patent contains a lengthy sequence listing. A copy of the sequence listing is available in electronic form from the USPTO web site (https://seqdata.uspto.gov/docdetail?docId=US12767975B2). An electronic copy of the sequence listing will also be available from the USPTO upon request and payment of the fee set forth in 37 CFR 1.19(b)(3).

What is claimed is:

1. A method of preparing a plurality of sample-barcoded anchor-domain-flanked gene specific DNA fragments from a template RNA sample, the method comprising:

contacting the template RNA sample with reverse primers of a set of GSPs (Gene Specific Primers), wherein the reverse primers comprise an anchor domain and a sample barcode domain common to the reverse primers of the set of GSPs, to produce a hybrid composition comprising RNA/anchored sample barcoded reverse primer hybrids;

removing unbound reverse primers from the hybrid composition to produce a hybrid enriched composition;

reverse transcribing the hybrid enriched composition to produce a cDNA composition; and contacting the cDNA composition with forward primers of the set, wherein the forward primers comprise an anchor domain, under primer extension reaction conditions to produce the plurality of sample-barcoded anchor-domain-flanked gene specific DNA fragments from the template RNA sample.

2. The method according to claim 1, wherein the reverse primers further comprise a unique molecular identifier (UMI) domain.

3. The method according to claim 1, wherein the template RNA sample is obtained from a single cell.

4. The method according to claim 3, wherein the method comprises obtaining the template RNA sample by isolating the single cell and then lysing the isolated single cell to produce the template RNA sample.

5. The method according to claim 4, wherein the cell is isolated and lysed in a well.

6. The method according to claim 4, wherein the cell is isolated and lysed in a droplet.

7. The method according to claim 6, wherein the droplet is produced using microfluidics.

8. The method according to claim 6, wherein the droplet is produced using a fluorescence activated cell sorter (FACS).

9. The method according to claim 1, wherein the method comprises a pooling step.

10. The method according to claim 9, wherein the pooling step comprises pooling the enriched hybrid composition with at least one additional enriched hybrid composition produced form at least one additional template RNA sample.

11. The method according to claim 1, wherein the method further comprises removing non-extended forward primers from the plurality of sample-barcoded anchor-domain-flanked gene specific DNA fragments.

12. The method according to claim 1, wherein the GSP domain of each forward primer ranges in length from 18 to 25 nucleotides (nt).

13. The method according to claim 1, wherein the GSP domain of each reverse primer ranges in length from 30 to 70 nt.

14. The method according to claim 1, wherein the flanking anchor domains comprise a universal priming site and the method further comprises amplifying the sample-barcoded anchor-domain-flanked gene specific DNA fragments comprising the anchor domains with universal forward and reverse primers having sequences complementary to the universal priming sites under amplification conditions sufficient to produce a barcoded amplicon composition comprising multiple product amplicons.

15. The method according to claim 14, wherein the universal forward and reverse primers further comprise Next-Generation Sequencing (NGS) adaptor domains.

16. The method according to claim 15, wherein the method further comprises adding NGS adaptor domains to the multiple product amplicons of the barcoded amplicon composition.

17. The method according claim 16, wherein the NGS adaptor domains are added to the multiple product amplicons of the barcoded amplicon composition by amplification.

18. The method according to claim 14, wherein the method further comprises sequencing the multiple product amplicons.

19. The method according to claim 18, wherein the multiple product amplicons are sequenced using an NGS protocol.

20. The method of claim 5, wherein the cell is deposited into the well using a cell sorter.

21. The method of claim 20, wherein the cell sorter is a fluorescence activated cell sorter (FACS).

22. The method according to claim 5, wherein the well is an individual well of a device comprising a plurality of wells.

23. The method according to claim 22, wherein the individual well contains the reverse primers of a set of GSPs.

24. The method according to claim 23, wherein the sample barcode domain common to the reverse primers of the set of GSPs is specific to the well.

* * * * *